US008673911B2

(12) United States Patent
Mallais et al.

(10) Patent No.: US 8,673,911 B2
(45) Date of Patent: Mar. 18, 2014

(54) INHIBITORS OF HISTONE DEACETYLASE

(75) Inventors: Tammy Mallais, Kirkland (CA); Oscar Moradei, Kirkland (CA); Alain Ajamian, Montreal (CA); Pierre Tessier, Hawkesbury (CA); David Smil, Montreal (CA); Sylvie Frechette, Verdun (CA); Silvana Leit, Kirkland (CA); Patrick Beaulieu, Laval (CA); Robert Deziel, Mount-Royal (CA); John Mancuso, Sherbrooke (CA)

(73) Assignee: MethylGene Inc., Montreal (CA)

( * ) Notice: Subject to any disclaimer, the term of this patent is extended or adjusted under 35 U.S.C. 154(b) by 114 days.

(21) Appl. No.: 12/740,616

(22) PCT Filed: Nov. 3, 2008

(86) PCT No.: PCT/CA2008/001911

§ 371 (c)(1),
(2), (4) Date: Sep. 20, 2010

(87) PCT Pub. No.: WO2009/055917

PCT Pub. Date: May 7, 2009

(65) Prior Publication Data

US 2011/0021771 A1 Jan. 27, 2011

Related U.S. Application Data

(60) Provisional application No. 60/985,060, filed on Nov. 2, 2007.

(51) Int. Cl.

| | |
|---|---|
| ***A61K 31/5377*** | (2006.01) |
| ***C07D 413/02*** | (2006.01) |
| ***A61K 31/4535*** | (2006.01) |
| ***C07D 417/02*** | (2006.01) |
| ***C07D 211/02*** | (2006.01) |
| ***C07D 401/02*** | (2006.01) |
| ***C07D 401/14*** | (2006.01) |
| ***A61K 31/426*** | (2006.01) |
| ***A61K 31/421*** | (2006.01) |
| ***A61K 31/415*** | (2006.01) |
| ***A61K 31/40*** | (2006.01) |
| ***A61K 31/381*** | (2006.01) |
| ***C07D 277/20*** | (2006.01) |
| ***C07D 263/30*** | (2006.01) |
| ***C07D 231/10*** | (2006.01) |
| ***C07D 333/02*** | (2006.01) |

(52) U.S. Cl.
USPC .................... 514/236.5; 514/236.8; 514/318; 514/340; 514/341; 514/365; 514/374; 514/406; 514/423; 514/438; 544/133; 544/140; 546/194; 546/201; 546/209; 546/270.4; 546/275.4; 548/200; 548/236; 548/364.7; 548/374.1; 548/530; 549/72

(58) Field of Classification Search
USPC ........... 514/236.5, 236.8, 318, 340, 341, 365, 514/374, 406, 423, 438; 544/133, 140; 546/194, 201, 209, 270.4, 275.4; 548/200, 236, 364.7, 374.1, 530; 549/72
See application file for complete search history.

(56) References Cited

U.S. PATENT DOCUMENTS

| | | | | |
|---|---|---|---|---|
| 7,094,791 | B2 * | 8/2006 | Cholody et al. | 514/326 |
| RE39,850 | E | 9/2007 | Delorme et al. | |
| 7,868,205 | B2 | 1/2011 | Moradei et al. | |
| 2005/0197336 | A1 | 9/2005 | Anandan et al. | |
| 2005/0250784 | A1 | 11/2005 | Anandan et al. | |
| 2006/0074119 | A1 * | 4/2006 | Andrews et al. | 514/394 |
| 2008/0132503 | A1 | 6/2008 | Moradei et al. | |
| 2008/0207590 | A1 | 8/2008 | Deziel et al. | |
| 2008/0227826 | A1 | 9/2008 | Frechette et al. | |

FOREIGN PATENT DOCUMENTS

| | | | | |
|---|---|---|---|---|
| CA | 2633100 | | 7/2007 | |
| EP | 0511021 | A1 | 10/1992 | |
| WO | 89/03818 | | 5/1989 | |
| WO | 03/076422 | A1 | 9/2003 | |
| WO | 2004/013130 | | 2/2004 | |
| WO | 2004/014899 | A1 | 2/2004 | |
| WO | WO 2004072051 | * | 8/2004 | 548/200 |
| WO | 2004/073599 | | 9/2004 | |

(Continued)

OTHER PUBLICATIONS

Herrero, M. Teresa. Novel applications of the hypervalent iodine chemistry. Synthesis of thiazolo-fused quinolinones. ARKIVOC (Gainesville, FL, United States) [online computer file] (2002), (5), 31-37.*

(Continued)

*Primary Examiner* — Samantha Shterengarts
(74) *Attorney, Agent, or Firm* — McDonnell Boehnen Hulbert & Berghoff LLP

(57) ABSTRACT

This invention relates to compounds and methods for the inhibition of HDAC enzymatic activity. More particularly, the invention provides for compounds of formula (I), (I) and N-oxides, hydrates, solvates, pharmaceutically acceptable salts, prodrugs and complexes thereof, and racemic and scalemic mixtures, diastereomers and enantiomers thereof, wherein L, M, n, R, W, X and Y are as defined in the specification.

(I)

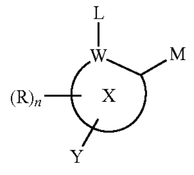

2 Claims, No Drawings

(56) References Cited

FOREIGN PATENT DOCUMENTS

| | | |
|---|---|---|
| WO | 2005/014588 | 2/2005 |
| WO | 2005/034880 | 4/2005 |
| WO | 2005/040161 | 5/2005 |
| WO | 2006/010749 | 2/2006 |
| WO | 2006/017214 | 2/2006 |
| WO | 2006/101454 | 9/2006 |
| WO | 2006/101455 | 9/2006 |
| WO | 2006/123121 | 11/2006 |
| WO | 2007/109178 | 9/2007 |
| WO | 2008/015263 | 9/2008 |
| WO | 2008/115262 | 9/2008 |

OTHER PUBLICATIONS

CAplus registry numbers: RN 860510-24-3, RN 63482-92-8, and RN 858490-34-3. Accessed in STN Jun. 15, 2012.*

[Database Registry Chemical Abstracts Service, Columbus, Ohio, Accession No. RN 131924-72-6, RN 131924-73-7, RN 131924-74-8, RN 131924-75-9, RN 131924-76-0, and RN 131924-77-1, Entered STN: Feb. 8, 1991.].*

Glover, SA et al., "N-alkoxy-N-acylnitrenium ions as possible intermediates in intramolecular aromatic substitution: novel formation of N-acyl-3,4-dihydro-1H-2,1-benzoxazines and N-acyl-4,5-dihydro-1H,3H-2,1-benzoxazepine" Journal of the Chemical Society, Perkin Transactions (1984), (10) 2225-2260.

Boldt, GE et al., "Identification of a Potent Botulinum Neurotoxin A Protease Inhibitor Using in Situ Lead Identification Chemistry" Organic Letters (2006) 8(8), 1729-1732.

Levin, J. I. et al., "Heteroaryl and Cycloalkyl Sulfonamide Hydroxamic Acid Inhibitors of Matrix Metalloproteinases", Bioorganic & Medicinal Chemistry Letters, 2001, 11(2), 239-242.

Vasilevsky, S. F. et al., "Heterocyclization of vic-substituted hydoxamic acid salts of acetylenylpyrazoles. A new procedure for the preparation of pyrazolo [3,4-c]pyridin-7-ones.", XP-002711452, 1 page, 2002.

Miura, J. et al., "Preparation of 3- or 5-phenylpyrazole derivatives as herbicides", XP002711475, 2 pages, 1988.

Tihanyi, E. et al., "Pyrazole-5-carboxylic acids", XP-002711476, 2 pages, 1980.

Belgodere, E. et al., "Imidazole derivatives with potential biological activity", XP-002711477, 2 pages, 1980.

* cited by examiner

INHIBITORS OF HISTONE DEACETYLASE

CROSS-REFERENCE TO RELATED APPLICATIONS

This application claims priority to U.S. provisional application No. 60/985,060, filed Nov. 2, 2007.

BACKGROUND OF THE INVENTION

1. Field of the Invention

This invention relates to compounds for the inhibition of histone deacetylase (HDAC). More particularly, the invention relates to compounds and methods for inhibiting HDAC enzymatic activity.

2. Description of Related Art

Histone deacetylases are involved in the epigenetic regulation of gene expression through chromatin remodeling. In eukaryotic cells, nuclear DNA associates with histones to form a compact complex called chromatin. The histones constitute a family of basic proteins which are generally highly conserved across eukaryotic species. The core histones, termed H2A, H2B, H3, and H4, associate to form a protein core. DNA winds around this protein core, with the basic amino acids of the histones interacting with the negatively charged phosphate groups of the DNA. Approximately 146 base pairs of DNA wrap around a histone core to make up a nucleosome particle, the repeating structural motif of chromatin.

Csordas, *Biochem. J.,* 286: 23-38 (1990) teaches that histones are subject to posttranslational acetylation of the N-terminal lysine residues, a reaction that is catalyzed by histone acetyl transferase (HAT1). Acetylation neutralizes the positive charge of the lysine side chain, and is thought to impact chromatin structure. Indeed, Taunton et al., *Science,* 272: 408-411 (1996), teaches that access of transcription factors to chromatin templates is enhanced by histone hyperacetylation. Taunton et al. further teaches that an enrichment in underacetylated histone H4 has been found in transcriptionally silent regions of the genome.

Histone acetylation is a reversible modification, with deacetylation being catalyzed by a family of enzymes termed histone deacetylases (HDACs). The molecular cloning of gene sequences encoding proteins with HDAC activity has established the existence of a set of discrete HDAC enzyme isoforms. Histone deacetylases play an important role in gene regulation in mammalian cells. Gray and Ekstrom, Expr. Cell. Res. 262: 75-83 (2001); Zhou et al., Proc. Natl. Acad. Sci. USA 98: 10572-10577 (2001); Kao et al. J. Biol. Chem. 277: 187-193 (2002) and Gao et al. J. Biol. Chem. 277: 25748-25755 (2002) teach that there are 11 members of the histone deacetylase (HDAC) family.

Class I histone deacetylases include HDAC1, HDAC2, HDAC3 and HDAC8. The Class I enzymes are expressed in a wide variety of tissues and are reported to be localized in the nucleus. Class II histone deacetylases include HDAC4, HDAC5, HDAC6, HDAC7, HDAC9 and HDAC10. The Class II enzymes have been described as limited in tissue distribution and they can shuttle between the nucleus and the cytoplasm. The Class II enzymes are further divided into Class IIa (HDAC4, HDAC5, HDAC7 and HDAC9) and Class IIb (HDAC6 and HDAC10). Recent classifications place HDAC11 in a class of its own.

Studies utilizing known HDAC inhibitors have established a link between acetylation and gene expression. Numerous studies have examined the relationship between HDAC and gene expression. Taunton et al., *Science* 272:408-411 (1996), discloses a human HDAC that is related to a yeast transcriptional regulator. Cress et al., *J. Cell. Phys.* 184:1-16 (2000), discloses that, in the context of human cancer, the role of HDAC is as a corepressor of transcription. Ng et al., *TIBS* 25: March (2000), discloses HDAC as a pervasive feature of transcriptional repressor systems. Magnaghi-Jaulin et al., *Prog. Cell Cycle Res.* 4:41-47 (2000), discloses HDAC as a transcriptional co-regulator important for cell cycle progression.

Richon et al., *Proc. Natl. Acad. Sci. USA,* 95: 3003-3007 (1998), discloses that HDAC activity is inhibited by trichostatin A (TSA), a natural product isolated from *Streptomyces hygroscopicus*, which has been shown to inhibit histone deacetylase activity and arrest cell cycle progression in cells in the G1 and G2 phases (Yoshida et al., *J. Biol. Chem.* 265: 17174-17179, 1990; Yoshida et al., *Exp. Cell Res.* 177: 122-131, 1988), and by a synthetic compound, suberoylanilide hydroxamic acid (SAHA). Yoshida and Beppu, *Exper. Cell Res.,* 177: 122-131 (1988), teaches that TSA causes arrest of rat fibroblasts at the $G_1$ and $G_2$ phases of the cell cycle, implicating HDAC in cell cycle regulation. Indeed, Finnin et al., *Nature,* 401: 188-193 (1999), teaches that TSA and SAHA inhibit cell growth, induce terminal differentiation, and prevent the formation of tumors in mice. Suzuki et al., U.S. Pat. No. 6,174,905, EP 0847992 and JP 258863/96, disclose benzamide derivatives that induce cell differentiation and inhibit HDAC. Delorme et al., WO 01/38322 and WO 2001/070675, disclose additional compounds that serve as HDAC inhibitors. Other inhibitors of histone deacetylase activity, including trapoxin, depudecin, FR901228 (Fujisawa Pharmaceuticals), and butyrate, have been found to similarly inhibit cell cycle progression in cells (Taunton et al., *Science* 272: 408-411, 1996; Kijima et al., *J. Biol. Chem.* 268(30): 22429-22435, 1993; Kwon et al., *Proc. Natl. Acad. Sci. USA* 95(7):3356-61, 1998).

These and other findings suggest that inhibition of HDAC activity represents a novel approach for intervening in cell cycle regulation and that HDAC inhibitors have great therapeutic potential in the study and/or treatment of diseases or conditions ameliorated by modulating HDAC activity. Inhibitors which are not selective for specific HDAC isotype(s) may have undesirable side effects than an HDAC inhibitor that is better able to target specific HDAC isoforms, and may thus be less desirable as an inhibitor or therapeutic agent. Identification of inhibitors selective for specific HDAC isotype(s) will yield novel strategies for understanding the role of histone deacetylases and treating diseases ameliorated by modulating by HDAC activity.

SUMMARY OF THE INVENTION

The present invention provides compounds and methods for the inhibition of HDAC enzymatic activity. The invention provides compounds and methods for treating diseases ameliorated by modulating by HDAC activity, such as cell proliferative diseases and conditions.

In a first aspect, the present invention provides compounds that are useful as inhibitors of HDAC and that have the Formula (I):

(I)

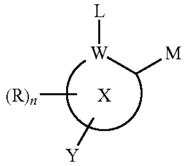

and N-oxides, hydrates, solvates, pharmaceutically acceptable salts, prodrugs and complexes thereof, and racemic and scalemic mixtures, diastereomers, tautomers and enantiomers thereof, wherein L, M, n, R, W, X and Y are as defined below. In this first aspect, the invention provides compounds of Formula I that are useful as HDAC inhibitors and, therefore, are useful research tools for the study of the role of HDAC in both normal and disease states.

In a second aspect, the invention provides a composition comprising a compound according to the present invention. In one embodiment, the composition further comprises an additional inhibitory agent.

In a third aspect, the invention provides a method of inhibiting HDAC activity, in one embodiment HDAC4, HDAC5, HDAC6, HDAC7, HDAC8, HDAC9 and/or HDAC11, the method comprising contacting the HDAC with a compound according to the present invention, or with a composition according to the present invention. Inhibition of HDAC can be in a cell or a multicellular organism. If in a cell, the method according to this aspect of the invention comprises contacting the cell with a compound according to the present invention, or with a composition according to the present invention. If in a multicellular organism, the method according to this aspect of the invention comprises administering to the organism a compound according to the present invention, or a composition according to the present invention. In one embodiment the organism is a mammal, for example a human.

The present invention provides compounds for use in the manufacture of a medicament for the treatment of diseases ameliorated by modulating by HDAC activity.

The foregoing merely summarizes the above aspects of the invention and is not intended to be limiting in nature. These aspects and other aspects and embodiments are described more fully below. The patent and scientific literature referred to herein establishes knowledge that is available to those with skill in the art. Each issued patent, patent application, and other publication cited herein is hereby incorporated by reference in its entirety. In the case of inconsistencies, the teachings of the present disclosure will prevail.

DETAILED DESCRIPTION OF THE INVENTION

The present invention provides compounds and methods for the inhibition of HDAC enzymatic activity. The invention also provides compounds and methods for treating diseases ameliorated by modulating by HDAC activity, such as cell proliferative diseases and conditions.

In one aspect, the invention provides compounds of the Formula (I):

(I)

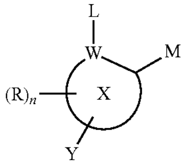

and N-oxides, hydrates, solvates, pharmaceutically acceptable salts, prodrugs and complexes thereof, and racemic and scalemic mixtures, diasteromers, tautomers and enantiomers thereof, wherein L, M, n, R, W, X and Y are as defined herein.

In the second aspect, the invention provides a composition comprising a compound according to the first aspect or any embodiment thereof and a pharmaceutically acceptable carrier.

In a third aspect, the invention provides a method of inhibiting HDAC activity, the method comprising contacting the HDAC, or a cell containing HDAC activity with an inhibition effective amount of a compound according to the present invention, or with an inhibition effective amount of a composition according to the present invention. Inhibition of HDAC activity can be in a cell or a multicellular organism. If in a multicellular organism, the method according to this aspect of the invention comprises administering to the organism an inhibition effective amount of a compound according to the present invention, or an inhibition effective amount of a composition according to the present invention. In one embodiment the organism is a mammal, for example a primate, such as a human. In one embodiment, the method further comprises concurrently or sequentially contacting the HDAC, or the cell, with an effective amount of an additional HDAC inhibitory agent, or if in a multicellular organism, concurrently or sequentially administering an inhibition effective amount of an additional HDAC inhibitory agent.

In one embodiment of the third aspect, the method comprises inhibiting a histone deacetylase selected from the group consisting of HDAC4, HDAC5, HDAC6, HDAC7, HDAC8, HDAC9 and/or HDAC11 in a cell comprising contacting the cell with a histone deacetylase inhibiting amount of a compound according to the present invention. In still another embodiment, the method comprises inhibiting a histone deacetylase selected from the group consisting of HDAC4, HDAC5, HDAC6, HDAC7, HDAC8, HDAC9 and/or HDAC11 in a cell comprising contacting the cell with a histone deacetylase inhibiting amount of a composition according to the present invention. According to this aspect, the compounds and compositions according to the invention are useful as tools for exploring the role of histone deacetylases, such as HDAC4, HDAC5, HDAC6, HDAC7, HDAC8, HDAC9 and/or HDAC11, in various disease conditions. In other embodiments of this aspect, the histone deacetylase is selected from the group consisting of HDAC4, HDAC5, HDAC7 and HDAC9

In some embodiments, the contacted cell is in an animal. Thus, the invention provides a method for treating a disease ameliorated by modulating by HDAC activity in an animal, comprising administering to an animal in need of such treatment a therapeutically effective amount of a compound according to the present invention, or a pharmaceutical composition thereof. In one embodiment, the animal is a mammal, for example a domesticated mammal or a primate. In another embodiment, the animal is a human.

In some embodiments the animal is administered an effective amount of a compound according to the present invention, or a pharmaceutical composition thereof, in combination (simultaneously or sequentially) with at least one other anti-disease agent, or a composition thereof. The term "anti-disease agent" includes any agent that is useful for the treatment of the particular disease for which treatment is desired.

For purposes of the present invention, the following definitions will be used (unless expressly stated otherwise).

Reference to "a compound of the formula (I), formula (II), etc.," (or equivalently, "a compound according to the first aspect", or "a compound of the present invention", and the like), herein is understood to include reference to N-oxides, hydrates, solvates, pharmaceutically acceptable salts, prodrugs and complexes thereof, and racemic and scalemic mixtures, diastereomers, enantiomers and tautomers thereof and unless otherwise indicated.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for 0, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—. Also, a number of moieties disclosed here may exist in multiple tautomeric forms, all of which are intended to be encompassed by any given tautomeric structure.

For simplicity, reference to a "$C_n$-$C_m$" heterocyclyl or "$C_n$-$C_m$" heteroaryl means a heterocyclyl or heteroaryl having from "n" to "m" annular atoms, where "n" and "m" are integers. Thus, for example, a $C_5$-$C_6$-heterocyclyl is a 5- or 6-membered ring having at least one heteroatom, and includes, for example, pyrrolidinyl ($C_5$) and piperidinyl ($C_6$); $C_6$-heteroaryl includes, for example, pyridyl and pyrimidyl.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$-hydrocarbyl" includes a covalent bond, methyl, ethyl, ethenyl, ethynyl, propyl, propenyl, propynyl, and cyclopropyl.

The term "aliphatic" is intended to mean both saturated, partially unsaturated and unsaturated, straight chain or branched aliphatic hydrocarbons. As will be appreciated by one of ordinary skill in the art, "aliphatic" is intended herein to include, but is not limited to, alkyl, alkenyl or alkynyl moieties.

The term "alkyl" is intended to mean a straight chain or branched aliphatic group having from 1 to 12 carbon atoms, alternatively 1-8 carbon atoms, and alternatively 1-6 carbon atoms. Other examples of alkyl groups have from 2 to 12 carbon atoms, alternatively 2-8 carbon atoms and alternatively 2-6 carbon atoms. Examples of alkyl groups include, without limitation, methyl, ethyl, propyl, isopropyl, butyl, isobutyl, sec-butyl, tert-butyl, pentyl, hexyl and the like. A "$C_0$" alkyl (as in "$C_0$-$C_3$alkyl") is a covalent bond.

The term "alkenyl" is intended to mean an unsaturated or partially unsaturated straight chain or branched aliphatic group with one or more carbon-carbon double bonds, having from 2 to 12 carbon atoms, alternatively 2-8 carbon atoms, and alternatively 2-6 carbon atoms. Examples of alkenyl groups include, without limitation, ethenyl, propenyl, butenyl, pentenyl, and hexenyl.

The term "alkynyl" is intended to mean an unsaturated or partially unsaturated straight chain or branched aliphatic group with one or more carbon-carbon triple bonds, having from 2 to 12 carbon atoms, alternatively 2-8 carbon atoms, and alternatively 2-6 carbon atoms. Examples of alkynyl groups include, without limitation, ethynyl, propynyl, butynyl, pentynyl, and hexynyl.

The terms "alkylene," "alkenylene," or "alkynylene" as used herein are intended to mean an alkyl, alkenyl, or alkynyl group, respectively, as defined hereinabove, that is positioned between and serves to connect two other chemical groups. Examples of alkylene groups include, without limitation, methylene, ethylene, propylene, and butylene. Examples of alkenylene groups include, without limitation, ethenylene, propenylene, and butenylene. Examples of alkynylene groups include, without limitation, ethynylene, propynylene, and butynylene.

The term "azolyl" as employed herein is intended to mean a five-membered saturated or unsaturated heterocyclic group containing two or more hetero-atoms, as ring atoms, selected from the group consisting of nitrogen, sulfur and oxygen, wherein at least one of the hetero-atoms is a nitrogen atom. Examples of azolyl groups include, but are not limited to, optionally substituted imidazolyl, oxazolyl, thiazolyl, pyrazolyl, isoxazolyl, isothiazolyl, 1,3,4-thiadiazolyl, 1,2,4-thiadiazolyl, 1,2,4-oxadiazolyl, and 1,3,4-oxadiazolyl.

The term "carbocycle" as employed herein is intended to mean a cycloalkyl or aryl moiety. The term "carbocycle" also includes a cycloalkenyl moiety having at least one carbon-carbon double bond.

The term "cycloalkyl" is intended to mean a saturated, partially unsaturated or unsaturated mono-, bi-, tri- or polycyclic hydrocarbon group having about 3 to 15 carbons, alternatively having 3 to 12 carbons, alternatively 3 to 8 carbons, alternatively 3 to 6 carbons, and alternatively 5 or 6 carbons. In certain embodiments, the cycloalkyl group is fused to an aryl, heteroaryl or heterocyclic group. Examples of cycloalkyl groups include, without limitation, cyclopenten-2-enone, cyclopenten-2-enol, cyclohex-2-enone, cyclohex-2-enol, cyclopropyl, cyclobutyl, cyclobutenyl, cyclopentyl, cyclopentenyl, cyclohexyl, cyclohexenyl, cycloheptyl, cyclooctyl, etc.

The term "heteroalkyl" is intended to mean a saturated, partially unsaturated or unsaturated, straight chain or branched aliphatic group, wherein one or more carbon atoms in the group are independently replaced by a moiety selected from the group consisting of O, S, N,N-alkyl, —S(O)—, —$S(O)_2$—, —$S(O)_2NH$—, or —$NHS(O)_2$—.

The term "aryl" is intended to mean a mono-, bi-, tri- or polycyclic aromatic moiety, for example a $C_6$-$C_{14}$aromatic moiety, for example comprising one to three aromatic rings. Alternatively, the aryl group is a $C_6$-$C_{10}$aryl group, alternatively a $C_6$aryl group. Examples of aryl groups include, without limitation, phenyl, naphthyl, anthracenyl, and fluorenyl.

The terms "aralkyl" or "arylalkyl" are intended to mean a group comprising an aryl group covalently linked to an alkyl group. If an aralkyl group is described as "optionally substituted", it is intended that either or both of the aryl and alkyl moieties may independently be optionally substituted or unsubstituted. For example, the aralkyl group is $(C_1$-$C_6)$alk ($C_6$-$C_{10}$)aryl, including, without limitation, benzyl, phenethyl, and naphthylmethyl. For simplicity, when written as "arylalkyl" this term, and terms related thereto, is intended to indicate the order of groups in a compound as "aryl-alkyl". Similarly, "alkyl-aryl" is intended to indicate the order of the groups in a compound as "alkyl-aryl".

The terms "heterocyclyl", "heterocyclic" or "heterocycle" are intended to mean a group which is a mono-, bi-, or polycyclic structure having from about 3 to about 14 atoms, wherein one or more atoms are independently selected from the group consisting of N, O, and S. The ring structure may be saturated, unsaturated or partially unsaturated. In certain embodiments, the heterocyclic group is non-aromatic, in which case the group is also known as a heterocycloalkyl. In certain embodiments, the heterocyclic group is a bridged heterocyclic group (for example, a bicyclic moiety with a methylene, ethylene or propylene bridge). In a bicyclic or polycyclic structure, one or more rings may be aromatic; for example one ring of a bicyclic heterocycle or one or two rings of a tricyclic heterocycle may be aromatic, as in indan and 9,10-dihydro anthracene. Examples of heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

In certain embodiments, the heterocyclic group is a heteroaryl group. As used herein, the term "heteroaryl" is intended to mean a mono-, bi-, tri- or polycyclic group having 5 to 18 ring atoms, alternatively 5 to 14 ring atoms, alternatively 5, 6, 9, or 10 ring atoms; for example having 6, 10, or 14 pi electrons shared in a cyclic array; and having, in addition to carbon atoms, between one or more heteroatoms selected from the group consisting of N, O, and S. The term "heteroaryl" is also intended to encompass the N-oxide derivative (or N-oxide derivatives, if the heteroaryl group contains more than one nitrogen such that more than one N-oxide derivative may be formed) of a nitrogen-containing heteroaryl group. For example, a heteroaryl group may be pyrimidinyl, pyridinyl, benzimidazolyl, thienyl, benzothiazolyl, benzofuranyl and indolinyl. Examples of heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, isoxazolyl, benzo[b]thienyl, naphtha[2,3-b]thianthrenyl, zanthenyl, quinolyl, benzothiazolyl, benzimidazolyl, beta-carbolinyl and perimidinyl. Illustrative examples of N-oxide derivatives of heteroaryl groups include, but are not limited to, pyridyl N-oxide, pyrazinyl N-oxide, pyrimidinyl N-oxide, pyridazinyl N-oxide, triazinyl N-oxide, isoquinolyl N-oxide and quinolyl N-oxide.

The terms "arylene," "heteroarylene," or "heterocyclylene" are intended to mean an aryl, heteroaryl, or heterocyclyl group, respectively, as defined hereinabove, that is positioned between and serves to connect two other chemical groups.

A heteroalicyclic group refers specifically to a non-aromatic heterocyclyl radical. A heteroalicyclic may contain unsaturation, but is not aromatic.

A heterocyclylalkyl group refers to a residue in which a heterocyclyl is attached to a parent structure via one of an alkylene, alkylidene, or alkylidyne radical. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. If a heterocyclylalkyl is described as "optionally substituted" it is meant that both the heterocyclyl and the corresponding alkylene, alkylidene, or alkylidyne radical portion of a heterocyclylalkyl group may be optionally substituted. A "lower heterocyclylalkyl" refers to a heterocyclylalkyl where the "alkyl" portion of the group has one to six carbons.

A heteroalicyclylalkyl group refers specifically to a heterocyclylalkyl where the heterocyclyl portion of the group is non-aromatic.

Other examples of heterocyclyls and heteroaryls include, but are not limited to, azepinyl, azetidinyl, acridinyl, azocinyl, benzidolyl, benzimidazolyl, benzofuranyl, benzofurazanyl, benzofuryl, benzothiofuranyl, benzothiophenyl, benzoxazolyl, benzothiazolyl, benzothienyl, benztriazolyl, benztetrazolyl, benzisoxazolyl, benzisothiazolyl, benzimidazolinyl, benzoxazolyl, benzoxadiazolyl, benzopyranyl, carbazolyl, 4aH-carbazolyl, carbolinyl, chromanyl, chromenyl, cinnolinyl, coumarinyl, decahydroquinolinyl, dibenzofuryl, 1,3-dioxolane, 2H,6H-1,5,2-dithiazinyl, dihydrofuro[2,3-b]tetrahydrofuran, dihydroisoindolyl, dihydroquinazolinyl (such as 3,4-dihydro-4-oxo-quinazolinyl), furanyl, furopyridinyl (such as furo[2,3-c]pyridinyl, furo[3,2-b]pyridinyl or furo[2,3-b]pyridinyl), furyl, furazanyl, hexahydrodiazepinyl, imidazolidinyl, imidazolinyl, imidazolyl, indazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolyl, isoquinolinyl, isothiazolidinyl, isothiazolyl, isoxazolinyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxetanyl, 2-oxoazepinyl, 2-oxopiperazinyl, 2-oxopiperidinyl, 2-oxopyrrolodinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolopyridyl, 2H-pyrrolyl, pyrrolyl, quinazolinyl, quinolyl, quinolinyl, quinoxalinyl, quinuclidinyl, tetrahydro-1,1-dioxothienyl, tetrahydrofuranyl, tetrahydrofuryl, tetrahydroisoquinolinyl, tetrahydroquinolinyl, tetrahydropyranyl, tetrazolyl, thiazolidinyl, 6H-1,2,5-thiadiazinyl, thiadiazolyl (e.g., 1,2,3-thiadiazolyl, 1,2,4-thiadiazolyl, 1,2,5-thiadiazolyl, 1,3,4-thiadiazolyl), thiamorpholinyl, thiamorpholinyl sulfoxide, thiamorpholuiyl sulfone, thianthrenyl, thiazolyl, thienyl, thienothiazolyl, thienooxazolyl, thienoimidazolyl, thiophenyl, triazinyl, triazinylazepinyl, triazolyl (e.g., 1,2,3-triazolyl, 1,2,4-triazolyl, 1,2,5-triazolyl, 1,3,4-triazolyl), and xanthenyl.

A "halohydrocarbyl" as employed herein is a hydrocarbyl moiety, in which from one to all hydrogens have been replaced with an independently selected halo.

Aromatic polycycles include, but are not limited to, bicyclic and tricyclic fused ring systems, including for example naphthyl and quinoline.

Non-aromatic polycycles include, but are not limited to, bicyclic and tricyclic fused ring systems where each ring is independently 4-9 membered and each ring independently contains zero, one or more double and/or triple bonds. Suitable examples of non-aromatic polycycles include, but are not limited to, decalin, octahydroindene, perhydrobenzocycloheptene and perhydrobenzo-[f]-azulene.

Polyheteroaryl groups include bicyclic and tricyclic fused rings systems where each ring is independently be 5 or 6 membered and independently contain one or more heteroatom, for example, 1, 2, 3 or 4 heteroatoms, independently chosen from O, N and S such that the fused ring system is aromatic. Suitable examples of polyheteroaryl ring systems include quinoline, isoquinoline, pyridopyrazine, pyrrolopyridine, furopyridine, indole, benzofuran, benzothiofuran, benzindole, benzoxazole, pyrroloquinoline, and the like.

Non-aromatic polyheterocyclic groups include but are not limited to bicyclic and tricyclic ring systems where each ring is independently 4-9 membered, independently contains one or more heteroatom, for example 1, 2, 3 or 4 heteroatoms, independently chosen from O, N and S, and independently contains zero, or one or more C—C double or triple bonds. Suitable examples of non-aromatic polyheterocycles include but are not limited to, hexitol, cis-perhydro-cyclohepta[b]pyridinyl, decahydro-benzo[f][1,4]oxazepinyl, 2,8-dioxabicyclo[3.3.0]octane, hexahydro-thieno[3,2-b]thiophene, perhydropyrrolo[3,2-b]pyrrole, perhydronaphthyridine, perhydrop-1H-dicyclopenta[b,e]pyran.

Mixed aryl and non-aryl polyheterocycle groups include but are not limited to bicyclic and tricyclic fused ring systems where each ring is independently 4-9 membered, and at least one ring contains one or more heteroatom independently chosen from O, N and S, and at least one of the rings must be aromatic. Suitable examples of mixed aryl and non-aryl polyheteorcycles include 2,3-dihydroindole, 1,2,3,4-tetrahydroquinoline, 5,11-dihydro-10H-dibenz[b,e][1,4]diazepine, 5H-dibenzo[b,e][1,4]diazepine, 1,2-dihydropyrrolo[3,4-b][1,5]benzodiazepine, 1,5-dihydropyrido[2,3-b][1,4]diazepin-4-one, 1,2,3,4,6,11-hexhydro-benzo[b]pyrido[2,3-e][1,4]diazepine-5-one, methylenedioxyphenyl, bis-methylenedioxyphenyl, 1,2,3,4-tetrahydronaphthalene, dibenzosuberane dihydroanthracene and 9H-fluorene.

As employed herein, and unless stated otherwise, when a moiety (e.g., alkyl, heteroalkyl, cycloalkyl, aryl, heteroaryl, heterocyclyl, etc.) is described as "optionally substituted" it is meant that the group optionally has from one to four, alternatively from one to three, alternatively one or two, independently selected non-hydrogen substituents. Suitable substituents include, without limitation, halo, hydroxy, oxo (e.g., an annular —CH— substituted with oxo is —C(O)—) nitro, halohydrocarbyl, hydrocarbyl, alkyl, cycloalkyl, heterocyclyl, aryl, heteroaryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Examples of substituents, which are themselves not further substituted (unless expressly stated otherwise) are:

(a) halo, hydroxy, cyano, oxo, carboxy, formyl, nitro, amino, amidino, guanidino, (b) $C_1$-$C_5$alkyl or alkenyl or arylalkyl imino, carbamoyl, azido, carboxamido, mercapto, hydroxy, hydroxyalkyl, alkylaryl, arylalkyl, $C_1$-$C_5$alkyl, $C_1$-$C_8$alkenyl, $C_1$-$C_8$alkoxy, $C_1$-$C_8$ alkyamino, $C_1$-$C_8$ alkoxycarbonyl, aryloxycarbonyl, $C_2$-$C_8$acyl, —C(O)—N($R^{30}$)-alkyl-cycloalkyl, —C(O)—N($R^{30}$)-alkyl-heterocyclyl, —C(O)—N($R^{30}$)-alkyl-aryl, —C(O)—N($R^{30}$)-alkyl-heteroaryl, —C(O)-cycloalkyl, —C(O)-heterocyclyl, —C(O)-aryl, —C(O)-heteroaryl, $C_2$-$C_8$acylamino, $C_1$-$C_8$alkylthio, arylalkylthio, arylthio, arylalkylsulfinyl, arylsulfinyl, $C_1$-$C_8$alkylsulfonyl, arylalkylsulfonyl, arylsulfonyl, $C_0$-$C_6$N-alkyl carbamoyl, $C_2$-$C_{15}$N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$heterocycle, $C_5$-$C_{15}$heteroaryl or any of these rings fused or spiro-fused to a cycloalkyl, heterocyclyl, or aryl, wherein each of the foregoing is further optionally substituted with one more moieties listed in (a), above; and (c) —$(CR^{32}R^{33})_s$—$NR^{30}R^{31}$, wherein s is from 0 (in which case the nitrogen is directly bonded to the moiety that is substituted) to 6, $R^{32}$ and $R^{33}$ are each independently hydrogen, halo, hydroxyl or $C_1$-$C_4$alkyl, and $R^{30}$ and $R^{31}$ are each independently hydrogen, cyano, oxo, hydroxyl, $C_1$-$C_8$alkyl, $C_1$-$C_8$heteroalkyl, $C_1$-$C_8$alkenyl, carboxamido, $C_1$-$C_3$alkyl-carboxamido, carboxamido-$C_1$-$C_3$alkyl, amidino, $C_2$-$C_5$hydroxyalkyl, $C_1$-$C_3$alkylaryl, aryl-$C_1$-$C_3$alkyl, $C_1$-$C_3$alkylheteroaryl, hetero aryl-$C_1$-$C_3$ alkyl, $C_1$-$C_3$alkylheterocyclyl, heterocyclyl-$C_1$-$C_3$alkyl $C_1$-$C_3$alkylcycloalkyl, cycloalkyl-$C_1$-$C_3$ alkyl, $C_2$-$C_8$alkoxy, $C_2$-$C_8$ alkoxy-$C_1$-$C_4$alkyl, $C_1$-$C_8$alkoxycarbonyl, aryloxycarbonyl, aryl-$C_1$-$C_3$ alkoxycarbonyl, heteroaryloxycarbonyl, heteroaryl-$C_1$-$C_3$alkoxycarbonyl, $C_1$-$C_8$acyl, $C_0$-$C_8$alkyl-carbonyl, aryl-$C_0$-$C_8$alkyl-carbonyl, heteroaryl-$C_0$-$C_8$alkyl-carbonyl, cycloalkyl-$C_0$-$C_8$alkyl-carbonyl, heterocyclyl-$C_0$-$C_8$alkyl-carbonyl, $C_0$-$C_8$alkyl-NH-carbonyl, aryl-$C_0$-$C_8$alkyl-NH-carbonyl, heteroaryl-$C_0$-$C_8$alkyl-NH-carbonyl, cycloalkyl-$C_0$-$C_8$alkyl-NH-carbonyl, heterocylclyl-$C_0$-$C_8$alkyl-NH-carbonyl, cycloalkyl-S(O)$_2$—, heterocyclyl-S(O)$_2$—, aryl-S(O)$_2$—, heteroaryl-S(O)$_2$—, $C_0$-$C_8$alkyl-O-carbonyl, aryl-$C_0$-$C_8$alkyl-O-carbonyl, heteroaryl-$C_0$-$C_8$alkyl-O-carbonyl, cycloalkyl-$C_0$-$C_8$alkyl-O-carbonyl, heterocyclyl-$C_0$-$C_8$alkyl-O-carbonyl, $C_1$-$C_8$alkylsulfonyl, arylalkylsulfonyl, arylsulfonyl, heteroarylalkylsulfonyl, heteroarylsulfonyl, $C_1$-$C_8$alkyl-NH-sulfonyl, arylalkyl-NH-sulfonyl, aryl-NH-sulfonyl, heteroarylalkyl-NH-sulfonyl, heteroaryl-NH-sulfonyl aroyl, aryl, cycloalkyl, heterocyclyl, heteroaryl, aryl-$C_1$-$C_3$ alkyl-, cycloalkyl-$C_1$-$C_3$ alkyl-, heterocyclyl-$C_1$-$C_3$alkyl-, heteroaryl-$C_1$-$C_3$alkyl-, or a protecting group, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents selected from the group consisting of (a) above, a protecting group, and ($X^{30}$—$Y^{31}$—), wherein said heterocyclyl may also be bridged (forming a bicyclic moiety with a methylene, ethylene or propylene bridge); wherein $X^{30}$ is selected from the group consisting of H, $C_1$-$C_8$alkyl, $C_2$-$C_8$alkenyl-, $C_2$-$C_8$alkynyl-, —$C_0$-$C_3$alkyl-$C_2$-$C_8$alkenyl-$C_0$-$C_3$alkyl, $C_0$-$C_3$alkyl-$C_2$-$C_8$alkynyl-$C_0$-$C_3$alkyl, $C_0$-$C_3$alkyl-O—$C_0$-$C_3$alkyl-, HO—$C_0$-$C_3$alkyl-, $C_0$-$C_4$alkyl-N($R^{30}$)—$C_0$-$C_3$alkyl-, N($R^{30}$)($R^{31}$)—$C_0$-$C_3$alkyl-, N($R^{30}$)($R^{31}$)—$C_0$-$C_3$alkenyl-, N($R^{30}$)($R^{31}$)—$C_0$-$C_3$alkynyl-, (N($R^{30}$)($R^{31}$))$_2$—C═N—, $C_0$-$C_3$alkyl-S(O)$_{0-2}$—$C_0$-$C_3$alkyl-, $CF_3$—$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocycyl are optionally substituted with from 1 to 3 substituents from (a); and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N $(R^{30})$—, —$N(R^{30})$—C(S)—, —C(S)—$N(R^{30})$—, —$N(R^{30})$—C(O)—$N(R^{31})$—, —$N(R^{30})$—$C(NR^{30})$—$N(R^{31})$—, —$N(R^{30})$—$C(NR^{31})$—, —$C(NR^{31})$—$N(R^{30})$—, —$N(R^{30})$—C(S)—$N(R^{31})$—, —$N(R^{30})$—C(O)—O—, —O—C(O)—$N(R^{31})$—, —$N(R^{30})$—C(S)—O—, —O—C(S)—$N(R^{31})$—, —$S(O)_{0-2}$—, —$SO_2N(R^{31})$—, —$N(R^{31})$—$SO_2$— and —$N(R^{30})$—$SO_2N(R^{31})$—.

A moiety that is substituted is one in which one or more (for example one to four, alternatively from one to three and alternatively one or two), hydrogens have been independently replaced with another chemical substituent. As a non-limiting example, substituted phenyls include 2-fluorophenyl, 3,4-dichlorophenyl, 3-chloro-4-fluoro-phenyl, 2-fluoro-3-propylphenyl. As another non-limiting example, substituted n-octyls include 2,4-dimethyl-5-ethyl-octyl and 3-cyclopentyl-octyl. Included within this definition are methylenes (—$CH_2$—) substituted with oxygen to form carbonyl —CO—.

When there are two optional substituents bonded to adjacent atoms of a ring structure, such as for example a phenyl, thiophenyl, or pyridinyl, the substituents, together with the atoms to which they are bonded, optionally form a 5- or 6-membered cycloalkyl or heterocycle having 1, 2, or 3 annular heteroatoms.

In certain embodiments, a group, such as a hydrocarbyl, heteroalkyl, heterocyclic and/or aryl group is unsubstituted.

In other embodiments, a group, such as a hydrocarbyl, heteroalkyl, heterocyclic and/or aryl group is substituted with from 1 to 4 (alternatively from one to three, and alternatively one or two) independently selected substituents.

Examples of substituents on alkyl groups include, but are not limited to, hydroxyl, halogen (e.g., a single halogen substituent or multiple halo substituents; in the latter case, groups such as —$CF_3$ or an alkyl group bearing $Cl_3$), oxo, cyano, nitro, alkyl, cycloalkyl, alkenyl, cycloalkenyl, alkynyl, heterocycle, aryl, —$OR^{a1}$, —$SR^{a1}$, —S(═O)$R^{e1}$, —$S(═O)_2R^{e1}$, —$P(═O)_2R^{e1}$, —$S(═O)_2OR^{e1}$, —$P(═O)_2R^{e1}$, —$NR^{b1}R^{c1}$, —$NR^{b1}S(═O)_2R^{e1}$, —$NR^{b1}P(═O)_2R^{e1}$, —$S(═O)_2NR^{b1}R^{c1}$, —$P(═O)_2NR^{b1}R^{c1}$, —C(═O)$OR^{e1}$, —C(═O)$R^{a1}$, —C(═O)$NR^{b1}R^{c1}$, —OC(═O)$R^{al}$, —OC(═O)$NR^{b1}R^{c1}$, —$NR^{b1}C$(═O)$OR^{e1}$, —$NR^{d1}C$(═O)$NR^{b1}R^{c1}$, —$NR^{d1}S(═O)_2NR^{b1}R^{c1}$, —$NR^{d1}P(═O)_2NR^{b1}R^{c1}$, —$NR^{b1}C$(═O)$R^{a1}$ or —$NR^{b1}P(═O)_2R^{e1}$, wherein $R^{a1}$ is hydrogen, alkyl, cycloalkyl, alkenyl, cycloalkenyl, alkynyl, heterocycle or aryl; $R^{b1}$, $R^{c1}$ and $R^{d1}$ are independently hydrogen, alkyl, cycloalkyl, heterocycle or aryl, or said $R^{b1}$ and $R^{c1}$ together with the N to which they are bonded optionally form a heterocycle; and $R^{e1}$ is alkyl, cycloalkyl, alkenyl, cycloalkenyl, alkynyl, heterocycle or aryl. In the aforementioned exemplary substituents, groups such as alkyl, cycloalkyl, alkenyl, alkynyl, cycloalkenyl, heterocycle and aryl can themselves be optionally substituted.

Examples of substituents on alkenyl and alkynyl groups include, but are not limited to, alkyl or substituted alkyl, as well as those groups recited as examples of alkyl substituents.

Examples of substituents on cycloalkyl groups include, but are not limited to, nitro, cyano, alkyl or substituted alkyl, as well as those groups recited about as examples of alkyl substituents. Other examples of substituents include, but are not limited to, spiro-attached or fused cyclic substituents, for example spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted. In certain embodiments, when a cycloalkyl is substituted by two $C_{1-6}$ alkyl groups, the two alkyl groups may combine together to form an alkylene chain, for example a $C_{1-3}$ alkylene chain. Cycloalkyl groups having this crosslinked structure include bicyclo[2.2.2]octanyl and norbornanyl.

Examples of substituents on cycloalkenyl groups include, but are not limited to, nitro, cyano, alkyl or substituted alkyl, as well as those groups recited as examples of alkyl substituents. Other examples of substituents include, but are not limited to, spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted. In certain embodiments, when a cycloalkenyl is substituted by two $C_{1-6}$ alkyl groups, the two alkyl groups may combine together to form an alkylene chain, for example a $C_{1-3}$ alkylene chain.

Examples of substituents on aryl groups include, but are not limited to, nitro, cycloalkyl or substituted cycloalkyl, cycloalkenyl or substituted cycloalkenyl, cyano, alkyl or substituted alkyl, as well as those groups recited above as examples of alkyl substituents. Other examples of substituents include, but are not limited to, fused cyclic groups, especially fused cycloalkyl, fused cycloalkenyl, fused heterocycle, or fused aryl, where the aforementioned cycloalkyl, cylcoalkenyl, heterocycle and aryl substituents can themselves be optionally substituted. Still other substituents on aryl groups (phenyl, as a non-limiting example) include, but are not limited to, haloalkyl and those groups recited as examples of alkyl substituents. In certain embodiments, when an aryl group is substituted by two $C_{1-6}$ alkyl groups, the two alkyl groups may combine together to form an alkylene chain, for example a $C_{1-3}$ alkylene chain.

Examples of substituents on heterocyclic groups include, but are not limited to, cycloalkyl, substituted cycloalkyl, cycloalkenyl, substituted cycloalkenyl, nitro, oxo (i.e., ═O), cyano, alkyl, substituted alkyl, as well as those groups recited as examples of alkyl substituents. Other substituents on heterocyclic groups include, but are not limited to, spiro-attached or fused cyclic substituents at any available point or points of attachment, for example spiro-attached cycloalkyl, spiro-attached cycloalkenyl, spiro-attached heterocycle (excluding heteroaryl), fused cycloalkyl, fused cycloakenyl, fused heterocycle and fused aryl, where the aforementioned cycloalkyl, cycloalkenyl, heterocycle and aryl substituents can themselves be optionally substituted. In certain embodiments, when a heterocyclic is substituted by two $C_{1-6}$ alkyl groups, the two alkyl groups may combine together to form an alkylene chain, for example a $C_{1-3}$ alkylene chain.

In certain embodiments, a heterocyclic group is substituted on carbon, nitrogen and/or sulfur at one or more positions. Examples of substituents on carbon include those groups recited as examples of alkyl substituents. Examples of substituents on nitrogen include, but are not limited to alkyl, aryl, aralkyl, alkylcarbonyl, alkylsulfonyl, arylcarbonyl, arylsulfonyl, alkoxycarbonyl, or aralkoxycarbonyl. Examples of substituents on sulfur include, but are not limited to, oxo and $C_{1-6}$alkyl. In certain embodiments, nitrogen and sulfur heteroatoms may independently be optionally oxidized and nitrogen heteroatoms may independently be optionally quaternized.

In certain embodiments, substituents on ring groups, such as aryl, heteroaryl, cycloalkyl and heterocyclyl, are selected from halogen, alkoxy and alkyl.

In certain embodiments, substituents on alkyl groups are selected from halogen and hydroxy.

Examples of substituents on aromatic polycycles include, but are not limited to, $C_1$-$C_6$alkyl, cycloalkylalkyl (e.g. cyclopropylmethyl), oxyalkyl, halo, nitro, amino, alkylamino, aminoalkyl, alkyl ketones, nitrile, carboxyalkyl, alkylsulfonyl, arylsulfonyl, aminosulfonyl and $OR^{aa}$, such as alkoxy, wherein $R^{aa}$ is selected from the group consisting of H, $C_1$-$C_6$alkyl, $C_4$-$C_9$cycloalkyl, $C_4$-$C_9$heterocycloalkyl, aryl, heteroaryl, arylalkyl, heteroarylalkyl and $(CH_2)_{0-6}Z^aR^{bb}$, wherein $Z^a$ is selected from the group consisting of O, $NR^{cc}$, S and S(O), and $R^{bb}$ is selected from the group consisting of H, $C_1$-$C_6$alkyl, $C_4$-$C_9$cycloalkyl, $C_4$-$C_9$heterocycloalkyl, $C_4$-$C_9$heterocycloalkylalkyl, aryl, mixed aryl and non-aryl polycycle, heteroaryl, arylalkyl, (e.g. benzyl), and heteroarylalkyl (e.g. pyridylmethyl); and $R^{cc}$ is selected from the group consisting of H, $C_1$-$C_6$alkyl, $C_4$-$C_9$cycloalkyl, $C_4$-$C_9$heterocycloalkyl, aryl, heteroaryl, arylalkyl (e.g. benzyl), heteroarylalkyl (e.g. pyridylmethyl) and amino acyl.

Examples of substituents on non-aromatic polycycles include, but are not limited to, oxo, $C_3$-$C_9$cycloalkyl, such as cyclopropyl, cyclobutyl, cyclopentyl, cyclohexyl and the like. Unless otherwise noted, non-aromatic polycycle substituents include both unsubstituted cycloalkyl groups and cycloalkyl groups that are substituted by one or more suitable substituents, including but not limited to, $C_1$-$C_6$alkyl, oxo, halo, hydroxy, aminoalkyl, oxyalkyl, alkylamino and $OR^{aa}$, such as alkoxy. In certain embodiments, substituents for such cycloalkyl groups include halo, hydroxy, alkoxy, oxyalkyl, alkylamino and aminoalkyl.

Examples of substituents on carbon atoms of polyheteroaryl groups include but are not limited to, straight and branched optionally substituted $C_1$-$C_6$alkyl, unsaturation (i.e., there are one or more double or triple C—C bonds), acyl, oxo, cycloalkyl, halo, oxyalkyl, alkylamino, aminoalkyl, acylamino, OR (for example alkoxy), and a substituent of the formula $—O—(CH_2CH{=}CH(CH_3)(CH_2))_{1-3}H$. Examples of suitable straight and branched $C_1$-$C_6$alkyl substituents include but are not limited to methyl, ethyl, n-propyl, 2-propyl, n-butyl, sec-butyl, t-butyl and the like. In certain embodiments, substituents are selected from halo, hydroxy, alkoxy, oxyalkyl, alkylamino and aminoalkyl. Examples of substitutions on nitrogen atoms include, for example N-oxide or $R^{cc}$. In certain embodiments, examples of substituents on nitrogen atoms include H, $C_1$-$C_4$alkyl, acyl, aminoacyl and sulfonyl. In certain embodiments, sulfur atoms are unsubstituted. Examples of substituents on sulfur atoms include but are not limited to oxo and lower alkyl.

Examples of substituents on carbon atoms of non-aromatic polyheterocyclic groups include but are not limited to straight and branched optionally substituted $C_1$-$C_6$alkyl, unsaturation (i.e., there are one or more double or triple C—C bonds), acyl, oxo, cycloalkyl, halo, oxyalkyl, alkylamino, aminoalkyl, acylamino and $OR^{aa}$, for example alkoxy. Examples of suitable straight and branched $C_1$-$C_6$alkyl substituents include but are not limited to methyl, ethyl, n-propyl, 2-propyl, n-butyl, sec-butyl, t-butyl and the like. In certain embodiments, substituents are selected from halo, hydroxy, alkoxy, oxyalkyl, alkylamino and aminoalkyl. Examples of substitutions on nitrogen atoms include, for example, N-oxide or $R^{cc}$. In certain embodiments, examples of N substituents include H, $C_1$-$C_4$ alkyl, acyl, aminoacyl and sulfonyl. In certain embodiments sulfur atoms are unsubstituted. Examples of S substituents include oxo and lower alkyl.

Examples of substituents on mixed aryl and non-aryl polyheterocycle groups include, but are not limited to, nitro or as described above for non-aromatic polycycle groups. In certain embodiments, substituents on carbon atoms include, but are not limited to, —N—OH, =N—OH, optionally substituted alkyl, unsaturation (i.e., there are one or more double or triple C—C bonds), oxo, acyl, cycloalkyl, halo, oxyalkyl, alkylamino, aminoalkyl, acylamino and $OR^{aa}$, for example alkoxy. In certain embodiments, substitutions on nitrogen atoms include, for example, N-oxide or $R^{cc}$. In other embodiments, examples of N substituents include H, $C_{1-4}$alkyl, acyl aminoacyl and sulfonyl. In certain embodiments, sulfur atoms are unsubstituted. Examples of S substituents include oxo and lower alkyl.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally optionally substituted. The term "sulfonamido" refers to a sulfonamide substituent attached by either the sulfur or the nitrogen atom. The term "amino" is meant to include $NH_2$, alkylamino, di-alkyl-amino, arylamino, and cyclic amino groups. The term "ureido" as employed herein refers to a substituted or unsubstituted urea moiety.

The term "radical" as used herein means a chemical moiety comprising one or more unpaired electrons.

Where optional substituents of a moiety are chosen from "one or more" groups it is to be understood that the moiety optionally has, unless otherwise stated, from one up to the maximum number of substitutable hydrogens on the moiety replaced with a substituent independently chosen from among the specified groups.

In addition, substituents on cyclic moieties (i.e., cycloalkyl, heterocyclyl, aryl, heteroaryl) include 5- to 6-membered mono- and 9- to 14-membered bi-cyclic moieties fused to the parent cyclic moiety to form a bi- or tri-cyclic fused ring system. Substituents on cyclic moieties also include 5- to 6-membered mono- and 9- to 14-membered bi-cyclic moieties attached to the parent cyclic moiety by a covalent bond to form a bi- or tri-cyclic bi-ring system. For example, an optionally substituted phenyl includes, but is not limited to, the following:

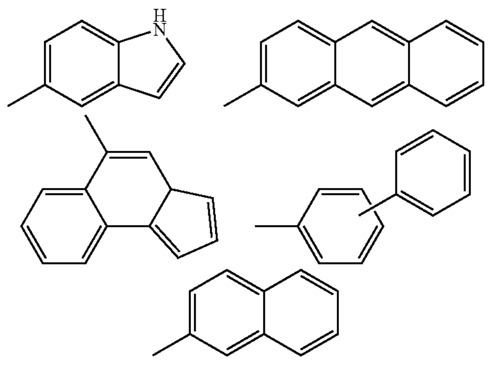

A saturated, unsaturated or partially unsaturated three- to eight-membered carbocyclic ring is for example a four- to seven-membered, alternatively a five- or six-membered, saturated, unsaturated or partially unsaturated carbocyclic ring. Examples of saturated, unsaturated or partially unsaturated three- to eight-membered carbocyclic rings include phenyl, cyclopropyl, cyclobutyl, cyclopentyl, cyclohexyl, and cycloheptyl.

A saturated, unsaturated or partially unsaturated three- to eight-membered heterocyclic ring contains at least one hetero atom selected from oxygen, nitrogen, and sulfur atoms. For example, a saturated, unsaturated or partially unsaturated three- to eight-membered heterocyclic ring can contain one or two heteroatoms with the remaining ring-constituting atoms being carbon atoms. The saturated, unsaturated or partially unsaturated three- to eight-membered heterocyclic ring is for example a saturated, unsaturated or partially unsaturated four- to seven-membered heterocyclic ring, alternatively a saturated, unsaturated or partially unsaturated five- or six-membered heterocyclic ring. Examples of saturated, unsaturated or partially unsaturated three- to eight-membered heterocyclic groups include thienyl, pyridyl, 1,2,3-triazolyl, imidazolyl, isoxazolyl, pyrazolyl, piperazinyl, piperazino, piperidyl, piperidino, morpholinyl, morpholino, homopiperazinyl, homopiperazino, thiomorpholinyl, thiomorpholino, tetrahydropyrrolyl, and azepanyl.

The terms "inhibition effective amount" or "histone deacetylase inhibiting amount" are meant to denote a dosage or amount sufficient to cause inhibition of histone deacetylase activity in vitro or in vivo. The histone deacetylase may be in a cell, which cell can be in a multicellular organism. The multicellular organism can be a plant or fungus, or an animal, for example a mammal, for example a human. The fungus may be infecting a plant or a mammal, for example a human, and could therefore be located in and/or on the plant or mammal. If the histone deacetylase is in a multicellular organism, the method according to this aspect of the invention comprises administering to the organism a compound or composition according to the present invention. Administration may be by any route, including, without limitation, parenteral, oral, sublingual, transdermal, topical, intranasal, intratracheal, or intrarectal. In certain embodiments, compounds of the invention are administered intravenously in a hospital setting. In certain other embodiments, administration may be by the oral route.

In certain embodiments, HDAC inhibition is specific, i.e., the HDAC inhibitor reduces a functional property or biological ability of a HDAC at a concentration that is lower than the concentration of the inhibitor that is required to produce another, unrelated biological effect. For example, the concentration of the inhibitor required for HDAC inhibitory activity is at least 2-fold lower, alternatively at least 5-fold lower, alternatively at least 10-fold lower, and alternatively at least 20-fold lower than the concentration required to produce an unrelated biological effect.

The term "therapeutically effective amount" as employed herein is an amount of a compound of the invention, that when administered to a patient, treats a disease. The amount of a compound of the invention which constitutes a "therapeutically effective amount" will vary depending on the compound, the disease, the disease state and its severity, the age, sex, health, size of the patient to be treated, the results desired, and the like. The therapeutically effective amount can be determined routinely by one of ordinary skill in the art. Optimal amounts can be determined based on monitoring of the patient's response to treatment.

The term "patient" as employed herein for the purposes of the present invention includes humans and other animals, for example mammals, and other organisms. Thus the compounds, compositions and methods of the present invention are applicable for example to both human therapy and veterinary applications. In one embodiment the patient is a mammal, for example a human.

The terms "treating", "treatment", or the like, as used herein covers the treatment of a disease-state in an organism and includes at least one of (i) preventing the disease-state from occurring, in particular, when such organism is predisposed to the disease-state but has not yet been diagnosed as having it; (ii) inhibiting the disease-state, i.e., partially or completely arresting its development; (iii) relieving the disease-state, i.e., causing regression of symptoms of the disease-state, or ameliorating a symptom of the disease; and (iv) reversal or regression of the disease-state, for example eliminating or curing of the disease. In certain embodiments of the present invention the organism is a mammal, for example a primate, for example a human. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art. In certain embodiments, the terms "treating", "treatment", or the like, as used herein covers the treatment of a disease-state in an organism and includes at least one of (ii), (iii) and (iv) above.

As used herein, the terms "histone deacetylase" and "HDAC" are intended to refer to any one of a family of enzymes that remove acetyl groups from a protein (for example, a histone, or tubulin). Unless otherwise indicated by context, the term "histone" is meant to refer to any histone protein, including H1, H2A, H2B, H3, H4, and H5, from any species. Examples of histone deacetylases include class II enzymes. For example the histone deacetylase is a human HDAC, including, but not limited to, HDAC-4, HDAC-5, HDAC-6, HDAC-7, HDAC-8, HDAC-9 and HDAC-10. In some other embodiments, the histone deacetylase is derived from a protozoal or fungal source.

The terms "histone deacetylase inhibitor" and "inhibitor of histone deacetylase" are intended to mean a compound having a structure as defined herein, which is capable of interacting with a histone deacetylase and inhibiting its enzymatic activity.

The term "inhibiting histone deacetylase enzymatic activity" is intended to mean reducing the ability of a histone deacetylase to remove an acetyl group from a protein, such as but not limited to a histone or tubulin. The concentration of inhibitor which reduces the activity of a histone deacetylase to 50% of that of the uninhibited enzyme is determined as the $IC_{50}$ value. In some embodiments, such reduction of histone deacetylase activity is at least 50%, alternatively at least about 75%, and alternatively at least about 90%. In other embodiments, histone deacetylase activity is reduced by at least 95%, alternatively by at least 99%.

In certain embodiments, such inhibition is specific, i.e., the histone deacetylase inhibitor reduces the ability of a histone deacetylase to remove an acetyl group from a protein at a concentration that is lower than the concentration of the inhibitor that is required to produce another, unrelated biological effect. For example, the concentration of the inhibitor required for histone deacetylase inhibitory activity is at least 2-fold lower, alternatively at least 5-fold lower, alternatively at least 10-fold lower, and alternatively at least 20-fold lower than the concentration required to produce an unrelated biological effect.

The term "protecting group" is intended to mean a group used in synthesis to temporarily mask the characteristic chemistry of a functional group because it interferes with another reaction. A good protecting group should be easy to put on, easy to remove and in high yielding reactions, and inert to the conditions of the reaction required. A protecting group or protective group is introduced into a molecule by chemical modification of a functional group in order to obtain chemoselectivity in a subsequent chemical reaction. One skilled in the art will recognize that during any of the processes for preparation of the compounds in the present invention, it may be necessary and/or desirable to protect sensitive or reactive groups on any of the molecules concerned. This may be achieved by means of conventional protecting groups, such as but not limited to Bn- (or $-CH_2Ph$), $-CHPh_2$, alloc (or $CH_2=CH-CH_2-O-C(O)-$), BOC—, -Cbz (or Z—), —F-moc, $-C(O)-CF_3$, N-Phthalimide, 1-Adoc-, TBDMS-, TBDPS-, TMS-, TIPS-, IPDMS-, $-SiR_3$, SEM-, t-Bu-, Tr-, THP- and Allyl- and those described in standard textbooks, such as Greene, T. W. et al., *Protective Groups in Organic Synthesis*, Wiley, N.Y. (1999). These protecting groups may be removed at a convenient stage using methods known from the art. When a functional group is termed "protected", this means that the group is in modified form to mitigate, especially preclude, undesired side reactions at the protected site.

The compounds of the present invention form salts which are also within the scope of this invention. Reference to a compound of the invention, for example a compound of Formula (I), herein is understood to include reference to salts thereof, unless otherwise indicated.

The term "salt(s)", as employed herein, denotes acidic and/or basic salts formed with inorganic and/or organic acids and bases. In addition, when a compound of Formula (I) contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic (exhibiting minimal or no undesired toxicological effects), physiologically acceptable) salts are preferred, although other salts are also useful, e.g., in isolation or purification steps which may be employed during preparation. Salts of the compounds of the invention may be formed, for example, by reacting a compound of the present invention with an amount of acid or base, such as an equivalent amount, in a medium such as one in which the salts precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfanotes (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl and butyl chlorides, bromides and iodides), dialkyl sulfates (e.g. dimethyl, diethyl, dibutyl and diamyl sulfates), long chain halides (e.g. decyl, lauryl, myristyl and stearyl chlorides, bromides and iodides), aralkyl halides (e.g. benzyl and phenethyl bromides), and others.

As used herein, the term "pharmaceutically acceptable salts" is intended to mean salts that retain the desired biological activity of the above-identified compounds and exhibit minimal or no undesired toxicological effects.

Another aspect of the invention provides compositions including a compound, N-oxide, hydrate, solvate, pharmaceutically acceptable salt, complex or prodrug of a compound according to the present invention as described herein, or a racemic mixture, diastereomer, enantiomer or tautomer thereof. For example, in one embodiment of the invention, a composition comprises a compound, N-oxide, hydrate, solvate, pharmaceutically acceptable salt, complex or prodrug of a compound according to the present invention as described herein present in at least about 30% enantiomeric or diastereomeric excess. In certain desirable embodiments of the invention, the compound, N-oxide, hydrates, solvate, pharmaceutically acceptable salt, complex or prodrug is present in at least about 50%, at least about 80%, or even at least about 90% enantiomeric or diastereomeric excess. In certain other desirable embodiments of the invention, the compound, N-oxide, hydrate, solvate, pharmaceutically acceptable salt, complex or prodrug is present in at least about 95%, alternatively at least about 98% and alternatively at least about 99% enantiomeric or diastereomeric excess. In other embodiments of the invention, a compound, N-oxide, hydrate, solvate, pharmaceutically acceptable salt, complex or prodrug is present as a substantially racemic mixture.

Some compounds of the invention may have chiral centers and/or geometric isomeric centers (E- and Z-isomers), and it is to be understood that the invention encompasses all such optical, enantiomeric, diastereoisomeric and geometric isomers. The invention also comprises all tautomeric forms of the compounds disclosed herein. Where compounds of the invention include chiral centers, the invention encompasses the enantiomerically and/or diasteromerically pure isomers of such compounds, the enantiomerically and/or diastereomerically enriched mixtures of such compounds, and the racemic and scalemic mixtures of such compounds. For example, a composition may include a mixture of enantiomers or diastereomers of a compound of Formula (I) in at least about 30% diastereomeric or enantiomeric excess. In certain embodiments of the invention, the compound is present in at least about 50% enantiomeric or diastereomeric excess, in at least about 80% enantiomeric or diastereomeric excess, or even in at least about 90% enantiomeric or diastereomeric excess. In certain embodiments of the invention, the compound is present in at least about 95%, alternatively in at least about 98% enantiomeric or diastereomeric excess, and alternatively in at least about 99% enantiomeric or diastereomeric excess.

The chiral centers of the present invention may have the S or R configuration. The racemic forms can be resolved by physical methods, such as, for example, fractional crystallization, separation or crystallization of diastereomeric derivates or separation by chiral column chromatography. The individual optical isomers can be obtained either starting from chiral precursors/intermediates or from the racemates by any suitable method, including without limitation, conventional methods, such as, for example, salt formation with an optically active acid followed by crystallization.

The present invention also includes prodrugs of compounds of the invention. The term "prodrug" is intended to mean a derivative of a compound of the present invention that requires a transformation, for example, within the body, to release or activate the parent compound. Prodrugs are frequently, although not necessarily, pharmacologically inactive until converted to the parent compound. A hydroxyl containing compound may be converted to, for example, a sulfonate, ester or carbonate prodrug, which may be hydrolyzed in vivo to provide the hydroxyl compound. An amino containing compound may be converted, for example, to a carbamate, amide, enamine, imine, N-phosphonyl, N-phosphoryl or N-sulfenyl prodrug, which may be hydrolyzed in vivo to provide the amino compound. A carboxylic acid compound may be converted to an ester (including silyl esters and thioesters), amide or hydrazide prodrug, which be hydrolyzed in vivo to provide the carboxylic acid compound. Prodrugs for drugs which have functional groups different than those listed above are well known to the skilled artisan. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of compounds of the invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like.

The compounds of the invention may be administered as is or as a prodrug, for example in the form of an in vivo hydrolyzable ester or in vivo hydrolyzable amide. An in vivo hydrolyzable ester of a compound of the invention containing carboxy or hydroxy group is, for example, a pharmaceutically acceptable ester which is hydrolyzed in the human or animal body to produce the parent acid or alcohol. Suitable pharmaceutically acceptable esters for carboxy include $C_1$-$C_6$alkoxymethyl esters (e.g., methoxymethyl), $C_1$-$C_6$alkanoyloxymethyl esters (e.g., for example pivaloyloxymethyl), phthalidyl esters, $C_3$-$C_8$cycloalkoxycarbonyloxy-$C_1$-$C_6$alkyl esters (e.g., 1-cyclohexylcarbonyloxyethyl); 1,3-dioxolen-2-onylmethyl esters (e.g., 5-methyl-1,3-dioxolen-2-onylmethyl; and $C_1$-$C_6$alkoxycarbonyloxyethyl esters (e.g., 1-methoxycarbonyloxyethyl) and may be formed at any appropriate carboxy group in the compounds of this invention.

An in vivo hydrolyzable ester of a compound of the invention containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl. Examples of substituents on benzoyl include morpholino and piperazino linked from a ring nitrogen atom via a methylene group to the 3- or 4-position of the benzoyl ring. A suitable value for an in vivo hydrolyzable amide of a compound of the invention containing a carboxy group is, for example, a N—$C_1$-$C_6$alkyl or N,N-di-$C_1$-$C_6$alkyl amide such as N-methyl, N-ethyl, N-propyl, N,N-dimethyl, N-ethyl-N-methyl or N,N-diethyl amide.

Upon administration to a subject, the prodrug undergoes chemical conversion by metabolic or chemical processes to yield a compound of the present invention, or a salt and/or solvate thereof. Solvates of the compounds of the present invention include, for example, hydrates.

Typically, in a prodrug, a polar functional group (e.g., a carboxylic acid, an amino group, a hydroxyl group, etc.) is masked by a promoiety, which is labile under physiological conditions. "Promoiety" refers to a form of protecting group that when used to mask a functional group within a compound molecule converts the drug into a prodrug. Typically, the promoiety will be attached to the compound via bond(s) that are cleaved by enzymatic or non-enzymatic means in vivo.

The terms "protect", "protected", and "protecting" are intended to refer to a process in which a functional group in a chemical compound is selectively masked by a non-reactive functional group in order to allow a selective reaction(s) to occur elsewhere on said chemical compound. Such non-reactive functional groups are herein termed "protecting groups". For example, the term "nitrogen protecting group", is intended to mean a group capable of selectively masking the reactivity of a nitrogen (N) group. The term "suitable protecting group" is intended to mean a protecting group useful in the preparation of the compounds of the present invention. Such groups are generally able to be selectively introduced and removed using mild reaction conditions that do not interfere with other portions of the subject compounds. Protecting groups that are suitable for use in the processes and methods of the present invention are well known, such as but not limited to, Bn- (or —$CH_2$Ph), —$CHPh_2$, alloc (or $CH_2$=CH—$CH_2$—O—C(O)—), BOC—, -Cbz (or Z—), —F-moc, —C(O)—$CF_3$, N-Phthalimide, 1-Adoc-, TBDMS-, TBDPS-, TMS-, TIPS-, IPDMS-, —$SiR_3$, SEM-, t-Bu-, Tr-, THP- and Allyl-. These protecting groups may be removed at a convenient stage using methods known from the art. The chemical properties of such protecting groups, methods for their introduction and their removal art known in the art and can be found for example in T. Greene and P. Wuls, *Protective Groups in Organic Synthesis* (3rd ed.), John Wiley & Sons, NY (1999), herein incorporated by reference in its entirety. The terms "deprotect", "deprotected", and "deprotecting" are intended to refer to the process of removing a protecting group from a compound.

Throughout the specification, certain embodiments of one or more chemical substituents are identified. Also encompassed are combinations of such embodiments. For example, the invention describes certain embodiments of L in the compounds and describes certain embodiments of group Y. Thus, as an example, also contemplated as within the scope of the invention are compounds in which certain examples of L are as described and in which certain examples of group Y are as described.

The foregoing merely summarizes one aspect and embodiments of the invention and is not intended to be limiting in nature. This aspect and embodiments are described more fully below.

Compounds

In one aspect, the invention provides compounds of the formula (I):

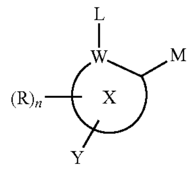

(I)

and N-oxides, hydrates, solvates, pharmaceutically acceptable salts, prodrugs and complexes thereof, and racemic and scalemic mixtures, tautomers, diastereomers and enantiomers thereof, wherein

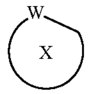

is selected from the group consisting of aryl, heteroaryl, cycloalkyl and heterocyclyl, wherein each aryl, heteroaryl, cycloalkyl and heterocyclyl moiety is optionally substituted;

W is selected from the group consisting of N, —C═ and —C($R^1$)—, wherein when

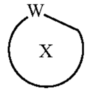

is cycloalkyl or heterocyclyl, then W is —C($R^1$)—;

M is selected from the group consisting of —C(O)N($R^1$)O$R^2$, —C(O)N$R^1R^2$, —C(O)OH, —C(O)O$R^1$, —C(O)$C_1$-$C_3$alkyl-S$R^1$, —NHC(O)$C_1$-$C_3$alkyl-S$R^1$, —NHC(O)$C_1$-$C_3$alkyl-O$R^1$, —C(O)$CH_2$—S(acetyl), —C(O)-heteroaryl, —C(O)-heterocyclyl, —C(NOH)N$R^1R^2$, —C(O)$C_1$-$C_3$alkyl-O$R^1$, —C(O)$C_1$-$C_3$alkyl-N$R^1R^2$, —C(O)$CF_3$, —C(O)C(O)O$R^1$, —C(O)C(O)N$R^1R^2$, —C(O)$C_1$-$C_4$alkyl, —N(OH)C(O)H, —N(O$R^1$)C(O)$R^2$, —N$R^1SO_2$N$R^1R^2$, —$SO_2$N$R^1$OH, —N(OH)C(O)N$R^1R^2$, —N$R^1$C(O)N(OH)$R^2$, —OC(O)N(OH)$R^2$, —C(NOH)N$R^1R^2$, and a Zn-chelating group;

or

M is —$C_1$-$C_2$alkyl-C(O)N($R^1$)O$R^2$, when

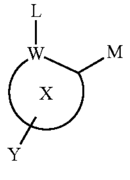

is

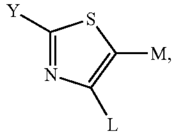

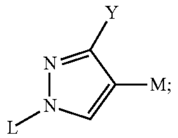

$R^1$ and $R^2$ is independently selected from the group consisting of —H, -alkyl, -aryl, -aryl-aryl, -hetetoaryl, heteroaryl-aryl, heteroaryl-heteroaryl, alkyl-heteroaryl and -alkyl-aryl, wherein each aryl and heteroaryl moiety is optionally substituted;

R is selected from the group consisting of H, alkyl, halo, hydroxy, nitro, $C_1$-$C_4$alkyl, —N$R^1R^2$, —O$R^1$, aryl, heteroaryl, alkyloxy and $CF_3$;

n is an integer from 0 to 1;

L is selected from the group consisting of aryl, heteroaryl, cycloalkyl, heterocyclyl, fused aryl, fused heterocyclyl, fused cycloalkyl, -alkenyl-aryl, -aryl-heteroaryl, -heteroaryl-aryl, -alkynyl-aryl, —O—$C_0$-$C_4$alkyl-aryl, -alkyl-aryl, —$SO_2$N$R^1$—$C_0$-$C_4$alkyl-aryl, —N$R^1$-aryl, —$CF_3$, -t-Bu, —N$R^1SO_2$-aryl, halo, —N($R^1$)C(O)-aryl, —S-heteroaryl and —S-aryl, wherein each aryl, heteroaryl, cycloalkyl and heterocyclyl moiety is optionally substituted with 1 to 3 independently selected substituents, and each of which is optionally fused to one or more aryl, heterocyclic or heteroaryl rings, or one or more saturated or partially unsaturated cycloalkyl or heterocyclyl rings, each of which ring is optionally substituted, wherein a cycloalkyl, heterocyclyl, aryl or heteroaryl moiety in

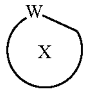

is optionally connected to a cycloalkyl, heterocyclyl, aryl or heteroaryl in L by a bond or by a bridging substituent;

Y is selected from the group consisting of H, halo, -aryl-heterocyclyl, -aryl-O—$C_0$-$C_4$alkyl-aryl, -aryl-aryl, —$C_1$-$C_4$alkyl, heteroalkyl, alkenyl, alkynyl, —N($R^a$)($R^b$), —N($R^c$)($R^d$), —O$R^e$, —S$R^s$, —$C_0$-$C_3$alkyl-aryl, —$C_0$-$C_3$alkyl-heteroaryl, —$C_0$-$C_3$alkyl-heterocyclyl, —$C_0$-$C_3$alkyl-cycloalkyl, —$C_2$-$C_4$alkenyl-aryl, —$C_2$-$C_4$alkenyl-heteroaryl, —$C_2$-$C_4$alkenyl-heterocyclyl, —$C_2$-$C_4$alkenyl-cycloalkyl, —$C_2$-$C_4$alkynyl-aryl, —$C_2$-$C_4$alkynyl-heteroaryl, —$C_2$-$C_4$alkynyl-heterocyclyl, —$C_2$-$C_4$alkynyl-cycloalkyl, —O—$C_0$-$C_3$alkyl-aryl, —O—$C_0$-$C_3$alkyl-heteroaryl, —O—$C_0$-$C_3$alkyl-cycloalkyl, —O—$C_0$-$C_3$alkyl-heterocycloalkyl, —C(O)NH—$C_0$-$C_3$alkyl-aryl, —C(O)NH—$C_0$-$C_3$alkyl-heteroaryl, —O—$C_0$-$C_3$alkyl-aryl-aryl, —O—$C_0$-$C_3$alkyl-heteroaryl-aryl, —O—$C_0$-$C_3$alkyl-aryl-heteroaryl, —O—$C_0$-$C_3$alkyl-heteroaryl-heteroaryl, —$S(O)_{0-2}$—$C_0$-$C_3$alkyl-aryl, —$S(O)_{0-2}$—$C_0$-$C_3$alkyl-heteroaryl-aryl, —$S(O)_{0-2}$—$C_0$-$C_3$alkyl-aryl-aryl, —$S(O)_{0-2}$—$C_0$-$C_3$alkyl-heteroaryl, —$S(O)_{0-2}$—$C_0$-$C_3$alkyl-aryl-heteroaryl, —$S(O)_{0-2}$—$C_0$-$C_3$alkyl-heteroaryl-heteroaryl, aryl-$C_0$-$C_3$alkyl-aryl, -heteroaryl-$C_0$-$C_3$alkyl-aryl, —$C_0$-$C_3$alkyl-aryl-$C_0$-$C_2$alkyl-N($R^e$)—$C_0$-$C_2$alkyl-aryl, —$C_0$-$C_3$alkyl-aryl-$C_0$-$C_2$alkyl-Nan-$C_0$-$C_2$alkyl-heteroaryl, —$C_0$-$C_3$alkyl-heteroaryl-$C_0$-$C_2$alkyl-N($R^e$)—$C_0$-$C_2$alkyl-aryl, —$C_0$-$C_3$alkyl-heteroaryl-$C_0$-$C_2$alkyl-Nan- $C_0$-$C_2$alkyl-heteroaryl, —$C_0$-$C_3$alkyl-aryl-$C_0$-$C_2$alkyl-N($R^e$)—$S(O)_2$—$C_0$-$C_2$alkyl-aryl, —$C_0$-$C_3$alkyl-aryl-$C_0$-$C_2$alkyl-N($R^e$)—$S(O)_2$—$C_0$-$C_2$alkyl-heteroaryl, —$C_0$-$C_3$alkyl-heteroaryl-$C_0$-$C_2$alkyl-N($R^e$)—$S(O)_2$—$C_0$-$C_2$alkyl-aryl, —$C_0$-$C_3$alkyl-heteroaryl-$C_0$-$C_2$alkyl-N($R^e$)—$S(O)_2$—$C_0$-$C_2$alkyl-heteroaryl, —N($R^e$)—$S(O)_2$—N($R^f$)H, —N($R^e$)—$S(O)_2$—$N(R^f)_2$, —N($R^e$)—C(O)H, —N($R^e$)—C(O)alkyl, —C(O)—N($R^e$)H, —C(O)—$N(R^e)_2$, —N($R^e$)—C(O)—$N(R^f)_2$, —N($R^e$)—C(O)—O-alkyl, —O—C(O)—N($R^e$)($R^f$), —OH, —O-alkyl, —O-aryl, —N($R^e$)—C(O)—$C_2$-$C_4$alkyl-O$R^e$, —O—$C_2$-$C_4$alkyl-N($R^e$)($R^f$), -heterocyclyl-$C_0$-$C_3$alkyl-aryl, -cycloalkyl-$C_0$-$C_3$alkyl-aryl, -aryl-$C_0$-$C_3$alkyl-heteroaryl, -heteroaryl-$C_0$-$C_3$alkyl-heteroaryl, -heterocyclyl-$C_0$-$C_3$alkyl-heteroaryl, -cycloalkyl-$C_0$-$C_3$alkyl-heteroaryl, -aryl-$C_0$-$C_3$alkyl-heterocyclyl, -heteroaryl-$C_0$-$C_3$alkyl-heterocyclyl, -heterocyclyl-$C_0$-$C_3$alkyl-heterocyclyl, -cycloalkyl-$C_0$-$C_3$alkyl-heterocyclyl, -heterocyclyl-$C_0$-$C_3$alkyl-O—$C_0$-$C_3$alkyl-aryl, -heterocyclyl-$C_0$-$C_3$alkyl-O—$C_0$-$C_3$alkyl-heteroaryl, -heterocyclyl-$C_0$-$C_3$alkyl-O—C(O)NH—$C_0$-$C_3$alkyl-aryl, -heterocyclyl-$C_0$-$C_3$alkyl-O—C(O)NH—$C_0$-$C_3$alkyl-heteroaryl, -heterocyclyl-$C_0$-$C_3$alkyl-heteroaryl-aryl, -heterocyclyl-$C_0$-$C_3$alkyl-heteroaryl-heteroaryl, -heterocyclyl-$C_0$-$C_3$alkyl-aryl-aryl, —NH$S(O)_2$—$C_0$-$C_3$alkyl-aryl, —NH$S(O)_2$—$C_0$-$C_3$alkyl-heteroaryl, —NHC(O)—$C_0$-$C_3$alkyl-aryl, -heterocyclyl-$C_0$-$C_3$alkyl-aryl, -heterocyclyl-$C_0$-$C_3$alkyl-heteroaryl, -heterocyclyl-C(O)-heterocyclyl, -heterocyclyl-C(O)—O-alkyl, -heterocyclyl-$S(O)_2$-alkyl, -heterocyclyl-$S(O)_2$—$C_0$-$C_3$alkyl-aryl, -heterocyclyl-$S(O)_2$—$C_0$-$C_3$alkyl-heteroaryl, -heterocyclyl-$C_1$-$C_4$alkyl-aryl, -heterocyclyl-$C_1$-$C_4$alkyl-heteroaryl, -heterocyclyl-$C_0$-$C_3$alkyl-aryl-heteroaryl, -heterocyclyl-$C_0$-$C_3$alkyl-heteroaryl-$C_0$-$C_3$alkyl-aryl, -heterocyclyl-$C_0$-$C_3$alkyl-heteroaryl-$C_0$-$C_3$alkyl-heteroaryl, -heterocyclyl-$C_0$-$C_3$alkyl-aryl-$C_0$-$C_3$alkyl-aryl, -heterocyclyl-$C_0$-$C_3$alkyl-aryl-$C_0$-$C_3$alkyl-heteroaryl, -heterocyclyl-$S(O)_2$—$C_0$-$C_3$alkyl-aryl, -heterocyclyl-$S(O)_2$—$C_0$-$C_3$alkyl-heteroaryl, -heterocyclyl-$S(O)_2$—$C_0$-$C_3$alkyl-alkyl, -heterocyclyl-$S(O)_2$—$C_0$-$C_3$alkyl-cycloalkyl, -heterocyclyl-$S(O)_2$—$C_0$-$C_3$alkyl-heterocyclyl, -heterocyclyl-C(O)—$C_0$-$C_3$alkyl-aryl, heterocyclyl-C(O)—$C_0$-$C_3$alkyl-heteroaryl, -heterocyclyl-C(O)—$C_0$-$C_3$alkyl-alkyl, -heterocyclyl-C(O)—$C_0$-$C_3$alkyl-cycloalkyl, -heterocyclyl-C(O)—$C_0$-$C_3$alkyl-heterocyclyl, -heterocyclyl-C(O)NH—$C_0$-$C_3$alkyl-aryl, -heterocyclyl-C(O)NH—$C_0$-$C_3$alkyl-heteroaryl, -heterocyclyl-C(O)NH—$C_0$-$C_3$alkyl-alkyl, -heterocyclyl-C(O)NH—$C_0$-$C_3$alkyl-cycloalkyl, -heterocyclyl-C(O)NH—$C_0$-$C_3$alkyl-heterocyclyl, -heterocyclyl-C(O)O—$C_0$-$C_3$alkyl-aryl, -heterocyclyl-C(O)O—$C_0$-$C_3$alkyl-heteroaryl, -heterocyclyl-C(O)O—$C_0$-$C_3$alkyl-alkyl, -heterocyclyl-C(O)O—$C_0$-$C_3$alkyl-cycloalkyl, -heterocyclyl-C(O)O—$C_0$-$C_3$alkyl-heterocyclyl, -heterocyclyl-$S(O)_2$—NH—$C_0$-$C_3$alkyl-aryl, -heterocyclyl-$S(O)_2$—NH—$C_0$-$C_3$alkyl-heteroaryl, -heterocyclyl-$S(O)_2$—NH—$C_0$-$C_3$alkyl-alkyl, -heterocyclyl-$S(O)_2$—NH—$C_0$-$C_3$alkyl-cycloalkyl, -heterocyclyl-$S(O)_2$—NH—$C_0$-$C_3$alkyl-heterocyclyl, —$C_0$-$C_3$alkyl-heterocyclyl-$C_2$-$C_4$alkenyl-aryl, —$C_0$-$C_3$alkyl-heterocyclyl-$CH(aryl)_2$, —$C_0$-$C_3$alkyl-heterocyclyl-$CH(heteroaryl)_2$, —$C_0$-$C_3$alkyl-heterocyclyl-CH(aryl)(heteroaryl), —$C_0$-$C_3$alkyl-aryl-O—$C_2$-$C_4$alkyl-heterocyclyl, —$C_0$-$C_3$alkyl-aryl-$C_0$-$C_3$alkyl-heterocyclyl-$C_0$-$C_3$alkyl-aryl, —$C_0$-$C_3$alkyl-heteroaryl-$C_0$-$C_3$alkyl-heterocyclyl-$C_0$-$C_3$alkyl-aryl, —$C_0$-$C_3$alkyl-aryl-$C_0$-$C_3$alkyl-heterocyclyl-$C_0$-$C_3$alkyl-heteroaryl, —$C_0$-$C_3$alkyl-heteroaryl-$C_0$-$C_3$alkyl-heterocyclyl-$C_0$-$C_3$alkyl-heteroaryl, —NH—C(O)-aryl, —NH—C(O)— heteroaryl, —$CH(aryl)_2$, —$CH(heteroaryl)_2$, —$C_0$-$C_3$alkyl-aryl-heterocyclyl, —$C_0$-$C_3$alkyl-aryl-heterocyclyl-$S(O)_2$-aryl, —$C_0$-$C_3$alkyl-heteroaryl-heterocyclyl-$S(O)_2$-aryl, —$C_0$-$C_3$alkyl-aryl-heterocyclyl-$S(O)_2$-heteroaryl, —$C_0$-$C_3$alkyl-heteroaryl-heterocyclyl-$S(O)_2$-heteroaryl, —$C_0$-$C_3$alkyl-aryl-$S(O)_2$-heterocyclyl-aryl, —$C_0$-$C_3$alkyl-heteroaryl-$S(O)_2$-heterocyclyl-aryl, —$C_0$-$C_3$alkyl-aryl-$S(O)_2$-heterocyclyl-heteroaryl, —$C_0$-$C_3$alkyl-heteroaryl-$S(O)_2$-heterocyclyl-heteroaryl, —$C_0$-$C_3$alkyl-aryl-heterocyclyl-C(O)-aryl, —$C_0$-$C_3$alkyl-heteroaryl-heterocyclyl-C(O)-aryl, —$C_0$-$C_3$alkyl-aryl-heterocyclyl-C(O)-heteroaryl, —$C_0$-$C_3$alkyl-heteroaryl-heterocyclyl-C(O)-heteroaryl, —$C_0$-$C_3$alkyl-aryl-C(O)-heterocyclyl-aryl, —$C_0$-$C_3$alkyl-heteroaryl-C(O)-heterocyclyl-aryl, —$C_0$-$C_3$alkyl-aryl-C(O)-heterocyclyl-heteroaryl, —$C_0$-$C_3$alkyl-heteroaryl-C(O)-heterocyclyl-heteroaryl, —$C_0$-$C_3$alkyl-aryl-heterocyclyl-C(O)N($R^e$)-aryl, —$C_0$-$C_3$alkyl-heteroaryl-heterocyclyl-C(O)N($R^e$)-aryl, —$C_0$-$C_3$alkyl-aryl-heterocyclyl-C(O)N($R^e$)-heteroaryl, —$C_0$-$C_3$alkyl-heteroaryl-heterocyclyl-C(O)N($R^e$)-heteroaryl, —$C_0$-$C_3$alkyl-aryl-N($R^e$)C(O)-heterocyclyl-aryl, —$C_0$-$C_3$alkyl-heteroaryl-N($R^e$)C(O)-heterocyclyl-aryl, —$C_0$-$C_3$alkyl-aryl-N($R^e$)C(O)-heterocyclyl-heteroaryl, —$C_0$-$C_3$alkyl-heteroaryl-N($R^e$)C(O)-heterocyclyl-heteroaryl, —$C_0$-$C_3$alkyl-aryl-heterocyclyl-C(O)O-aryl, —$C_0$-$C_3$alkyl-heteroaryl-heterocyclyl-C(O)O-aryl, —$C_0$-$C_3$alkyl-aryl-heterocyclyl-C(O)O-heteroaryl, —$C_0$-$C_3$alkyl-heteroaryl-heterocyclyl-C(O)O-heteroaryl, —$C_0$-$C_3$alkyl-aryl-OC(O)-heterocyclyl-aryl, —$C_0$-$C_3$alkyl-heteroaryl-OC(O)-heterocyclyl-aryl, —$C_0$-$C_3$alkyl-aryl-OC(O)-heterocyclyl-heteroaryl, —$C_0$-$C_3$alkyl-heteroaryl-OC(O)-heterocyclyl-heteroaryl, aromatic polycycles, non-aromatic polycycles, polyheteroaryl groups, non-aromatic polyheterocyclic, mixed aryl and non-aryl polyheterocycle, —$Z^1$—Z—$Z^2$-D, —CH($OR^1$)—Z—$Z^3$—Z-D, —C($R^1$)($R^2$)—Z—$Z^3$—Z-D, —$C(F)_2$—Z—$Z^3$—Z-D, fused heterocyclyl, —C(O)—N($R^1$)—$C_0$-$C_3$alkyl-aryl-O-aryl, —C(O)—N($R^1$)—$C_0$-$C_3$alkyl-aryl-$S(O)_{0-2}$-aryl, —C(O)—N($R^1$)—$C_0$-$C_3$alkyl-aryl-N($R^2$)-aryl, —C(O)—N($R^1$)—$C_0$-$C_3$alkyl-aryl-O-heteroaryl, —C(O)—N($R^1$)—$C_0$-$C_3$alkyl-aryl-$S(O)_{0-2}$-heteroaryl, —C(O)—N($R^1$)—$C_0$-$C_3$alkyl-aryl-N($R^2$)-heteroaryl, —C(O)—N($R^1$)—$C_0$-$C_3$alkyl-heteroaryl-O-aryl, —C(O)—N($R^1$)—$C_0$-$C_3$alkyl-heteroaryl-$S(O)_{0-2}$-aryl, —C(O)—N($R^1$)—$C_0$-$C_3$alkyl-heteroaryl-N($R^2$)-aryl, —C(O)—N($R^1$)—$C_0$-$C_3$alkyl-heteroaryl-O-heteroaryl, —C(O)—N($R^1$)—$C_0$-$C_3$alkyl-heteroaryl-$S(O)_{0-2}$-heteroaryl, —C(O)—N($R^1$)—$C_0$-$C_3$alkyl-heteroaryl-N($R^2$)-heteroaryl, wherein each aryl, heteroaryl, cycloalkyl and heterocyclyl moiety is optionally substituted, wherein $Z^1$ is selected from the group consisting of chemical bond, alkyl, aryl, heterocyclyl, bridged heterocyclyl, spiro heterocyclyl, cycloalkyl, heteroaryl, —C(F)($R^1$)—, —C($OR_2$)($R^1$)—, —C(aryl)($R^1$)—, —C(heteroaryl)($R^1$)—, —C(heterocyclyl)($R^1$)—, —C(cycloalkyl)($R^1$)—, —C(alkyl)($R^1$)—, —C(alkenyl)($R^1$)—, —C(alkynyl)($R^1$)—, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted;

Z is selected from the group consisting of chemical bond, —O—, —N($R^1$)—, —N($R^a$)($R^b$), —N($R^e$)—, —N($C_2$-$C_4$alkyl-O$R^1$)—, —C(O)—, —C(NO$R^1$)—, —C(H)(F)—, —C(H)(CON($R^1$)($R^2$))—CON($R^1$)($R^2$)—, —C(H)(N($R^1$)($R^2$)), —C(O)N($R^1$)($R^2$)—, —C(H)(CON($R^e$)($R^f$))—C(O)N($R^1$)($R^2$)—, —C(H)(N($R^e$)($R^f$)—C(O)N($R^1$)($R^2$)—, —C(H)(heteroaryl)-C(O)N($R^1$)($R^2$)—, —C(H)(heteroaryl-aryl)-C(O)N($R^1$)($R^2$)—, —C(H)(heteroaryl-heteroaryl)-C(O)N($R^1$)($R^2$)—, —C(O)—C(O)N($R^1$)—, —S(O)$_{0-2}$—, —N($R^1$)S(O)$_2$—, —S(O)$_2$N($R^1$)—, —N($R^1$)S(O)$_2$N($R^2$)—, —N($R^1$)C(O)—, —C(O)N($R^1$)—, —OC(O)—, —C(O)O—, —N($R^1$)C(N$R^2$)—, —C(N$R^2$)N($R^1$)—, —N($R^1$)C(O)N($R^2$)—, —N($R^1$)C(O)O—, —OC(O)N($R^1$)—, —N($R^1$)C(S)—, —C(S)N($R^1$)—, —N($R^1$)C(S)N($R^2$)—, —N($R^1$)C(S)O—, —OC(S)N($R^1$)—, —O—$C_2$-$C_4$alkyl-N($R^1$)—, —N($R^1$)—$C_2$-$C_4$alkyl-O—, —O—$C_2$-$C_4$alkyl-O—, —O—$C_1$-$C_4$alkyl-S(O)$_2$N($R^1$)—, —S(O)$_2$N($R^1$)—$C_2$-$C_4$alkyl-O—, —O—$C_2$-$C_4$alkyl-N($R^1$)S(O)$_2$—, —N($R^1$)S(O)$_2$—$C_1$-$C_4$alkyl-O—, —C(O)—$C_1$-$C_4$alkyl-N($R^1$)—, —N($R^1$)—$C_1$-$C_4$alkyl-C(O)—, —O—$C_1$-$C_4$alkyl-C(O)N($R^1$)—, —C(O)N($R^1$)—$C_2$-$C_4$alkyl-O—, —O—$C_2$-$C_4$alkyl-N($R^1$)C(O)—, —N($R^1$)C(O)—$C_1$-$C_4$alkyl-O—, —O—$C_1$-$C_4$alkyl-C(O)—, —C(O)—$C_1$-$C_4$alkyl-O—, —N($R^1$)—$C_1$-$C_4$alkyl-C(O), —C(O)—$C_1$-$C_4$alkyl-N($R^1$)—, —O—$C_1$-$C_4$alkyl-C(S)—, —C(S)—$C_1$-$C_4$alkyl-O—, —N($R^1$)—$C_1$-$C_4$alkyl-C(S), —C(S)—$C_1$-$C_4$alkyl-N($R^1$)—, —N($R^1$)—$C_1$-$C_4$alkyl-C(S)—, —O—$C_1$-$C_4$alkyl-C(S)N($R^1$)—, —C(S)N($R^1$)—$C_2$-$C_4$alkyl-O—, —O—$C_2$-$C_4$alkyl-N($R^1$)—C(S)—, —N($R^1$)C(S)—$C_1$-$C_4$alkyl-O—, —N($R^1$)—$C_1$-$C_4$alkyl-S(O)$_2$—, —O—$C_1$-$C_4$alkyl-S(O)$_2$N($R^1$)—, —S(O)$_2$N($R^1$)—$C_2$-$C_4$alkyl-O—, —O—$C_2$-$C_4$alkyl-N($R^1$)S(O)$_2$—, —N($R^1$)S(O)$_2$—$C_1$-$C_4$alkyl-O—, —O—$C_2$-$C_4$alkyl-OC(O)N($R^1$)—, —O—$C_2$-$C_4$alkyl-OC(S)N($R^1$)—;

$Z^2$ is selected from the group consisting of chemical bond, alkyl, alkenyl, —C(F)($R^1$)—, —C(O$R^2$)($R^1$)—, —C(aryl)($R^1$)—, —C(heteroaryl)($R^1$)—, —C(heterocyclyl)($R^1$)—, —C(cycloalkyl)($R^1$)—, —C(alkyl)($R^1$)—, —C(alkenyl)($R^1$)—, —C(alkynyl)($R^1$)—, wherein each alkyl, aryl, alkenyl or alkynyl moiety is optionally substituted;

$Z^3$ is selected from the group consisting of chemical bond, $C_2$-$C_5$alkyl, aryl, heterocyclyl, bridged heterocyclyl, spiro heterocyclyl, cycloalkyl or heteroaryl, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of each ring is optionally substituted;

D is selected from the group consisting of H, aryl, heteroaryl, alkyl, cycloalkyl and heterocyclyl, bridged heterocyclyl, spiro heterocyclyl, aryl-heterocyclyl, -aryl-$C_0$-$C_3$alkyl-O—$C_0$-$C_3$alkyl-aryl, -aryl-$C_0$-$C_3$alkyl-O—$C_0$-$C_3$alkyl-heteroaryl, -heteroaryl-$C_0$-$C_3$alkyl-O—$C_0$-$C_3$alkyl-aryl, -heteroaryl-$C_0$-$C_3$alkyl-O-$C_0$-$C_3$alkyl-heteroaryl, -aryl-$C_0$-$C_3$alkyl-N($R^1$)—$C_0$-$C_3$alkyl-aryl, -aryl-$C_0$-$C_3$alkyl-N($R^1$)—$C_0$-$C_3$alkyl-heteroaryl, -heteroaryl-$C_0$-$C_3$alkyl-N($R^1$)—$C_0$-$C_3$alkyl-aryl, -heteroaryl-$C_0$-$C_3$alkyl-N($R^1$)—$C_0$-$C_3$alkyl-heteroaryl, aromatic polycycle, non-aromatic polycycle, polyheteroaryl group, non-aromatic polyheterocyclic, mixed aryl and non-aryl polyheterocycle, each of which is optionally substituted and each of which is optionally fused to one or more aryl or heteroaryl rings, or one or more saturated or partially unsaturated cycloalkyl or heterocyclyl rings, each of which ring is optionally substituted;

$R^a$ and $R^b$ together with the nitrogen to which they are bound form a 4 to 7 membered heterocyclyl having 1 or 2 annular heteroatoms, or a 5 to 8 membered bridged heterocyclyl having 1 or 2 annular heteroatoms, the heterocyclyl being optionally substituted with 1-3 substituents independently selected from the group consisiting of H, OH, oxo (i.e., =O), —N($R^1$)($R^2$), $C_1$-$C_6$alkyl, aryl, heteroaryl, —$C_1$-$C_6$alkyl-aryl, —$C_1$-$C_6$alkyl-heteroaryl, —$C_1$-$C_3$ alkoxy-$C_1$-$C_3$alkyl, —$C_2$-$C_3$alkyl-OH, —$C_2$-$C_3$alkyl-O—$C_1$-$C_4$alkyl, —$C_5$-$C_6$cycloalkyl, —$C_0$-$C_3$alkyl-N(H)—C(O)—$C_1$-$C_3$alkyl, —$C_0$-$C_3$alkyl-N(H)—C(O)-haloalkyl, —$C_0$-$C_3$alkyl-NHC(O)O—$C_1$-$C_3$alkyl-aryl, —$C_0$-$C_3$alkyl-$CF_3$, —$C_0$-$C_3$alkyl-NHC(O)O—$C_1$-$C_3$alkyl-heteroaryl and —$C_0$-$C_3$alkyl-$NH_2$, wherein said heterocyclyl also is optionally fused to an aryl or heteroaryl, wherein each aforementioned aryl, heteroaryl, cycloalkyl and heterocyclyl moiety is optionally substituted;

each $R^c$ and $R^d$ is independently selected from the group consisting of H, —$C_1$-$C_6$alkyl, —$C_2$-$C_3$alkyl-O$R^e$, —C(O)O$R^1$, —C(O)N$R^1R^2$, —C(S)O$R^1$, —C(S)N$R^1R^2$, —C(O)$R^1$, —C(S)$R^1$, —S(O)$_2R^1$, —S(O)$_2$N$R^1R^2$, aryl, heteroaryl, -heteroaryl-heteroaryl, -heteroaryl-aryl, -aryl-heteroaryl, —C(O)-aryl, —$C_1$-$C_3$-alkoxy-$C_1$-$C_3$-alkyl, —$C_2$-$C_3$alkyl-O$R^2$, —$C_2$-$C_3$alkyl-N$R^aR^b$, —$C_2$-$C_3$alkyl-N$R^eR^f$, —$CH_2$—C($CH_3$)$_2$—N$R^aR^b$ and —$CH_2$—C($CH_3$)$_2$—N$R^eR^f$, in which each aryl and heteroaryl is optionally substituted with one, two or three substituents independently selected from amino, $OCH_3$ and OH;

each $R^e$ and $R^f$ is independently selected from the group consisting of —H, -alkyl, -aryl, -aryl-aryl, -hetetoaryl, heterocyclyl, heteroaryl-aryl, heteroaryl-heteroaryl, —$C_1$-$C_6$alkyl-C(O)N$R^1R^2$, —C(O)-alkyl, —C(O)heteroaryl, —C(O)cycloalkyl, —C(O)aryl, —C(O)O-alkyl, —C(O)Oheteroaryl, —C(O)Ocycloalkyl, —C(O)Oaryl, —C(O)N($R^1$)-alkyl, —C(O)N($R^1$)heteroaryl, —C(O)(N$R^1$)cycloalkyl, —C(O)N($R^1$)aryl and —C(O)$CF_3$; and each $R^s$ is independently selected from the group consisting of —H, $C_1$-$C_6$alkyl, aryl, heteroaryl, heterocyclyl, cycloalkyl and a protecting group, wherein each cycloalkyl, heterocyclyl, aryl, alkyl and heteroaryl moiety is optionally substituted, provided that Formula (I) excludes the following compounds N-hydroxybiphenyl-2-carboxamide, 2-benzyl-N-hydroxybenzamide, N-hydroxy-2-phenoxybenzamide, N-hydroxy-2-(phenylamino)benzamide, N-hydroxy-4-phenyl-1H-pyrrole-3-carboxamide, N-hydroxy-4-(naphthal en-1-yl)-1H-pyrrole-3-carboxamide, N-hydroxy-4-(naphthalen-2-yl)-1H-pyrrole-3-carboxamide and provided that Formula (I) excludes compounds having the formula

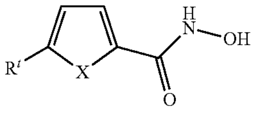

or

-continued

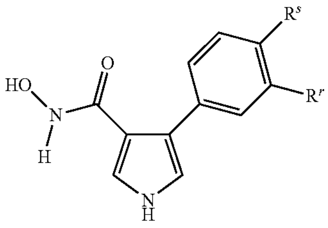

wherein $R^t$ is

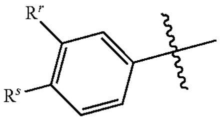,
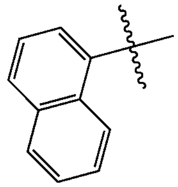
or

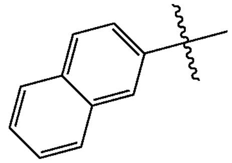, $R^r$ and $R^s$ are independently H, lower haloalkyl, $-CO_2H$, $-NO_2$, lower alkyl carboxylate, lower alkoxy or —CN, and X is S or O.

In one embodiment of the present invention, the invention provides compounds of the Formula (Ia):

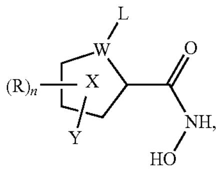

wherein groups L, W, X, Y, R and n are as described for Formula (I).

In one embodiment of Formula (Ia),

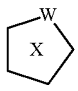

is selected from the group consisting of

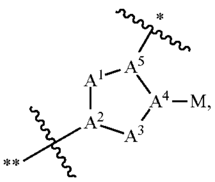
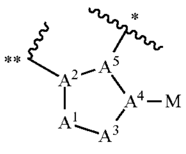
and

-continued

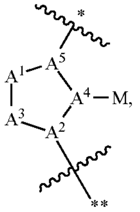

wherein $A^1$, $A^2$, $A^3$, $A^4$ and $A^5$ form a 5-membered heteroaryl ring, wherein $A^1$ and $A^3$ are selected from the group consisting of carbon, nitrogen, —S— and —O—, $A^4$ is carbon and $A^2$ and $A^5$ are nitrogen or carbon, provided that at least one of $A^2$ and $A^5$ is carbon, and wherein * represents the point of attachment to group L and ** represents the point of attachment to group Y.

In another embodiment of the present invention, the invention provides compounds of the Formula (Ib):

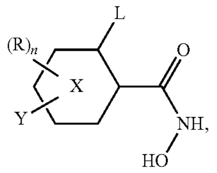

wherein groups L, X, Y, R and n are as described for Formula (I).

In one embodiment of Formula (Ib),

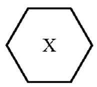

is selected from the group consisting of (a)

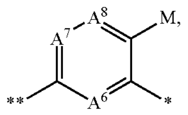

(b)

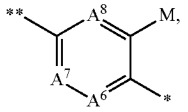

(c)

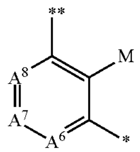
and (d)

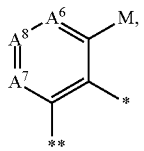

wherein $A^6$, $A^7$ and $A^8$ form part of a 6-membered aryl or heteroaryl ring, wherein $A^6$, $A^7$ and $A^8$ are independently carbon and/or nitrogen, provided that at least one of $A^6$, $A^7$ and $A^8$ in structures (c) and (d) is carbon, and wherein * represents the point of attachment to group L and ** represents the point of attachment to group Y.

In an embodiment of the present invention,

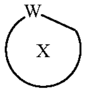

is an aryl group, for example a 6-membered group.

In another embodiment of the present invention,

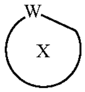

is a phenyl group.

In another embodiment of the present invention,

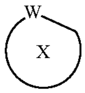

is a heteroaryl group, for example a 5- or 6-membered heteroaryl group.

In another embodiment of the present invention,

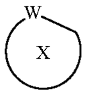

is imidazothiazolyl, benzofuranyl or benzothienyl for example, imidazo[2,1-b]thiazolyl.

In another embodiment of the present invention,

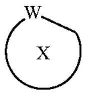

is benzothienyl.

In another embodiment of the present invention,

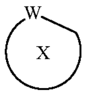

is

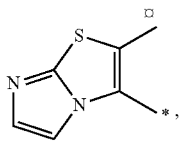

wherein * represents the point of attachment of L and ¤ represents the point of attachment of M.

In another embodiment of the present invention,

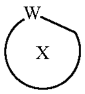

is a 5-membered heteroaryl group.

In another embodiment of the present invention,

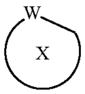

is a 5-membered heteroaryl group selected from the group consisting of oxazolyl, thienyl, pyrazolyl, thiazolyl and isoxazolyl.

In another embodiment

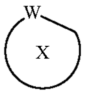

is selected from the group consisting of pyrazolyl, thiazolyl and thienyl.

In another embodiment of the present invention,

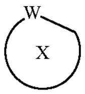

is pyridyl or pryimidyl.

In another embodiment of the present invention,

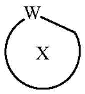

is selected from group consisting of

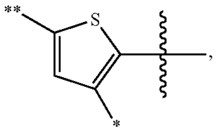, 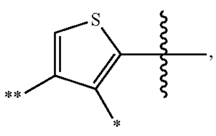,

-continued
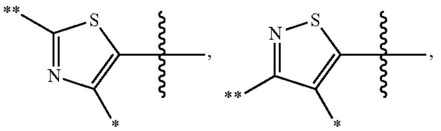
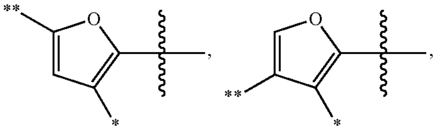
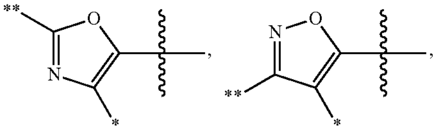
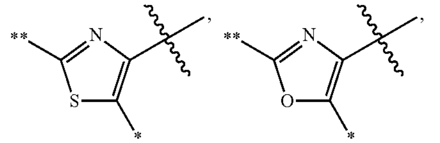
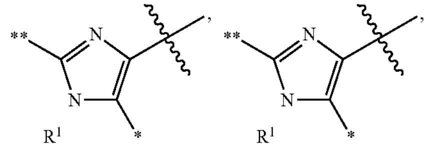
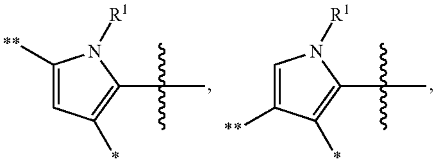
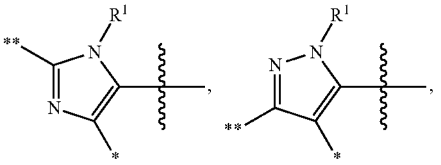
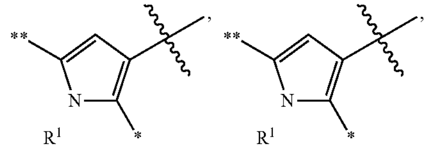
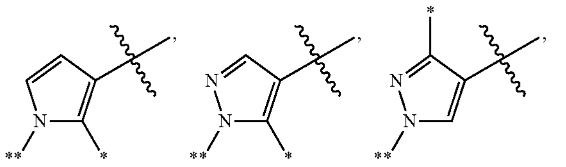
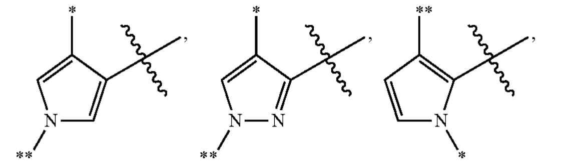
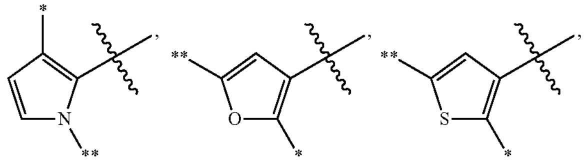
-continued
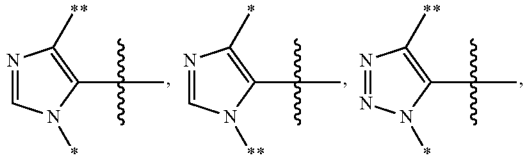
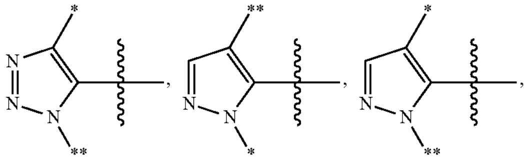
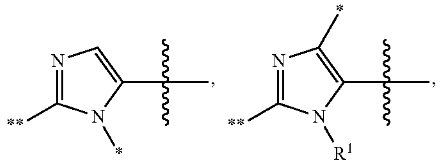
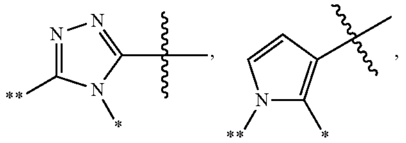
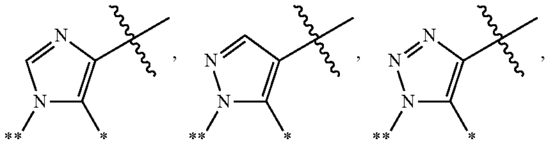
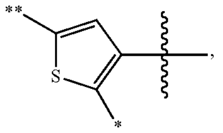
and
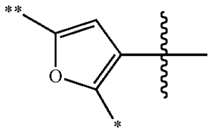
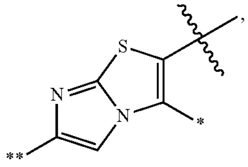
wherein ⌇ represents the point of attachment to group M, * represents the point of attachment to group L and ** represents the point of attachment to group Y.
In another embodiment of the present invention,
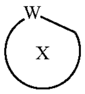
is selected from group consisting of
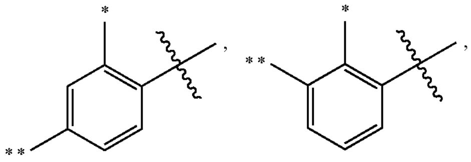

-continued

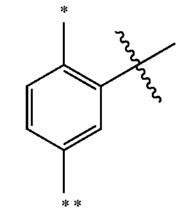

and

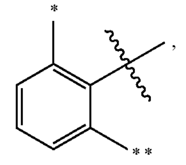

, wherein represents the point of attachment to group M, * represents the point of attachment to group L and ** represents the point of attachment to group Y.

In another embodiment of the present invention,

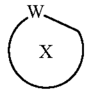

is selected from group consisting of

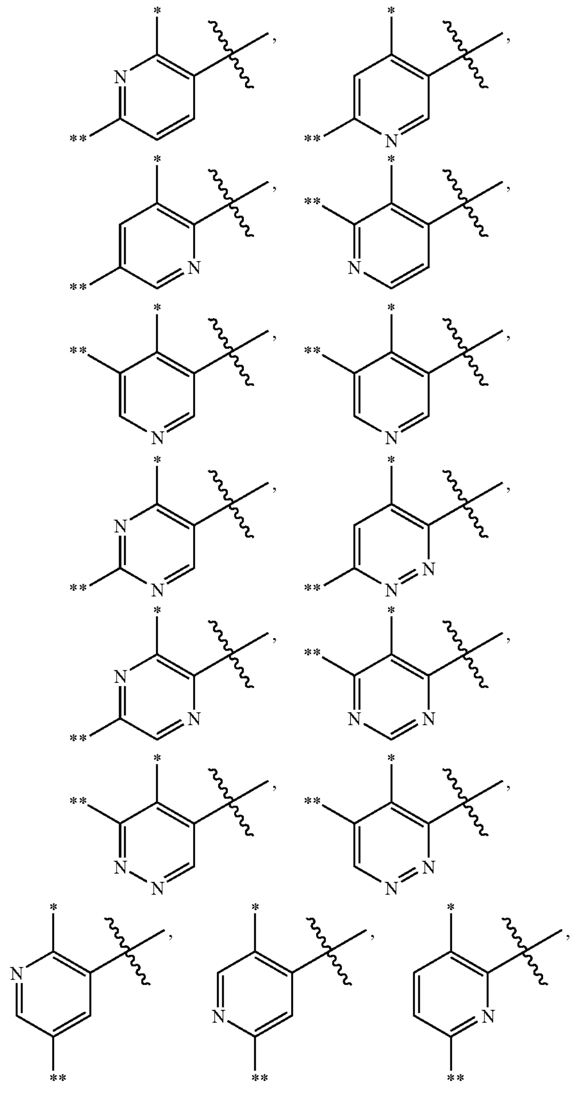

-continued

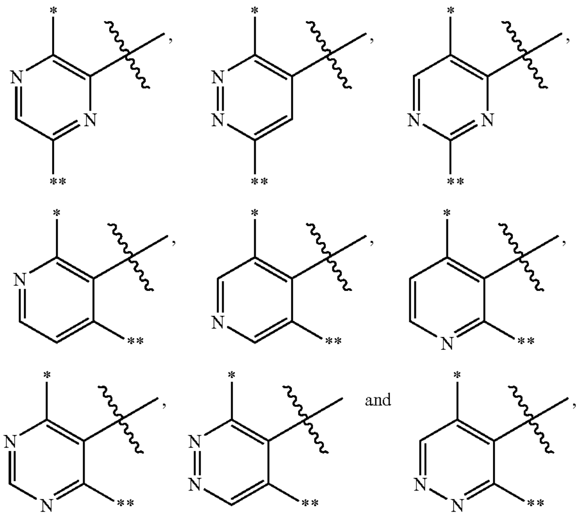

wherein represents the point of attachment to group M, * represents the point of attachment to group L and ** represents the point of attachment to group Y.

In another embodiment of the present invention,

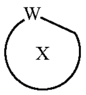

is selected from group consisting of

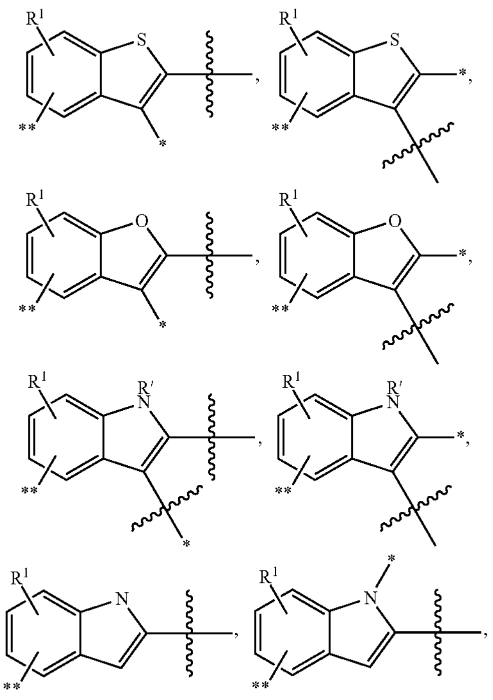

-continued

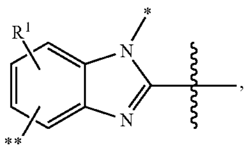

, and

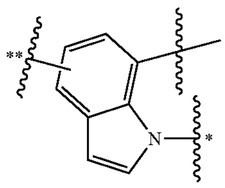

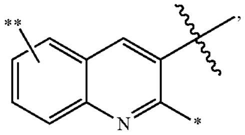

wherein ~ represents the point of attachment to group M, * represents the point of attachment to group L and ** represents the point of attachment to group Y.

In another embodiment of the present invention,

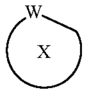

is

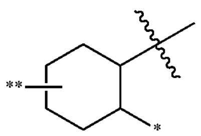

or

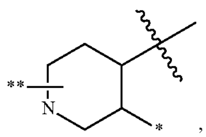

, wherein ~ represents the point of attachment to group M, * represents the point of attachment to group L and ** represents the point of attachment to group Y.

In another embodiment of the present invention,

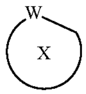

is selected from group consisting of

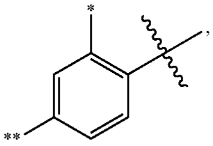

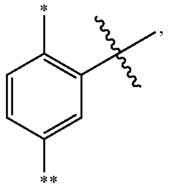

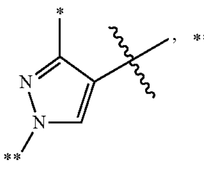

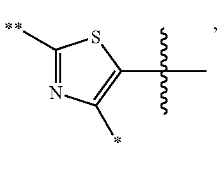

-continued

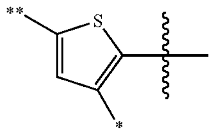

and

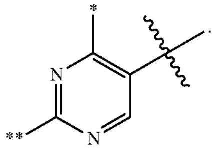

wherein ~ represents the point of attachment to group M, * represents the point of attachment to group L and ** represents the point of attachment to group Y.

In another embodiment of the present invention, W is

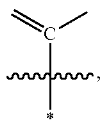

wherein * is the point of attachment of group L.

In another embodiment of the present invention, M is —C(O)N($R^1$)O$R^2$ or —N(OH)—C(O)H.

In another embodiment of the present invention, M is —C(O)N($R^1$)O$R^2$, for example, —C(O)NHOH.

In another embodiment of the present invention, $R^1$ is H or alkyl.

In another embodiment of the present invention, $R^2$ is H.

In another embodiment of the present invention, R is H.

In another embodiment of the present invention, n is 0.

In another embodiment of the present invention, L is selected from the group consisting of aryl, heteroaryl, cycloalkyl, heterocyclyl, fused aryl, fused heterocyclyl, fused cycloalkyl, -alkenyl-aryl, -aryl-heteroaryl, -heteroaryl-aryl, -alkynyl-aryl, —O—$C_0$-$C_4$alkyl-aryl, -alkyl-aryl, —$SO_2$—N($R^1$)—$C_0$-$C_4$alkyl-aryl, —N($R^1$)-aryl, —$CF_3$, -t-Bu, —$NR_1SO_2$-aryl, halo, —N($R^1$)C(O)-aryl and —S-aryl, wherein each aryl, heteroaryl, cycloalkyl and heterocyclyl moiety is optionally substituted.

In another embodiment of the present invention, L is selected from the group consisting of aryl, heteroaryl, cycloalkyl, heterocyclyl, fused aryl, fused heterocyclyl, fused cycloalkyl, -alkenyl-aryl, -aryl-heteroaryl, -heteroaryl-aryl, -alkynyl-aryl, —O—$C_0$-$C_4$alkyl-aryl, -alkyl-aryl, —$SO_2$N($R^1$)—$C_0$-$C_4$alkyl-aryl, —N($R^1$)-aryl, —$CF_3$, -t-Bu, —$NR_1SO_2$-aryl, halo, —N($R^1$)C(O)-aryl and —S-aryl, wherein each aryl, heteroaryl, cycloalkyl and heterocyclyl moiety is optionally substituted with 1, 2 or 3 moieties independently selected from the group consisting of phenyl (which itself is optionally substituted with alkyl), halo, alkyl, alkoxy, $NO_2$, pyrrolyl, thienyl, amino, dialkylamino, morpholinyl and —C(NOH)$NH_2$, and each of which is optionally fused to one or more aryl, heterocyclic or heteroaryl rings, or one or more saturated or partially unsaturated cycloalkyl or heterocyclyl rings, each of each ring is optionally substituted.

In another embodiment of the present invention, L is selected from the group consisting of aryl, heteroaryl, cycloalkyl, alkenyl-aryl, —O—$C_0$-$C_4$alkyl-aryl, -alkyl-aryl, —S$(O)_2$N($R^1$)—$C_0$-$C_4$alkyl-aryl, —N($R^1$)-aryl, —$CF_3$, —N($R^1$)—S$(O)_2$-aryl, fused aryl, fused heterocyclyl and fused cycloalkyl, halo, —N($R^1$)C(O)-aryl and —S-aryl, wherein each aryl, heteroaryl, cycloalkyl and heterocyclyl moiety is optionally substituted, and each of which is optionally fused to one or more aryl, heteroaryl or heterocyclyl rings, or one or more saturated or partially unsaturated cycloalkyl or heterocyclyl rings, each of which ring is optionally substituted.

In another embodiment of the present invention, L is selected from the group consisting of aryl, heteroaryl, cycloalkyl, alkenyl-aryl, —O—$C_0$-$C_4$alkyl-aryl, -alkyl-aryl, —$S(O)_2N(R^1)$—$C_0$-$C_4$alkyl-aryl, —$N(R^1)$-aryl, —$CF_3$, —$N(R^1)$—$S(O)_2$-aryl, fused aryl, fused heterocyclyl, fused cycloalkyl, halo, —$N(R^1)C(O)$-aryl and —S-aryl, wherein each aryl, heteroaryl, heterocyclyl and cycloalkyl moiety is optionally substituted.

In another embodiment of the present invention, L is selected from the group consisting of aryl, heteroaryl, cycloalkyl, alkenyl-aryl, —O—$C_0$-$C_4$alkyl-aryl, -alkyl-aryl, —$S(O)_2N(R^1)$—$C_0$-$C_4$alkyl-aryl, —$N(R^1)$-aryl, —$CF_3$, —$N(R^1)$—$S(O)_2$-aryl, fused aryl, fused heterocyclyl, fused cycloalkyl, halo, —$N(R^1)C(O)$-aryl and —S-aryl, wherein each aryl, heteroaryl, cycloalkyl and heterocyclyl moiety is optionally substituted with 1, 2 or 3 moieties independently selected from the group consisting of phenyl (which itself is optionally substituted with alkyl), halo, alkyl, alkoxy, $NO_2$, pyrrolyl, thienyl, amino, dialkylamino, morpholinyl and —$C(NOH)NH_2$.

In another embodiment of the present invention, L is selected from the group consisting of aryl, heteroaryl, cycloalkyl, alkenyl-aryl, —O—$C_0$-$C_4$alkyl-aryl, -alkyl-aryl, —$S(O)_2N(R^1)$—$C_0$-$C_4$alkyl-aryl, —$N(R^1)$-aryl, —$N(R^1)$—$S(O)_2$-aryl, fused aryl, fused heterocyclyl, fused cycloalkyl, —$N(R^1)C(O)$-aryl and —S-aryl, wherein each aryl, heteroaryl, cycloalkyl and heterocyclyl moiety is optionally fused to one or more aryl, heteroaryl or heterocyclyl rings, or one or more saturated or partially unsaturated cycloalkyl or heterocyclyl rings, each of which ring is optionally substituted.

In another embodiment of the present invention, L is selected from the group consisting of phenyl, heteroaryl, cycloalkyl, alkenyl-phenyl, —O—$C_0$-$C_4$alkyl-phenyl, -alkyl-phenyl, —$S(O)_2N(R^1)$—$C_0$-$C_4$alkyl-phenyl, —$N(R^1)$-phenyl, —$CF_3$, —$N(R^1)$—$S(O)_2$-phenyl, fused phenyl, fused heterocyclyl, fused cycloalkyl, halo, —$N(R^1)C(O)$-phenyl and —S-phenyl, wherein each phenyl, heteroaryl, cycloalkyl and heterocyclyl moiety is optionally substituted, wherein said heteroaryl is selected from the group consisting of thienyl, pyrrolyl, pyridinyl and furanyl, and each of which is optionally fused to one or more aryl, heteroaryl or heterocyclyl rings, or one or more saturated or partially unsaturated cycloalkyl or heterocyclyl rings, each of which ring is optionally substituted.

In another embodiment of the present invention, L is selected from the group consisting of phenyl, heteroaryl, cycloalkyl, alkenyl-phenyl, —O—$C_0$-$C_4$alkyl-phenyl, -alkyl-phenyl, —$S(O)_2N(R^1)$—$C_0$-$C_4$alkyl-phenyl, —$N(R^1)$-phenyl, —$CF_3$, —$N(R^1)$—$S(O)_2$-phenyl, fused phenyl, fused heterocyclyl, fused cycloalkyl, halo, —$N(R^1)C(O)$-phenyl and —S-phenyl, wherein each phenyl, heteroaryl, heterocyclyl and cycloalkyl moiety is optionally substituted, and wherein said heteroaryl is selected from the group consisting of thienyl, pyrrolyl, pyridinyl and furanyl.

In another embodiment of the present invention, L is selected from the group consisting of phenyl, heteroaryl, cycloalkyl, alkenyl-phenyl, —O—$C_0$-$C_4$alkyl-phenyl, -alkyl-phenyl, —$S(O)_2N(R^1)$—$C_0$-$C_4$alkyl-phenyl, —$N(R^1)$-phenyl, —$CF_3$, —$N(R^1)$—$S(O)_2$-phenyl, fused phenyl, fused heterocyclyl, fused cycloalkyl, halo, —$N(R^1)C(O)$-phenyl and —S-phenyl, wherein said heteroaryl is selected from the group consisting of thienyl, pyrrolyl, pyridinyl and furanyl and wherein each phenyl, heteroaryl, cycloalkyl and heterocyclyl moiety is optionally substituted with 1, 2 or 3 moieties independently selected from the group consisting of phenyl (which itself is optionally substituted with alkyl), halo, alkyl, alkoxy, $NO_2$, pyrrolyl, thienyl, amino, dialkylamino, morpholinyl and —$C(NOH)NH_2$.

In another embodiment of the present invention, L is selected from the group consisting of phenyl, heteroaryl, cycloalkyl, alkenyl-phenyl, —O—$C_0$-$C_4$alkyl-phenyl, -alkyl-phenyl, —$S(O)_2N(R^1)$—$C_0$-$C_4$alkyl-phenyl, —$N(R^1)$-phenyl, —$N(R^1)$—$S(O)_2$-phenyl, fused phenyl, fused heterocyclyl, fused cycloalkyl, —$N(R^1)C(O)$-phenyl and —S-phenyl, wherein said heteroaryl is selected from the group consisting of thienyl pyrrolyl, pyridinyl and furanyl and wherein each phenyl, heteroaryl, cycloalkyl and heterocyclyl moiety is optionally fused to one or more aryl, heteroaryl or heterocyclyl rings, or one or more saturated or partially unsaturated cycloalkyl or heterocyclyl rings, each of which ring is optionally substituted.

In another embodiment of the present invention, L is selected from the group consisting of aryl, heteroaryl, —O—$C_0$-$C_4$alkyl-aryl, -alkyl-aryl, —$N(R^1)SO_2$-aryl, —$SO_2N(R^1)$—$C_0$-$C_4$alkyl-aryl, —$N(R^1)$-aryl, -alkenyl-aryl and -alkynyl-aryl, wherein each aryl and heteroaryl group is optionally substituted with 1, 2 or 3 independently selected substituents.

In another embodiment of the present invention, L is selected from the group consisting of aryl, heteroaryl, —O—$C_0$-$C_4$alkyl-aryl, -alkyl-aryl, —$N(R^1)SO_2$-aryl, —$SO_2N(R^1)$—$C_0$-$C_4$alkyl-aryl, —$N(R^1)$-aryl, -alkenyl-aryl and -alkynyl-aryl, wherein each aryl and heteroaryl group is optionally substituted with 1, 2 or 3 substituents independently selected from the group consisting of hydroxy, amino, —NH-alkyl, —$N(alkyl)_2$, —O-alkyl, halo, $C_1$-$C_6$alkyl, aryl, heteroaryl, optionally substituted heteroaryl, nitro, cyano, $C_2$-$C_6$alkoxy, $C_1$-$C_6$alkylamino and $CF_3$.

In another embodiment of the present invention, L is selected from the group consisting of aryl, heteroaryl, -aryl-aryl, heterocyclyl, -alkynyl-aryl, —O—$C_0$-$C_4$alkyl-aryl, -alkyl-aryl, —$SO_2$—$N(R^1)$—$C_0$-$C_4$alkyl-aryl, —$N(R^1)$-aryl, —O-alkyl-aryl, -heteroaryl-aryl and —S-aryl, wherein each aryl, heteroaryl and heterocyclyl moiety is optionally substituted with 1 to 3 independently selected substituents, and each of which is optionally fused to one or more aryl, heterocyclic or heteroaryl rings, or one or more saturated or partially unsaturated cycloalkyl or heterocyclyl rings, each of which ring is optionally substituted.

In another embodiment of the present invention, L is selected from the group consisting of aryl, heteroaryl, -aryl-aryl, heterocyclyl, -alkynyl-aryl, —O—$C_0$-$C_4$alkyl-aryl, -alkyl-aryl, —$SO_2$—$N(R^1)$—$C_0$-$C_4$alkyl-aryl, —$N(R^1)$-aryl, —O-alkyl-aryl, -heteroaryl-aryl and —S-aryl, wherein each aryl, heteroaryl and heterocyclyl moiety is optionally substituted with 1 to 3 substituents (for example 1 or 2 substituents), independently selected from the group consisting of alkoxy, nitro, halo, alkyl, heterocyclyl and -heteroaryl-alkyl.

In another embodiment of the present invention, L is selected from the group consisting of phenyl, thienyl, -phenyl-phenyl, -alkynyl-phenyl, pyrrole, benzo[d]thiazole, —O-phenyl, -alkyl-phenyl, pyridine, —$SO_2$—NH-alkyl-phenyl, —NH-phenyl, —O-alkyl-phenyl, thienyl-phenyl, pyrrole and —S-phenyl, wherein each aryl, heteroaryl and heterocyclyl moiety is optionally substituted with 1 to 3 independently selected substituents, and each of which is optionally fused to one or more aryl, heterocyclic or heteroaryl rings, or one or more saturated or partially unsaturated cycloalkyl or heterocyclyl rings, each of which ring is optionally substituted.

In another embodiment of the present invention, L is selected from the group consisting of phenyl, thienyl, -phenyl-phenyl, -alkynyl-phenyl, pyrrole, benzo[d]thiazole, —O- phenyl, -alkyl-phenyl, pyridine, —$SO_2$—NH-alkyl-phenyl, —NH-phenyl, —O-alkyl-phenyl, thienyl-phenyl, pyrrole and —S-phenyl, wherein each aryl, heteroaryl and heterocyclyl moiety is optionally substituted with 1 to 3 substituents (for example 1 or 2 substituents), independently selected from the group consisting of alkoxy, nitro, halo, alkyl, heterocyclyl and -heteroaryl-alkyl.

In another embodiment of the present invention, L is aryl or heteroaryl, each of which is optionally substituted with 1, 2 or 3 independently selected substituents.

In another embodiment of the present invention, L is phenyl, thienyl or pyridyl, each of which is optionally substituted with 1, 2 or 3 independently selected substituents.

In another embodiment of the present invention, Y is selected from the group consisting of H, halo, alkoxy, aryl, alkyl, heterocyclyl, heteroaryl, —N($R^1$)—C(O)-alkyl-aryl, —C(O)—N($R^1$)-aryl-O-aryl, —N($R^1$)—$SO_2$-aryl, -alkyl-aryl, -alkyl-heteroaryl, -aryl-heterocyclyl, -heterocyclyl-alkyl-aryl, heterocyclyl-alkyl-heteroaryl, -heterocyclyl-C(O)-aryl, —CH$(aryl)_2$, -heterocyclyl-C(O)-alkyl, -heterocyclyl-C(O)-heterocyclyl, -heterocyclyl-C(O)—O-alkyl, -heterocyclyl-$SO_2$-alkyl, -heterocyclyl-$SO_2$-aryl, -heterocyclyl-alkyl-heteroaryl, -heterocyclyl-$SO_2$-aryl-N($R^1$)—C(O)-alkyl, -alkyl-O-aryl, -alkyl-O—C(O)—N($R^1$)-alkyl-aryl, -alkyl-N($R^1$)-alkyl-aryl, —C(O)—N($R^1$)-aryl, —N($R^1$)—C(O)—O-alkyl-aryl, —N($R^1$)—$SO_2$-alkyl-aryl, —N($R^1$)—$SO_2$-aryl and —N($R^1$)—$SO_2$-heteroaryl, wherein each aryl, heteroaryl and heterocyclyl moiety is optionally substituted with 1 to 3 independently selected substituents, and each of which is optionally fused to one or more aryl, heterocyclic or heteroaryl rings, or one or more saturated or partially unsaturated cycloalkyl or heterocyclyl rings, each of which ring is optionally substituted.

In another embodiment of the present invention, Y is selected from the group consisting of H, halo, alkoxy, aryl, alkyl, heterocyclyl, heteroaryl, —N($R^1$)—C(O)-alkyl-aryl, —C(O)—N($R^1$)-aryl-O-aryl, —N($R^1$)—$SO_2$-aryl, -alkyl-aryl, -alkyl-heteroaryl, -aryl-heterocyclyl, -heterocyclyl-alkyl-aryl, heterocyclyl-alkyl-heteroaryl, -heterocyclyl-C(O)-aryl, —CH$(aryl)_2$, -heterocyclyl-C(O)-alkyl, -heterocyclyl-C(O)-heterocyclyl, -heterocyclyl-C(O)—O-alkyl, -heterocyclyl-$SO_2$-alkyl, -heterocyclyl-$SO_2$-aryl, -heterocyclyl-alkyl-heteroaryl, heterocyclyl-$SO_2$-aryl-N($R^1$)—C(O)-alkyl, -alkyl-O-aryl, -alkyl-O—C(O)—N($R^1$)-alkyl-aryl, -alkyl-N($R^1$)-alkyl-aryl, —C(O)—N($R^1$)-aryl, —N($R^1$)—C(O)—O-alkyl-aryl, —N($R^1$)—$SO_2$-alkyl-aryl, —N($R^1$)—$SO_2$-aryl and —N($R^1$)—$SO_2$-heteroaryl, wherein each aryl, heteroaryl and heterocyclyl moiety is optionally substituted with 1 to 3 substituents independently selected from the group consisting of alkoxy, alkyl, —N($R^a$)($R^b$), —O-alkyl-heterocyclyl.

In another embodiment of the present invention, Y is selected from the group consisting of H, alkoxy, phenyl, —NH—C(O)-alkyl-phenyl, alkyl, halo, thienyl, —C(O)—NH-phenyl-O-phenyl, dibenzo[b,f][1,4]oxazepine, dibenzo [b,f][1,4]oxazepine-11-(10H)-one, —NH—$SO_2$-phenyl, -alkyl-phenyl, pyridine, -phenyl-morpholine, benzothiophene, benzo[d][1,3]dioxole, piperidine, -piperidine-alkyl-phenyl, -piperidine-C(O)-phenyl, 2,3-dihydrobenzofuran, -piperidine-alkyl-pyridine, —CH$(phenyl)_2$, -piperidine-C(O)-alkyl, -piperidine-C(O)-pyrrolidine, -piperidine-C(O)—O-alkyl, -piperidine-$SO_2$-alkyl, -piperidine-$SO_2$-phenyl, -piperidine-alkyl-indole, -piperidine-$SO_2$-phenyl-NH—C(O)-alkyl, wherein each aryl, heteroaryl, cycloalkyl and heterocyclyl moiety is optionally substituted with 1 to 3 independently selected substituents, and each of which is optionally fused to one or more aryl, heterocyclic or heteroaryl rings, or one or more saturated or partially unsaturated cycloalkyl or heterocyclyl rings, each of which ring is optionally substituted.

In another embodiment of the present invention, Y is selected from the group consisting of H, alkoxy, phenyl, —NH—C(O)-alkyl-phenyl, alkyl, halo, thienyl, —C(O)—NH-phenyl-O-phenyl, dibenzo[b,f][1,4]oxazepine, dibenzo [b,f][1,4]oxazepine-11-(10H)-one, —NH—$SO_2$-phenyl, -alkyl-phenyl, pyridine, -phenyl-morpholine, benzothiophene, benzo[d][1,3]dioxole, piperidine, -piperidine-alkyl-phenyl, -piperidine-C(O)-phenyl, 2,3-dihydrobenzo furan, -piperidine-alkyl-pyridine, —CH$(phenyl)_2$, -piperidine-C(O)-alkyl, -piperidine-C(O)-pyrrolidine, -piperidine-C(O)—O-alkyl, -piperidine-$SO_2$-alkyl, -piperidine-$SO_2$-phenyl, -piperidine-alkyl-indole, -piperidine-$SO_2$-phenyl-NH—C(O)-alkyl, wherein each aryl, heteroaryl, cycloalkyl and heterocyclyl moiety is optionally substituted with 1 to 3 substituents independently selected from the group consisting of alkoxy, alkyl, —N($R^a$)($R^b$), —O-alkyl-heterocyclyl.

In another embodiment of the present invention, Y is selected from the group consisting of H, halo, -aryl-heterocyclyl, -aryl-O—$C_0$-$C_4$alkyl, -aryl-O—$C_0$-$C_4$alkyl-aryl, —$C_1$-$C_4$alkyl, —$OR^e$, —$C_0$-$C_3$ alkyl-aryl, —$C_0$-$C_3$alkyl-heteroaryl, —$C_0$-$C_3$alkyl-heterocyclyl, aromatic polycycle, non-aromatic polycycle, mixed aromatic and non-aromatic polycycle and fused heterocyclyl, wherein each aryl, heteroaryl, heterocyclyl and polycycle is optionally substituted.

In another embodiment of the present invention, Y is selected from the group consisting of H, halo, -aryl-heterocyclyl, -aryl-O—$C_0$-$C_4$alkyl, -aryl-O—$C_0$-$C_4$alkyl-aryl, —$C_1$-$C_4$alkyl, —$C_0$-$C_3$alkyl-aryl, —$C_0$-$C_3$alkyl-heteroaryl and —$C_0$-$C_3$alkyl-heterocyclyl, wherein each aryl, heteroaryl and heterocyclyl is optionally substituted with 1, 2 or 3 moieties independently selected from the group consisting of alkoxy, alkyl, fused cycloalkyl, halo and acetyl.

In another embodiment of the present invention, Y is selected from the group consisting of H, halo, -aryl-heterocyclyl, -aryl-O—$C_0$-$C_4$alkyl, -aryl-O—$C_0$-$C_4$alkyl-aryl, —$C_1$-$C_4$alkyl, —$C_0$-$C_3$alkyl-aryl, —$C_0$-$C_3$alkyl-heteroaryl, —$C_0$-$C_3$alkyl-heterocyclyl, aromatic polycycle, non-aromatic polycycle, mixed aromatic and non-aromatic polycycle and fused heterocyclyl, wherein said aryl is a 6-membered aryl group, for example phenyl, and wherein each aryl, heteroaryl, heterocyclyl and polycycle is optionally substituted.

In another embodiment of the present invention, Y is selected from the group consisting of H, halo, -aryl-heterocyclyl, -aryl-O—$C_0$-$C_4$alkyl, -aryl-O—$C_0$-$C_4$alkyl-aryl, —$C_1$-$C_4$alkyl, —$C_0$-$C_3$alkyl-aryl, —$C_0$-$C_3$alkyl-heteroaryl, —$C_0$-$C_3$alkyl-heterocyclyl, aromatic polycycle, non-aromatic polycycle, mixed aromatic and non-aromatic polycycle and fused heterocyclyl, wherein said aryl is a 6-membered aryl group, for example phenyl, wherein each aryl, heteroaryl, heterocyclyl and polycycle is optionally substituted with 1, 2 or 3 moieties independently selected from the group consisting of alkoxy, alkyl, fused cycloalkyl, halo and acetyl.

In another embodiment of the present invention, Y is selected from the group consisting of H, halo, -aryl-heterocyclyl, -aryl-O—$C_0$-$C_4$alkyl, -aryl-O—$C_0$-$C_4$alkyl-aryl, —$C_1$-$C_4$alkyl, —$OR^e$, —$C_0$-$C_3$alkyl-aryl, —$C_0$-$C_3$alkyl-heteroaryl, —$C_0$-$C_3$alkyl-heterocyclyl, aromatic polycycle, non-aromatic polycycle, mixed aromatic and non-aromatic polycycle and fused heterocyclyl, wherein said heteroaryl group is a 5- or 6-membered heteroaryl group, for example thienyl or pyridinyl, wherein each aryl, heteroaryl, heterocyclyl and polycycle is optionally substituted.

In another embodiment of the present invention, Y is selected from the group consisting of H, halo, -aryl-heterocyclyl, -aryl-O—$C_0$-$C_4$alkyl, -aryl-O—$C_0$-$C_4$alkyl-aryl, —$C_1$-$C_4$alkyl, $OR^e$, —$C_0$-$C_3$ alkyl-aryl, —$C_0$-$C_3$alkyl-heteroaryl, —$C_0$-$C_3$alkyl-heterocyclyl, aromatic polycycle, non-aromatic polycycle, mixed aromatic and non-aromatic polycycle and fused heterocyclyl, wherein said heteroaryl group is a 5- or 6-membered heteroaryl group, for example thiophene or pyridine, wherein each aryl, heteroaryl, heterocyclyl and polycycle is optionally substituted with 1, 2 or 3 moieties independently selected from the group consisting of alkoxy, alkyl, fused cycloalkyl, halo and acetyl.

In another embodiment of the present invention, Y is H, aryl (for example phenyl) or -aryl-heterocyclyl (for example -phenyl-morpholinyl) wherein said aryl and heterocyclyl are optionally substituted.

In another embodiment of the present invention, Y is H, aryl (for example phenyl) or -aryl-heterocyclyl (for example -phenyl-morpholinyl) wherein said aryl and heterocyclyl are optionally substituted with 1, 2 or 3 moieties independently selected from the group consisting of alkoxy, alkyl, fused cycloalkyl, halo and acetyl.

In another embodiment of the present invention, Y is optionally substituted aryl, for example optionally substituted phenyl.

In another embodiment of the present invention, Y is optionally substituted aryl, for example optionally substituted phenyl with 1, 2 or 3 moieties independently selected from the group consisting of alkoxy, alkyl, fused cycloalkyl, halo and acetyl.

In another embodiment of the present invention, Y is selected from the group consisting of —$Z^1$—Z—$Z^2$-D, —$C_0$-$C_2$alkyl-Z—$Z^3$—Z-D, —CH($OR^1$)—Z—$Z^3$—Z-D, —C($R^1$)($R^2$)—Z—$Z^3$—Z-D and —$C(F)_2$—Z—$Z^3$—Z-D, wherein each aryl, heteroaryl, cycloalkyl and heterocyclyl moiety therein is optionally substituted.

In another embodiment of the present invention, Y is selected from the group consisting of —$Z^1$—Z—$Z^2$-D, wherein each aryl, heteroaryl, cycloalkyl and heterocyclyl moiety therein is optionally substituted.

In another embodiment of the present invention, Y is selected from the group consisting of —$C_0$-$C_2$alkyl-Z—$Z^3$—Z-D, wherein each aryl, heteroaryl, cycloalkyl and heterocyclyl moiety therein is optionally substituted.

In another embodiment of the present invention, Y is selected from the group consisting of aromatic polycyle, non-aromatic polycycle, mixed aromatic and non-aromatic polycycle and fused heterocyclyl, each of which is optionally substituted.

In another embodiment of the present invention, each aryl, heterocyclyl, cycloalkyl, and heteroaryl group in Y is optionally substituted with 1, 2 or 3 substituents independently selected from the group consisting of H, halo, OH, —$OCH_3$, —CN, —$S(O)_{0-2}$—$C_1$-$C_4$alkyl, —$CF_3$, —$OCF_3$, alkyl, —$NH_2$, —$N(alkyl)_2$, —NH(alkyl), —N(aryl)(alkyl), —N(-alkyl-aryl)(alkyl), —N(heteroaryl)(alkyl), —N(-alkyl-heteroalkylaryl)(alkyl), —NH(aryl), —NH(-alkyl-aryl), —NH (heteroaryl), —NH(-alkyl-heteroalkylaryl), —N(—$C_2$-$C_4$ alkyl-O-alkyl) (alkyl), —NH(—$C_2$-$C_4$alkyl-O-alkyl), —$NO_2$, —O—$C_1$-$C_4$alkyl, —$C_0$-$C_4$alkyl-aryl, —$C_0$-$C_4$alkyl-heteroaryl, —$C_0$-$C_4$alkyl-heterocyclyl, —$C_0$-$C_4$alkyl-cycloalkyl, —$NHS(O)_2$-alkyl, —$S(O)_2$NH-alkyl, —$NR^aR^b$, —$NR^cR^b$, —$OR^e$, —$OR^s$, $C_2$-$C_4$alkyl-$NR^cR^d$, —$S(O)_{0-2}R^e$, —$(CR^{32}R^{33})_s$—$NR^{30}R^{31}$, and ($X^{30}$—$Y^{31}$—), wherein $R^{30}$ and $R^{31}$ are each independently hydrogen, cyano, oxo, hydroxyl, $C_1$-$C_8$alkyl, $C_1$-$C_8$hetero alkyl, $C_1$-$C_9$alkenyl, carboxamido-, $C_1$-$C_3$ alkyl-carboxamido-, carboxamido-$C_1$-$C_3$alkyl-, amidino-, $C_2$-$C_5$hydroxyalkyl-, $C_1$-$C_3$ alkyl-aryl-, aryl-$C_1$-$C_3$ alkyl-, $C_1$-$C_3$ alkyl-heteroaryl-, heteroaryl-$C_1$-$C_3$alkyl-, $C_1$-$C_3$ alkyl-heterocyclyl-, heterocyclyl-$C_1$-$C_3$alkyl-, $C_1$-$C_3$alkyl-cycloalkyl-, cycloalkyl-$C_1$-$C_3$alkyl-, $C_2$-$C_3$alkoxy-, $C_2$-$C_8$alkoxy-$C_1$-$C_4$alkyl-, $C_1$-$C_8$alkoxy-carbonyl-, aryloxy-carbonyl-, aryl-$C_1$-$C_3$alkoxy-carbonyl-, heteroaryloxy-carbonyl-, heteroaryl-$C_1$-$C_3$alkoxy-carbonyl-, $C_1$-$C_8$acyl, $C_0$-$C_5$alkyl-carbonyl-, aryl-$C_0$-$C_8$alkyl-carbonyl-, heteroaryl-$C_0$-$C_8$alkyl-carbonyl-, cycloalkyl-$C_0$-$C_8$alkyl-carbonyl-, $C_0$-$C_8$alkyl-NH-carbonyl-, aryl-$C_0$-$C_8$alkyl-NH-carbonyl-, heteroaryl-$C_0$-$C_8$alkyl-NH-carbonyl-, cycloalkyl-$C_0$-$C_8$alkyl-NH-carbonyl-, $C_0$-$C_8$alkyl-O-carbonyl-, aryl-$C_0$-$C_8$alkyl-O-carbonyl-, heteroaryl-$C_0$-$C_8$alkyl-O-carbonyl-, cycloalkyl-$C_0$-$C_8$alkyl-O-carbonyl-, $C_1$-$C_8$alkylsulfonyl-, aryl-alkyl-sulfonyl-, aryl-sulfonyl-, heteroaryl-alkyl-sulfonyl-, heteroaryl-sulfonyl-, $C_1$-$C_8$alkyl-NH-sulfonyl-, aryl-alkyl-NH-sulfonyl-, aryl-NH-sulfonyl-, heteroaryl-alkyl-NH-sulfonyl-, heteroaryl-NH-sulfonyl, aroyl-, aryl-, cycloalkyl-, heterocyclyl-, heteroaryl-, aryl-$C_1$-$C_3$alkyl-, cyclo alkyl-$C_1$-$C_3$alkyl-, heterocyclyl-$C_1$-$C_3$alkyl-, heteroaryl-$C_1$-$C_3$alkyl-, or protecting group, each of which is optionally substituted with one or more substituents selected from halo, cyano, oxo, carboxy, formyl, nitro, amino, amidino and guanidino, or $R^{30}$ and $R^{31}$ taken together with the N to which they are attached form a heterocyclyl or heteroaryl, each of which is optionally substituted with from 1 to 3 substituents selected from the group consisting of halo, cyano, oxo, carboxy, formyl, nitro, amino, amidino, guanidino, a protecting group, and ($X^{30}$—$Y^{31}$—), in which $X^{30}$ is selected from the group consisting of $C_1$-$C_8$alkyl-, $C_2$-$C_8$alkenyl-, $C_2$-$C_8$alkynyl-, $C_0$-$C_3$alkyl-$C_2$-$C_8$alkenyl-$C_0$-$C_3$alkyl-, $C_0$-$C_3$alkyl-$C_2$-$C_8$alkynyl-$C_0$-$C_3$alkyl-, $C_0$-$C_3$alkyl-O—$C_0$-$C_3$alkyl-, HO—$C_0$-$C_3$alkyl-, $C_0$-$C_4$alkyl-N($R^{30}$)—$C_0$-$C_3$alkyl-, N($R^{30}$)($R^{31}$)—$C_0$-$C_3$alkyl-, N($R^{30}$)($R^{31}$)—$C_0$-$C_3$alkenyl-, N($R^{30}$)($R^{31}$)—$C_0$-$C_3$alkynyl-, $(N(R^{30})(R^{31}))_2$—C═N—, $C_0$-$C_3$alkyl-S$(O)_{0-2}$—$C_0$-$C_3$alkyl-, $CF_3$—$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$ alkyl-, N($R^{30}$)($R^{31}$)-heterocyclyl-$C_1$-$C_3$ alkyl-, wherein the aryl, cycloalkyl, heteroaryl and heterocycyl are optionally substituted with from 1 to 3 substituents selected from halo, cyano, oxo, carboxy, formyl, nitro, amino, amidino and guanidino; and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C($NR^{30}$)—N($R^{31}$)—, —N($R^{30}$)—C($NR^{31}$)—, —C($NR^{35}$—N($R^{30}$), —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)—N($R^{31}$)—, —$S(O)_{0-2}$—, —$SO_2$N($R^{31}$)—, —N($R^{31}$)—$SO_2$— and —N($R^{30}$)—$SO_2$N($R^{31}$)—; and $R^{32}$ and $R^{33}$ are independently selected from hydrogen, halo and hydroxyl.

In another embodiment of the present invention, Y is selected from the group consisting of aryl, heterocyclyl, cycloalkyl and heteroaryl, each of which is optionally substituted with 1, 2 or 3 substituents (alternatively 1 or 2 substituents, alternatively 1 substituent) independently selected from the group consisting of H, halo, ═O, OH, $C_1$-$C_3$-hydrocarbyl, —$OCH_3$, —CN, —$S(O)_{0-2}$—$C_1$-$C_4$alkyl, —$CF_3$, —$OCF_3$, alkyl, —$NH_2$, —$N(alkyl)_2$, —NH(alkyl), —N(aryl)(alkyl), —N(-alkyl-aryl)(alkyl), —N(heteroaryl)(alkyl), —N(-alkyl-heteroalkylaryl)(alkyl), —NH(aryl), —NH(heteroaryl), —NH(-alkyl-heteroalkylaryl), —N(—$C_2$-$C_4$alkyl-O-alkyl)(alkyl), —NH(—$C_2$-$C_4$alkyl-O-alkyl), —$NO_2$, —O—$C_1$-$C_4$alkyl, —$C_0$-$C_4$alkyl-aryl, —$C_0$-$C_4$alkyl-heteroaryl, —$C_0$-$C_4$alkyl-heterocyclyl, —$C_0$-$C_4$alkyl-cycloalkyl, —NHS$(O)_2$-alkyl, —S$(O)_2$NH-alkyl, —$NR^aR^b$, —$NR^eR^d$, —$OR^e$, —$C_2$-$C_4$alkyl-$NR^aR^b$, $C_2$-$C_4$alkyl-NR-$^cR^d$, —S$(O)_{0-1}R^e$, —($CR^{32}R^{33}$), —$NR^{30}R^{31}$, and ($X^{30}$—$Y^{31}$—), wherein $R^{30}$ and $R^{31}$ are each independently hydrogen, cyano, oxo, hydroxyl, $C_1$-$C_8$alkyl, $C_1$-$C_8$hetero alkyl, $C_1$-$C_8$alkenyl, carboxamido-, $C_1$-$C_3$ alkyl-carboxamido-, carboxamido-$C_1$-$C_3$ alkyl-, amidino-, $C_2$-$C_8$hydroxyalkyl-, $C_1$-$C_3$ alkyl-aryl-, aryl-$C_1$-$C_3$alkyl-, $C_1$-$C_3$ alkyl-hetero aryl-, heteroaryl-$C_1$-$C_3$alkyl-, $C_1$-$C_3$ alkyl-heterocyclyl-, heterocyclyl-$C_1$-$C_3$ alkyl-, $C_1$-$C_3$alkyl-cycloalkyl-, cycloalkyl-$C_1$-$C_3$alkyl-, $C_2$-$C_5$alkoxy-, $C_2$-$C_8$alkoxy-$C_1$-$C_4$alkyl-, $C_1$-$C_8$alkoxy-carbonyl-, aryloxy-carbonyl-, aryl-$C_1$-$C_3$ alkoxy-carbonyl-, heteroaryloxy-carbonyl-, heteroaryl-$C_1$-$C_3$alkoxy-carbonyl-, $C_1$-$C_8$acyl, $C_0$-$C_8$alkyl-carbonyl-, aryl-$C_0$-$C_8$alkyl-carbonyl-, heteroaryl-$C_0$-$C_8$alkyl-carbonyl-, cycloalkyl-$C_0$-$C_8$alkyl-carbonyl-, $C_0$-$C_8$alkyl-NH-carbonyl-, aryl-$C_0$-$C_8$alkyl-NH-carbonyl-, heteroaryl-$C_0$-$C_8$alkyl-NH-carbonyl-, cycloalkyl-$C_0$-$C_8$alkyl-NH-carbonyl-, $C_0$-$C_8$alkyl-O-carbonyl-, aryl-$C_0$-$C_8$alkyl-O-carbonyl-, heteroaryl-$C_0$-$C_8$alkyl-O-carbonyl-, cycloalkyl-$C_0$-$C_8$alkyl-O-carbonyl-, $C_1$-$C_8$alkylsulfonyl-, aryl-alkyl-sulfonyl-, aryl-sulfonyl-, heteroaryl-alkyl-sulfonyl-, heteroaryl-sulfonyl-, $C_1$-$C_8$alkyl-NH-sulfonyl-, aryl-alkyl-NH-sulfonyl-, aryl-NH-sulfonyl-, heteroaryl-alkyl-NH-sulfonyl-, heteroaryl-NH-sulfonyl, aroyl-, aryl-, cycloalkyl-, heterocyclyl-, heteroaryl-, aryl-$C_1$-$C_3$ alkyl-, cyclo alkyl-$C_1$-$C_3$ alkyl-, heterocyclyl-$C_1$-$C_3$alkyl-, heteroaryl-$C_1$-$C_3$alkyl-, or protecting group, each of which is optionally substituted with one or more substituents selected from halo, cyano, oxo, carboxy, formyl, nitro, amino, amidino and guanidino, or $R^{30}$ and $R^{31}$ taken together with the N to which they are attached form a heterocyclyl or heteroaryl, each of which is optionally substituted with from 1 to 3 substituents selected from the group consisting of halo, cyano, oxo, carboxy, formyl, nitro, amino, amidino, guanidino, a protecting group, and ($X^{30}$—$Y^{31}$—), in which $X^{30}$ is selected from the group consisting of $C_1$-$C_8$alkyl-, $C_2$-$C_8$alkenyl-, $C_2$-$C_5$alkynyl-, $C_0$-$C_3$alkyl-$C_2$-$C_8$alkenyl-$C_0$-$C_3$alkyl-, $C_0$-$C_3$alkyl-$C_2$-$C_8$alkynyl-$C_0$-$C_3$alkyl-, $C_0$-$C_3$alkyl-O—$C_0$-$C_3$alkyl-, HO—$C_0$-$C_3$alkyl-, $C_0$-$C_4$alkyl-N($R^{30}$)—$C_0$-$C_3$alkyl-, N($R^{30}$)($R^{31}$)—$C_0$-$C_3$alkyl-, N($R^{30}$)($R^{31}$)—$C_0$-$C_3$alkenyl-, N($R^{30}$)($R^{31}$)—$C_0$-$C_3$alkynyl-, $(N(R^{30})(R^{31}))_2$—C═N—, $C_0$-$C_3$alkyl-S$(O)_{0-2}$—$C_0$-$C_3$alkyl-, $CF_3$—$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocycyl are optionally substituted with from 1 to 3 substituents selected from halo, cyano, oxo, carboxy, formyl, nitro, amino, amidino and guanidino; and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C($NR^{30}$)—N($R^{31}$)—, —N($R^{30}$)—C($NR^{31}$)—, —C($NR^{31}$)—N($R^{30}$), —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)—N($R^{31}$)—, —S$(O)_{0-2}$—, —$SO_2$N($R^{31}$)—, —N($R^{31}$)—$SO_2$— and —N($R^{30}$)—$SO_2$N($R^{31}$)—; and $R^{32}$ and $R^{33}$ are independently selected from hydrogen, halo and hydroxyl.

In another embodiment of the present invention $R^e$ is alkyl.

In another embodiment of the present invention, each aryl, heteroaryl, heterocyclyl, and cycloalkyl moiety of L is optionally substituted with the group

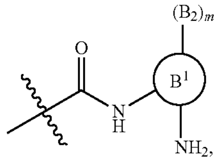

wherein

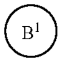

is an aryl or heteroaryl;

m is an integer from 0 to 3; and $B^2$ is selected from the group consisting of H, alkyl, aryl, hereoaryl, halo, —CN, amide, carboxyl, alkoxy, —$SO_2$NHalkyl, —$SO_2NH_2$, —$SO_2N(alkyl)_2$, —$_2$NHalkyl-SO, —$NH_2SO_2$, —$N(alkyl)_2SO_2$ and haloalkyl, wherein each aryl, alkyl and heteroaryl moiety is optionally substituted.

In another embodiment of the present invention, L is selected from the group consisting of aryl, heteroaryl, heterocyclyl and cycloalkyl (for example aryl, for example, phenyl), each of which is optionally substituted with the group

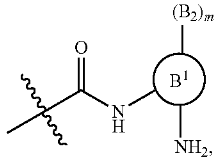

wherein $B^1$ is an aryl or heteroaryl;

m is an integer from 0 to 3; and $B^2$ is selected from the group consisting of H, alkyl, aryl, hereoaryl, halo, —CN, amide, carboxyl, alkoxy, —$SO_2$NHalkyl, —$SO_2NH_2$, —$SO_2N(alkyl)_2$, —$_2$NHalkyl-SO, —$NH_2SO_2$, —$N(alkyl)_2SO_2$ and haloalkyl, wherein each aryl, alkyl and heteroaryl moiety is optionally substituted.

In another embodiment of the present invention,

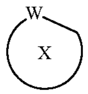

is

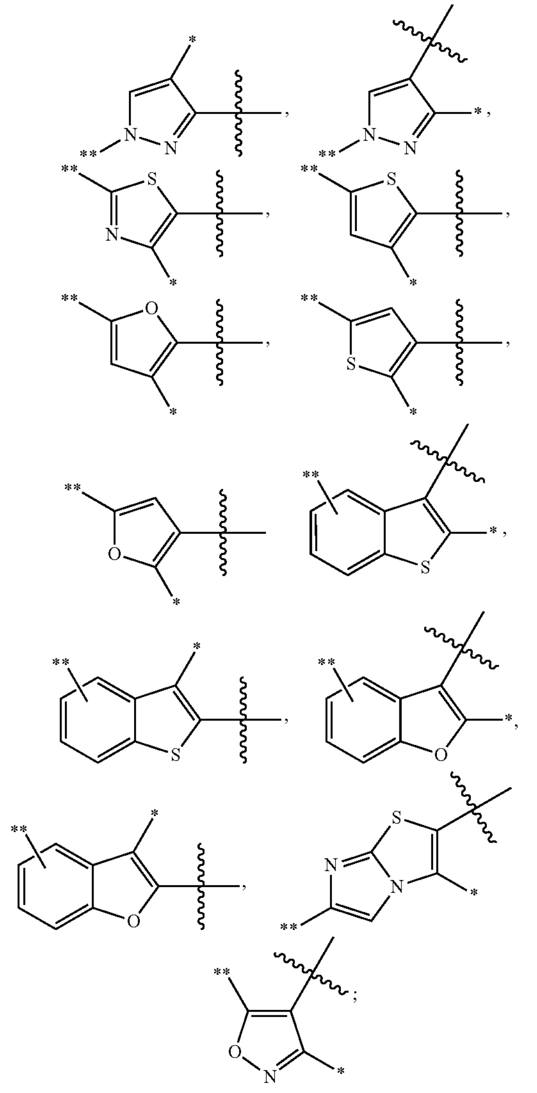

or

M is —C(O)NHOH;

n is 1;

R is H;

L is aryl or —N($R^1$)$SO_2$-aryl, wherein said aryl moiety is optionally substituted;

Y is aryl, alkyl, heteroaryl, or -aryl-$C_0$-$C_3$alkyl-heterocyclyl, wherein said aryl and heteroaryl moieties are optionally substituted; and $R^1$ is H;

wherein ⌇ represents the point of attachment to group M, * represents the point of attachment to group L and ** represents the point of attachment to group Y.

In another embodiment of the present invention,

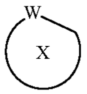

is

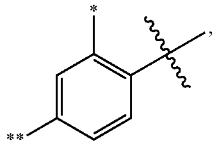, 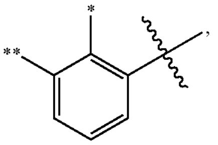,

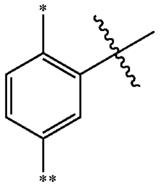 or 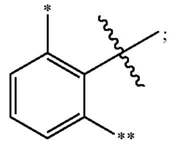;

M is —C(O)NHOH;

R is H or —$OR^1$;

L is aryl, -aryl-aryl, heteroaryl, —$C_2$-$C_4$alkynyl-aryl, —$C_2$-$C_4$alkenyl-aryl, —O—$C_0$-$C_4$alkyl-aryl, —$C_0$-$C_4$alkyl-aryl, —$NR_1SO_2$—$C_0$-$C_4$alkyl-aryl, -aryl-heteroaryl or -heteroaryl-aryl, wherein each said aryl moiety is optionally substituted, and optionally fused to one or more aryl or heteroaryl rings, or one or more saturated or partially unsaturated cycloalkyl or heterocyclyl rings, each of which ring is optionally substituted, wherein an aryl moiety in

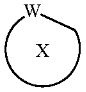

is optionally connected to an aryl or heteroaryl in L by a bond;

Y is H, aryl, heteroaryl or alkyl, wherein said aryl and heteroaryl moieties are optionally substituted; and $R^1$ is H or alkyl, wherein ⌇ represents the point of attachment to group M, * represents the point of attachment to group L and ** represents the point of attachment to group Y.

In another embodiment of the present invention,

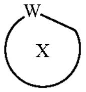

is

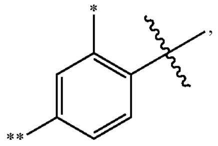, 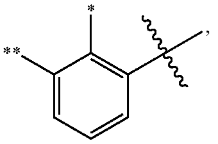,

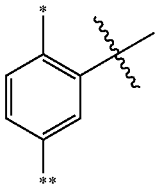 or 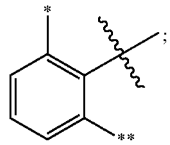;

M is —C(O)NHOH or —C(O)$OR^1$;

R is H or —$OR^1$;

L is aryl, optionally substituted with

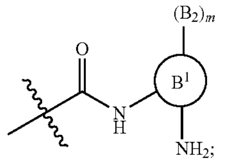

wherein $B^1$ is aryl;

m is 1;

$B^2$ is heretoaryl;

Y is H; and $R^1$ is H or alkyl, wherein ⌇ represents the point of attachment to group M, * represents the point of attachment to group L and ** represents the point of attachment to group Y.

In another embodiment of the present invention,

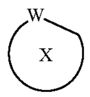

is phenyl, thienyl, thiazolyl, pyrazolyl or oxazolyl;

M is —C(O)NHOH;

L is phenyl, thienyl or pyridine, each of which is optionally substituted; and

Y is —$Z^1$—Z—$Z^2$-D;

wherein $Z^1$ is selected from the group consisting of chemical bond, alkyl, aryl, heterocyclyl, bridged heterocyclyl, spiro heterocyclyl, cycloalkyl, heteroaryl, —C(F)$R^1$—, —C($OR^2$)$R^1$—, —C(aryl)$R^1$—, —C(heteroaryl)$R^1$—, —C(heterocyclyl)$R^1$—, —C(cycloalkyl)$R^1$—, —C(alkyl)$R^1$—, —C(alkenyl)$R^1$— and —C(alkynyl)$R^1$—, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted;

Z is selected from the group consisting of chemical bond —O—, —$NR^1$—, —$NR^aR^b$, —$NR^c$—, —N($C_2$-$C_4$alkyl-$OR^1$)—, —C(O)—, —C($NOR^1$)—, —CHF—, —CH($CONR^1R^2$)—$CONR^1R^2$—, —CH($NR^1R^2$)—$CONR^1R^2$—, —CH($CONR^eR^f$)—$CONR^1R^2$—, —CH($NR^eR^f$)—$CONR^1R^2$—, —CH(heteroaryl)-$CONR^1R^2$—, —CH(heteroaryl-aryl)-$CONR^1R^2$—, —CH(heteroaryl-heteroaryl)-$CONR^1R^2$—, —C(O)—C(O)$NR^1$—, —$S(O)_{0-2}$—, —$NR^1S(O)_2$—, —$S(O)_2NR^1$—, —$NR^1S(O)_2NR^2$—, —$NR^1$C(O)—, —C(O)$NR^1$—, —OC(O)—, —C(O)O—, —$NR^1$C($NR^2$)—, —C($NR^2$)$NR^1$—, —$NR^1$C(O)$NR^2$—, —$NR^1$C(O)O—, —OC(O)$NR^1$— $NR^1$C(S)—, —C(S)$NR^1$—, —$NR^1$C(S)$NR^2$—, —$NR^1$C(S)O—, —OC(S)$NR^1$—, —O—$C_2$-$C_4$alkyl-$NR^1$— $NR^1$—$C_2$-$C_4$alkyl-O—, —$NR^c$—$C_2$-$C_4$alkyl-O—, —O—$C_1$-$C_4$alkyl —$S(O)_2NR^1$—, —$S(O)_2NR^1$—$C_2$-$C_4$alkyl-O—, —O—$C_2$-$C_4$alkyl-$NR^1S(O)_2$—, —$NR^1S(O)_2$—$C_1$-$C_4$alkyl-O—, —C(O)—$C_1$-$C_4$alkyl-$NR^1$— $NR^1$—$C_1$-$C_4$alkyl-C(O)—, —O—$C_1$-$C_4$alkyl-C(O)$NR^1$—C(O)$NR^1$—$C_2$-$C_4$alkyl-O—, —O—$C_2$-$C_4$alkyl-$NR_1$C(O)—, —$NR^1$C(O)—$C_1$-$C_4$alkyl-O—, —O—$C_1$-$C_4$alkyl-C(O)—, —C(O)—$C_1$-$C_4$alkyl-O—, —$NR^1$—$C_1$-$C_4$alkyl-C(O), —C(O)—$C_1$-$C_4$alkyl-$NR^1$—, —O—$C_1$-$C_4$alkyl-C(S)—, —C(S)—$C_1$-$C_4$alkyl-O—, —$NR^1$—$C_1$-$C_4$alkyl-C(S), —C(S)—$C_1$-$C_4$alkyl-$NR^1$—, —$NR^1$—$C_1$-$C_4$alkyl-C(S)—, —O—$C_1$-$C_4$alkyl-C(S)$NR^1$—, —C(S)$NR_1$—$C_2$-$C_4$alkyl-O—, —O—$C_2$-$C_4$alkyl-$NR^1$C(S)—, —$NR^1$C(S)—$C_1$-$C_4$alkyl-O—, —$NR^1$—$C_1$-$C_4$alkyl-$S(O)_2$—, —O—$C_1$-$C_4$alkyl-$S(O)_2NR^1$—, —$S(O)_2NR^1$—$C_2$-$C_4$alkyl-O—, —O—$C_2$-$C_4$alkyl-$NR^1S(O)_2$—, —$NR^1S(O)_2$—$C_1$-$C_4$alkyl-O—, —O—$C_2$-$C_4$alkyl-OC(O)$NR^1$— and —O—$C_2$-$C_4$alkyl-OC(S)$NR^1$—;

$Z^2$ is selected from the group consisting of chemical bond, alkyl, alkenyl, —C(F)$R^1$—, —C($OR^2$)$R^1$—, —C(aryl)$R^1$—, —C(heteroaryl)$R^1$—, —C(heterocyclyl)$R^1$—, —C(cycloalkyl)$R^1$—, —C(alkyl)$R^1$—, —C(alkenyl)$R^1$—, —C(alkynyl)$R^1$—, wherein each alkyl, aryl, alkenyl or alkynyl moiety is optionally substituted; and D is selected from the group consisting of H, aryl, heteroaryl, alkyl, cycloalkyl, heterocyclyl, bridged heterocyclyl, spiro heterocyclyl, aryl-heterocyclyl, -aryl-$C_0$-$C_3$alkyl-O—$C_0$-$C_3$alkyl-aryl, -aryl-$C_0$-$C_3$alkyl-O—$C_0$-$C_3$alkyl-heteroaryl, -heteroaryl-$C_0$-$C_3$alkyl-O-$C_0$-$C_3$alkyl-aryl, -heteroaryl-$C_0$-$C_3$alkyl-O—$C_0$-$C_3$alkyl-heteroaryl, -aryl-$C_0$-$C_3$alkyl-$NR^1$—$C_0$-$C_3$alkyl-aryl, -aryl-$C_0$-$C_3$alkyl-$NR^1$—$C_0$-$C_3$alkyl-heteroaryl, -heteroaryl-$C_0$-$C_3$alkyl-$NR^1$—$C_0$-$C_3$alkyl-aryl, -heteroaryl-$C_0$-$C_3$alkyl-$NR^1$—$C_0$-$C_3$alkyl-heteroaryl, each of which is optionally substituted and each of which is optionally fused to one or more aryl or heteroaryl rings, or one or more saturated or partially unsaturated cycloalkyl or heterocyclyl rings, each of each ring is optionally substituted.

In another embodiment of the present invention,

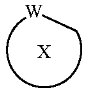

is phenyl, thienyl, benzofuranyl, benzothienyl, thiazolyl, pyrazolyl or oxazolyl;

M is —C(O)NHOH;

L is phenyl, thienyl or pyridine each of which is optionally substituted; and

Y is —$Z^1$—Z—$Z^2$-D;

wherein, $Z^1$ is selected from the group consisting of chemical bond,

Z is selected from the group consisting of —O—, —$NR_1$—, —$NR^aR^b$, —C(O)—, —C($NOR^1$)—, —CHF—, —CH($CONR^1R^2$)—$CONR^1R^2$—, —CH($NR^1R^2$)—$CONR^1R^2$—, —CH($CONR^eR^f$)—$CONR^1R^2$—, —CH($NR^eR^f$)—$CONR^1R^2$—, —CH(heteroaryl)-$CONR^1R^2$—, —CH(heteroaryl-aryl)-$CONR^1R^2$—, —CH(heteroaryl-heteroaryl)-$CONR^1R^2$—, —C(O)—C(O)$NR^1$—, —$S(O)_{0-2}$—, —$NR^1S(O)_2$—, —$S(O)_2NR^1$—, —$NR^1S(O)_2NR^2$—, —$NR^1$C(O)—, —C(O)$NR^1$—, —OC(O)—, —C(O)O—, —$NR^1$C($NR^2$)—, —C($NR^2$)$NR^1$—, —$NR^1$C(O)$NR^2$—, —$NR^1$C(O)O—, —OC(O)$NR^1$—, —$NR^1$C(S)—, —C(S)$NR^1$—, —$NR^1$C(S)$NR^2$—, —$NR^1$C(S)O—, —OC(S)$NR^1$—, —O—$C_2$-$C_4$alkyl-$NR^1$—, —$NR^1$—$C_2$-$C_4$alkyl-O—, —$NR^c$—$C_2$-$C_4$alkyl-O—, —O—$C_1$-$C_4$alkyl —$S(O)_2NR^1$—, —$S(O)_2NR^1$—$C_2$-$C_4$alkyl-O—, —O—$C_2$-$C_4$alkyl-$NR^1S(O)_2$—, —$NR^1S(O)_2$—$C_1$-$C_4$alkyl-O—, —C(O)—$C_1$-$C_4$alkyl-$NR^1$—, —$NR^1$—$C_1$-$C_4$alkyl-C(O)—, —O—$C_1$-$C_4$alkyl-C(O)$NR^1$—C(O)$NR^1$—$C_2$-$C_4$alkyl-O—, —O—$C_2$-$C_4$alkyl-$NR^1$C(O)—, —$NR^1$C(O)—$C_1$-$C_4$alkyl-O—, —O—$C_1$-$C_4$alkyl-C(O)—, —C(O)—$C_1$-$C_4$alkyl-O—, —$NR^1$—$C_1$-$C_4$alkyl-C(O), —C(O)—$C_1$-$C_4$alkyl-$NR^1$—, —O—$C_1$-$C_4$alkyl-C(S)—, —C(S)—$C_1$-$C_4$alkyl-O—, —$NR^1$—$C_1$-$C_4$alkyl-C(S), —C(S)—$C_1$-$C_4$alkyl-$NR^1$—, —$NR^1$—$C_1$-$C_4$alkyl-C(S)—, —O—$C_1$-$C_4$alkyl-C(S)$NR^1$—, —C(S)$NR^1$—$C_2$-$C_4$alkyl-O—, —O—$C_2$-$C_4$alkyl-$NR^1$C(S)—, —$NR^1$C(S)—$C_1$-$C_4$alkyl-O—, —$NR^1$—$C_1$-$C_4$alkyl-$S(O)_2$—, —O—$C_1$-$C_4$alkyl-$S(O)_2NR^1$—$S(O)_2NR^1$—$C_2$-$C_4$alkyl-O—, —O—$C_2$-$C_4$alkyl-$NR^1S(O)_2$—, —$NR^1S(O)_2$—$C_1$-$C_4$alkyl-O—, —O—$C_2$-$C_4$alkyl-OC(O)$NR^1$—, —O—$C_2$-$C_4$alkyl-OC(S)$NR^1$—;

$Z^2$ is selected from the group consisting of chemical bond, alkyl, alkenyl, —C(F)$R^1$—, —C($OR^2$)$R^1$—C(aryl)$R^1$—, —C(heteroaryl)$R^1$—, —C(heterocyclyl)$R^1$—, —C(cycloalkyl)$R^1$—, —C(alkyl)$R^1$—, —C(alkenyl)$R^1$—, —C(alkynyl)$R^1$—, wherein each alkyl, aryl, alkenyl or alkynyl moiety is optionally substituted;

D is selected from the group consisting of H, aryl, heteroaryl, alkyl, cycloalkyl and heterocyclyl, bridged heterocyclyl, spiro heterocyclyl, aryl-heterocyclyl, -aryl-$C_0$-$C_3$alkyl-O—$C_0$-$C_3$alkyl-aryl, -aryl-$C_0$-$C_3$alkyl-O—$C_0$-$C_3$alkyl-heteroaryl, -heteroaryl-$C_0$-$C_3$alkyl-O—$C_0$-$C_3$alkyl-aryl, -heteroaryl-$C_0$-$C_3$alkyl-O—$C_0$-$C_3$alkyl-heteroaryl, -aryl-$C_0$-$C_3$alkyl-$NR^1$—$C_0$-$C_3$alkyl-aryl, -aryl-$C_0$-$C_3$alkyl-$NR^1$—$C_0$-$C_3$alkyl-heteroaryl, -heteroaryl-$C_0$-$C_3$alkyl-$NR^1$—$C_0$-$C_3$alkyl-aryl, -heteroaryl-$C_0$-$C_3$alkyl-$NR^1$—$C_0$-$C_3$alkyl-heteroaryl, each of which is optionally substituted and each of which is optionally fused to one or more aryl or heteroaryl rings, or one or more saturated or partially unsaturated cycloalkyl or heterocyclyl rings, each of which ring is optionally substituted.

In another embodiment of the present invention,

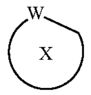

is phenyl, thienyl, benzothienyl, benzofuranyl, thiazolyl, pyrazolyl or oxazolyl;

M is —C(O)NHOH;

L is phenyl, thienyl, benzothienyl or pyridine, each of which is optionally substituted;

Y is —Z—$Z^3$—Z-D;

each Z is independently selected from the group consisting of chemical bond, —O—, —$NR^1$—, —$NR^aR^b$, —C(O)—, —C($NOR^1$)—, —CHF—, —CH($CONR^1R^2$)—$CONR^1R^2$—, —CH($NR^1R^2$)—$CONR^1R^2$—, —CH($CONR^eR^f$)—$CONR^1R^2$—, —CH($NR^eR^f$)—$CONR^1R^2$—, —CH(heteroaryl)-$CONR^1R^2$—, —CH(heteroaryl-aryl)-$CONR^1R^2$—, —CH(heteroaryl-heteroaryl)-$CONR^1R^2$—, —C(O)—C(O)$NR^1$—, —$S(O)_{0-2}$—, —$NR^1S(O)_2$—, —$S(O)_2NR^1$—, —$NR^1S(O)_2NR^2$—, —$NR^1$C(O)—, —C(O)$NR^1$—, —OC(O)—, —C(O)O—, —$NR^1$C($NR^2$)—, —C($NR^2$)$NR^1$—, —$NR^1$C(O)$NR^2$—, —$NR^1$C(O)O—, —OC(O)$NR^1$—, —$NR^1$C(S)—, —C(S)$NR^1$—, —$NR^1$C(S)$NR^2$—, —$NR^1$C(S)O—, —OC(S)$NR^1$—, —O—$C_2$-$C_4$alkyl-$NR^1$—, —$NR^1$—$C_2$-$C_4$alkyl-O—, —O—$C_1$-$C_4$alkyl —$S(O)_2NR^1$—, —$S(O)_2NR^1$—$C_2$-$C_4$alkyl-O—, —O—$C_2$-$C_4$alkyl-$NR^1S(O)_2$—, —$NR^1S(O)_2$—$C_1$-$C_4$alkyl-O—, —C(O)—$C_1$-$C_4$alkyl-$NR^1$—, —$NR^1$—$C_1$-$C_4$alkyl-C(O)—, —O—$C_1$-$C_4$alkyl-C(O)$NR^1$—, —C(O)$NR^1$—$C_2$-$C_4$alkyl-O—, —O—$C_2$-$C_4$alkyl-$NR^1$C(O)—, —$NR^1$C(O)—$C_1$-$C_4$alkyl-O—, —O—$C_1$-$C_4$alkyl-C(O)—, —C(O)—$C_1$-$C_4$alkyl-O—, —$NR^1$—$C_1$-$C_4$alkyl-C(O), —C(O)—$C_1$-$C_4$alkyl-$NR^1$—, —O—$C_1$-$C_4$alkyl-C(S)—, —C(S)—$C_1$-$C_4$alkyl-O—, —$NR^1$—$C_1$-$C_4$alkyl-C(S), —C(S)—$C_1$-$C_4$alkyl-$NR^1$—$NR^1$—$C_1$-$C_4$alkyl-C(S)—, —O—$C_1$-$C_4$alkyl-C(S)$NR^1$—, —C(S)$NR^1$—$C_2$-$C_4$alkyl-O—, —O—$C_2$-$C_4$alkyl-$NR^1$C(S)—, —$NR^1$C(S)—$C_1$-$C_4$alkyl-O—, —$NR^1$—$C_1$-$C_4$alkyl-$S(O)_2$—, —O—$C_1$-$C_4$alkyl-$S(O)_2NR^1$—, —$S(O)_2NR^1$—$C_2$-$C_4$alkyl-O—, —O—$C_2$-$C_4$alkyl-$NR^1S(O)_z$—, —$NR^1S(O)_2$—$C_1$-$C_4$alkyl-O—, —O—$C_2$-$C_4$alkyl-OC(O)$NR^1$—, —O—$C_2$-$C_4$alkyl-OC(S)$NR^1$—;

$Z^3$ is selected from the group consisting of a chemical bond, $C_2$-$C_5$alkyl, aryl, heterocyclyl, bridged heterocyclyl, spiro heterocyclyl, cycloalkyl and heteroaryl, wherein each aryl, heteroaryl, cycloalkyl and heterocyclyl moiety is optionally substituted and each of which is optionally fused to one or more aryl or heteroaryl rings, or one or more saturated or partially unsaturated cycloalkyl or heterocyclyl rings, each of which ring is optionally substituted; and D is selected from the group consisting of H, aryl, heteroaryl, alkyl, cycloalkyl and heterocyclyl, bridged heterocyclyl, spiro heterocyclyl, aryl-heterocyclyl, -aryl-$C_0$-$C_3$alkyl-O—$C_0$-$C_3$alkyl-aryl, -aryl-$C_0$-$C_3$alkyl-O—$C_0$-$C_3$alkyl-heteroaryl, -heteroaryl-$C_0$-$C_3$alkyl-O—$C_0$-$C_3$alkyl-aryl, -heteroaryl-$C_0$-$C_3$alkyl-O—$C_0$-$C_3$alkyl-heteroaryl, -aryl-$C_0$-$C_3$alkyl-$NR^1$—$C_0$-$C_3$alkyl-aryl, -aryl-$C_0$-$C_3$alkyl-$NR^1$—$C_0$-$C_3$alkyl-heteroaryl, -heteroaryl-$C_0$-$C_3$alkyl-$NR^1$—$C_0$-$C_3$alkyl-aryl, -heteroaryl-$C_0$-$C_3$alkyl-$NR^1$—$C_0$-$C_3$alkyl-heteroaryl, aromatic polycycle, non-aromatic polycycle, polyheteroaryl group, non-aromatic polyheterocyclic and mixed aryl and non-aryl polyheterocycle, each of which is optionally substituted and each of which is optionally fused to one or more aryl or heteroaryl rings, or one or more saturated or partially unsaturated cycloalkyl or heterocyclyl rings, each of which ring is optionally substituted.

In another embodiment of the present invention,

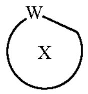

is aryl or heteroaryl;

W is —C=;

M is —C(O)N($R^1$)$OR^2$ or —N(OH)C(O)H;

$R^1$ and $R^2$ are as described for Formula (I);

n is 0;

L is selected from the group consisting of aryl, —N($R^1$)C(O)-aryl, —O-alkyl-aryl, —$CF_3$, heteroaryl, —N($R^1$)$SO_2$-aryl, -alkynyl-aryl, -alkyl-aryl, —$SO_2$—N($R^1$)-alkyl-aryl, —N($R^1$)— alkyl, -aryl-aryl, —O-aryl, —N($R^1$)-aryl, —O-alkyl-aryl, -heteroaryl-aryl, aryl-heteroaryl and fused heterocycle, wherein said aryl, heteroaryl and fused heterocycle are optionally substituted;

Y is selected from the group consisting of H, —$OR^e$, aryl, alkyl, halo, heteroaryl and -heterocycle-C(O)-alkyl, wherein said aryl and heteroaryl are optionally substituted; and $R^e$ is alkyl.

In another embodiment of the present invention,

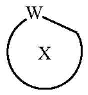

is aryl or heteroaryl;

W is —C=;

M is —C(O)N($R^1$)O$R^2$ or —N(OH)C(O)H;

$R^1$ and $R^2$ are as described for Formula (I);

n is 0;

L is selected from the group consisting of aryl, —N($R^1$)C(O)-aryl, —O-alkyl-aryl, —$CF_3$, heteroaryl, —N($R^1$)$SO^2$-aryl, -alkynyl-aryl, -alkyl-aryl, —$SO^2$—N($R^1$)-alkyl-aryl, —N($R^1$)-alkyl, -aryl-aryl, —O-aryl, —N($R^1$)-aryl, —O-alkyl-aryl, -heteroaryl-aryl, aryl-heteroaryl and fused heterocycle, wherein said aryl, heteroaryl and fused heterocycle are optionally substituted, for example with 1 or 2 substituents independently selected from the group consisting of halo, phenyl, alkyl, alkoxy, fused heterocycle, $NO_2$, pyrrolyl, thienyl and fused phenyl, wherein said phenyl, fused heterocycle, pyrrolyl, thienyl and fused phenyl are themselves further optionally substituted with alkyl;

Y is selected from the group consisting of H, —O$R^e$, aryl, alkyl, halo, heteroaryl and -heterocycle-C(O)-alkyl, wherein said aryl and heteroaryl are optionally substituted with a substituent selected from the group consisting of alkyl, alkoxy and fused heterocycle; and $R^e$ is alkyl.

In another embodiment of the present invention,

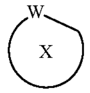

is selected from the group consisting of phenyl, pyrazolyl, thiazolyl, isoxazolyl, thienyl, benzofuranyl, benzothienyl and pyrimidinyl, alternatively phenyl, pyrazolyl, thiazolyl, thienyl and benzothienyl;

W is —C═;

M is —C(O)N($R^1$)O$R^2$ or —N(OH)C(O)H, for example —C(O)N($R^1$)O$R^2$;

$R^1$ and $R^2$ are as described for Formula (I), alternatively are H or alkyl;

n is 0;

L is selected from the group consisting of phenyl, —N($R^1$)C(O)-aryl, —O-alkyl-aryl, —$CF_3$, heteroaryl, —N($R^1$)—$SO_2$-aryl, -alkynyl-aryl, -alkyl-aryl, —$SO_2$—N($R^1$)-alkyl-aryl, —N($R^1$)— alkyl, -aryl-aryl, —O-aryl, —N($R^1$)-aryl, -heteroaryl-aryl, —S-aryl and fused heterocycle, wherein said aryl, heteroaryl and fused heterocycle are optionally substituted;

Y is selected from the group consisting of H, -01e, aryl, alkyl, halo, heteroaryl, —N($R^1$)—C(O)-alkyl-aryl, —C(O)—N($R^1$)-aryl-O-aryl, dibenzo[b,f][1,4]oxazepine, dibenzo[b,f][1,4]oxazepine-11-(10H)-one, —N($R^1$)—$SO_2$-aryl, -alkyl-aryl, -alkyl-O-aryl, -aryl-heterocycle, benzo[d][1,3]dioxole, heterocycle, -heterocyclyl-alkyl-aryl, -heterocyclyl-C(O)-aryl, 2,3-dihydrobenzofuan, -heterocyclyl-alkyl-heteroaryl, —CH-$(aryl)_2$, -heterocyclyl-C(O)-heteroaryl, -heterocyclyl-C(O)—O-alkyl, -heterocyclyl-$SO_2$-alkyl, -heterocyclyl-$SO_2$-aryl, -heterocyclyl-$SO_2$-aryl-N($R^1$)—C(O)-alkyl, -alkyl-O—C(O)—N($R^1$)-alkyl-aryl, -alkyl-N($R^1$)-alkyl-aryl, —C(O)—N($R^1$)-aryl, —N($R^1$)—C(O)-alkyl-aryl, —N($R^1$)—$SO_2$-aryl, —N($R^1$)—$SO_2$-alkyl-aryl, —N($R^1$)—$SO_2$-heteroaryl and -heterocyclyl-C(O)-alkyl, wherein said aryl and heteroaryl are optionally substituted; and $R^e$ is alkyl.

In another embodiment of the present invention,

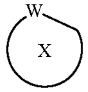

is selected from the group consisting of phenyl, pyrazolyl, thiazolyl, isoxazolyl, thienyl, benzofuranyl, benzothienyl and pyrimidinyl, alternatively phenyl, pyrazolyl, thiazolyl, thienyl and benzothienyl;

W is —C═;

M is —C(O)N($R^1$)O$R^2$ or —N(OH)C(O)H, for example —C(O)N($R^1$)O$R^2$;

$R^1$ and $R^2$ are as described for Formula (I), alternatively are H or alkyl;

n is 0;

L is selected from the group consisting of phenyl, —N($R^1$)C(O)-aryl, —O-alkyl-aryl, —$CF_3$, heteroaryl, —N($R^1$)—$SO_2$-aryl, -alkynyl-aryl, -alkyl-aryl, —$SO_2$—N($R^1$)-alkyl-aryl, —N($R^1$)— alkyl, -aryl-aryl, —O-aryl, —N($R^1$)-aryl, -heteroaryl-aryl, —S-aryl and fused heterocycle, wherein said aryl, heteroaryl and fused heterocycle are optionally substituted, for example with 1 or 2 substituents independently selected from the group consisting of halo, phenyl, alkyl, alkoxy, fused heterocycle, $NO_2$, pyrrole, thiophene and fused phenyl, wherein said phenyl, fused heterocycle, pyrrolyl, thienyl and fused phenyl are themselves further optionally substituted with alkyl;

Y is selected from the group consisting of H, —O$R^e$, aryl, alkyl, halo, heteroaryl, —N($R^1$)—C(O)-alkyl-aryl, —C(O)—N($R^1$)-aryl-O-aryl, dibenzo[b,f][1,4]oxazepine, dibenzo[b][1,4]oxazepine-11-(10H)-one, —N($R^1$)—$SO_2$-aryl, -alkyl-aryl, -alkyl-O-aryl, -aryl-heterocycle, benzo[d][1,3]dioxole, heterocycle, -heterocyclyl-alkyl-aryl, -heterocyclyl-C(O)-aryl, 2,3-dihydrobenzofuan, -heterocyclyl-alkyl-heteroaryl, —CH-$(aryl)_2$, -heterocyclyl-C(O)-heteroaryl, -heterocyclyl-C(O)—O-alkyl, -heterocyclyl-$SO_2$-alkyl, -heterocyclyl-$SO_2$-aryl, -heterocyclyl-$SO_2$-aryl-N($R^1$)—C(O)-alkyl, -alkyl-O—C(O)—N($R^1$)-alkyl-aryl, -alkyl-N($R^1$)-alkyl-aryl, —C(O)—N($R^1$)-aryl, —N($R^1$)—C(O)-alkyl-aryl, —N($R^1$)—$SO_2$-aryl, —N($R^1$)—$SO_2$-alkyl-aryl, —N($R^1$)—$SO_2$-heteroaryl and -heterocyclyl-C(O)-alkyl, wherein said aryl and heteroaryl are optionally substituted with a substituent selected from the group consisting of alkyl, alkoxy, —$CF_3$, optionally substituted phenyl, —N($R^a$)($R^b$), —O-alkyl-morpholine and fused heterocycle; and $R^e$ is alkyl.

In another embodiment of the present invention,

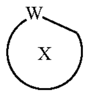

is selected from the group consisting of phenyl, pyrazolyl, thiazolyl, isoxazolyl, thienyl, benzofuranyl, benzothienyl and pyrimidinyl, alternatively phenyl, pyrazolyl, thiazolyl, thienyl and benzothienyl;

W is —C═;

M is —C(O)N($R^1$)O$R^2$ or —N(OH)C(O)H, for example —C(O)N($R^1$)O$R^2$;

$R^1$ and $R^2$ are as described for Formula (I), alternatively are H or alkyl;

n is 0;

L is selected from the group consisting of phenyl, —N($R^1$)C(O)-phenyl, —O-alkyl-phenyl, —$CF_3$, benzothiazolyl, —N($R^1$)$SO_2$-phenyl, -alkynyl-phenyl, thienyl, pyrrolyl, -alkyl-phenyl, pyridine, —$SO_2$—N($R^1$)-alkyl-phenyl, —N($R^1$)-alkyl, -phenyl-phenyl, —O-phenyl, —N($R^1$)-aryl, -thienyl-phenyl, —S-phenyl and fused heterocycle, wherein said phenyl, benzothiazolyl, thienyl, pyrrolyl, pyridine and fused heterocycle are optionally substituted;

Y is selected from the group consisting of H, —$OR^e$, phenyl, alkyl, halo, pyrrolyl, thienyl, —N($R^1$)—C(O)-alkyl-phenyl, —C(O)—N($R^1$)-phenyl-O-phenyl, dibenzo[b,f][1,4]oxazepine, dibenzo[b,f][1,4]oxazepine-11-(10H)-one, —N($R^1$)—$SO_2$-phenyl, -alkyl-phenyl, -alkyl-O-phenyl, pyridinyl, -phenyl-morpholine, benzothiophene, benzo[d][1,3]dioxole, piperidinyl, -piperidine-alkyl-phenyl, -piperidine-C(O)-phenyl, 2,3-dihydrobenzofuan, -piperidine-alkyl-pyridine, —CH-$(phenyl)_2$, piperidine-C(O)-pyrrolidine, -piperidine-C(O)—O-alkyl, -piperidine-$SO_2$-alkyl, -piperidine-$SO_2$-phenyl, -piperidine-alkyl-indole, -piperidine-$SO_2$-phenyl-N($R^1$)—C(O)-alkyl, -alkyl-O—C(O)—N($R^1$)-alkyl-phenyl, -alkyl-N($R^1$)-alkyl-phenyl, —C(O)—N($R^1$)-phenyl, —N($R^1$)—C(O)-alkyl-phenyl, —N($R^1$)—$SO_2$-phenyl, —N($R^1$)—$SO_2$-alkyl-phenyl, —N($R^1$)—$SO_2$-thienyl and -piperidine-C(O)-alkyl, wherein said phenyl, pyrrolyl, pyridinyl, benzothiophene, piperidinyl, indole and thienyl are optionally substituted; and $R^e$ is alkyl.

In another embodiment of the present invention,

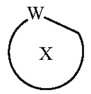

is selected from the group consisting of phenyl, pyrazolyl, thiazolyl, isoxazolyl, thienyl, benzofuranyl, benzothienyl and pyrimidinyl, alternatively phenyl, pyrazolyl, thiazolyl, thienyl and benzothienyl;

W is

M is —C(O)N($R^1$)$OR^2$ or —N(OH)C(O)H, for example —C(O)N($R^1$)$OR^2$;

$R^1$ and $R^2$ are as described for Formula (I), alternatively are H or alkyl;

n is 0;

L is selected from the group consisting of phenyl, —N($R^1$)C(O)-phenyl, —O-alkyl-phenyl, —$CF_3$, benzothiazolyl, —N($R^1$)$SO_2$-phenyl, -alkynyl-phenyl, thienyl, pyrrolyl, -alkyl-phenyl, pyridine, —$SO_2$—N($R^1$)-alkyl-phenyl, —N($R^1$)-alkyl, -phenyl-phenyl, —O-phenyl, —N($R^1$)-aryl, -thienyl-phenyl, —S-phenyl and fused heterocycle, wherein said phenyl, benzothiazolyl, thienyl, pyrrolyl, pyridine and fused heterocycle are optionally substituted, for example with 1 or 2 substituents independently selected from the group consisting of halo, phenyl, alkyl, alkoxy, fused heterocycle, $NO_2$, pyrrole, thiophene and fused phenyl, wherein said phenyl, fused heterocycle, pyrrolyl, thienyl and fused phenyl are themselves further optionally substituted with alkyl;

Y is selected from the group consisting of H, —$OR^e$, phenyl, alkyl, halo, pyrrolyl, thienyl, —N($R^1$)—C(O)-alkyl-phenyl, —C(O)—N($R^1$)-phenyl-O-phenyl, dibenzo[b,f][1,4]oxazepine, dibenzo[b,f][1,4]oxazepine-11-(10H)-one, —N($R^1$)—$SO_2$-phenyl, -alkyl-phenyl, -alkyl-O-phenyl, pyridinyl, -phenyl-morpholine, benzothiophene, benzo[d][1,3]dioxole, piperidinyl, -piperidine-alkyl-phenyl, -piperidine-C(O)-phenyl, 2,3-dihydrobenzofuan, -piperidine-alkyl-pyridine, —CH-$(phenyl)_2$, piperidine-C(O)-pyrrolidine, -piperidine-C(O)—O-alkyl, -piperidine-$SO_2$-alkyl, -piperidine-$SO_2$-phenyl, -piperidine-alkyl-indole, -piperidine-$SO_2$-phenyl-N($R^1$)—C(O)-alkyl, -alkyl-O—C(O)—N($R^1$)-alkyl-phenyl, -alkyl-N($R^1$)-alkyl-phenyl, —C(O)—N($R^1$)-phenyl, —N($R^1$)—C(O)-alkyl-phenyl, —N($R^1$)—$SO_2$-phenyl, —N($R^1$)—$SO_2$-alkyl-phenyl, —N($R^1$)—$SO_2$-thienyl and -piperidine-C(O)-alkyl, wherein said phenyl, pyrrolyl, pyridinyl, benzothiophene, piperidinyl, indole and thienyl are optionally substituted with a substituent selected from the group consisting of alkyl, alkoxy, —$CF_3$, optionally substituted phenyl, —N($R^a$)($R^b$), —O-alkyl-morpholine and fused heterocycle; and $R^e$ is alkyl.

In another embodiment of the present invention, the invention provides compounds of the Formula (Ic):

(Ic)

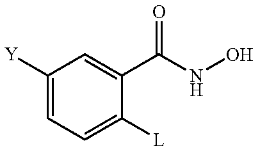

wherein

L is selected from the group consisting of aryl, heteroaryl, -aryl-aryl, -alkynyl-aryl, —O—$C_0$-$C_4$alkyl-aryl, -alkyl-aryl, —$SO_2$—N($R^1$)—$C_0$-$C_4$alkyl-aryl, —N($R^1$)-aryl and -heteroaryl-aryl, wherein each aryl and heteroaryl moiety is optionally substituted with 1 to 3 independently selected substituents, and each of which is optionally fused to one or more aryl, heterocyclic or heteroaryl rings, or one or more saturated or partially unsaturated cycloalkyl or heterocyclyl rings, each of which ring is optionally substituted;

$R^1$ is selected from the group consisting of —H, -alkyl, -aryl, -aryl-aryl, -hetetoaryl, heteroaryl-aryl, heteroaryl-heteroaryl, alkyl-heteroaryl and -alkyl-aryl, wherein each aryl and heteroaryl moiety is optionally substituted; and Y is H, —O-alkyl or optionally substituted aryl.

In another embodiment of the present invention, the invention provides compounds of the Formula (Id):

(Id)

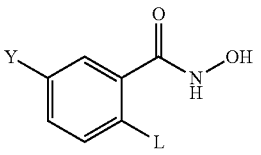

wherein

L is selected from the group consisting of phenyl, thienyl, -phenyl-phenyl, -alkynyl-phenyl, pyrrole, benzo[d]thiazole, —O-phenyl, -alkyl-phenyl, pyridine, —$SO_2$—N(H)—$C_0$-$C_4$alkyl-phenyl, —N(H)-phenyl, —O-alkyl-phenyl and -thienyl-phenyl, wherein each said phenyl, thienyl, pyrrole, benzo[d]thiazole and pyridine moiety is optionally substituted with 1 to 3 independently selected substituents, and each of which is optionally fused to one or more aryl, heterocyclic or heteroaryl rings, or one or more saturated or partially unsaturated cycloalkyl or heterocyclyl rings, each of which ring is optionally substituted; and Y is H, —O-alkyl or optionally substituted phenyl.

In another embodiment of the present invention, the invention provides compounds of the Formula (Ie):

(Ie)

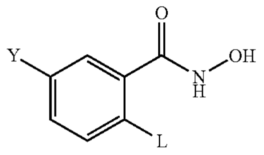

wherein

L is selected from the group consisting of phenyl, thienyl, -phenyl-phenyl, -alkynyl-phenyl, pyrrole, benzo[d]thiazole, —O-phenyl, -alkyl-phenyl, pyridine, —$SO_2$—N(H)—$C_0$-$C_4$alkyl-phenyl, —N(H)-phenyl, —O-alkyl-phenyl and -thienyl-phenyl, wherein each said phenyl, thienyl, pyrrole, benzo[d]thiazole and pyridine moiety is optionally substituted with 1 to 3 substituents independently selected from the group consisting of halo, alkyl, alkoxy, nitro, pyrrole and fused heterocycle; and Y is H, —O-alkyl or optionally substituted phenyl.

In another embodiment of the present invention, the invention provides compounds of the Formula (If):

(If)

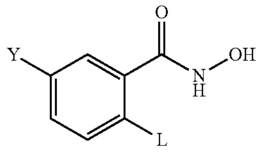

wherein

L is selected from the group consisting of phenyl, thienyl, -phenyl-phenyl, -alkynyl-phenyl, pyrrole, benzo[d]thiazole, —O-phenyl, -alkyl-phenyl, pyridine, —$SO_2$—N(H)—$C_0$-$C_4$alkyl-phenyl, —N(H)-phenyl, —O-alkyl-phenyl and -thienyl-phenyl, wherein (1) each said phenyl moiety is optionally substituted with 1 to 3 substituents independently selected from the group consisting of halo, alkyl, alkoxy, nitro, pyrrole and fused heterocycle, (2) each said pyrrole, thienyl and benzo[d]thiazole is substituted with 1 to 2 independently selected alkyl, and (3) said pyridine is substituted with 1 to 2 independently selected alkoxy; and Y is H, —O-alkyl or optionally substituted phenyl.

In another embodiment of the present invention, the invention provides compounds of the Formula (Ig):

(Ig)

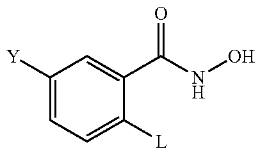

wherein

L is selected from the group consisting of aryl and heteroaryl, wherein each aryl and heteroaryl moiety is optionally substituted with 1 to 3 independently selected substituents, and each of which is optionally fused to one or more aryl, heterocyclic or heteroaryl rings, or one or more saturated or partially unsaturated cycloalkyl or heterocyclyl rings, each of which ring is optionally substituted; and Y is H.

In another embodiment of the present invention, the invention provides compounds of the Formula (Ih):

(Ih)

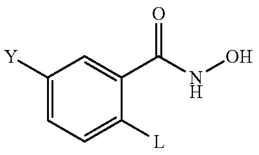

wherein

L is selected from the group consisting of phenyl, pyrrole and thienyl, each of which is optionally substituted with 1 to 3 independently selected substituents, and each of which is optionally fused to one or more aryl, heterocyclic or heteroaryl rings, or one or more saturated or partially unsaturated cycloalkyl or heterocyclyl rings, each of which ring is optionally substituted; and Y is H.

In another embodiment of the present invention, the invention provides compounds of the Formula (Ii):

(Ii)

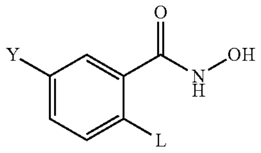

wherein

L is selected from the group consisting of phenyl, pyrrole and thienyl, each of which is optionally substituted with 1 to 3 substituents independently selected from the group consisting of alkoxy, nitro, halo, alkyl, optionally substituted aryl and optionally substituted heteroaryl; and Y is H.

In another embodiment of the present invention, the invention provides compounds of the Formula (Ij):

(Ij)

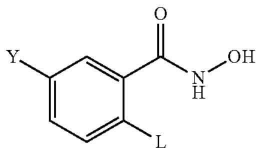

wherein

L is selected from the group consisting of (1) phenyl optionally substituted with a substituent selected from the group consisting of alkoxy, nitro, halo and optionally substituted heteroaryl (for example -thienyl-alkyl), (2) pyrrole and (3) thienyl optionally substituted with alkyl; and Y is H.

In another embodiment of the present invention, the invention provides compounds of the Formula (Ik):

(Ik)

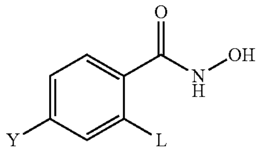

wherein

L is aryl or heteroaryl, each of which is optionally substituted;

Y is selected from the group consisting of aryl, —$C_1$-$C_4$alkyl, halo, heteroaryl, —N($R^1$)—C(O)-alkyl-aryl, —C(O)—N($R^1$)—$C_0$-$C_3$alkyl-aryl-O-aryl, optionally substituted dibenzo[b][1,4]oxazepine and —N($R^1$)S(O)$_2$-aryl, wherein said aryl and heteroaryl moieties are optionally substituted; and $R^1$ is selected from the group consisting of —H, -alkyl, -aryl, -aryl-aryl, -hetetoaryl, heteroaryl-aryl, heteroaryl-heteroaryl, alkyl-heteroaryl and -alkyl-aryl, wherein each aryl and heteroaryl moiety is optionally substituted.

In another embodiment of the present invention, the invention provides compounds of the Formula (Il):

(Il)

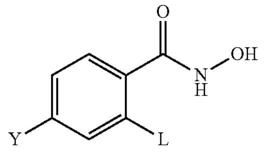

wherein

L is phenyl or thienyl, each of which is optionally substituted; and

Y is selected from the group consisting of phenyl, —$C_1$-$C_4$alkyl, halo, thienyl, —N(H)—C(O)-alkyl-phenyl, —C(O)—N(H)—$C_0$-$C_3$alkyl-phenyl-O-phenyl, optionally substituted dibenzo[b,f][1,4]oxazepine, optionally substituted dibenzo[b,f][1,4]oxazepine-11-(10H)-one and —N(H)S(O)$_2$-phenyl, wherein said phenyl and thienyl moieties are optionally substituted.

In another embodiment of the present invention, the invention provides compounds of the Formula (Im):

(Im)

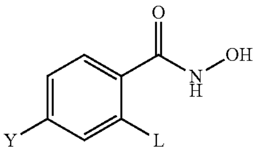

wherein

L is phenyl or thienyl, each of which is optionally substituted with one or more independently selected alkoxy or alkyl; and Y is selected from the group consisting of phenyl, —$C_1$-$C_4$alkyl, halo, thienyl, —N(H)—C(O)-alkyl-phenyl, —C(O)—N(H)—$C_0$-$C_3$alkyl-phenyl-O-phenyl, optionally substituted dibenzo[b,f][1,4]oxazepine, optionally substituted dibenzo[b,f][1,4]oxazepine-11-(10H)-one and —N(H)S(O)$_2$-phenyl, wherein said phenyl and thienyl moieties are optionally substituted with one or more substituents selected from the group consisting of alkyoxy, alkyl and optionally substituted phenyl.

In another embodiment of the present invention, the invention provides compounds of the Formula (In):

(In)

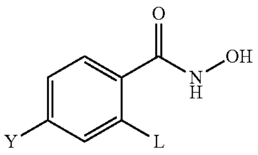

wherein

L is phenyl optionally substituted with alkoxy, or thienyl optionally substituted with alkyl; and Y is selected from the group consisting of phenyl, —$C_1$-$C_4$alkyl, halo, thienyl, —N(H)—C(O)-alkyl-phenyl, —C(O)—N(H)—$C_0$-$C_3$alkyl-phenyl-O-phenyl; optionally substituted dibenzo[b][1 ,4]oxazepine, optionally substituted dibenzo[b,f][1,4]oxazepine-11-(10H)-one and —N(H)S(O)$_2$-phenyl, wherein said phenyl moieties are optionally substituted with one or more alkyoxy, and said thienyl moieties are optionally substituted with alkyl and optionally substituted phenyl (for example phenyl substituted with amino, alkylamino or dialkylamino).

In another embodiment of the present invention, the invention provides compounds of the Formula (In):

(In)

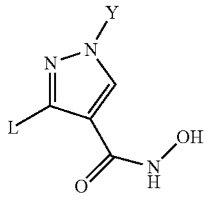

wherein

L is optionally substituted aryl; and

Y is aryl, —$C_0$-$C_3$alkyl-aryl or heteroaryl, wherein said aryl and heteroaryl moieties are optionally substituted.

In another embodiment of the present invention, the invention provides compounds of the Formula (Io):

(Io)

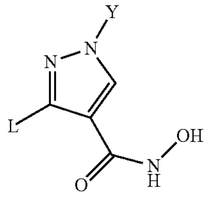

wherein

L is optionally substituted phenyl; and

Y is phenyl, —$C_0$-$C_3$alkyl-phenyl or pyridinyl, wherein said phenyl and pyridinyl moieties are optionally substituted.

In another embodiment of the present invention, the invention provides compounds of the Formula (Ip):

(Ip)

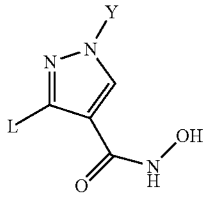

wherein

L is phenyl optionally substituted with halo; and

Y is phenyl, —$C_0$-$C_3$alkyl-phenyl or pyridinyl, wherein said phenyl and pyridinyl moieties are optionally substituted.

In another embodiment of the present invention, the invention provides compounds of the Formula (Iq):

(Iq)

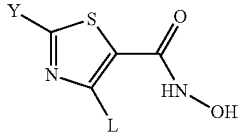

wherein

L is optionally substituted aryl; and

Y is selected from the group consisting of aryl, -aryl-heterocyclyl, heteroaryl, -heterocyclyl-$C_0$-$C_3$alkyl-aryl, —$C_0$-$C_3$alkyl-heterocyclyl, —C(O)-heterocyclyl, -heterocyclyl-C(O)—$C_0$-$C_3$alkyl-heterocyclyl, -heterocyclyl-C(O)O—$C_0$-$C_3$alkyl-alkyl, -heterocyclyl-S$(O)_2$—$C_0$-$C_3$alkyl-alkyl, -heterocyclyl-S$(O)_2$—$C_0$-$C_3$alkyl-aryl, -heterocyclyl-$C_0$-$C_3$alkyl-heteroaryl, -heterocyclyl-C(O)—$C_0$-$C_3$alkyl-aryl, -heterocyclyl-C(O)-alkyl, and —CH$(aryl)_2$, wherein each aryl, heterocyclyl and heteroaryl moiety is optionally substituted with 1 to 3 independently selected substituents, and each of which is optionally fused to one or more aryl, heterocyclic or heteroaryl rings, or one or more saturated or partially unsaturated cycloalkyl or heterocyclyl rings, each of which ring is optionally substituted.

In another embodiment of the present invention, the invention provides compounds of the Formula (Ir):

(Ir)

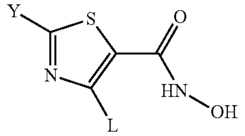

wherein

L is optionally substituted phenyl;

Y is selected from the group consisting of phenyl, -phenyl-heterocyclyl, benzothiophene, benzo[d][1,3]dioxole, piperidine, pyridine, piperidine-alkyl-aryl, piperidine-C(O)-aryl, 2,3-dihydrobenzofuran, thienyl, -piperidine-$C_1$-$C_3$ alkyl-heterocyclyl, —CH$(phenyl)_2$, -piperidine-C(O)-alkyl, -piperidine-C(O)-heterocyclyl, -piperidine-C(O)—O-alkyl, -piperidine-$SO_2$-alkyl, -piperidine-$SO_2$-aryl, -piperidine-alkyl-heteroaryl, -piperidine-$SO_2$-aryl-N($R^1$)—C(O)-alkyl, —wherein each of said phenyl, heterocyclyl, benzothiophene, benzo[d][1,3]dioxole, piperidine, pyridine, aryl, 2,3-dihydrobenzofuran, thienyl and heteroaryl moieties is optionally substituted with 1 to 3 independently selected substituents, and each of which is optionally fused to one or more aryl, heterocyclic or heteroaryl rings, or one or more saturated or partially unsaturated cycloalkyl or heterocyclyl rings, each of which ring is optionally substituted;

$R^1$ is selected from the group consisting of —H, -alkyl, -aryl, -aryl-aryl, -hetetoaryl, heteroaryl-aryl, heteroaryl-heteroaryl, alkyl-heteroaryl and -alkyl-aryl, wherein each aryl and heteroaryl moiety is optionally substituted.

In another embodiment of the present invention, the invention provides compounds of the Formula (Is):

(Is)

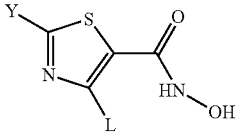

wherein

L is optionally substituted phenyl; and

Y is selected from the group consisting of phenyl, -phenyl-morpholine, benzothiophene, benzo[d][1,3]dioxole, piperidine, pyridine, piperidine-alkyl-phenyl, piperidine-C(O)-phenyl, 2,3-dihydrobenzofuran, thienyl, -piperidine-$C_1$-$C_3$alkyl-pyridine, —CH$(phenyl)_2$, -piperidine-C(O)-alkyl, -piperidine-C(O)-pyrrolidine, -piperidine-C(O)—O-alkyl, -piperidine-$SO_2$-alkyl, -piperidine-$SO_2$-phenyl, -piperidine-alkyl-indole and -piperidine-$SO_2$-phenyl-N(H)—C(O)-alkyl, wherein each of said phenyl, morpholine, benzothiphene, benzo[d][1,3]dioxole, piperidine, pyridine, 2,3-dihydrobenzofuran, pyrrolidine, indole and thienyl moieties is optionally substituted with 1 to 3 independently selected substituents, and each of which is optionally fused to one or more aryl, heterocyclic or heteroaryl rings, or one or more saturated or partially unsaturated cycloalkyl or heterocyclyl rings, each of which ring is optionally substituted.

In another embodiment of the present invention, the invention provides compounds of the Formula (It):

(It)

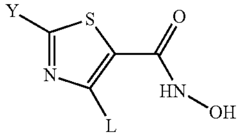

wherein

L is phenyl optionally substituted with halo; and

Y is selected from the group consisting of phenyl, -phenyl-morpholine, benzothiophene, benzo[d][1,3]dioxole, piperidine, pyridine, piperidine-alkyl-phenyl, piperidine-C(O)-phenyl, 2,3-dihydrobenzofuran, thienyl, -piperidine-$C_1$-$C_3$alkyl-pyridine, —CH$(phenyl)_2$, -piperidine-C(O)-alkyl, -piperidine-C(O)-pyrrolidine, -piperidine-C(O)—O-alkyl, -piperidine-$SO_2$-alkyl, -piperidine-$SO_2$-phenyl, -piperidine-alkyl-indole and -piperidine-$SO_2$-phenyl-N(H)—C(O)-alkyl, wherein each said phenyl moiety is optionally substituted with 1 to 3 independently selected alkoxy or —O-alkyl-heterocyclyl (for example, —O-alkyl-morpholine).

In another embodiment of the present invention, the invention provides compounds of the Formula (Iu):

(Iu)

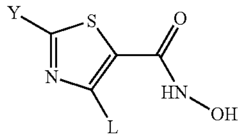

wherein

L is phenyl optionally substituted with halo; and

Y is optionally substituted piperidine.

In another embodiment of the present invention, the invention provides compounds of the Formula (Iv):

(Iv)

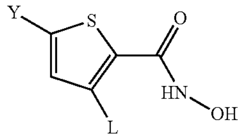

wherein

L is optionally substituted phenyl;

Y is aryl, -alkyl-O-aryl, —$C_0$-$C_3$alkyl-aryl, -alkyl-O—C(O)—N($R^1$)-alkyl-aryl, -alkyl-N($R^1$)-alkyl-aryl and —C(O)—N($R^1$)-aryl, wherein each aryl moiety is optionally substituted with 1 to 3 independently selected substituents, and is optionally fused to one or more aryl, heterocyclic or heteroaryl rings, or one or more saturated or partially unsaturated cycloalkyl or heterocyclyl rings, each of which ring is optionally substituted; and $R^1$ is selected from the group consisting of —H, -alkyl, -aryl, -aryl-aryl, -hetetoaryl, heteroaryl-aryl, heteroaryl-heteroaryl, alkyl-heteroaryl and -alkyl-aryl, wherein each aryl and heteroaryl moiety is optionally substituted.

In another embodiment of the present invention, the invention provides compounds of the Formula (Iw):

(Iw)

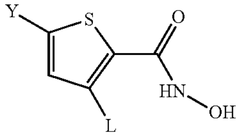

wherein

L is optionally substituted phenyl; and

Y is phenyl, -alley-O-phenyl, —$C_0$-$C_3$alkyl-phenyl, -alkyl-O—C(O)—N(H)-alkyl-phenyl, -alkyl-O—C(O)—N(alkyl)-alkyl-phenyl, -alkyl-N(H)-alkyl-phenyl, -alkyl-N(alkyl)-alkyl-phenyl and —C(O)—N(H)-phenyl, wherein each phenyl moiety is optionally substituted with 1 to 3 independently selected substituents, and is optionally fused to one or more aryl, heterocyclic or heteroaryl rings, or one or more saturated or partially unsaturated cycloalkyl or heterocyclyl rings, each of which ring is optionally substituted.

In another embodiment of the present invention, the invention provides compounds of the Formula (Ix):

(Ix)

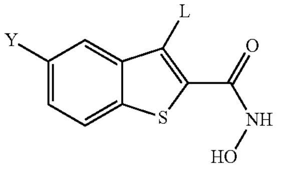

wherein

L is optionally substituted phenyl;

Y is selected from the group consisting of H, —N($R^1$)—C(O)—O-alkyl-aryl, —N($R^1$)—S$(O)_2$-aryl, —N($R^1$)—S$(O)_2$-alkyl-aryl and —N($R^1$)—S$(O)_2$-heteroaryl, wherein each aryl and heteroaryl moiety is optionally substituted with 1 to 3 independently selected substituents, and is optionally fused to one or more aryl, heterocyclic or heteroaryl rings, or one or more saturated or partially unsaturated cycloalkyl or heterocyclyl rings, each of which ring is optionally substituted; and $R^1$ is selected from the group consisting of —H, -alkyl, -aryl, -aryl-aryl, -hetetoaryl, heteroaryl-aryl, heteroaryl-heteroaryl, alkyl-heteroaryl and -alkyl-aryl, wherein each aryl and heteroaryl moiety is optionally substituted.

In another embodiment of the present invention, the invention provides compounds of the Formula (Iy):

(Iy)

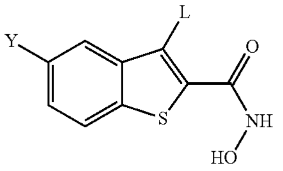

wherein

L is optionally substituted phenyl; and

Y is selected from the group consisting of H, —N(H)—C(O)—O-alkyl-phenyl, —N(H)—S$(O)_2$-phenyl, —N(H)—S$(O)_2$-alkyl-phenyl and —N(H)—S$(O)_2$-thiophene, wherein each phenyl and thiophene moiety is optionally substituted with 1 to 3 independently selected substituents, and is optionally fused to one or more aryl, heterocyclic or heteroaryl rings, or one or more saturated or partially unsaturated cycloalkyl or heterocyclyl rings, each of which ring is optionally substituted.

In another embodiment of the present invention, the invention provides compounds of the Formula (Iz):

(Iz)

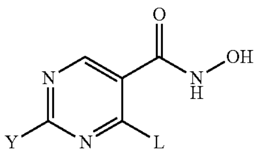

wherein

L is —S-aryl, aryl or heteroaryl, wherein each aryl and heteroaryl moiety is optionally substituted with 1 to 3 independently selected substituents, and is optionally fused to one or more aryl, heterocyclic or heteroaryl rings, or one or more saturated or partially unsaturated cycloalkyl or heterocyclyl rings, each of which ring is optionally substituted; and Y is optionally substituted aryl.

In another embodiment of the present invention, the invention provides compounds of the Formula (Iaa):

(Iaa)

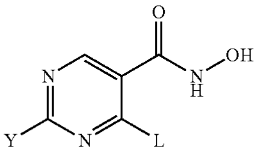

wherein

L is —S-phenyl, phenyl or pyridine, wherein each phenyl and pyridine moiety is optionally substituted with 1 to 3 independently selected substituents, and is optionally fused to one or more aryl, heterocyclic or heteroaryl rings, or one or more saturated or partially unsaturated cycloalkyl or heterocyclyl rings, each of which ring is optionally substituted; and Y is phenyl optionally substituted with halo.

In another aspect of the invention, the invention provides compounds of the Formula (II):

(II)

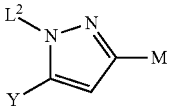

and N-oxides, hydrates, solvates, pharmaceutically acceptable salts, prodrugs and complexes thereof, and racemic and scalemic mixtures, tautomers, diastereomers and enantiomers thereof, wherein $L^2$ is selected from the group consisting of H, —$C_0$-$C_3$alkyl-aryl, —$C_0$-$C_3$alkyl-heteroaryl, —$C_1$-$C_6$alkyl, in which each aryl and heteroaryl is optionally substituted with one, two or three substituents independently selected from halo, heterocyclyl, $CF_3$, amino, $OCH_3$ and OH; and Y and M are defined for Formula (I).

In another embodiment of the present invention, the compound is a compound selected from the group consisting of N-hydroxy-2-(thiophen-2-yl)benzamide, N-hydroxy-5-methoxy-2-(thiophen-2-yl)benzamide, 4'-fluoro-N-hydroxy-2'-methylbiphenyl-2-carboxamide, N-hydroxy-2',3'-dimethoxybiphenyl-2-carboxamide, N-hydroxy-2-(phenylethynyl)benzamide, 2-(benzo[d][1,3]dioxol-5-yl)-N-hydroxybenzamide, N-hydroxy-3'-methoxybiphenyl-2-carboxamide, 4'-fluoro-N-hydroxybiphenyl-2-carboxamide, N-hydroxy-2-(1H-pyrrol-1-yl)benzamide, 2-(2,5-dimethyl-1H-pyrrol-1-yl)-N-hydroxybenzamide, N-hydroxy-2'-methoxybiphenyl-2-carboxamide, N-hydroxy-2-(4-methylthiophen-3-yl)benzamide, N-hydroxy-2-(2-methylbenzo[d]thiazol-5-yl)benzamide, 2-((4-fluoro-3-methylphenyl)ethynyl)-N-hydroxybenzamide, N-hydroxy-2-phenethylbenzamide, N-hydroxy-3'-nitrobiphenyl-2-carboxamide, N-hydroxy-2-(2-methoxypyridin-3-yl)benzamide, 2-(N-benzylsulfamoyl)-N-hydroxybenzamide, 3'-fluoro-N-hydroxybiphenyl-2-carboxamide, N-hydroxy-3'-(1H-pyrrol-1-yl)biphenyl-2-carboxamide, N-hydroxydibenzo[b,d]furan-4-carboxamide, N-hydroxy-3'-methoxy-5-methylbiphenyl-2-carboxamide, 5-fluoro-N-hydroxy-3'-methoxybiphenyl-2-carboxamide, N-hydroxy-3'-(4-methylthiophen-3-yl)biphenyl-2-carboxamide, ethyl 3'(2-amino-5-(thiophen-2-yl)phenylcarbamoyl)biphenyl-2-carboxylate, N3'-(2-amino-5-(thiophen-2-yl)phenyl)-N2-hydroxybiphenyl-2,3'-dicarboxamide, 2-(benzyloxy)-N-hydroxybenzamide, N-hydroxy-1,3-diphenyl-1H-pyrazole-4-carboxamide, N-hydroxy-2-(5-phenylthiophen-2-yl)benzamide, N-hydroxy-2,4-bis(4-methylthiophen-3-yl)benzamide, N-hydroxy-2,4-diphenylthiazole-5-carboxamide, N-hydroxy-5-methyl-3-phenylisoxazole-4-carboxamide, N-hydroxy-5-phenyl-3-(phenylsulfonamido)thiophene-2-carboxamide, N-hydroxy-2,5-diphenylthiophene-3-carboxamide, 3-(4-bromophenyl)-N-hydroxy-1-(4-methoxyphenyl)-1H-pyrazole-4-carboxamide, (Z)-5-(dibenzo[b,f][1,4]oxazepin-11-yl)-N-hydroxybiphenyl-2-carboxamide, N2-hydroxy-N-5-(2-phenoxyphenyl)biphenyl-2,5-dicarboxamide,

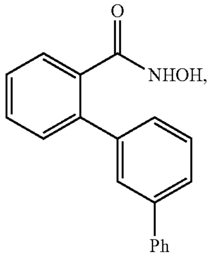
,
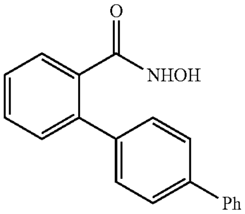
,
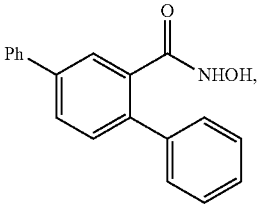
,
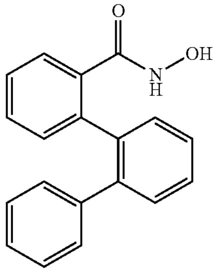
,
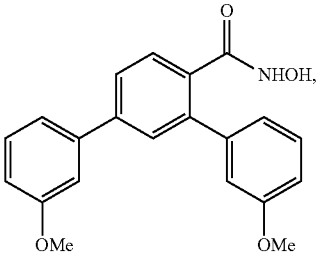
,
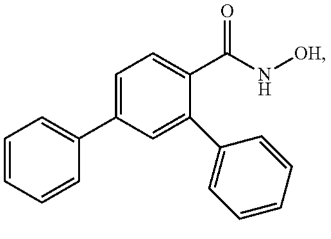
, 1-benzyl-N-hydroxy-3-phenyl-1H-pyrazole-4-carboxamide, 1-(4-(benzyloxy)phenyl)-N-hydroxy-3-phenyl-1H-pyrazole-4-carboxamide, 3-(4-fluorophenyl)-N-hydroxy-1-phenyl-1H-pyrazole-4-carboxamide, N-hydroxy-2-(4-morpholinophenyl)-4-phenylthiazole-5-carboxamide, 2-(benzo[b]thiophen-3-yl)-N-hydroxy-4-phenylthiazole-5-carboxamide, N-hydroxy-3-phenyl-1-(pyridin-2-yl)-1H-pyrazole-4-carboxamide,
N-hydroxy-2,5-diphenyloxazole-4-carboxamide,
N-hydroxy-2,5-diphenylthiazole-4-carboxamide,
N-hydroxy-4-phenyl-2-(2-phenylacetamido)thiazole-5-carboxamide,
N-hydroxy-3-phenylbenzofuran-2-carboxamide,
5-(4-dimethylaminophenyl)-N-hydroxybiphenyl-2-carboxamide,
N-hydroxy-4-phenyl-2-(piperidin-1-yl)thiazole-5-carboxamide,
N2-hydroxy-N5-phenylbiphenyl-2,5-dicarboxamide,
N-hydroxy-2-phenylbenzofuran-3-carboxamide,
N-hydroxy-4-phenyl-2-(pyridin-3-yl)thiazole-5-carboxamide,
2-(3,4-dihydroquinolin-1(2H)-yl)-N-hydroxy-4-phenylthiazole-5-carboxamide,
N-hydroxy-4-phenyl-2-(pyridin-4-yl)thiazole-5-carboxamide,
N5-(2-aminophenyl)-$N^2$-hydroxybiphenyl-2,5-dicarboxamide,
5-(1H-benzo[d]imidazol-2-yl)-N-hydroxybiphenyl-2-carboxamide,
N-hydroxy-5-(phenoxymethyl)-3-phenylthiophene-2-carboxamide,
N-hydroxy-3-phenyl-5-(phenylsulfonamido)benzo[b]thiophene-2-carboxamide,
N-hydroxy-1-phenyl-5-(trifluoromethyl)-1H-pyrazole-4-carboxamide,
3-chloro-N-hydroxy-5-phenylthiophene-2-carboxamide,
N2-hydroxy-N5-(2-phenoxyphenyl)biphenyl-2,5-dicarboxamide,
5-benzyl-N-hydroxy-3-phenylthiophene-2-carboxamide,
benzyl 2-(hydroxycarbamoyl)-3-phenylbenzo[b]thiophen-5-ylcarbamate,
2-(1-benzylpiperidin-4-yl)-N-hydroxy-4-phenylthiazole-5-carboxamide and 2-(1-benzoylpiperidin-4-yl)-N-hydroxy-4-phenylthiazole-5-carboxamide.

Some examples of the compounds according to the first aspect of the invention are listed in the tables and schemes below. These examples merely serve to exemplify some of the compounds of the first aspect of the invention and do not limit the scope of the invention.

SYNTHETIC SCHEMES AND EXPERIMENTAL PROCEDURES

The compounds of the invention can be prepared according to the reaction schemes for the examples illustrated below utilizing methods known to one of ordinary skill in the art. These schemes serve to exemplify some procedures that can be used to make the compounds of the invention. One skilled in the art will recognize that other general synthetic procedures may be used. The compounds of the invention can be prepared from starting components that are commercially available. Any kind of substitutions can be made to the starting components to obtain the compounds of the invention according to procedures that are well known to those skilled in the art.

Scheme 1

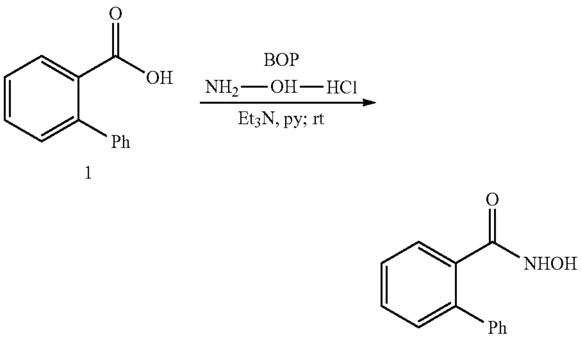

1

2: Example 1a

Example 1a

N-hydroxybiphenyl-2-carboxamide 2

N-hydroxybiphenyl-2-carboxamide 2

A solution of 2-biphenylcarboxylic acid 1 (0.25 g, 1.261 mmol), BOP (0.558 g, 1.261 mmol), hydroxylamine hydrochloride (0.088 g, 1.261 mmol) and triethylamine (0.527 mL, 3.78 mmol) was stirred in pyridine (5 mL) at room temperature overnight then diluted with DCM, washed with water (2×), dried over $MgSO_4$, filtered and solvent evaporated to provide title compound 2 (8.8 mg, 3% yield) as a white solid after purification by Biotage (50 to 100% EtOAc in Hexane) followed by trituration ($Et_2O$). $^1H$ NMR (400 MHz, DMSO-$d_6$) δ (ppm): 10.77 (s, 1H), 8.97 (s, 1H), 7.52 to 7.42 (m, 1H), 7.40 to 7.33 (m, 8H). LRMS (ESI): (calc.) 213.23 (found) 214.2 (MH)+

TABLE 1

Compounds according to Scheme 1.

| Ex | Compound | Structure | Name | Characterization |
|---|---|---|---|---|
| 1b | 3 | 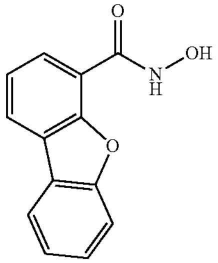 [SMILES: O=C(NO)c1cccc2c1oc1ccccc12] | N-hydroxydibenzo[b,d]furan-4-carboxamide | (DMSO-d6) δ (ppm) 1H: 11.11 (bs, 1H), 9.33 (bs, 1H), 8.29 (dd, J = 7.6, 1.2 Hz, 1H), 8.20 (dd, J = 7.8, 0.6 Hz, 1H), 7.77 (d, J = 5.1 Hz, 1H), 7.75 (dd, J = 5.5, 1.2 Hz, IH), 7.57 (td, J = 7.2, 1.4 Hz, IH), 7.48 (t, J = 7.8 Hz, 1H), 7.44 (td, J = 6.7, 1.2 Hz, 1H). LRMS (ES1): (calc.) 227.22 (found) 228.1 (MH)+ |

TABLE 1-continued

| Compounds according to Scheme 1. | | | | |
|---|---|---|---|---|
| Ex | Compound | Structure | Name | Characterization |
| 1c | 4 | 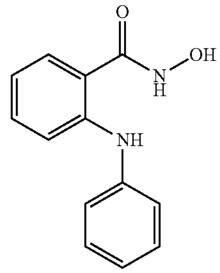 [SMILES: O=C(NO)c1ccccc1Nc1ccccc1] | N-hydroxy-2-(phenylamino) benzamide | (s(DMSO-d6) δ (ppm) 1H: 11.24 (s, 1H), 9.24 (s, 1H), 9.11 (s, 1H), 7.47 (d, J =7.6 Hz, 1H), 7.34-7.27 (m, 4H), 7.13 (dd, J = 8.6, 1.0 Hz, 2H), 6.95 (tt, J = 7.2, 1.0 Hz, 1H), 6.81 (td, J = 6.7, 1.8 Hz, 1H). LRMS (ESI): (calc.) 228.25 (found) 229.1 (MH)+ |
| 1d | 5 | 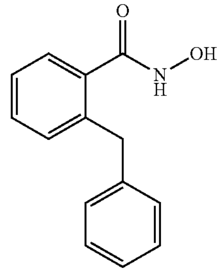 [SMILES: O=C(NO)c1ccccc1Cc1ccccc1] | 2-benzyl-N-hydroxybenzamide | (DMSO-d6) δ (ppm) 1H: 10.93 (s, 1H), 9.09 (s, 1H), 7.34 (td, J = 7.4, 2.1 Hz, 1H), 7.27 (td, J = 7.6, 1.6 Hz, 1H), 7.25-7.14 (m, 7H), 4.07 (s, 2H). LRMS (ESI): (calc.) 227.26 (found) 228.1 (MH)+ |
| 1e | 6 | 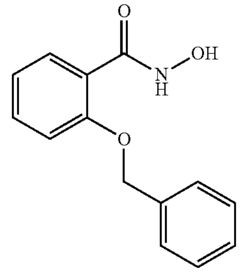 [SMILES: O=C(NO)c1ccccc1OCc1ccccc1] | 2-(benzyloxy)-N-hydroxybenzamide | (DMSO-d6) δ (ppm) 1H: 10.63 (d, J = 1.4 Hz, 1H), 9.10 (d, J = 1.8 Hz, 1H), 7.50 (dd, J = 7.6, 1.8 Hz, 1H), 7.48 (d, J = 7.4 Hz, 2H), 7.42-7.36 (m, 3H), 7.32 (tt, J = 7.2, 1.4 Hz, 1H), 7.14 (d, J = 7.8 Hz, 1H), 7.00 (td, J = 7.6, 1.0 Hz, 1H), 5.21 (s, 2H). LRMS (ESI): (calc.) 243.26 (found) 244.1 (MH)+ |

Scheme 2

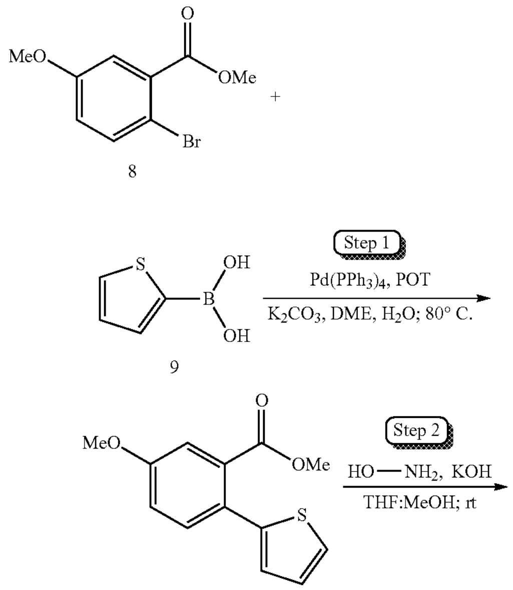

8

9

10

-continued

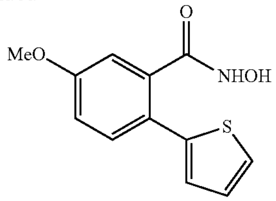

11: Example 2a

Example 2a

N-hydroxy-5-methoxy-2-(thiophen-2-yl)benzamide 11

Step 1: methyl 5-methoxy-2-(thiophen-2-yl)benzoate 10

To a degassed solution of methyl 2-bromo-5-methoxybenzoate 8 (0.25 g, 1.020 mmol), 2-thiophene boronic acid 9 (0.170 g, 1.326 mmol), tri-o-tolylphosphine (0.093 g, 0.306 mmol), and $K_2CO_3$ (0.423 g, 3.06 mmol) in DME (3 mL) and water (1 mL) was added $Pd(Ph_3P)_4$ (0.077 g, 0.066 mmol) and the reaction mixture was placed in a preheated oil bath at 85° C. and stirred overnight. The next morning the reaction was complete by HPLC therefore it was solvent evaporated, diluted with DCM, washed with water, brine, dried over $MgSO_4$, filtered and solvent evaporated to provide compound 10 (0.13 g, 52% yield) as a colorless oil after purification by Biotage (0 to 10% EtOAc in Hexane). LRMS (ESI): (calc.) 248.05 (found) 249.1 (MH)+

Step 2:
N-hydroxy-5-methoxy-2-(thiophen-2-yl)benzamide
11

To a stirring solution of methyl 5-methoxy-2-(thiophen-2-yl)benzoate 10 (0.13 g, 0.524 mmol) and a solution of 50% hydroxylamine in water (0.53 mL, 0.524 mmol) in THF (1 mL) and MeOH (1 mL) was added KOH (0.117 g, 2.094 mmol) and the reaction mixture was allowed to stir at room temperature for 3 hours. The reaction mixture was solvent evaporated, diluted with DCM, washed with 5% $KHSO_4$, brine, dried over $MgSO_4$, filtered and solvent evaporated to provide title compound 11 (50 mg, 38% yield) as a white solid after trituration (overnight, DCM). $^1H$ NMR (400 MHz, DMSO-$d_6$) δ (ppm): 10.87 (s, 1H), 9.06 (s, 1H), 7.49 (d, J=1.2 Hz, 1H), 7.45 (dd, J=15.5, 1.2 Hz, 1H), 7.14 (dd, J=3.5, 1.2 Hz, 1H), 7.05 to 7.02 (m, 2H), 6.84 (d, J=2.7 Hz, 1H), 3.78 (s, 3H). LRMS (ESI): (calc.) 249.05 (found) 250.1 (MH)+

TABLE 2

Compounds according to Scheme 2.

| Ex. | Compound | Structure | Name | Characterization | Steps |
|---|---|---|---|---|---|
| 2b | 12 | 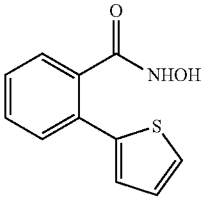 | N-hydroxy-2-(thiophen-2-yl)benzamide | $^1H$ NMR (400 MHz, DMSO-$d_6$) δ (ppm): 10.88 (s, 1H), 9.07 (s, 1H), 7.56 (dd, J = 5.3, 1.2 Hz, 1H), 7.53 to 7.50 (m, 1H), 7.46 (dt, J = 7.2, 1.6 Hz, 1H), 7.36 (dt, J = 7.6, 1.6 Hz, 1H), 7.31 to 7.29 (m, 1H), 7.25 (dd, J = 3.5, 0.98 Hz, 1H), 7.08 (dd, J = 5.1, 3.7 Hz, 1H). LRMS (ESI): (calc.) 219.26 (found) 220.1 (MH)+ | 1 and 2 |
| 2c | 13 | 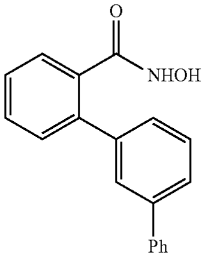 | | $^1H$ NMR (400 MHz, DMSO-$d_6$) δ (ppm): 10.81 (d, J = 1.8 Hz, 1H), 9.01 (d, J = 2.0 Hz, 1H), 7.70-7.35 (m, 13H). LRMS (ESI): (calc.) 289.33 (found) 290.1 (MH)+ | 1 and 2 |
| 2d | 14 | 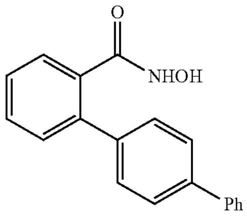 | | $^1H$ NMR (400 MHz, DMSO-$d_6$) δ (ppm): 10.82 (s, 1H), 9.00 (s, 1H), 7.71 to 7.68 (m, 3H), 7.52 to 7.37 (m, 10H). LRMS (ESI): (calc.) 289.33 (found) 290.1 (MH)+ | 1 and 2 |
| 2e | 15 | 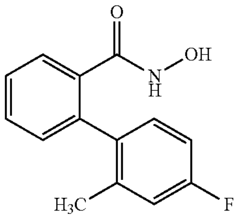 [SMILES: Cc1cc(F)ccc1-c1ccccc1C(=O)NO] | 4'-fluoro-N-hydroxy-2'-methylbiphenyl-2-carboxamide | $^1H$ NMR (400 MHz, DMSO-$d_6$) δ (ppm): 10.70 (s, 1H), 8.88 (s, 1H), 7.49-7.43 (m, 1H), 7.41-7.38 (m, 2H), 7.16 (d, J = 7.2 Hz, 1H), 7.07 (t, J = 8.4 Hz, 1H), 7.05 (dd, J = 10.2, 2.7 Hz, 1H), 6.97 (td, J = 8.6, 2.5 Hz, 1H), 2.04 (s, 3H). LRMS (ESI): (calc.) 245.25 (found) 246.1 (MH)+ | 1 and 2 |
| 2f | 16 | 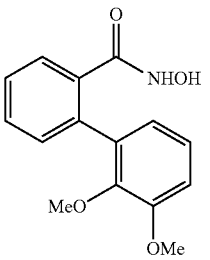 | N-hydroxy-2',3'-dimethoxy-biphenyl-2-carboxamide | $^1H$ NMR (400 MHz, DMSO-$d_6$) δ (ppm): 10.72 (s, 1H), 8.85 (s, 1H), 7.43-7.37 (m, 3H), 7.22 (d, J = 7.2 Hz, 1H), 7.12-6.98 (m, 2H), 6.73-6.72 (m, 1H), 3.48 (s, 3H), 3.31 (s, 3H). calc (273.10) MS (m/z): 274.1 (M + H). | 1 and 2 |

TABLE 2-continued

| Compounds according to Scheme 2. | | | | | |
|---|---|---|---|---|---|
| Ex. | Compound | Structure | Name | Characterization | Steps |
| 2g | 17 | 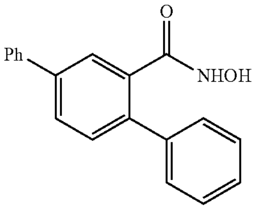 | | $^1$H NMR (400 MHz, DMSO-$d_6$) δ (ppm): 10.92 (s, 1H), 9.05 (s, 1H), 7.81 (dd, J = 8.1, 2.1 Hz, 1H), 7.74 (dd, J = 7.8, 1.2 Hz, 2H), 7.63 (d, J = 2.2 Hz, 1H), 7.53-7.35 (m, 9H). LRMS (ESI): (calc.) 289.33 (found) 290.1 (MH)+ | 1 and 2 |
| 2h | 18 | 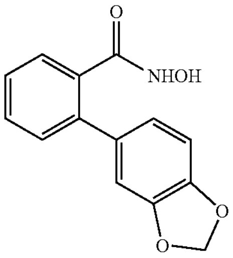 | 2-(benzo[d] [l,3]dioxol-5-yl)-N-hydroxy-benzamide | $^1$H NMR (400 MHz, DMSO-$d_6$) δ (ppm): 10.74 (s, 1H), 9.00 (s, 1H), 7.47 (td, J = 7.4, 1.8 Hz, 1H), 7.39-7.32 (m, 3H), 6.95-6.93 (m, 2H), 6.86 (dd, J = 7.9, 1.9 Hz, 1H), 6.04 (s, 2H). LRMS (ESI): (calc.) 257.07 258.0 (MH)+ | 1 and 2 |
| 2i | 19 | 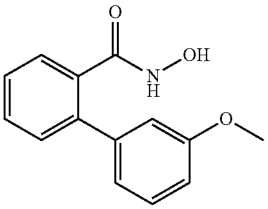 [SMILES: COc1cccc(-c2ccccc2C(=O)NO)c1] | N-hydroxy-3'-melhoxybipheny 1-2-carboxamide | $^1$H NMR (400 MHz, DMSO-$d_6$) δ (ppm): 10.77 (s, 1H), 8.99 (s, 1H), 7.52-7.48 (m, 1H), 7.42-7.39 (m, 2H), 7.37 (td, J = 8.0, 1.2 Hz, 1H), 7.30 (t, J = 8.0 Hz, 1H), 6.97 (dd, J = 3.1, 1.0 Hz, 1H), 6.96 (s, 1H), 6.91 (ddd, J = 7.2, 2.5, 1.0 Hz, 1H), 3.77 (s, 3H). LRMS (ESI): (calc.) 243.26 244.1 (MH)+ | 1 and 2 |
| 2j | 20 | 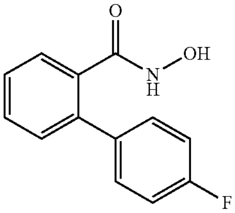 [SMILES: O=C(NO)c1ccccc1-c1ccc(F)cc1] | 4'-fluoro-N-hydroxybiphenyl-2-carboxamide | $^1$H NMR (400 MHz, DMSO-$d_6$) δ (ppm): 10.79 (s, 1H), 8.99 (s, 1H), 7.51 (td, J = 7.6, 1.6 Hz, 1H), 7.44-7.36 (m, 3H), 7.40 (d, J = 8.4 Hz, 2H), 7.23 (t, J = 9.0 Hz, 2H). LRMS (ESI): (calc.) 231.22 (found) 232.1 (MH)+ | 1 and 2 |
| 2k | 21 | 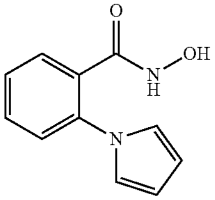 [SMILES: O=C(NO)c1ccccc1-n1cccc1] | N-hydroxy-2-(lH-pyrrol-1-yl)benzamide | $^1$H NMR (400 MHz, DMSO-$d_6$) δ (ppm): 10.90 (s, 1H), 9.21 (s, 1H), 7.53 (ddd, J = 9.0, 6.3, 2.7 Hz, 1H), 7.41 (d, J = 7.8 Hz, 1H), 7.39 (s, 1H), 7.37 (td, J = 7.6, 1.2 Hz, 1H), 6.99 (t, J = 2.2 Hz, 2H), 6.19 (t, J = 2.2 Hz, 2H). LRMS (ESI): (calc.) 202.21 (found) 203.1 (MH)+ | 2 |
| 2l | 22 | 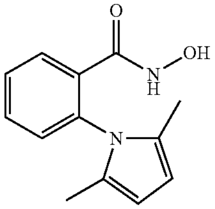 [SMILES: Cc1ccc(C)n1-c1ccccc1C(=O)NO] | 2-(2,5-dimethyl-lH-pyrrol-1-yl)-N-hydroxy-benzamidc | $^1$H NMR (400 MHz, DMSO-$d_6$) δ (ppm): 10.66 (s, 1H), 9.04 (s, 1H), 7.56 (ddd, J = 7.6, 6.7, 2.7 Hz, 1H), 7.52-7.48 (m, 2H), 7.16 (dd, J = 7.2, 1.0 Hz, 1H), 5.68 (s, 2H), 1.88 (s, 6H). LRMS (ESI): (calc.) 230.26 (found) 231.1 (MH)+ | 2 |

TABLE 2-continued

| Compounds according to Scheme 2. | | | | | |
|---|---|---|---|---|---|
| Ex. | Compound | Structure | Name | Characterization | Steps |
| 2m | 23 | 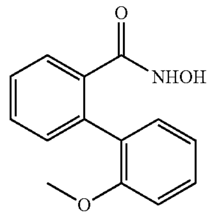 | N-hydroxy-2'-methoxybiphenyl-2-carboxamide | $^1$H NMR (400 MHz, DMSO-$d_6$) δ (ppm): 10.63 (s, 1H), 8.78 (s, 1H), 7.48-7.44 (m, 1H), 7.39-7.36 (m, 2H), 7.31-7.26 (m, 2H), 7.17 (dd, J = 7.4, 1.8 Hz, 1H), 7.00 (d, J = 7.8 Hz, 1H), 6.95 (td, J = 7.2, 1.0 Hz, 1H), 3.67 (s, 3H). LRMS (ESI): (calc.) 243.26 (found) 244.1 (MH)+ | 1 and 2 |
| 2n | 24 | 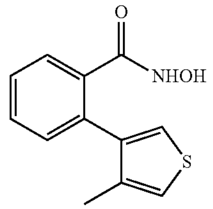 | N-hydroxy-2-(4-methylthiophen-3-yl)benzamide | $^1$H NMR (400 MHz, DMSO-$d_6$) δ (ppm): 10.67 (s, 1H), 8.94 (s, 1H), 7.47-7.39 (m, 3H), 7.26-7.24 (m, 2H), 7.17 (s, 1H), 2.04 (s, 3H). LRMS (ESI): (calc.) 233.29 (found) 234.1 (MH)+ | 1 and 2 |
| 2o | 25 | 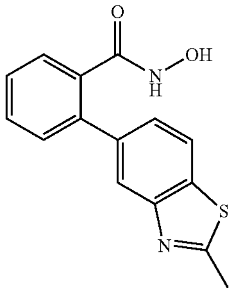 [SMILES: Cc1nc2cc(-c3ccccc3C(=O)NO)ccc2s1] | N-hydroxy-2-(2-methylbenzo[d]thiazol-5-yl) benzamide | $^1$H NMR (400 MHz, DMSO-$d_6$) δ (ppm): 10.81 (s, 1H), 8.98 (s, 1H), 8.04 (d. J = 8.2 Hz. 1H), 7.90 (d, J = 1.8 Hz, 1H), 7.54 to 7.39 (m, 5H), 2.81 (s, 3H). LRMS (ESI): (calc.) 284.33 (found) 285.1 (MH)+ | 1 and 2 |
| 2p | 26 | 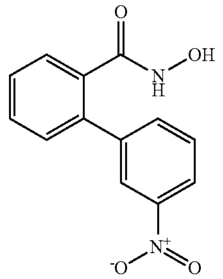 | N-hydroxy-3'-nitrobiphenyl-2-carboxamide | $^1$H NMR (400 MHz, DMSO-$d_6$) δ (ppm): 10.88 (s, 1H), 9.02 (d, J = 1.6 Hz, 1H), 8.24 to 8.21 (m, 1H), 8.19 to 8.18 (m, 2H), 7.83 to 7.81 (m, 1H), 7.73 to 7.69 (m, 1H), 7.60 to 7.56 (m, 1H), 7.52 to 7.45 (m, 2H). LRMS (ESI): (calc.) 258.23 (found) 259.1 (MH)+ | 1 and 2 |
| 2q | 27 | 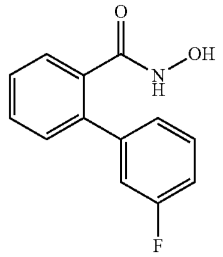 [SMILES: O=C(NO)c1ccccc1-c1cccc(F)c1] | 3'-fluoro-N-hydroxybiphenyl-2-carboxamide | $^1$H NMR (400 MHz, DMSO-$d_6$) δ (ppm): 10.82 (s, 1H), 9.03 (s, 1H), 7.53 to 7.51 (m, 1H), 7.47 to 7.36 (m, 5H), 7.24 to 7.17 (m, 2H). LRMS (ESI): (calc.) 231.22 (found) 232.1 (MH)+ | 1 and 2 |

TABLE 2-continued

| Compounds according to Scheme 2. | | | | | |
|---|---|---|---|---|---|
| Ex. | Compound | Structure | Name | Characterization | Steps |
| 2r | 28 | 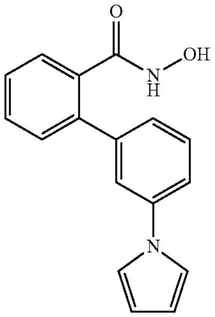 [SMILES: O=C(NO)c1ccccc1-c1cccc(-n2cccc2)c1] | N-hydroxy-3'-(lH-pyrrol-1-yl)biphenyl-2-carboxamide | $^1$H NMR (400 MHz, DMSO-$d_6$) δ (ppm): 10.83 (s, 1H), 9.05 (s, J = 1.6 Hz, 1H), 7.56 to 7.37 (m, 9H), 7.26 (d, J = 7.4 Hz, 1H), 6.28 (t, J = 2.2 Hz, 2H). LRMS (ESI): (calc.) 278.31 (found) 279.2 (MH)+ | 1 and 2 |
| 2s | 29 | 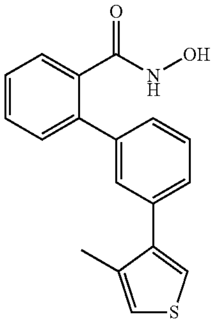 [SMILES: Cc1cscc1-c1cccc(-c2ccccc2C(=O)NO)c1] | N-hydroxy-3'-(4-methyl-thiophen-3-yl) biphcnyl-2-carboxamidc | $^1$H NMR (400 MHz, DMSO-$d_6$) δ (ppm): 10.82 (d, 1H), 9.01 (s, 1H), 7.55 to 7.37 (s, 9H), 7.29 to 7.28 (m, 1H), 2.27 (d, J = 0.78 Hz, 3H). LRMS (ESI): (calc.) 309.38 (found) 310.1 (MH)+ | 1 and 2 |
| 2t | 30 | 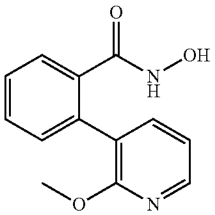 [SMILES: COc1ncccc1-c1ccccc1C(=O)NO] | N-hydroxy-2-(2-methoxypyridin-3-yl)benzamide | $^1$H NMR (400 MHz, DMSO-$d_6$) δ (ppm): 10.80 (s, 1H), 8.82 (s, 1H), 8.22 (dd, 1H), 7.58 (dd, 1H), 7.50 (m, 1H), 7.40 (m, 2H), 7.32 (d, 1H), 7.01 (m, 1H), 3.78 (s, 3H). LRMS (ESI): (calc.) 244.25 (found) 245.1 (MH)+ | 1 and 2 |
| 2u | 31 | 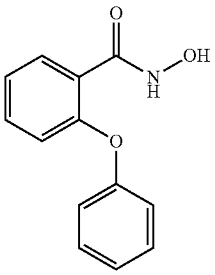 [SMILES: O=C(NO)c1ccccc1Oc1ccccc1] | N-hydroxy-2-phenoxy-benzamide | $^1$H NMR (400 MHz, DMSO-$d_6$) δ (ppm): 10.83 (s, 1H), 9.12 (s, 1H), 7.51 (dd, J = 7.4, 1.6 Hz, 1H), 7.44-7.40 (m, 1H), 7.39 (dd, J = 8.6, 7.4 Hz, 2H), 7.19 (td, J = 7.4, 1.0 Hz, 1H), 7.14 (tt, J = 7.4, 1.0 Hz, 1H), 7.01 (dd, J = 8.6, 1.0 Hz, 2H), 6.85 (dd, J = 8.4, 1.0 Hz, 1H). LRMS (ESI): (calc.) 229.23 (found) 230.1 (MH)+ | 2 |
| 2v | 32 | 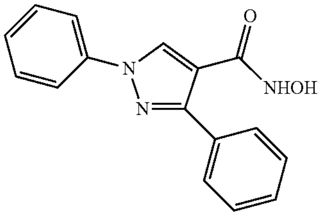 | N-hydroxy-1,3-diphenyl-1H-pyrazole-4-carboxamidc | $^1$H NMR (400 MHz, DMSO-$d_6$) δ (ppm): 8.54 (s, 1H), 7.84 (d, J = 7.8 Hz, 4H), 7.52 (t, J = 7.6 Hz, 2H), 7.45-7.35 (m, 4H). LRMS (ESI): (calc.) 279.3 (found) 280.3 (MH)+ | 2 |

TABLE 2-continued

Compounds according to Scheme 2.

| Ex. | Compound | Structure | Name | Characterization | Steps |
|---|---|---|---|---|---|
| 2w | 33 | 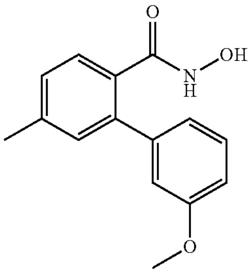 [SMILES: COc1cccc(-c2cc(C)ccc2C(=O)NO)c1] | N-hydroxy-3'-methoxy-5-mcthylbiphenyl-2-carboxamide | $^1$H NMR (400 MHz, DMSO-$d_6$) δ (ppm): 10.70 (s, 1H), 8.95 (s, 1H), 7.25 (m, 4H), 6.95 (m, 2H), 6.90 (m, 1H), 3.80 (s, 3H), 2.38 (s, 3H). LRMS (ESI): (calc.) 257.58 (found) 258.2 (MH)+ | 1 and 2 |
| 2x | 96 | 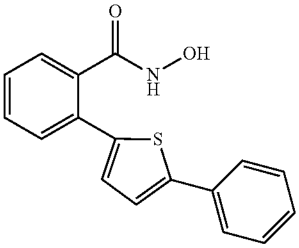 [SMILES: O=C(NO)c1ccccc1-c1ccc(-c2ccccc2)s1] | N-hydroxy-2-(5-phenylthiophen-2-yl)benzamide | $^1$H NMR (400 MHz, DMSO-$d_6$) δ (ppm): 10.96 (d, J = 1.4 Hz, IH), 9.15 (d, J = 1.6 Hz, 1H), 7.68 (dd, J = 8.4, 1.2 Hz, 2H), 7.59 (dd, J = 7.8, 0.8 Hz, 1H). 7.51 (d, J = 3.7 Hz, 1H), 7.50 (td, J = 7.8, 1.6 Hz, 1H), 7.44 (t, J = 7.4 Hz, 2H), 7.40 (td, J = 7.4, 1.02 Hz, 1H), 7.34 (dd, J = 7.6, 1.4 Hz, 1H), 7.33 (tt, J = 7.4, 1.2 Hz, 1H), 7.27 (d, J = 3.9 Hz, 1H). LRMS (ESI): (calc.) 295.36; (found) 296.1 (MH)+ | 1 and 2 |
| 2y | 97 | 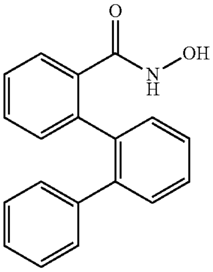 [SMILES: O=C(NO)c1ccccc1-c1ccccc1-c1ccccc1] | | $^1$H NMR (400 MHz, CD3OD) δ (ppm): 7.39-7.37 (m, 3H), 7.34-7.30 (m, 2H), 7.28-7.22 (m, 4H), 7.15-7.10 (m, 4H). LRMS (ESI): (calc.) 289.33 (found) 290.2 (MH)+ | 1 and 2 |
| 2z | 98 | 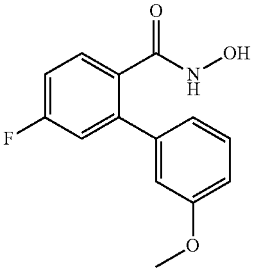 [SMILES: COc1cccc(-c2cc(F)ccc2C(=O)NO)c1] | 5-fluoro-N-hydroxy-3'-methoxybipheny l-2-carboxamidc | $^1$H NMR (400 MHz, DMSO-$d_6$) δ (ppm): 10.80 (s, 1H), 9.05 (s, 1H), 7.42 (m, 1H), 7.28 (m, 3H), 6.98 (m, 2H), 6.94 (dd, 1H), 3.78 (s, 3H). LRMS (ESI): (calc.) 261.25 (found) 262.1 (MH)+ | 1 and 2 |

Scheme 3

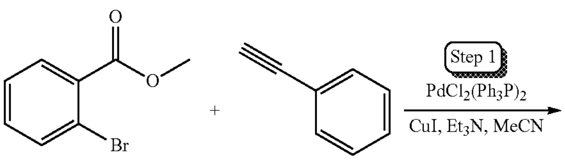

34 35

-continued

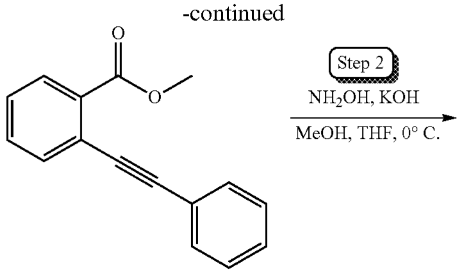

36

-continued

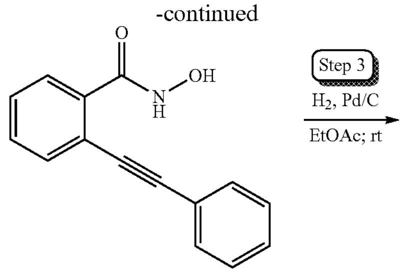

37: Example 3a

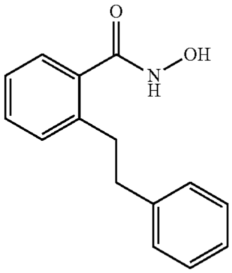

38: Example 3b

Example 3a

N-hydroxy-2-(phenylethynyl)benzamide 37

Example 3b

N-hydroxy-2-phenethylbenzamide 38

Step 1: Methyl 2-(phenylethynyl)benzoate 36

To a solution of methyl 2-bromobenzoate 34 (166 μL, 1.163 mmol) in acetonitrile (2906 μL) was added triethylamine (972 μL, 6.98 mmol) and phenylacetylene 35 (140 μl, 1.279 mmol). Then copper (I) iodide (11.07 mg, 0.058 mmol), and bis(triphenylphosphine)-palladium(II) chloride (20.40 mg, 0.029 mmol), were successively added, degassing between and after each addition of catalysts. The mixture was stirred at 75° C. overnight. The reaction mixture was partitioned between EtOAc and 1M HCl. The aqueous layer was extracted with fresh EtOAc and the combined organic layers were washed with water, brine, dried over $MgSO_4$. The residue was purified via Biotage using EtOAc/Hex ((0:100 to 10:90); 25+S column), to afford compound 36 (157 mg, 57%). LRMS (ESI): (calc.) 236.08 (found) 237.2 (MH)+

Step 2: N-hydroxy-2-(phenylethynyl)benzamide 37

In a 100 mL round-bottomed flask was added methyl 2-(phenylethynyl)benzoate 36 (157 mg, 0.665 mmol) in THF (1.33 mL) and MeOH (1.33 mL) and the solution was cooled to 0° C. Then, a 50% aqueous solution of hydroxylamine (2195 mg, 33.2 mmol) was added followed by a 4M aqueous solution of KOH (0.33 mL, 1.329 mmol) and the resulting colorless solution was stirred at 0° C. and allowed to slowly warm to rt for 20 h. The reaction mixture was partitioned between EtOAc and $H_2O$. The aqueous layer was extracted with EtOAc (2×) and the combined organic layers were washed with brine, dried over $MgSO_4$, filtered and concentrated in vacuo. The yellow oil was crystallized in $Et_2O$ and the filtrate was evaporated and triturated again in $Et_2O$. The solids were combined to afford title compound 37 (67 mg, 43% yield) as a white solid. $^1H$ NMR (400 MHz, DMSO-$d_6$) δ (ppm): 10.98 (s, 1H), 9.20 (s, 1H), 7.61 (d, J=7.4 Hz, 1H), 7.55-7.43 (m, 814). LRMS (ESI): (calc.) 237.25 (found) 238.2 (MH)+

Step 3: N-hydroxy-2-phenethylbenzamide 38

A solution of N-hydroxy-2-(phenylethynyl)benzamide 37 (40 mg, 0.169 mmol) in EtOAc (1533 μL) and MeOH (153 pit) was degassed under vacuum and put under $N_2$ atmosphere (3 cycles). Then a suspension of Pd/C (17.94 g, 0.017 mmol) in EtOAc (1 mL) was added and the resulting suspension was degassed and put under $H_2$ atmosphere (3 cycles) and the resulting black suspension was stirred at 21° C. for 2 h. The reaction mixture was filtered through Celite®. The filtrate was concentrated in vacuo then crystallized from a mixture of $Et_2O$ and hexane to afford title compound 38 (25 mgs, 62% yield) as a white solid. $^1H$ NMR: (DMSO-$d_6$) δ (ppm): 10.90 (s, 1H), 9.10 (s, 1H), 7.37-7.22 (m, 8H), 7.18 (t, J=7.2 Hz, 1H), 2.93 (dt, J=9.8, 6.3 Hz, 2H), 2.84 (dt, J=9.7, 5.7 Hz, 2H). LRMS (ESI): (calc.) 241.29 (found) 242.22 (MH)+

TABLE 3

Compounds according to Scheme 3.

| Ex. | Compound | Structure | Name | Characterization | Steps |
|---|---|---|---|---|---|
| 3c | 39 | 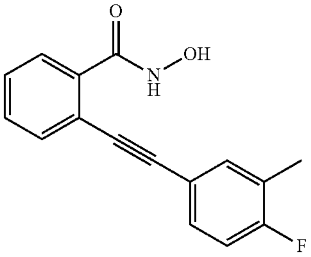 [SMILES: Cc1cc(C#Cc2ccccc2C(=O)NO)ccc1F] | 2-((4-fluoro-3-methylphenyl) elhynyl)-N-hydroxy benzamide | $^1H$ NMR (400 MHz, DMSO-$d_6$) δ (ppm): 10.97 (s, 1H), 9.20 (s, 1H), 7.58 (d, J = 7.2 Hz, 1H), 7.51-7.44 (m, 4H), 7.39 (ddd, J = 8.4, 5.1 2.2 Hz, 1H), 7.22 (t, J = 9.6 Hz, 1H), 2.25 (s, 3H). LRMS (ESI): (calc.) 269.27 (found) 270.1 (MH)+ | 1,2,3 |

Scheme 4

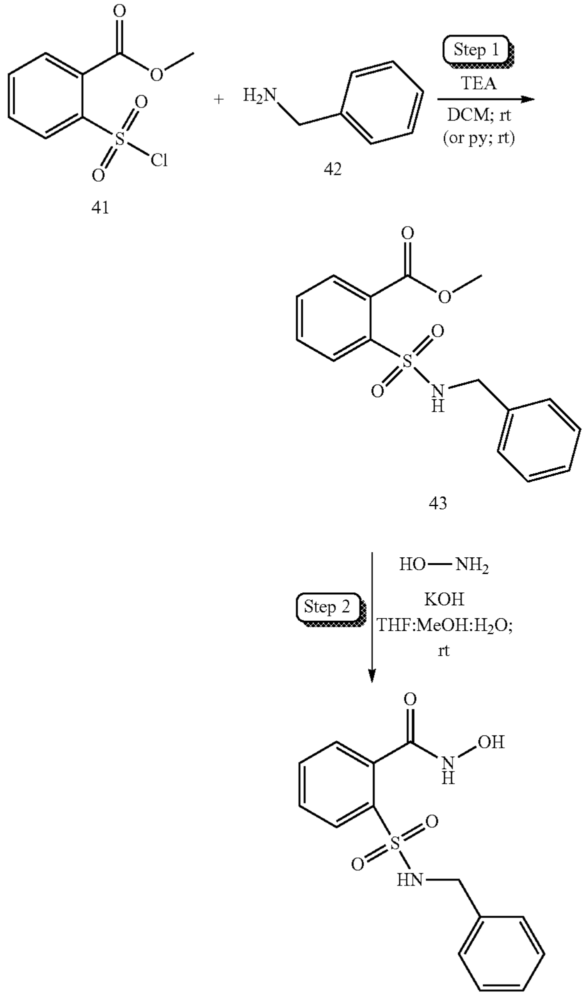

41 42 43

44: Example 4a

Example 4a

2-(N-benzylsulfamoyl)-N-hydroxybenzamide 44

Step 1: methyl 2-(N-benzylsulfamoyl)benzoate 43

To a solution of benzylamine 42 (0.140 mL, 1.278 mmol) in DCM (2.557 mL) was added triethylamine (0.535 mL, 3.84 mmol) and methyl 2-(chlorosulfonyl)benzoate 41 (300 mg, 1.278 mmol) and the resulting colorless solution was stirred at rt for 20 h. The reaction mixture was partitioned between DCM and $H_2O$. The organic layer was washed with 1M HCl, saturated $NaHCO_3$, and brine, dried over $MgSO_4$, filtered and concentrated. The crude mixture was purified by Biotage using EtOAc/Hex ((20:80 to 40:60); 25+S column) to afford compound 43 (49 mgs, 13% yield) as a colorless oil. LRMS (ESI): (calc.) 305.07 (found) 306.2 (MH)+

Step 2: 2-(N-benzylsulfamoyl)-N-hydroxybenzamide 44

In a 50 mL round-bottomed flask was added methyl 2-(N-benzylsulfamoyl)benzoate 43 (49 mg, 0.160 mmol) in THF (321 μl) and MeOH (321 μl) and the solution was cooled to 0° C. Then, a 50% aqueous solution of hydroxylamine (530 mg, 8.02 mmol) was added, followed by a 4M aqueous solution of KOH (80 μl, 0.321 mmol) and the resulting colorless solution was stirred at 0° C., allowing to slowly warm to rt and stirred for 18 h. The reaction mixture was partitioned between EtOAc and $H_2O$. The aqueous layer was extracted with EtOAc and combined organic layers were washed with brine, dried over $MgSO_4$, filtered and concentrated in vacuo to provide a colorless oil. A solid was obtained by successive dissolution in $Et_2O$/Hex mixture and concentration which was triturated in $Et_2O$ to afford title compound 44 (18 mgs, 37% yield) as a white solid. $^1H$ NMR (400 MHz, DMSO-$d_6$) δ (ppm): 11.25 (s, 1H), 9.34 (s, 1H), 7.83 (dd, J=7.6, 1.2 Hz, 1H), 7.67 (td, J=7.4, 1.4 Hz, 1H), 7.61 (td, J=7.6, 1.6 Hz, 1H), 7.50 (dd, J=7.4, 1.6 Hz, 1H), 7.49 (bs, 1H), 7.27-7.18 (m, 5H), 4.05 (d, J=5.9 Hz, 2H). LRMS (ESI): (calc.) 306.34 (found) 307.14 (MH)+

TABLE 4

Compound according to Scheme 4.

| Ex. | Compound | Structure | Name | Characterization |
|---|---|---|---|---|
| 4b | 45 | 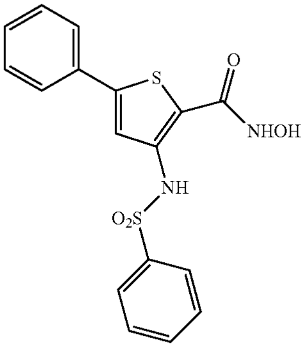 | N-hydroxy-5-phenyl-3-(phenyl-sulfonamido) thiophene-2-carboxamide | $^1H$ NMR (400 MHz, DMSO-$d_6$) δ (ppm): 7.89-7.86 (m, 2H), 7.68-7.63 (m, 3H), 7.60-7.54 (m, 3H), 7.49-7.40 (m, 3H). LRMS (ESI): (calc.) 374.4 (found) 375.3 (MH)+ |

Scheme 5

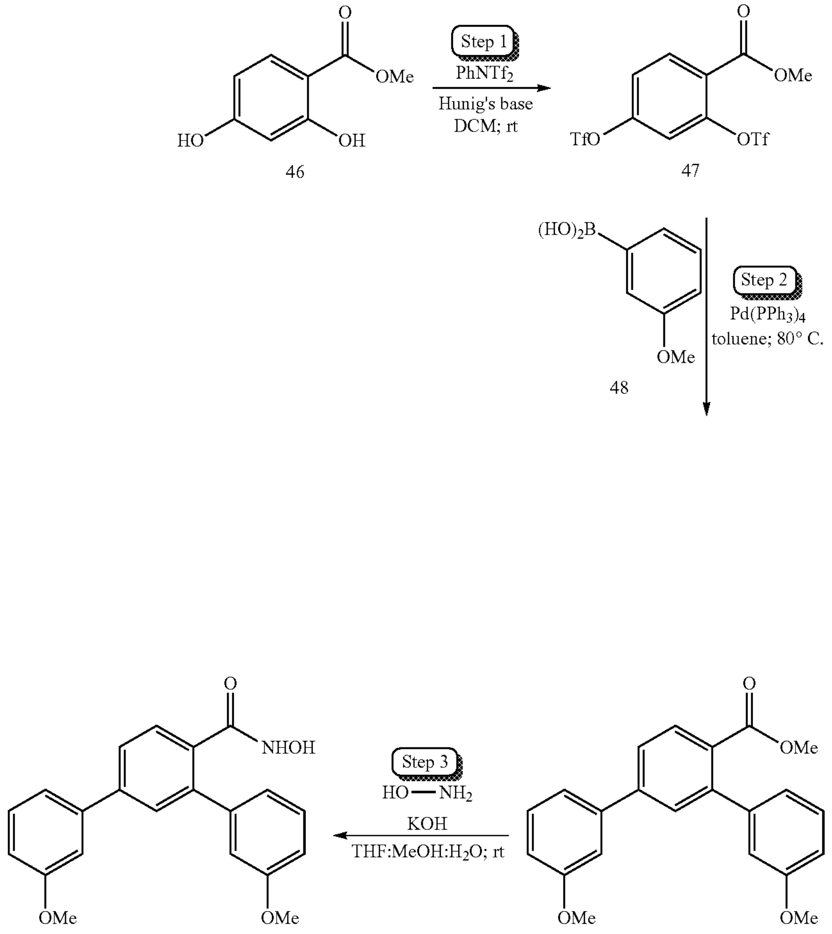

46 47 48 49 50: Example 5a

Example 5a

Compound 50

Step 1: Methyl 2,4-bis(trifluoromethylsulfonyloxy)benzoate 47

A solution of methyl 2,4-dihydroxybenzoate 46 (0.5 g, 2.97 mmol), N-phenyltrifluoro-methanesulfonamide (2.125 g, 5.95 mmol) and DIPEA (1.039 mL, 5.95 mmol) in DCM (15 mL) was stirred at room temperature for 2 days then washed with saturated $NaHCO_3$, brine, dried over $MgSO_4$, filtered and solvent evaporated to provide methyl 2,4-bis(trifluoromethylsulfonyloxy)benzoate 47 (1.14 g, 89% yield) after purification by Biotage (0 to 10% EtOAc in Hexane). LRMS (ESI): (calc.) 431.94 (found) 455.0 (MNa)+

Step 2: Compound 49

To a degassed solution of methyl 2,4-bis(trifluoromethylsulfonyloxy)benzoate 47 (0.3 g, 0.694 mmol), 3-methoxyphenylboronic acid 48 (0.422 g, 2.78 mmol) and potassium carbonate (0.288 g, 2.082 mmol) in toluene (7 mL) was added $Pd(Ph_3P)_4$ (0.241 g, 0.208 mmol). The reaction mixture was stirred at 90° C. for 2 h, cooled to rt, diluted with EtOAc, washed with $NaHCO_3$, brine, dried over $Na_2SO_4$ and purified by flash chromatography (10% EtOAc/Hex) to afford compound 49 (0.22 g, 91% yield) as a colorless oil.

Step 3: Compound 50

To a solution of compound 49 (0.22 g, 0.631 mmol), in methanol (1.263 ml) and THF (1.263 ml) was added potassium hydroxide (0.316 ml, 1.263 mmol) followed by the addition of a 50% solution of hydroxylamine in water (2.086 g, 31.6 mmol). The mixture was stirred at rt for 18 h. It was then diluted with $H_2O$ and extracted with EtOAc. The organic phase was dried over $Na_2SO_4$ and concentrated. The crude product was purified by flash chromatography (5% MeOH/DCM) to afford title compound 50 (46 mg, 21% yield) as light brown solid. $^1H$ NMR (DMSO) d(ppm) 111: 10.82 (s, 1H), 9.01 (s, 1H), 7.69 (dd, 1H), 7.64 (d, 1H), 7.35 (m, 4H), 7.25 (m, 1H), 7.60 (m, 2H), 6.95 (m, 2H), 3.82 (s, 3H), 3.78 (s, 3H). LRMS (ESI): (calc.) 349.38 (found) 350.3 (MH)+

TABLE 5
| Compounds according to Scheme 5. | | | | |
|---|---|---|---|---|
| Ex. | Compound | Structure | Name | Characterization |
| 5b | 51 | 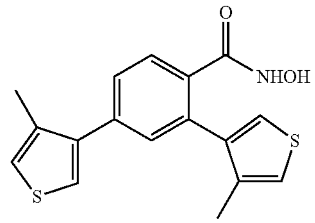 | N-hydroxy-2,4-bis(4-methylthiophen-3-yl)benzamide | $^1$H NMR (400 MHz, DMSO-$d_6$) δ (ppm): 10.72 (s, 1 H), 8.98 (s, 1 H), 7.58 (d, 1 H), 7.45 (m, 2 H), 7.28 (m, 3 H), 7.18 (m, 1 H), 2.26 (s, 3 H), 2.09 (s, 3 H). LRMS (ESI): (calc.) 329.44 (found) 330.1 (MH)+ |
| 5c | 52 | 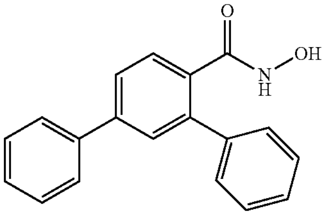 [SMILES: O=C(NO)c1ccc(-c2ccccc2)cc1-c1ccccc1] | | $^1$H NMR (400 MHz, DMSO-$d_6$) δ (ppm): 10.82 (s, 1 H), 9.01 (s, 1 H), 7.75 (m, 2 H), 7.70 (dd, 1 H), 7.63 9 d, 1 H), 7.48 (m, 5 H), 7.40 (m, 4 H). LRMS (ESI): (calc.) 289.33 (found) 290.2 (MH)+ |
Scheme 6
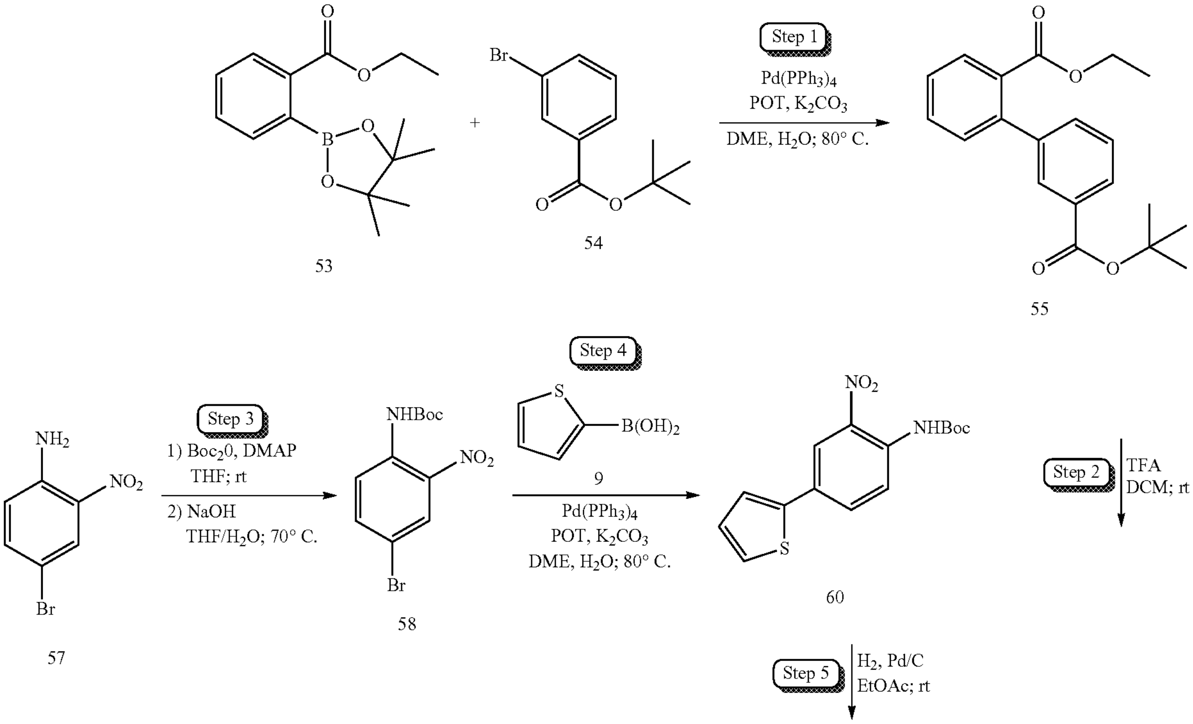

-continued

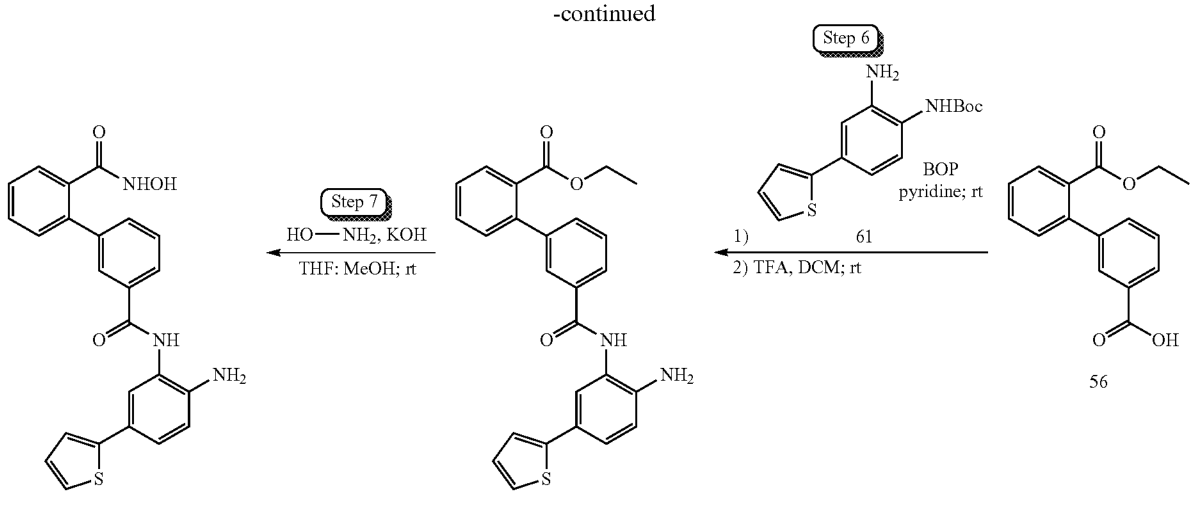

63: Example 6b

62: Example 6a

56

Example 6a

Ethyl 3'-(2-amino-5-(thiophen-2-yl)phenylcarbamoyl)biphenyl-2-carboxylate 62

Example 6b

N3'-(2-amino-5-(thiophen-2-yl)phenyl)-N2-hydroxy-biphenyl-2,3'-dicarboxamide 63

Step 1: 3'-tert-butyl 2-ethyl biphenyl-2,3'-dicarboxylate 55

The procedure was followed as outlined in Scheme 2, Step 1 replacing compounds 8 and 9 with compounds 54 and 53 to afford 3'-tert-butyl 2-ethyl biphenyl-2,3'-dicarboxylate 55 (0.2 g, 63% yield) as a light yellow oil.

Step 2: 2'-(ethoxycarbonyl)biphenyl-3-carboxylic Acid 56

To a solution of 3'-tert-butyl 2-ethyl biphenyl-2,3'-dicarboxylate 55 (0.2 g, 0.613 mmol) in DCM (2 ml), trifluoroacetic acid (0.472 ml, 6.13 mmol) was added and stirred at rt for 5 h. It was then concentrated in vacuo, taken up in DCM and concentrated again (2×). The crude compound was then dried overnight on the vacuum pump to afford compound 56 (0.166 g, 100% yield) as a white solid.

Step 3: tert-butyl 4-bromo-2-nitrophenylcarbamate 58

To a stirring solution of 4-bromo-2-nitroaniline 57 (10.0 g, 46.1 mmol) and di-tert-butyl dicarbonate (20.11 g, 92.2 mmol) in THF (100 mL) was added a catalytic amount of DMAP and the reaction mixture was allowed to stir at room temperature for 18 h. The solvent was removed then the crude di-Boc intermediate (MS: 439/441 (M+Na)) was placed under vacuum then taken up in THF (46 mL). To this was added a solution of 2N NaOH (46 mL) and the reaction mixture was heated to 70° C. for 4 h. Solid NaOH (1.8 g) was added and the solution was further heated for 18 h then solvent evaporated to remove the THF and the resulting yellow solid was filtered (washed with water) to afford tert-butyl 4-bromo-2-nitrophenylcarbamate 58 (15.38 g, >100% yield (not dry)). LRMS (ESI): (calc.) 316.1 (found) 339.0/341.0 (MNa)+

Step 4: tert-butyl 2-nitro-4-(thiophen-2-yl)phenylcarbamate 60

The procedure was followed as outlined in Scheme 2, Step 1 replacing compound 8 with compound 58 to afford tert-butyl 2-nitro-4-(thiophen-2-yl)phenylcarbamate 60 (3.3 g, 77% yield) as a yellow solid. LRMS (ESI): (calc.) 320.08 (found) 343.1 (MNa)+

Step 5: tert-butyl 2-amino-4-(thiophen-2-yl)phenylcarbamate 61

The procedure was followed as outlined in Scheme 3, Step 3 replacing compound 37 with compound 60 to afford tert-butyl 2-amino-4-(thiophen-2-yl)phenylcarbamate 61 (2.75 g, 92% yield) as a yellow solid. LRMS (ESI): (calc.) 290.11 (found) 235.1 (M(-tBu)Na)+

Step 6: ethyl 3'-(2-(tert-butoxycarbonylamino)-5-(thiophen-2-yl)phenylcarbamoyl)biphenyl-2-carboxylate 62

To a solution of 2'-(ethoxycarbonyl)biphenyl-3-carboxylic acid 56 (0.166 g, 0.614 mmol) in pyridine (3 ml), tert-butyl 2-amino-4-(thiophen-2-yl)phenylcarbamate 61 (0.4 g, 1.378 mmol) and BOP (0.815 g, 1.843 mmol) were added. The reaction mixture was stirred at rt for 2 days, concentrated and diluted with DCM then washed with $NaHCO_3$, brine and dried with $Na_2SO_4$. Flash purification (5% EtOAc/DCM) afforded the tert-Boc intermediate (0.333 g, 0.614 mmol) which was taken up in DCM (1.75 mL). Neat trifluoroacetic acid (0.946 mL, 12.28 mmol) was added and the reaction mixture was allowed to stir at room temperature for 1 h then diluted with DCM and a solution of KOH in brine (0.672 g, in 10 mL brine) and stirred until pH>9. The organic phase was separated and dried over $Na_2SO_4$. Flash purification (15% EtOAc/DCM) afforded title compound 62 (0.195 g, 72% yield) as a light brown solid. $^1H$ NMR: (DMSO) d(ppm) 1H, 9.83 (s, 1H), 8.02 (d, 1H), 7.98 (s, 1H), 7.80 (dd, 1H), 7.66 (t, 1H), 7.55 (m, 4H), 7.45 (d, 1H), 7.36 (dd, 1H), 7.31 (dd, 1H), 7.24 (dd, 1H), 7.05 (dd, 1H), 6.82 (d, 1H), 5.15 (s, 2H), 4.09 (m, 2H), 1.02 (t, 3H). LRMS (ESI): (calc.) 442.53 (found) 443.2 (MH)+

Step 7: N3'-(2-amino-5-(thiophen-2-yl)phenyl)-N2-hydroxybiphenyl-2,3'-dicarboxamide 63

To a solution of ethyl 3'-(2-amino-5-(thiophen-2-yl)phenylcarbamoyl)biphenyl-2-carboxylate 62 (0.195 g, 0.441 mmol), in methanol (1.102 ml) and THF (1.102 ml), potassium hydroxide (0.220 ml, 0.881 mmol) was added followed by a 50% hydroxylamine solution in water (1.455 g, 22.03 mmol). The mixture was stirred at rt for 18 h. It was then diluted with aqueous $NaHCO_3$, and extracted with EtOAc. The organic phase was dried over $Na_2SO_4$ and concentrated. The crude product was purified by flash chromatography (15% MeOH/DCM) to afford title compound 63 (0.04 g, 21% yield) as a white solid. $^1$H NMR: (DMSO) d(ppm) 1H, 10.80 (s, 1H), 9.80 (s, 1H), 9.01 (s, 1H), 8.04 (s, 1H), 7.98 (d, 1H), 7.55 (m, 5H), 7.44 (m, 2H), 7.35 (d, 1H), 7.30 (dd, 1H), 7.25 (d, 1H), 7.04 (m, 1H), 6.82 (d, 1H), 5.18 (s, 2H). LRMS (ESI): (calc.) 429.49 (found) 430.2 (MH)+.

Scheme 7

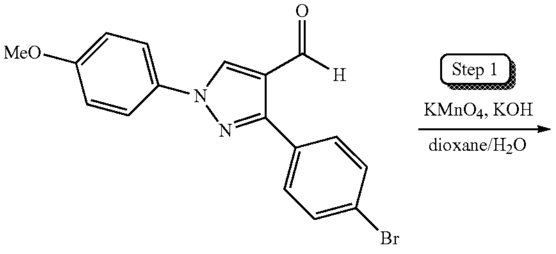

64

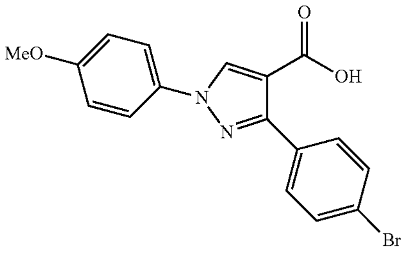

65

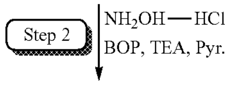

-continued

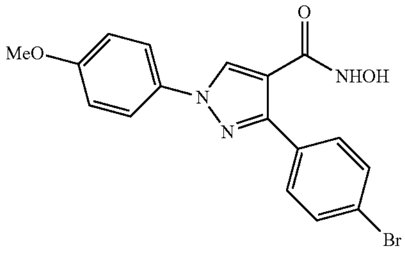

66: Example 7a

Example 7a 3-(4-bromophenyl)-N-hydroxy-1-(4-methoxyphenyl)-1H-pyrazole-4-carboxamide 66

Step 1: 3-(4-bromophenyl)-1-(4-methoxyphenyl)-1H-pyrazole-4-carboxylic acid 65

Procedure involves adding first KOH (0.177 g, 3.15 mmol) and then potassium permanganate (0.498 g, 3.15 mmol) to a suspension of aldehyde 64 (0.750 g, 2.1 mmol) in dioxane/water (8.5/2.1 mLs). The resulting solution was stirred at r.t. for 1 h prior to dilution with aq. HCl until pH=1, and extraction with EtOAc. The combined organic extracts were dried with anhydrous $Na_2SO_4$, filtered, and concentrated. The residue was taken up in EtOAc, and triturated with hexanes to afford compound 65 (0.622 g, 79% yield) as a white solid which was collected by filtration. LRMS (ESI): (calc.) 372.01 (found) 375.2 (MH)+

Step 2: 3-(4-bromophenyl)-N-hydroxy-1-(4-methoxyphenyl)-1H-pyrazole-4-carboxamide 66

A solution of 3-(4-bromophenyl)-1-(4-methoxyphenyl)-1H-pyrazole-4-carboxylic acid 65 (0.30 g, 0.804 mmol), hydroxylamine hydrochloride (0.112 g, 1.608 mmol), BOP (0.427 g, 0.965 mmol) and triethylamine (0.336 mLs, 2.412 mmol) in pyridine (10 mLs) was stirred at room temperature for 2 h. All solvents were then removed under reduced pressure, and the residue diluted with brine and aq. HCl until pH=1. Following extraction with EtOAc, the combined organic extracts were dried with anhydrous $Na_2SO_4$, filtered, and concentrated. The residue was purified by column chromatography on silica gel using 50-100% EtOAc/hexanes as the eluent to afford title compound 66 (10 mgs, 3% yield) as a light orange solid.

1H NMR: (MeOD-d4) 8.46 (s, 1H), 7.84-7.73 (m, 4H), 7.64-7.57 (m, 2H), 7.13-7.06 (m, 2H), 3.89 (s, 3H). LRMS (ESI): (calc.) 388.2 (found) 386.1/388.1 (MH)-

Scheme 8

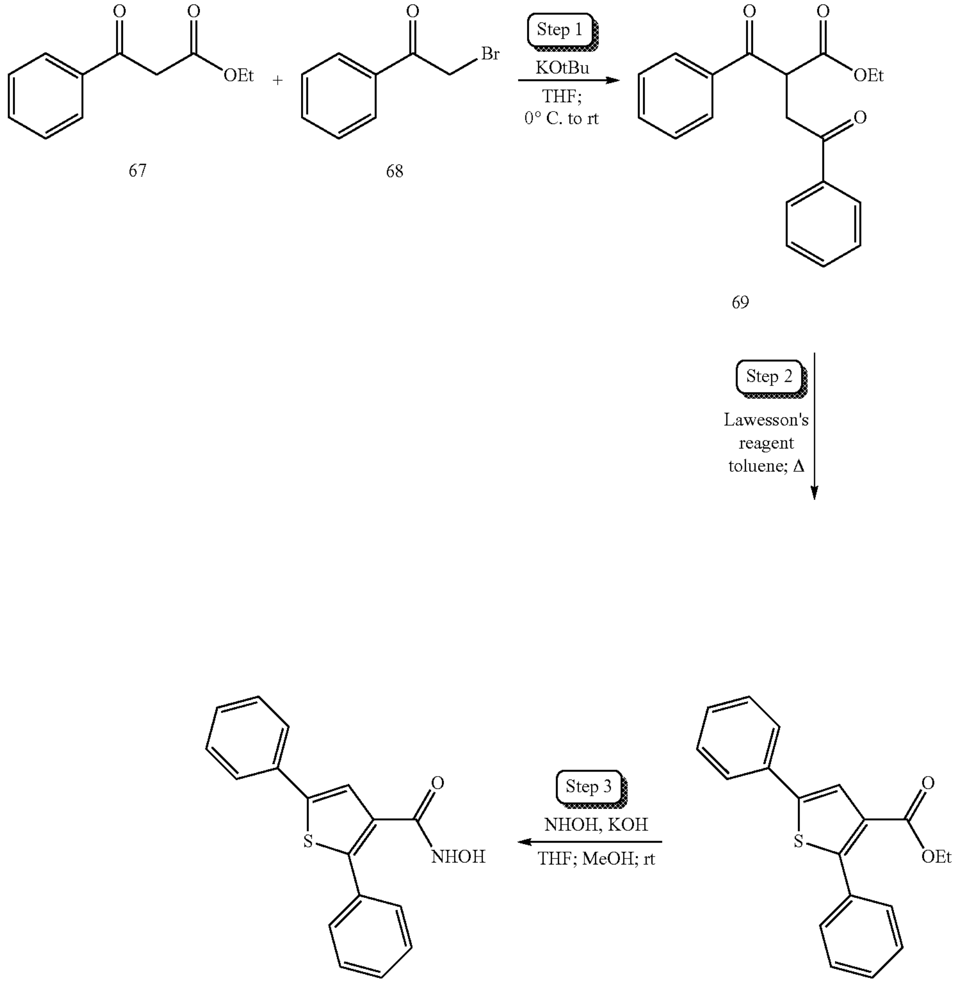

67 68 69

71: Example 8a 70

Example 8a

N-hydroxy-2,5-diphenylthiophene-3-carboxamide 71

Step 1: Ethyl 2-benzoyl-4-oxo-4-phenylbutanoate 69

To a stirring solution of ethyl 3-oxo-3-phenylpropanoate 67 (0.754 g, 3.92 mmol) in THF cooled to 0° C. was added potassium tert-butoxide (0.556 g, 4.71 mmol) and the reaction mixture was stirred for 10 minutes followed by the addition of 2-bromo-1-phenylethanone 68 (0.859 g, 4.32 mmol). The reaction mixture was allowed to stir at room temperature for 90 minutes then quenched with ethanol (2) and poured into ethyl acetate and layer separated. The organic layer was washed with water, brine, dried over $Na_2SO_4$, then purified by ISCO (40 g column, 0 to 35% ethyl acetate in hexane) to afford compound 69 (0.812 g, 67% yield) as a yellow oil. LRMS (ESI): (calc.) 310.12 (found) 311.08 (MH)+

Step 2: ethyl 2,5-diphenylthiophene-3-carboxylate 70

To a stirring solution of ethyl 2-benzoyl-4-oxo-4-phenylbutanoate 69 (0.812 g, 2.62 mmol) in toluene (20 mLs) was added Lawesson's reagent (1.270 g, 3.14 mmol) and the reaction mixture was refluxed for 4 h then concentrated. The crude residue was purified by ISCO (40 g column, 0 to 30% ethyl acetate in hexane) to afford ethyl 2,5-diphenylthiophene-3-carboxylate 70 (0.44 g 55% yield) as a yellow oil. LRMS (ESI): (calc.) 308.09 (found) 309.27 (MH)+

Step 3: N-hydroxy-2,5-diphenylthiophene-3-carboxamide 71

To a stirring solution of ethyl 2,5-diphenylthiophene-3-carboxylate 70 (0.440 g, 1.427 mmol) in methanol (7 mL) and THF (7 mL) was added 50% hydroxylamine in water (1.4 mL, 23.31 mmol) and the resulting mixture was stirred at room temperature for 45 minutes then concentrated to one third volume. The solution was neutralized with 3N HCl to pH 7 and the desired product was filtered then purified by Gilson (55 to 95% MeOH in $H_2O$) to afford the title compound 71 (87 mg, 21% yield) as a white solid. $^1H$ NMR: (DMSO-d6) d(ppm) 1H, 10.96 (s, 1H), 9.14 (s, 1H), 7.71-7.69 (m, 2H), 7.57-7.55 (m, 3H), 7.48-7.34 (m, 6H) LRMS (ESI): (calc) 295.36 (found) 296.22 (MH)+

Scheme 9

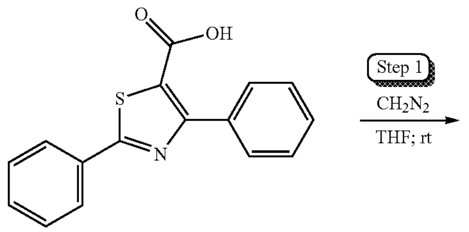

72

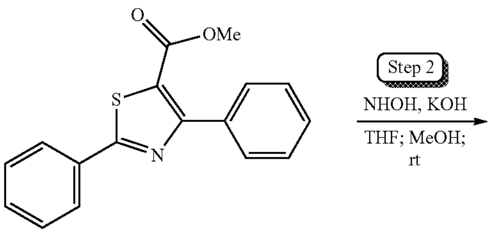

73

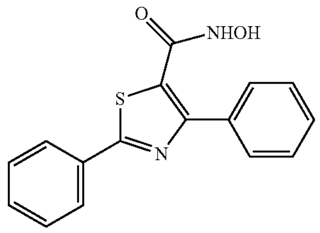

74: Example 9a

Example 9a

N-hydroxy-2,4-diphenylthiazole-5-carboxamide 74

Step 1: methyl 2,4-diphenylthiazole-5-carboxylate 73

To a pre-cooled (0° C.) solution of 2,4-Diphenyl-1,3-thiazole-5-carboxylic acid 72 (400 mg, 1.422 mmol) in EtOAc (7.109 ml) was added a 0.5 M solution of diazomethane (5.69 ml, 2.84 mmol) in $Et_2O$ (freshly prepared) (c.a. 5 mL) and the resulting white suspension was stirred at 0° C. for 1 h. TLC showed completion. Then, the small amount of white solid left was filtered off and the filtrate was concentrated in vacuo to afford methyl 2,4-diphenylthiazole-5-carboxylate 73 (0.449 g, 107% yield).

Step 2: N-hydroxy-2,4-diphenylthiazole-5-carboxamide 74

A 100 mL round-bottomed flask was charged with methyl 2,4-diphenylthiazole-5-carboxylate 73 (420 mg, 1.422 mmol) in MeOH (2.844 ml) and THF (2.84 ml) and the solution was cooled down to 0° C. Then a 50% aqueous solution of hydroxylamine (4697 mg, 71.1 mmol) and 4M potassium hydroxide solution (0.427 ml, 1.706 mmol) were added and the reaction mixture was allowed to warm up to rt while stirring for 18 h. The reaction mixture was partitioned between EtOAc and water. The aqueous layer was extracted with fresh EtOAc and the combined organic layers were washed with 1M HCl, sat $NaHCO_3$, and brine, dried over $MgSO_4$, filtered and concentrated. The resulting solid was triturated ($Et_2O$) to afford the title compound 74 (0.303 g, 72% yield). $^1$H NMR: (DMSO-d6) d(ppm) 1H, 11.29 (s, 1H), 9.44 (s, 1H), 8.03 (dd, J=6.3, 2.7 Hz, 2H), 7.84 (d, J=7.0 Hz, 2H), 7.56-7.55 (m, 3H), 7.50-7.43 (m, 3H). LRMS (ESI): (calc.) 296.34 (found) 297.1 (MH)+

TABLE 6

Compound according to Scheme 9.

| Ex | Compound | Structure | Name | Characterization |
|---|---|---|---|---|
| 9b | 75 | 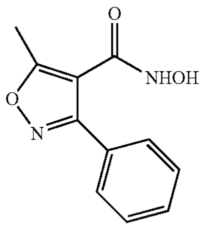 | N-hydroxy-5-methyl-3-phenylisoxazole-4-carboxamide | $^1$H NMR (400 MHz, CD3OD) δ (ppm): 7.47-7.45 (m, 2 H), 7.34-7.29 (m, 3 H), 2.55 (s, 3 H) LRMS (ESI): (calc.) 218.0 (found) 219.0 (MH)+ |

Scheme 10

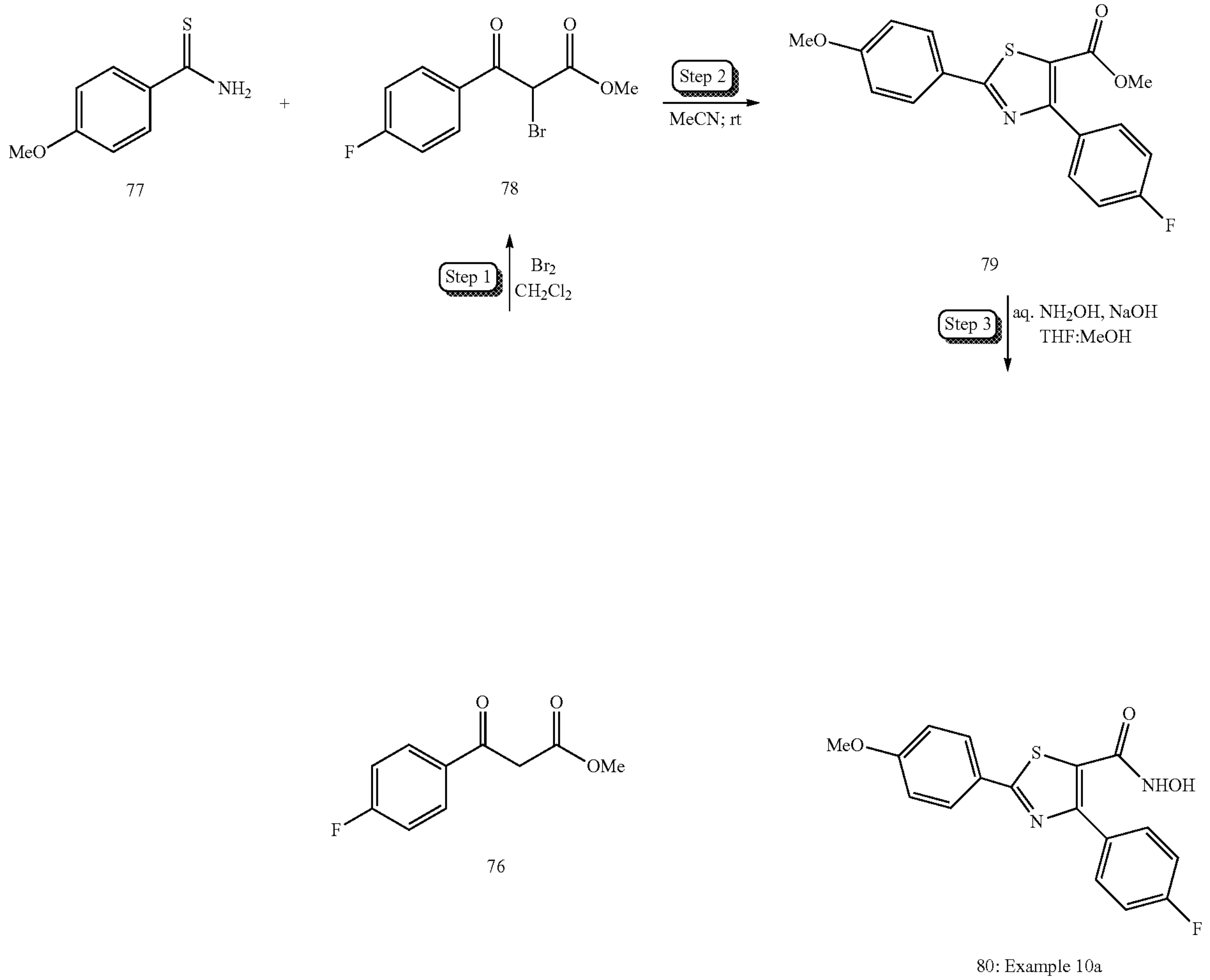

Example 10a

4-(4-fluorophenyl)-N-hydroxy-2-(4-methoxyphenyl) thiazole-5-carboxamide 80

Step 1: methyl 2-bromo-3-(4-fluorophenyl)-3-oxopropanoate 78

To a solution of methyl 3-(4-fluorophenyl)-3-oxopropanoate 76 (1 equiv, 500 mg, 2.55 mmol) in DCM (17 mL) was added a solution of bromine (1.3 equiv, 530 mg, 3.31 mmol) in DCM (1.5 mL) in a drop wise manner at 0° C. The reaction mixture was stirred further for an additional 1 h and then treated with 10% aqueous $K_2CO_3$ (5 mL) solution. The organic phase was separated, dried over $Na_2SO_4$, filtered and concentrated under reduced pressure to afford methyl 2-bromo-3-(4-fluorophenyl)-3-oxopropanoate 78 (700 mg, 100% yield). LRMS (ESI): (calc) 273.96 (found) 275.108 (MH+)+.

Step 2: methyl 4-(4-fluorophenyl)-2-(4-methoxyphenyl)thiazole-5-carboxylate 79

To a stirring solution of methyl 2-bromo-3-(4-fluorophenyl)-3-oxopropanoate 78 (1 equiv, 1.15 g, 4.2 mmol) in MeCN at room temperature was added 4-methoxybenzothioamide 77 (1 equiv, 700 mg, 4.2 mmol) and the reaction mixture was stirred for 18 h. The solvent was evaporated and the residue purified by trituration with diethyl ether to afford methyl 4-(4-fluorophenyl)-2-(4-methoxyphenyl)thiazole-5-carboxylate 79 (320 mg, 22% yield). LRMS (ESI): (calc) 343.37 (found) 344.235 (MH+)+.

Step 3: 4-(4-fluorophenyl)-N-hydroxy-2-(4-methoxyphenypthiazole-5-carboxamide 80

The procedure was followed as outlined in Scheme 5, Step 3 replacing compound 49 with compound 79 to afford title compound 4-(4-fluorophenyl)-N-hydroxy-2-(4-methoxyphenyl)thiazole-5-carboxamide 80 (86% yield) after overnight trituration in water. $^1H$ NMR (400 MHz, CD3OD) δ (ppm): 7.95 (d, J=8.8 Hz, 2H), 7.85 (m, 2H), 7.18 (t, J=8.8, Hz, 2H), 7.04 (d, 8.8 Hz, 2H), 3.87 (s, 3H). LRMS (ESI): (calc) 344.36 (found) 345.2 (MH+)+.

TABLE 6

| Compounds according to Scheme 10 | | | | |
|---|---|---|---|---|
| Ex | Compound | Structure | Name | Characterization |
| 10b | 81 | 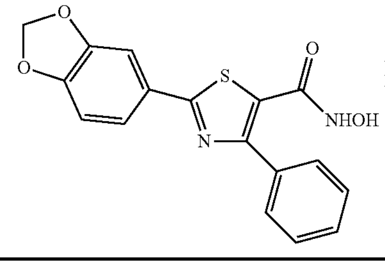 | 2-(benzo[d][1,3]-dioxol-5-yl)-N-hydroxy-4-phenylthiazole-5-carboxamide | (CD3OD) δ (ppm) 1 H: 7.85 (d, J = 7.2 Hz, 2 H), 7.53 (m, 2 H), 7.44-7.34 (m, 3 H), 6.92 (d, J = 8.0 Hz, 1 H), 6.05 (s, 2 H) LRMS (ESI): (calc.) 340.0 (found) 341.2 (MH)+ |

Scheme 11

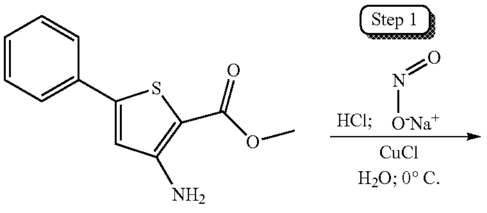

82

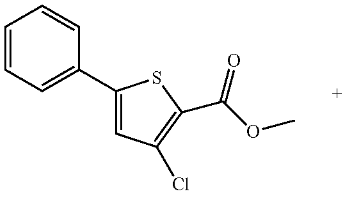

83

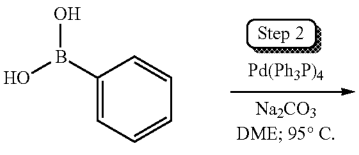

84

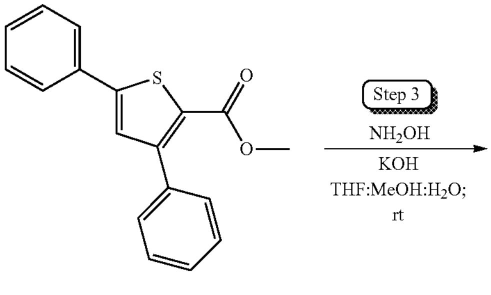

85

-continued

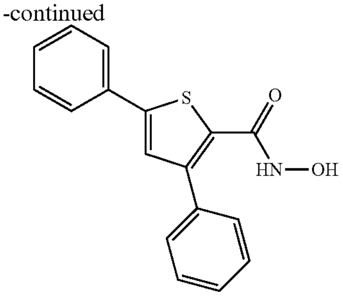

86: Example 11a

Example 11a

N-hydroxy-3,5-diphenylthiophene-2-carboxamide 86

Step 1: methyl 3-chloro-5-phenylthiophene-2-carboxylate 83

To a stirring solution of methyl 3-amino-5-phenylthiophene-2-carboxylate 82 (1.166 g, 5 mmol) in water (14 mL) and concentrated hydrochloric acid (7 mL) cooled to 0° C. was added a solution of sodium nitrite (0.431 g, 6.25 mmol) in water (2 mL). The reaction mixture was stirred for 30 min then the resulting solution was poured into a solution of CuCl (1.732 g, 17.50 mmol) in concentrated hydrochloric acid (20 mL) still at 0° C. The reaction was allowed to slowly warm to room temperature over 4 h then poured into ice cold water and extracted with ether (3×). The combined organic phases were washed with water, dried over $Na_2SO_4$, filtered and concentrated under reduced pressure to afford methyl 3-chloro-5-phenylthiophene-2-carboxylate 83 as a white solid (0.850 mg, 67% yield) after purification by ISCO (40 g column, 5 to 40% ethyl acetate in hexane). LRMS (ESI): (calc) 252.72 (found) 253.06 (MH)+

Step 2: methyl 3,5-diphenylthiophene-2-carboxylate 85

The procedure was followed as outlined in Scheme 2, Step 1 replacing compounds 8 and 9 with compounds 83 and 84 to afford methyl 3,5-diphenylthiophene-2-carboxylate 85 (90% yield) as a white solid after purification by ISCO (12 g column, 0 to 30% ethyl acetate in hexane). LRMS (ESI): (calc) 294.37 (found) 295.21 (MH)+

Step 3:
N-hydroxy-3,5-diphenylthiophene-2-carboxamide 86

The procedure was followed as outlined in Scheme 5, Step 3 replacing compound 49 with compound 85 to afford title compound N-hydroxy-3,5-diphenylthiophene-2-carboxamide 86 (21% yield) as a white solid after purification by Gilson (60 to 95% MeOH in water). $^1$H NMR (400 MHz, DMSO-$d_6$) δ (ppm): 10.96 (s, 1H), 9.22 (s, 1H), 7.76-7.74 (m, 2H), 7.70 (s, 1H), 7.57-7.54 (m, 2H), 7.48-7.34 (m, 6H). LRMS (ESI): (calc) 295.36 (found) 296.19 (MH)+

Scheme 12

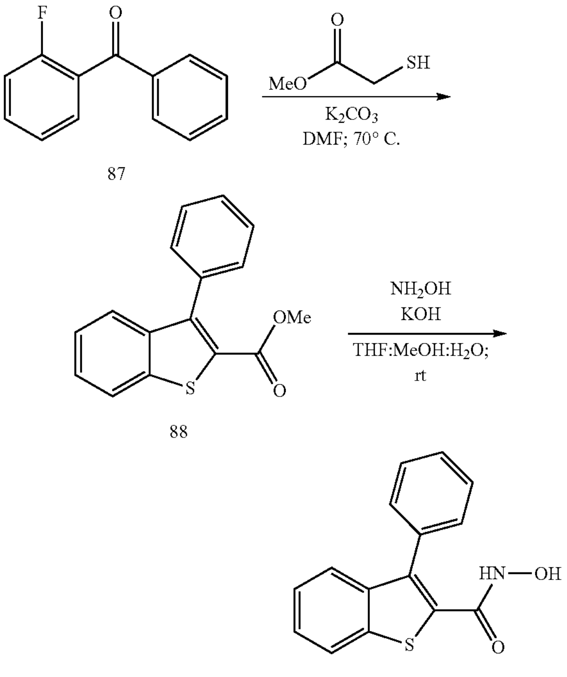

87

88

89: Example 12a

Example 12a

N-hydroxy-3,5-diphenylthiophene-2-carboxamide 89

Step 1: methyl
3-phenylbenzo[b]thiophene-2-carboxylate 88

To a stirring solution of (2-fluorophenyl)(phenyl)methanone 87 (2 g, 9.99 mmol) and methyl 2-mercaptoacetate in DMF (30 mL) was added potassium carbonate (4.14 g, 30.0 mmol) and the reaction mixture was stirred at 70° C. for 16 h. The solvent was removed under reduced pressure and the resulting residue was diluted with ethyl acetate and washed with water. The organic layer was dried over $Na_2SO_4$, filtered and concentrated under reduced pressure to afford methyl 3-phenylbenzo[b]thiophene-2-carboxylate 88 as a white oily solid (0.62 g, 23% yield) after purification by ISCO (0 to 40% ethyl acetate in hexane). LRMS (ESI): (calc) 268.33 (found) 269.156 (MH)+

Step 2:
N-hydroxy-3,5-diphenylthiophene-2-carboxamide 89

The procedure was followed as outlined in Scheme 5, Step 3 replacing compound 49 with compound 88 to afford title compound N-hydroxy-3,5-diphenylthiophene-2-carboxamide 89 (10% yield) as a white solid after purification by ISCO (0 to 100% Ethyl acetate in hexane) followed by recrystallization from MeCN and water. $^1$H NMR (400 MHz, DMSO-$d_6$) δ (ppm): 10.85 (br s, 1H), 9.22 (br s, 1H), 8.08 (d, J=7.8 Hz, 1H), 7.58-7.41 (m, 8H). LRMS (ESI): (calc) 269.32 (found) 270.1 (MH)+.

Scheme 13

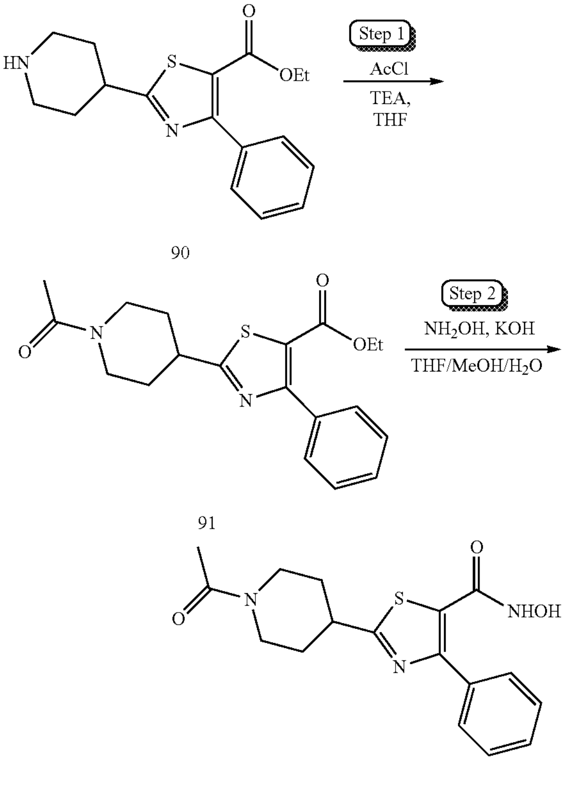

90

91

92: Example 13a

Example 13a

N-hydroxy-3,5-diphenylthiophene-2-carboxamide 92

Step 1: ethyl 2-(1-acetylpiperidin-4-yl)-4-phenylthiazole-5-carboxylate 91

To prepare compound 90, the procedure was followed as outlined in Scheme 10, Step 2 replacing compounds 77 and 78 with compounds tent-butyl 4-carbamothioylpiperidine-1-carboxylate and ethyl 2-bromo-3-oxo-3-phenylpropanoate to afford compound 90 (0.790 g, 21% yield) as a white solid. To a stirring solution of ethyl 4-phenyl-2-(piperidin-4-yl)thiazole-5-carboxylate 90 (0.235 g, 0.743 mmol) in THF (8 mL) was added acetyl chloride (1.11 mL, 0.891 mmol) and the reaction was stirred at room temperature for 2 h. The solution was diluted with brine and extracted with ethyl acetate. The combined organics were dried over $Na_2SO_4$, filtered and concentrated under reduced pressure to afford ethyl 2-(1-acetylpiperidin-4-yl)-4-phenylthiazole-5-carboxylate 91 as a light yellow oil (0.196 g, 74% yield) after purification by flash chromatography (0 to 10% MeOH in ethyl acetate). LRMS (ESI): (calc) 358.45 (found) 359.3 (MH)+

Step 2: N-hydroxy-3,5-diphenylthiophene-2-carboxamide 92

The procedure was followed as outlined in Scheme 5, Step 3 replacing compound 49 with compound 91 to afford title compound N-hydroxy-3,5-diphenylthiophene-2-carboxamide 92 (20% yield) as a beige solid after purification by flash chromatography (0 to 30% MeOH in ethyl acetate). $^1$H NMR (400 MHz, CD3OD) δ (ppm): 7.82-7.73 (m, 2H), 7.50-7.38 (m, 3H), 4.60 (d, J=13.3 Hz, 1H), 4.05 (d, J=13.3 Hz, 1H), 3.44-3.29 (m, 2H), 2.94-2.83 (m, 1H), 2.28-2.14 (m, 5H), 1.94-1.68 (m, 2H). LRMS (ESI): (calc) 345.42 (found) 346.3 (MH)+

Scheme 14

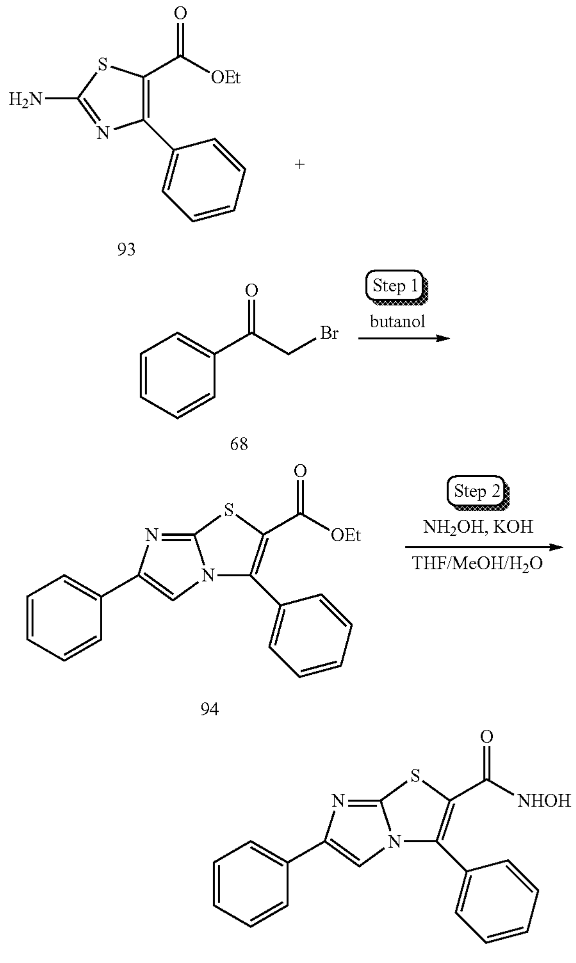

93

68

94

95: Example 14a

Example 14a

N-hydroxy-3,6-diphenylimidazo[2,1-b]thiazole-2-carboxamide 95

Step 1: ethyl 3,6-diphenylimidazo[2,1-b]thiazole-2-carboxylate 94

A solution of ethyl 2-amino-4-phenylthiazole-5-carboxylate 93 (0.7 g, 2.82 mmol) and 3-(2-bromoacetyl)benzene-1-ylium 68 (0.34 mL, 2.82 mmol) was stirred at 120° C. in butanol (9 mL) for 3 d. The solution was cooled to room temperature, diluted with brine and extracted with ethyl acetate. The combined organics were dried over $Na_2SO_4$, filtered and concentrated under reduced pressure to afford ethyl 3,6-diphenylimidazo[2,1-b]thiazole-2-carboxylate 94 (0.18 g, 18% yield) as a tan solid after purification by flash chromatography (0 to 30% MeOH in ethyl acetate) followed by trituration in hexane. LRMS (ESI): (calc) 348.42 (found) 349.2 (MH)+

Step 2: N-hydroxy-3,6-diphenyl imidazo[2,1-b]thiazole-2-carboxamide 95

The procedure was followed as outlined in Scheme 5, Step 3 replacing compound 49 with compound 94 to afford title compound N-hydroxy-3,6-diphenylimidazo[2,1-b]thiazole-2-carboxamide 95 (83% yield) as a beige solid after purification by trituration (ethyl acetate and hexane). $^1$H NMR (400 MHz, DMSO-d$_6$) δ (ppm): 8.20 (br s, 1H), 7.97-7.92 (m, 2H), 7.76-7.70 (m, 2H), 7.67-7.61 (m, 3H), 7.45-7.39 (m, 2H), 7.34-7.28 (m, 1H) LRMS (ESI): (calc) 335.4 (found) 336.3 (MH)+.

Scheme 15

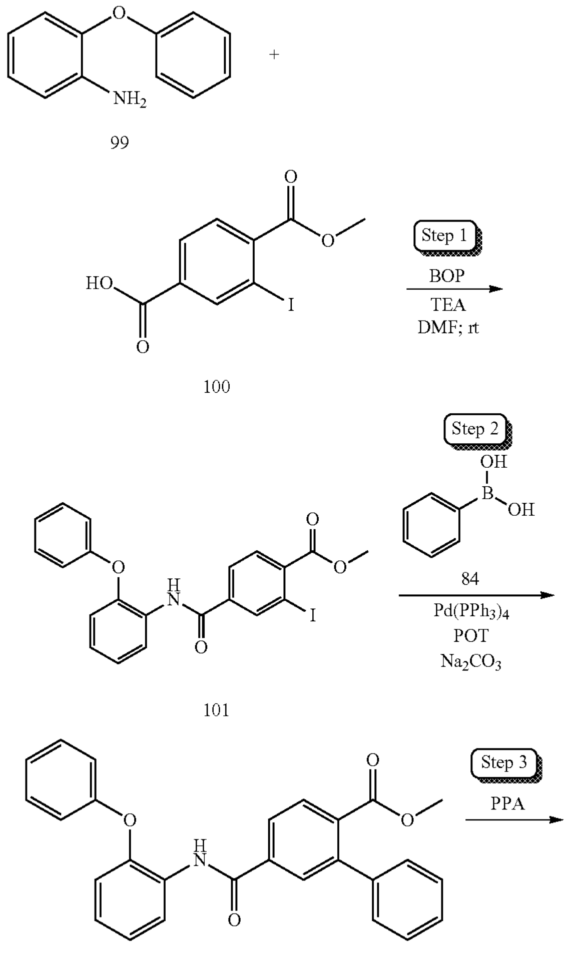

99

100

84

101

102

-continued

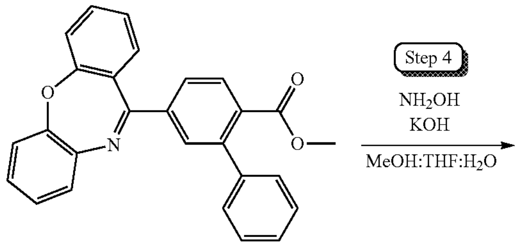

103

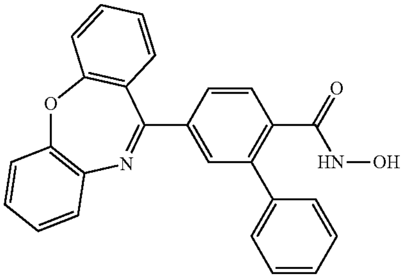

104: Example 15a

Example 15a (Z)-5-(dibenzo[b,f][1,4]oxazepin-11-yl)-N-hydroxy-biphenyl-2-carboxamide 104

Step 1: methyl 2-iodo-4-(2-phenoxyphenylcarbamoyl)benzoate 101

To a stirring solution of 2-phenoxyaniline 99 (0.813 g, 4.39 mmol) and 3-iodo-4-(methoxycarbonyl)benzoic acid 100 (1.28 g, 4.18 mmol) in DMF (15 mL) was added BOP (1.942 g, 4.39 mmol) and TEA (1.166 mL, 8.36 mmol), the reaction mixture was stirred at room temperature for 1 h then poured into water. The desired product was extracted with ethyl acetate and the combined organic layers were washed with water, brine, dried over $Na_2SO_4$, filtered and solvent evaporated to provide methyl 2-iodo-4-(2-phenoxyphenylcarbamoyl)benzoate 101 (1.382 g, 70% yield) as a red foam after purification by flash chromatography (0 to 40% ethyl acetate in hexane).

LRMS (ESI): (calc.) 473.26 (found) 474.21 (MH)+

Step 2: methyl 5-(2-phenoxyphenylcarbamoyl)biphenyl-2-carboxylate 102

The procedure was followed as outlined in Scheme 2, Step 1 replacing compounds 8 and 9 with compounds 101 and 84 to afford 5-(2-phenoxyphenylcarbamoyl)biphenyl-2-carboxylate 102 (1.07 g, 87% yield) as an orange foam after purification by ISCO (40 g column, 0 to 40% ethyl acetate in hexane).

LRMS (ESI): (calc.) 423.46 (found) 424.16 (MH)+

Step 3: (Z)-methyl 5-(dibenzo[b,f][1,4]oxazepin-11-yl)biphenyl-2-carboxylate 103

To a stirring solution of methyl 5-(2-phenoxyphenylcarbamoyl)biphenyl-2-carboxylate 102 (0.723 g, 1.7 mmol) in DCM (3 mL) was added PPA (40 g, 1.7 mmol). The reaction was heated to slowly distill off the DCM then stirred at 110° C. for 1 h. The reaction mixture was cooled to room temperature, poured into ice water then extracted with DCM. The combined organic layers were washed with water, dried over $Na_2SO_4$, filtered and solvent evaporated to provide 103 as a yellow solid (0.537 g, 78% yield) after purification by ISCO (5 to 30% ethyl acetate in hexane).

LRMS (ESI): (calc.) 405.44 (found) 406.38 (MH)+

Step 4: (Z)-5-(dibenzo[b,f][1,4]oxazepin-11-yl)-N-hydroxybiphenyl-2-carboxamide 104

The procedure was followed as outlined in Scheme 5, Step 3 replacing compound 49 with compound 103 to afford title compound (Z)-5-(dibenzo[b,f][1,4]oxazepin-11-yl)-N-hydroxybiphenyl-2-carboxamide 104 (3% yield) as a white solid after purification by Gilson (55 to 95% MeOH in water).

$^1$H NMR (400 MHz, CD3OD) δ (ppm): 7.84 (d, J=1.6 Hz, 1H), 7.78 (d, J=8.0, 2.0 Hz, 1H), 7.63-7.58 (m, 2H), 7.52-7.49 (m, 2H), 7.46-7.35 (m, 5H), 7.30-7.20 (m, 5H). LRMS (ESI): (calc) 406.43 (found) 407.35 (MH)+

TABLE 7

Other compounds according to Scheme 15.

| Ex. | Cpd # | Structure | Name | Characterization |
|---|---|---|---|---|
| 15b | 105 | 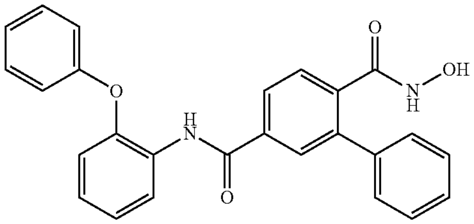 [SMILES: O=C(Nc1ccccc1Oc1ccccc1)c1ccc(C(=O)NO)c(-c2ccccc2)c1] | N2-hydroxy-N5-(2-phenoxyphenyl) biphenyl-2,5-dicarboxamide | $^1$H NMR (400 MHz, MeOH-$d_4$) δ (ppm): 7.87 (dd, J = 7.2, 2.4 Hz, 1 H), 7.75 (dd, J = 8.0, 1.6 Hz, 1 H), 7.64 (d, J = 1.6 Hz, 1 H), 7.52 (d, J = 8.0 Hz, 1 H), 7.44-7.37 (m, 5 H), 7.30-7.22 (m, 4 H), 7.07 (dd, J = 1.8 Hz, 1 H), 7.02-6.99 (m, 1 H), 6.96-6.94 (m, 2 H) LRMS (ESI): (calc.) 424.45 (found) 425.29 (MH)+ |

The following additional compounds were prepared according to the procedures described herein and/or according to knowledge available to one of skill in the art.

TABLE 8

| Cpd | Structure | Name | Characterization |
| --- | --- | --- | --- |
| 106 | 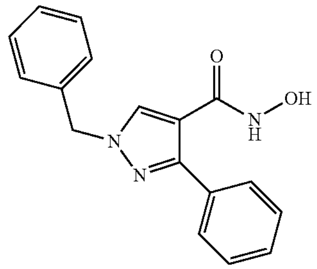 [SMILES: O=C(NO)c1cn(Cc2ccccc2)nc1-c1ccccc1] | 1-benzyl-N-hydroxy-3-phenyl 1H-pyrazole-4-carboxamide | $^1$H NMR (400 MHz, DMSO-d6) δ (ppm): 10.81 (s, 1 H), 9.00 (s, 1 H), 8.17 (s, 1 H), 7.79-7.74 (m, 2 H), 7.44-7.32 (m, 8 H), 5.41 (s, 2 H) LRMS (ESI): (calc.) 293.3 (found) 294.3 (MH)+ |
| 107 | 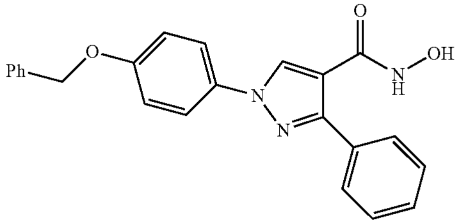 [SMILES: O=C(NO)c1cn(-c2ccc(OCc3ccccc3)cc2)nc1-c1ccccc1] | 1-(4-(benzyloxy) phenyl)-N-hydroxy-3-phenyl-1H-pyrazole-4-carboxamide | $^1$H NMR (400 MHz, DMSO-d6) δ (ppm): 10.87 (s, 1 H), 9.10 (s, 1 H), 8.67 (s, 1 H), 7.86-7.78 (m, 4 H), 7.50-7.32 (m, 8 H), 7.18 (d, J = 9.2 Hz, 2 H), 5.17 (s, 2 H). LRMS (ESI): (calc.) 385.4 (found) 386.4 (MH)+ |
| 108 | 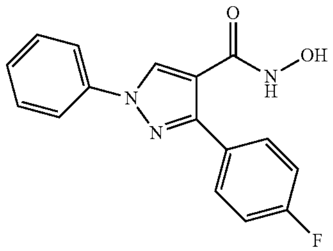 [SMILES: O=C(NO)c1cn(-c2ccccc2)nc1-c1ccc(F)cc1] | 3-(4-fluorophenyl)-N-hydroxy-1-phenyl-1H-pyrazole-4-carboxamide | $^1$H NMR (400 MHz, DMSO-d6) δ (ppm): 10.97 (br s, 1 H), 9.18 (br s, 1 H), 8.84 (s, 1 H), 8.01-7.91 (m, 4 H), 7.63-7.56 (m, 2 H), 7.45-7.40 (m, 1 H), 7.36-7.28 (m, 2 H) LRMS (ESI): (calc.) 297.3 (found) 298.2 (MH)+ |
| 109 | 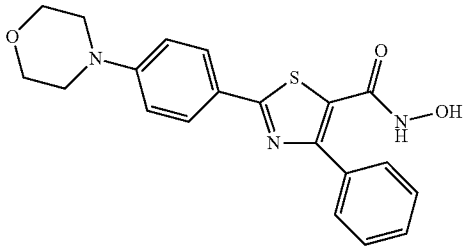 [SMILES: O=C(NO)c1sc(-c2ccc(N3CCOCC3)cc2)nc1-c1ccccc1] | N-hydroxy-2-(4-morpholino-phenyl)-4-phenylthiazole-5-carboxamide | $^1$H NMR (400 MHz, CD3OD) δ (ppm): 7.90 (d, J = 8.8 Hz, 2 H), 7.80 (d, J = 8.0 Hz, 2 H), 7.47-7.40 (m, 3 H), 7.04 (d, J = 8.8 Hz, 2 H), 3.84 (t, J = 5.2 Hz, 4 H), 3.28 (t, J = 4.8 Hz, 4 H) LRMS (ESI): (calc.) 381.1 (found) 382.3 (MH)+ |
| 110 | 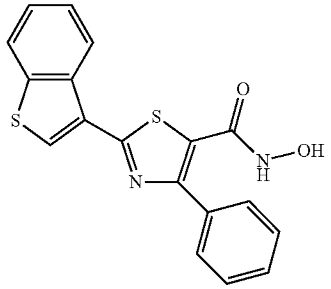 [SMILES: O=C(NO)c1sc(-c2csc3ccccc23)nc1-c1ccccc1] | 2-(benzo[b]thiophen-3-yl)-N-hydroxy-4-phenylthiazole-5-carboxamide | $^1$H NMR (400 MHz, CD3OD) δ (ppm): 8.81 (d, J = 8.0 Hz, 1 H), 8.35 (s, 1 H), 7.99 (d, J= 8.0 Hz, 1 H), 7.91 (d, J = 6.8 Hz, 2 H), 7.56-7.41 (m, 5 H) LRMS (ESI): (calc.) 352.0 (found) 353.2 (MH)+ |
| 111 | 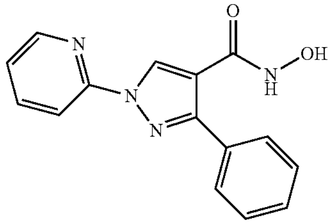 [SMILES: O=C(NO)c1cn(-c2ccccn2)nc1-c1ccccc1] | N-hydroxy-3-phenyl-1-(pyridin-2-yl)-1H-pyrazole-4-carboxamide | $^1$H NMR (400 MHz, DMSO-d6) δ (ppm): 11.09 (br s, 1 H), 9.17 (s, 1 H), 8.95 (s, 1 H), 8.62-8.56 (m, 1 H), 8.13-8.04 (m, 2 H), 7.94-7.88 (m, 2 H), 7.52-7.44 (m, 4 H) LRMS (ESI): (calc.) 280.3 (found) 281.1 (MH)+ |

TABLE 8-continued

| Cpd | Structure | Name | Characterization |
|---|---|---|---|
| 112 | 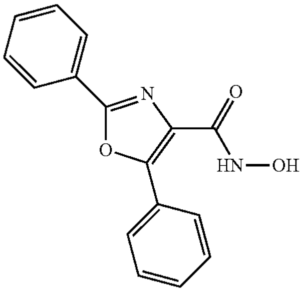 | N-hydroxy-2,5-diphenyloxazole-4-carboxamide | $^{1}$H NMR (400 MHz, DMSO-d6) δ (ppm): 11.24 (s, 1 H), 9.23 (s, 1 H), 8.28-8.25 (m, 2 H), 8.15-8.13 (m, 2 H), 7.62-7.58 (m, 3 H), 7.56-7.46 (m, 3 H)<br>LRMS (ESI): (calc) 280.28 (found) 281.17 (MH)+ |
| 113 | 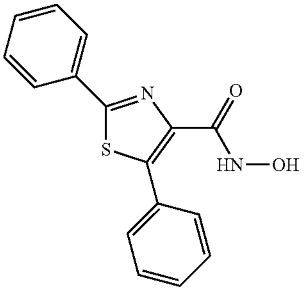 | N-hydroxy-2,5-diphenylthiazole-4-carboxamide | $^{1}$H NMR (400 MHz, DMSO-d6) δ (ppm): 11.24 (s, 1 H), 9.22 (s, 1 H), 8.05-8.03 (m, 2 H), 7.63-7.61 (m, 2 H), 7.55-7.54 (m, 3 H), 7.48-7.44 (m, 3 H)<br>LRMS (ESI): (calc) 296.34 (found) 297.18 (MH)+ |
| 114 | 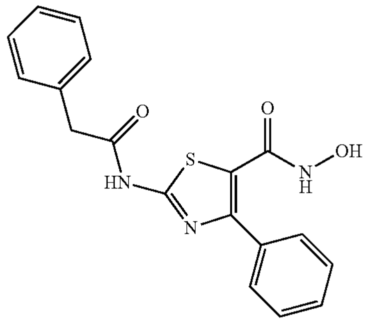 [SMILES: O=C(Cc1ccccc1)Nc1nc(-c2ccccc2)c(C(=O)NO)s1] | N-hydroxy-4-phenyl-2-(2-phenylacetamido) thiazole-5-carboxamide | $^{1}$H NMR (400 MHz, CD3OD) δ (ppm): 7.80-7.75 (m, 2 H), 7.46-7.28 (m, 9 H), 3.84 (s, 2 H)<br>LRMS (ESI): (calc.) 353.4 (found) 354.3 (MH)+ |
| 115 | 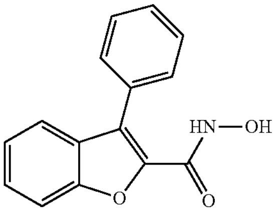 [SMILES: O=C(NO)c1oc2ccccc2c1-c1ccccc1] | N-hydroxy-3-phenylbenzofuran-2-carboxamide | $^{1}$H NMR (400 MHz, DMSO-d6) δ (ppm): 11.45 (br s, 1 H), 9.27 (br s, 1 H), 7.70-7.35 (m, 9 H)<br>LRMS (ESI): (calc.) 253.3 (found) 254.1 (MH)+ |
| 116 | 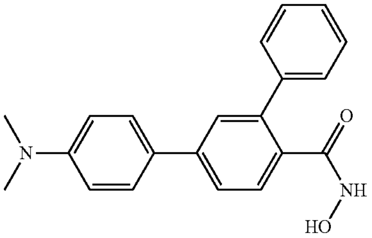 [SMILES: CN(C)c1ccc(-c2ccc(C(=O)NO)c(-c3ccccc3)c2)cc1] | 5-(4-dimethylamino-phenyl)-N-hydroxybiphenyl-2-carboxamide | $^{1}$H NMR (400 MHz, CD3OD) δ (ppm): 7.74 (s, 0.38 H), 6.83-6.54 (m, 10 H), 6.04 (d, J = 9.0 Hz, 2 H), 2.18 (s, 6 H).<br>LRMS (ESI): (calc.) 332.4 (found) 333.3 (MH)+ |

TABLE 8-continued

| Cpd | Structure | Name | Characterization |
|---|---|---|---|
| 117 | 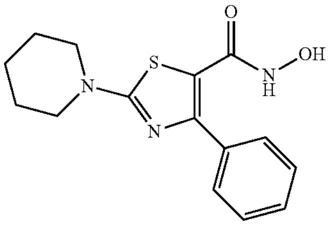 [SMILES: O=C(NO)c1sc(N2CCCCC2)nc1-c1ccccc1] | N-hydroxy-4-phenyl-2-(piperidin-1-yl)thiazole-5-carboxamide | $^1$H NMR (400 MHz, DMSO-d6) δ (ppm): 10.71 (br s, 1 H), 9.13 (s, 1 H), 7.72-7.67 (m, 2 H), 7.44-7.36 (m, 3 H), 3.54-3.47 (m, 4 H), 1.69-1.60 (m, 6 H) LRMS (ESI): (calc.) 303.4 (found) 304.2 (MH)+ |
| 118 | 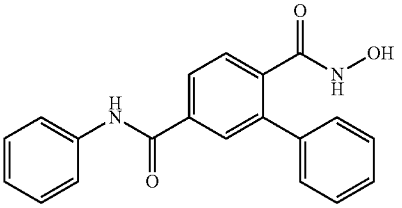 [SMILES: O=C(Nc1ccccc1)c1ccc(C(=O)NO)c(-c2ccccc2)c1] | $N^2$-hydroxy-$N^5$-phenylbiphenyl-2,5-dicarboxamide | $^1$H NMR (400 MHz, DMSO-d6) δ (ppm): 10.92 (s, 1 H), 10.38 (s, 1 H), 9.10 (s, 1 H), 7.98-7.96 (m, 2 H), 7.78 (dd, J = 8.8, 1.2 Hz, 2 H), 7.54-7.34 (m, 8 H), 7.14-7.10 (m, 1 H) LRMS (ESI): (calc) 332.35 (found) 333.33 (MH)+ |
| 119 | 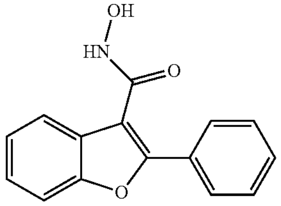 [SMILES: O=C(NO)c1c(-c2ccccc2)oc2ccccc12] | N-hydroxy-2-phenylbenzofuran-3-carboxamide | $^1$H NMR (400 MHz, DMSO-d6) δ (ppm): 11.17 (s, 1 H), 9.35 (s, 1 H), 7.92-7.89 (m, 2 H), 7.69 (d, J = 8.2 Hz, 1 H), 7.60-7.33 (m, 6 H). LRMS (ESI): (calc.) 253.3 (found) 252.1 (M − H)− |
| 120 | 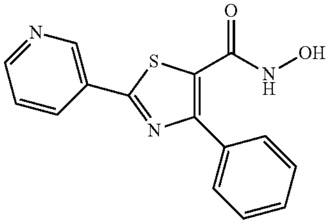 [SMILES: O=C(NO)c1sc(-c2cccnc2)nc1-c1ccccc1] | N-hydroxy-4-phenyl-2-(pyridin-3-yl)thiazole-5-carboxamide | $^1$H NMR (400 MHz, DMSO-d6) δ (ppm): 11.38 (br s, 1 H), 9.52 (s, 1 H), 9.25 (d, J = 2.2 Hz, 1 H), 8.81-8.76 (m, 1 H), 8.49-8.42 (m, 1 H), 7.96-7.86 (m, 2 H), 7.66-7.61 (m, 1 H), 7.59-7.45 (m, 3 H) LRMS (ESI): (calc.) 297.3 (found) 298.1 (MH)+ |
| 121 | 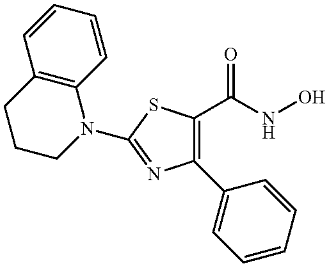 [SMILES: O=C(NO)c1sc(N2CCCc3ccccc32)nc1-c1ccccc1] | 2-(3,4-dihydroquinolin-1(2H)-yl)-N-hydroxy-4-phenylthiazole-5-carboxamide | $^1$H NMR (400 MHz, CD3OD) δ (ppm): 7.94-7.88 (m, 1 H), 7.79-7.72 (m, 2 H), 7.48-7.38 (m, 3 H), 7.29-7.20 (m, 2 H), 7.14-7.07 (m, 1 H) 4.01 (t, J = 6.1 Hz, 2 H, 2.84 (t, J = 6.3 Hz, 2 H), 2.10-2.02 (m, 2 H) LRMS (ESI): (calc.) 351.4 (found) 352.3 (MH)+ |
| 122 | 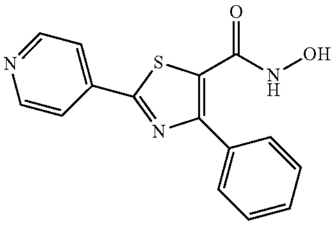 [SMILES: O=C(NO)c1sc(-c2ccncc2)nc1-c1ccccc1] | N-hydroxy-4-phenyl-2-(pyridin-4-yl)thiazole-5-carboxamide | $^1$H NMR (400 MHz, DMSO-d6) δ (ppm): 11.39 (br s, 1 H), 9.56 (s, 1 H), 8.89-8.76 (m, 2 H), 8.06-7.98 (m, 2 H), 7.94-7.85 (m, 2 H), 7.58-7.45 (m, 3 H) LRMS (ESI): (calc.) 297.3 (found) 298.2 (MH)+ |

TABLE 8-continued

| Cpd | Structure | Name | Characterization |
|---|---|---|---|
| 123 | 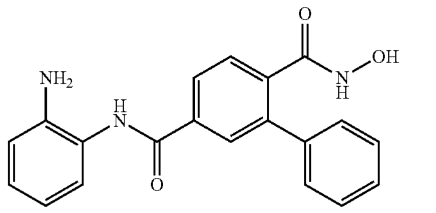 [SMILES: Nc1ccccc1NC(=O)c1ccc(C(=O)NO)c(-c2ccccc2)c1] | $N^5$-(2-aminophenyl)-$N^2$-hydroxybiphenyl-1-2,5-dicarboxamide | $^1$H NMR (400 MHz, DMSO-d6) δ (ppm): 10.91 (s, 1 H), 9.84 (s, 1 H), 9.08 (s, 1 H), 8.02-7.96 (m, 2 H), 7.51-7.39 (m, 6 H), 7.15 (d, J = 8.0 Hz, 1 H), 6.98 (t, J = 7.2 Hz, 1 H), 6.78 (d, J = 8.0 Hz, 1 H), 6.60 (t, J = 7.6 Hz, 1 H), 4.94 (s, 2 H) LRMS (ESI): (calc) 347.37 (found) 348.30 (MH)+ |
| 124 | 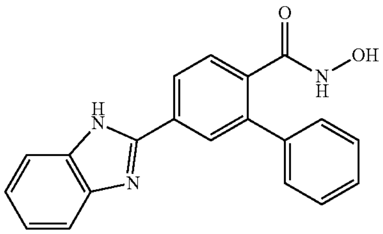 [SMILES: O=C(NO)c1ccc(-c2nc3ccccc3[nH]2)cc1-c1ccccc1] | 5-(1H-benzo[d]imidazol-2-yl)-N-hydroxybiphenyl-2-carboxamide | $^1$H NMR (400 MHz, DMSO-d6) δ (ppm): 13.06 (s, 1 H), 10.91 (s, 1 H), 9.08 (s, 1 H), 8.22-8.20 (m, 2 H), 7.68 (d, J = 7.6 Hz, 1 H), 7.57-7.39 (m, 7 H), 7.26-7.19 (m, 2 H) LRMS (ESI): (calc) 329.35 (found) 330.34 (MH)+ |
| 125 | 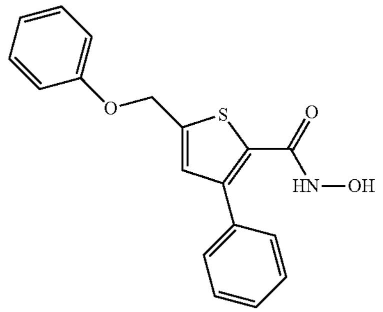 [SMILES: O=C(NO)c1sc(COc2ccccc2)cc1-c1ccccc1] | N-hydroxy-5-(phenoxymethyl)-3-phenylthiophene-2-carboxamide | $^1$H NMR (400 MHz, DMSO-d6) δ (ppm): 10.94 (s, 1 H), 9.19 (s, 1 H), 7.48-7.30 (m, 8 H), 7.06-7.04 (m, 2 H), 6.99-6.95 (m, 1 H), 5.33 (s, 2 H) LRMS (ESI): (calc) 325.38 (found) 326.31 (MH)+ |
| 126 | 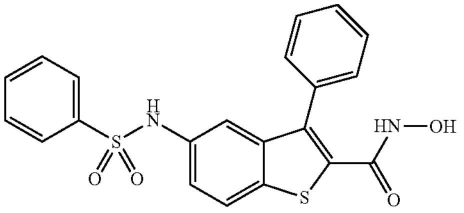 [SMILES: O=C(NO)c1sc2ccc(NS(=O)(=O)c3ccccc3)cc2c1-c1ccccc1] | N-hydroxy-3-phenyl-5-(phenylsulfonamido) benzo[b] thiophene-2-carboxamide | $^1$H NMR (400 MHz, DMSO-d6) δ (ppm): 10.83 (br s, 1 H), 10.33 (br s, 1 H), 9.21 (s, 1 H), 7.95 (d, J = 8.4 Hz, 1 H), 7.69-7.44 (m, 8 H), 7.23-7.21 (m, 4 H). LRMS (ESI): (calc.) 424.5 (found) 425.4 (MH)+ |
| 127 | 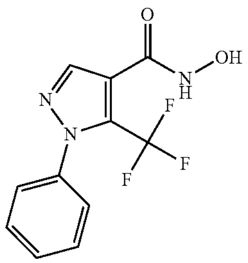 [SMILES: O=C(NO)c1cnn(-c2ccccc2)c1C(F)(F)F] | N-hydroxy-1-phenyl-5-(trifluoromethyl)-1H-pyrazole-4-carboxamide | $^1$H NMR (400 MHz, CD3OD) δ (ppm): 7.92 (s, 1 H), 7.58-7.55 (m, 3 H), 7.48-7.46 (m, 2 H) LRMS (ESI): (calc.) 271.2 (found) 270.1 (MH)– |
| 128 | 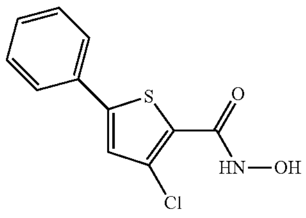 [SMILES: O=C(NO)c1sc(-c2ccccc2)cc1Cl] | 3-chloro-N-hydroxy-5-phenylthiophene-2-carboxamide | $^1$H NMR (400 MHz, DMSO-d6) δ (ppm): 11.01 (s, 1 H), 9.35 (s, 1 H), 7.74-7.71 (m, 2 H), 7.62 (s, 1 H), 7.49-7.39 (m, 3 H) LRMS (ESI): (calc) 253.70 (found) 254.08 (MH)+ |

TABLE 8-continued

| Cpd | Structure | Name | Characterization |
|---|---|---|---|
| 129 | 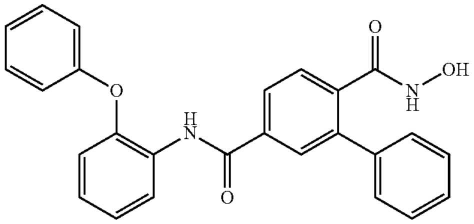 [SMILES: O=C(Nc1ccccc1Oc1ccccc1)c1ccc(C(=O)NO)c(-c2ccccc2)c1] | $N^2$-hydroxy-$N^5$-(2-phenoxyphenyl) biphenyl-2,5-dicarboxamide | $^1$H NMR (400 MHz, CD3OD) δ (ppm): 7.87 (dd, J = 7.2, 2.4 Hz, 1 H), 7.75 (dd, J = 8.0, 1.6 Hz, 1 H), 7.64 (d, J = 1.6 Hz, 1 H), 7.52 (d, J = 8.0 Hz, 1 H), 7.44-7.37 (m, 5 H), 7.30-7.22 (m, 4 H), 7.07 (dd, J = 1.8 Hz, 1 H), 7.02-6.99 (m, 1 H), 6.96-6.94 (m, 2 H) LRMS (ESI): (calc) 424.45 (found) 425.29 (MH)+ |
| 130 | 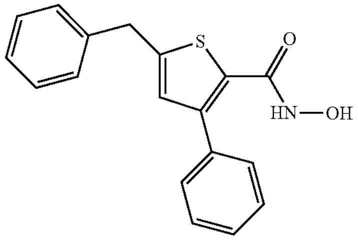 [SMILES: O=C(NO)c1sc(Cc2ccccc2)cc1-c1ccccc1] | 5-benzyl-N-hydroxy-3-phenylthiophene-2-carboxamide | $^1$H NMR (400 MHz, DMSO-d6) δ (ppm): 10.78 (s, 1 H), 9.09 (s, 1 H), 7.44-7.30 (m, 9 H), 7.27-7.22 (m, 1 H), 7.08 (s, 1 H), 4.16 (s, 2 H) LRMS (ESI): (calc) 309.38 (found) 310.26 (MH)+ |
| 131 | 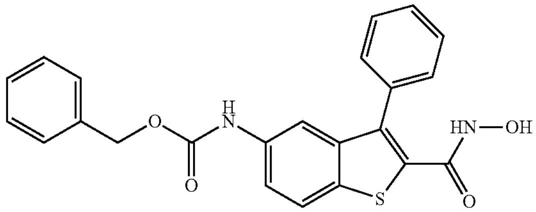 [SMILES: O=C(Nc1ccc2sc(C(=O)NO)c(-c3ccccc3)c2c1)OCc1ccccc1] | benzyl 2-(hydroxycarbamoyl)-3-phenylbenzo[b] thiophen-5-ylcarbamate | $^1$H NMR (400 MHz, DMSO-d6) δ (ppm): 10.83 (br s, 1 H), 9.90 (br s, 1 H), 9.20 (br s, 1 H), 7.98-7.89 (m, 2 H), 7.54-7.30 (m, 11 H), 5.12 (s, 2 H). LRMS (ESI): (calc.) 418.5 (found) 419.3 (MH)+ |
| 132 | 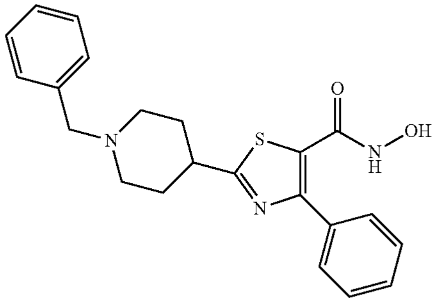 [SMILES: O=C(NO)c1sc(C2CCN(Cc3ccccc3)CC2)nc1-c1ccccc1] | 2-(1-benzylpiperidin-4-yl)-N-hydroxy-4-phenylthiazole-5-carboxamide | $^1$H NMR (400 MHz, CD3OD) δ (ppm): 7.80-7.76 (m, 2 H), 7.49-7.26 (m, 8 H), 3.54 (s, 2 H), 3.13-3.03 (m, 1 H), 2.96-2.89 (m, 2 H), 2.20-2.05 (m, 4 H), 1.84-1.72 (m, 2 H) LRMS (ESI): (calc.) 393.5 (found) 394.4 (MH)+ |
| 133 | 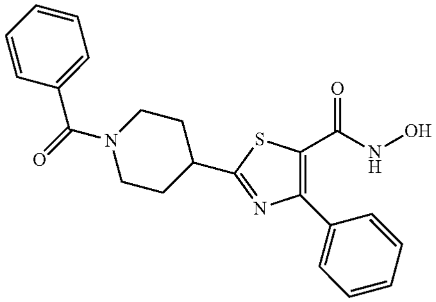 [SMILES: O=C(NO)c1sc(C2CCN(C(=O)c3ccccc3)CC2)nc1-c1ccccc1] | 2-(1-benzoylpiperidin-4-yl)-N-hydroxy-4-phenylthiazole-5-carboxamide | ($^1$H NMR (400 MHz, CD3OD) δ (ppm): 7.81-7.75 (m, 2 H), 7.54-7.41 (m, 8 H), 4.81-4.70 (m, 1 H), 3.96-3.82 (m, 1 H), 3.50-3.40 (m, 3 H), 2.38-2.27 (m, 1 H), 2.20-2.10 (m, 1 H), 2.00-1.80 (m, 2 H) LRMS (ESI): (calc.) 407.5 (found) 408.3 (MH)+ |
| 134 | 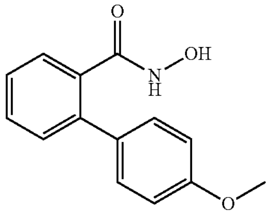 [SMILES: COc1ccc(-c2ccccc2C(=O)NO)cc1] | N-hydroxy-4'-methoxybiphenyl-2-carboxamide | (DMSO-d6) d (ppm) 1 H: 10.73 (s, 1 H), 8.96 (s, 1 H), 7.50-7.46 (m, 1 H), 7.38-7.32 (m, 3 H), 7.34 (d, J = 8.8 Hz, 2 H), 6.95 (d, J= 8.8 Hz, 2 H), 3.78 (s, 3 H). LRMS (ESI): (calc.) 243.26 (found) 244.2 (MH)+ |

TABLE 8-continued

| Cpd | Structure | Name | Characterization |
|---|---|---|---|
| 135 | 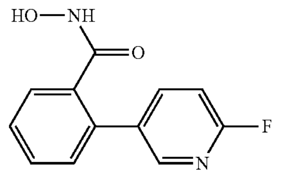 [SMILES: O=C(NO)c1ccccc1-c1ccc(F)nc1] | 2-(6-fluoropyridin-3-yl)-N-hydroxybenzamide | (DMSO) δ ppm) 1 H: 10.85 (s, 1 H), 9.05 (s, 1 H), 8.21 (d, 1 H), 7.96 (t, 1 H), 7.55 (m, 1 H), 7.43 (m, 3 H), 7.24 (dd, 1 H). LRMS (ESI): (calc.) 232.21 (found) 233.1 (MH)+ |
| 136 | 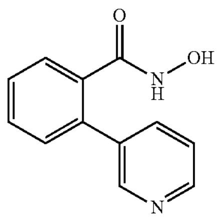 [SMILES: O=C(NO)c1ccccc1-c1cccnc1] | N-hydroxy-2-(pyridin-3-yl)benzamide | (DMSO-d6) δ ppm) 1 H: 10.88 (s, 1 H), 9.04 (d, J = 1.2 Hz, 1 H), 8.57 (dd, J = 0.8, 2.3 Hz, 1 H), 8.54 (dd, J = 1.7, 4.9 Hz, 1 H), 7.77 (dt, J = 2.3, 7.6 Hz, 1 H), 7.55 (dd, J = 1.7, 7.6 Hz, 1 H), 7.47-7.42 (m, 4 H) LRMS (ESI): (calc.) 214.22 (found) 215.1 (MH)+ |
| 137 | 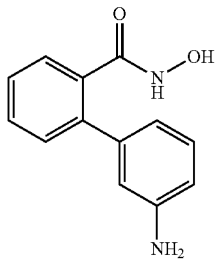 [SMILES: Nc1cccc(-c2ccccc2C(=O)NO)c1] | 3'-amino-N-hydroxybiphenyl-2-carboxamide | (DMSO-d6) δ ppm) 1 H: 10.66 (s, 1 H), 8.91 (s, 1 H), 7.45 (dd, J = 1.9, 7.6 Hz, 1 H), 7.37-7.29 (m, 3 H), 6.99 (t, J = 7.6 Hz, 1 H), 6.59 (t, J = 1.9 Hz, 1 H), 6.54-6.50 (m, 2 H), 5.07 (bs, 2 H) LRMS (ESI): (calc.) 228.25 (found) 229.1 (MH)+ |
| 138 | 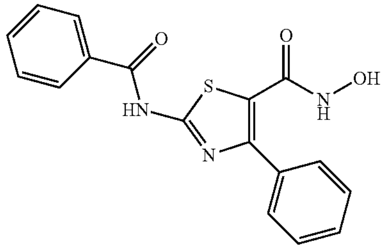 [SMILES: O=C(Nc1nc(-c2ccccc2)c(C(=O)NO)s1)c1ccccc1] | 2-benzamido-N-hydroxy-4-phenylthiazole-5-carboxamide | (DMSO-d6) d (ppm) 1 H: 13.03 (br s, 1 H), 8.21-8.16 (m, 1 H), 8.02-7.96 (m, 2 H), 7.83-7.76 (m, 1 H), 7.74-7.40 (m, 6 H) LRMS (ESI): (calc.) 339.4 (found) 340.3 (MH)+ |
| 139 | 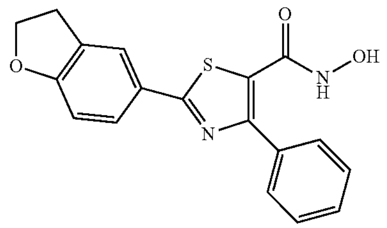 [SMILES: O=C(NO)c1sc(-c2ccc3c(c2)CCO3)nc1-c1ccccc1] | 2-(2,3-dihydrobenzofuran-5-yl)-N-hydroxy-4-phenylthiazole-5-carboxamide | (DMSO-d6) d (ppm) 1 H: 11.20 (s, 1 H), 9.37 (s, 1 H), 7.89-7.74 (m, 4 H), 7.46-7.37 (m, 3 H), 6.89 (d, J = 8.4 Hz, 1 H), 4.61 (t, J = 8.8 Hz, 2 H), 3.26 (t, J = 8.8 Hz, 2 H). LRMS (ESI): (calc.) 338.4 (found) 339.3 (MH)+ |
| 140 | 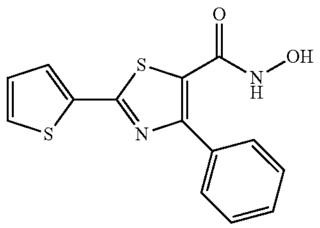 [SMILES: O=C(NO)c1sc(-c2cccs2)nc1-c1ccccc1] | N-hydroxy-4-phenyl-2-(thiophen-2-yl)thiazole-5-carboxamide | (DMSO-d6) d (ppm) 1 H: 11.30 (br s, 1 H), 9.47 (s, 1 H), 7.90-7.77 (m, 4 H), 7.56-7.44 (m, 3 H), 7.29-7.24 (m, 1 H) LRMS (ESI): (calc.) 302.4 (found) 303.1 (MH)+ |

TABLE 8-continued

| Cpd | Structure | Name | Characterization |
| --- | --- | --- | --- |
| 141 | 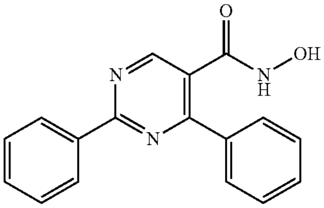 [SMILES: O=C(NO)c1cnc(-c2ccccc2)nc1-c1ccccc1] | N-hydroxy-2,4-diphenylpyrimidine-5-carboxamide | (DMSO-d6) d (ppm) 1 H: 11.26 (br s, 1 H), 9.45 (s, 1 H), 8.93 (s, 1 H), 8.57-8.51 (m, 2 H), 8.01-7.95 (m, 2 H), 7.65-7.56 (m, 6 H) LRMS (ESI): (calc.) 291.3 (found) 292.2 (MH)+ |
| 142 | 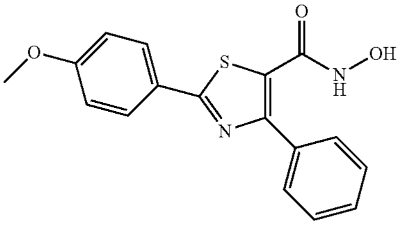 [SMILES: COc1ccc(-c2nc(-c3ccccc3)c(C(=O)NO)s2)cc1] | N-hydroxy-2-(4-methoxyphenyl)-4-phenylthiazole-5-carboxamide | (DMSO-d6) d (ppm) 1 H: 11.21 (s, 1 H), 9.38 (s, 1 H), 7.94 (d, J = 8.8 Hz, 2 H), 7.81 (d, J = 7.3 Hz, 2 H), 7.47-7.37 (m, 3 H), 7.08 (d, J = 8.8 Hz, 2 H), 3.83 (s, 3 H). LRMS (ESI): (calc.) 326.4 (found) 327.3 (MH)+ |
| 143 | 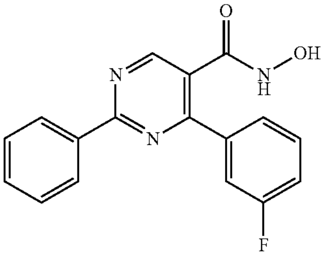 [SMILES: O=C(NO)c1cnc(-c2ccccc2)nc1-c1cccc(F)c1] | 4-(3-fluorophenyl)-N-hydroxy-2-phenylpyrimidine-5-carboxamide | (DMSO-d6) d (ppm) 1 H: 11.29 (br s, 1 H), 9.51 (s, 1 H), 8.98 (s, 1 H), 8.58-8.50 (m, 2 H), 7.81-7.72 (m, 2 H), 7.68-7.59 (m, 4 H), 7.51-7.44 (m, 1 H) LRMS (ESI): (calc.) 309.3 (found) 310.3 (MH)+ |
| 144 | 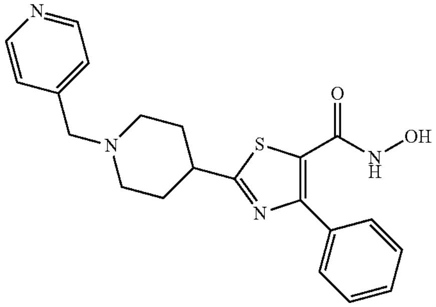 [SMILES: O=C(NO)c1sc(C2CCN(Cc3ccncc3)CC2)nc1-c1ccccc1] | N-hydroxy-4-phenyl-2-(1-(pyridin-4-ylmethyl)piperidin-4-yl)thiazole-5-carboxamide | (DMSO-d6) δ ppm) 1 H: 8.55 (dd, J = 4.5, 1.6 Hz, 2 H), 7.82-7.75 (m, 2 H), 7.50-7.37 (m, 5 H), 3.59 (s, 2 H), 3.15-3.05 (m, 1 H), 2.95-2.88 (m, 2 H), 2.24-2.06 (m, 4 H), 1.87-1.76 (m, 2 H) LRMS (ESI): (calc.) 394.5 (found) 395.4 (MH)+ |
| 145 | 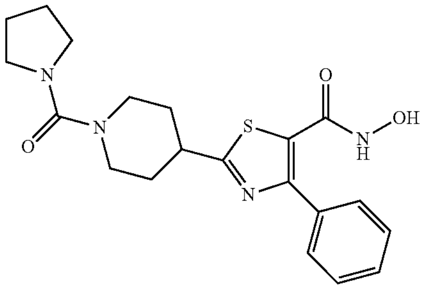 [SMILES: O=C(NO)c1sc(C2CCN(C(=O)N3CCCC3)CC2)nc1-c1ccccc1] | N-hydroxy-4-phenyl-2-(1-(pyrrolidine-1-carbonyl)piperidin-4-yl)thiazole-5-carboxamide | (MeOD-d4) δ ppm) 1 H: 7.80-7.74 (m, 2 H), 7.49-7.40 (m, 3 H), 3.95-3.88 (m, 2 H), 3.46-3.40 (m, 4 H), 3.35-3.28 (m, 1 H), 3.05-2.92 (m, 2 H), 2.22-2.15 (m, 2 H), 1.94-1.80 (m, 6 H) LRMS (ESI): (calc.) 400.5 (found) 401.4 (MH)+ |
| 146 | 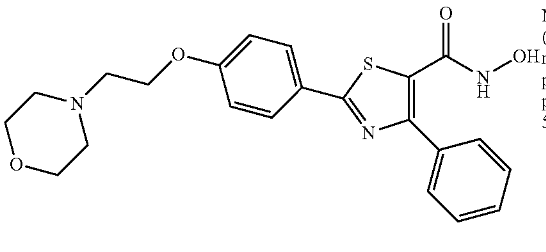 | N-hydroxy-2-(4-(2-morpholinoethoxy)phenyl)-4-phenylthiazole-5-carboxamide | (DMSO-d6) δ ppm) 1 H: 11.23 (br s, 1 H), 9.40 (br s, 1 H), 7.94 (d, J = 8.8 Hz, 2 H), 7.82 (d, J = 7.0 Hz, 2 H), 7.49-7.39 (m, 3 H), 7.10 (d, J = 9.0 Hz, 2 H), 4.17 (t, J = 5.7 Hz, 2 H), 3.58 (t, J = 5.7 Hz, 4 H), 2.72 (t, J = 5.6 Hz, 2 H), 2.49-2.48 (m, 4 H). LRMS (ESI): (calc.) 425.5 (found) 426.4 (MH)+ |

TABLE 8-continued

| Cpd | Structure | Name | Characterization |
|---|---|---|---|
| 147 | 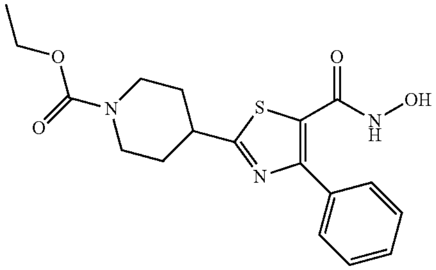 [SMILES: CCOC(=O)N1CCC(c2nc(-c3ccccc3)c(C(=O)NO)s2)CC1] | ethyl 4-(5-(hydroxycarbamoyl)-4-phenylthiazol-2-yl)piperidine-1-carboxylate | (DMSO-d6) δ ppm) 1 H: 7.86-7.79 (m, 2 H), 7.48-7.37 (m, 3 H), 4.14-4.04 (m, 4 H), 3.36-3.24 (m, 1 H), 3.10-2.90 (m, 2 H), 2.15-2.06 (m, 2 H), 1.70-1.58 (m, 2 H), 1.23 (t, J = 7.0 Hz, 3 H) LRMS (ESI): (calc.) 375.4 (found) 376.4 (MH)+ |
| 148 | 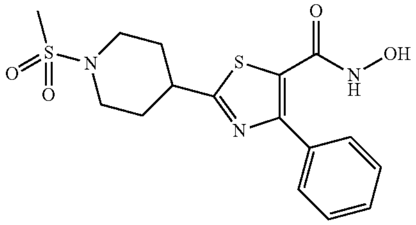 [SMILES: CS(=O)(=O)N1CCC(c2nc(-c3ccccc3)c(C(=O)NO)s2)CC1] | N-hydroxy-2-(1-(methylsulfonyl) piperidin-4-yl)-4-phenylthiazole-5-carboxamide | (MeOD-d4) δ ppm) 1 H: 7.80-7.75 (m, 2 H), 7.50-7.40 (m, 3 H), 3.90-3.82 (m, 2 H), 3.32-3.22 (m, 1 H), 3.04-2.94 (m, 2 H), 2.90 (s, 3 H), 2.35-2.25 (m, 2 H), 2.03-1.90 (m, 2 H) LRMS (ESI): (calc.) 381.5 (found) 382.1 (MH)+ |
| 149 | 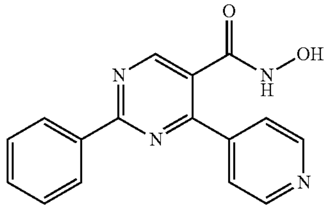 [SMILES: O=C(NO)c1cnc(-c2ccccc2)nc1-c1ccncc1] | N-hydroxy-2-phenyl-4-(pyridin-4-yl)pyrimidine-5-carboxamide | (DMSO-d6) δ ppm) 1 H: 11.33 (br s, 1 H), 9.52 (s, 1 H), 9.05 (s, 1 H), 8.82 (dd, J = 4.5, 1.8 Hz, 2 H), 8.56-8.51 (m, 2 H), 7.87 (dd, J = 4.3, 1.6 Hz, 2 H), 7.68-7.60 (m, 3 H) LRMS (ESI): (calc.) 292.3 (found) 293.1 (MH)+ |
| 150 | 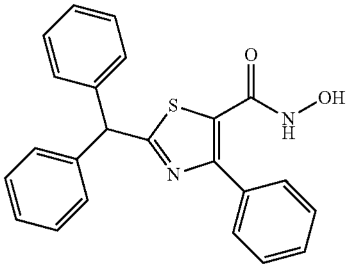 [SMILES: O=C(NO)c1sc(C(c2ccccc2)c2ccccc2)nc1-c1ccccc1] | 2-benzhydryl-N-hydroxy-4-phenylthiazole-5-carboxamide | (DMSO-d6) d (ppm) 1 H: 11.19 (s, 1 H), 9.38 (s, 1 H), 7.79-7.74 (m, 3 H), 7.59-7.51 (m, 2 H), 7.49-7.30 (m, 10 H), 6.09 (s, 1 H) LRMS (ESI): (calc.) 386.5 (found) 387.3 (MH)+ |
| 151 | 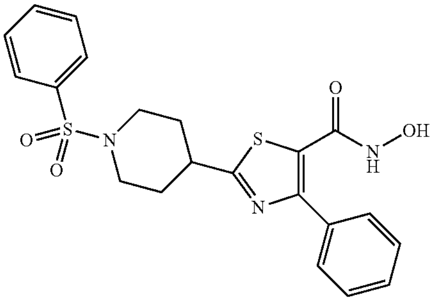 [SMILES: O=C(NO)c1sc(C2CCN(S(=O)(=O)c3ccccc3)CC2)nc1-c1ccccc1] | N-hydroxy-4-phenyl-2-(1-(phenylsulfonyl) piperidin-4-yl)thiazole-5-carboxamide | (DMSO-d6) d (ppm) 1 H: 7.85-7.67 (m, 7 H), 7.47-7.37 (m, 3 H), 3.79-3.71 (m, 2 H), 3.19-3.10 (m, 1 H), 2.55-2.50 (m, 2 H), 2.21-2.12 (m, 2 H), 1.84-1.69 (m, 2 H) LRMS (ESI): (calc.) 443.5 (found) 444.3 (MH)+ |
| 152 | 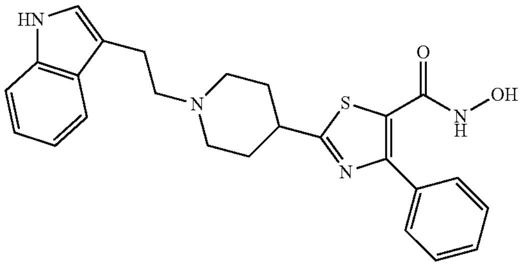 [SMILES: O=C(NO)c1sc(C2CCN(CCc3c[nH]c4ccccc34)CC2)nc1-c1ccccc1] | 2-(1-(2-(1H-indol-3-yl)ethyl)piperidin-4-yl)-N-hydroxy-4-phenylthiazole-5-carboxamide | (MeOD-d4) d (ppm) 1 H: 7.81-7.75 (m, 2 H), 7.63-7.59 (m, 1 H), 7.49-7.36 (m, 4 H), 7.17-7.11 (m, 2 H), 7.08-7.03 (m, 1 H), 3.50-3.42 (m, 2 H), 3.35-3.30 (m, 1 H), 3.19-3.02 (m, 4 H), 2.80-2.67 (m, 2 H), 2.38-2.29 (m, 2 H), 2.17-2.03 (m, 2 H) LRMS (ESI): (calc.) 446.6 (found) 447.3 (MH)+ |

TABLE 8-continued

| Cpd | Structure | Name | Characterization |
|---|---|---|---|
| 153 | 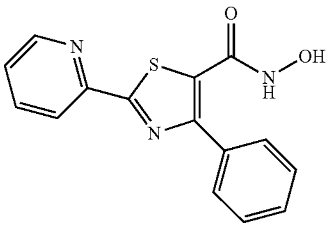 [SMILES: O=C(NO)c1sc(-c2ccccn2)nc1-c1ccccc1] | N-hydroxy-4-phenyl-2-(pyridin-2-yl)thiazole-5-carboxamide | (MeOD-d4) d (ppm) 1 H: 8.63 (d, J = 4.3 Hz, 1 H), 8.31 (d, J = 7.8 Hz, 1 H), 8.02-7.95 (m, 1 H), 7.93-7.86 (m, 2 H), 7.55-7.42 (m, 4 H) LRMS (ESI): (calc.) 297.3 (found) 298.1 (MH)+ |
| 154 | 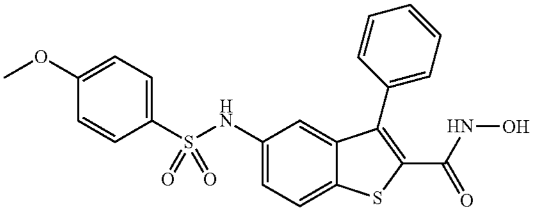 [SMILES: COc1ccc(S(=O)(=O)Nc2ccc3sc(C(=O)NO)c(-c4ccccc4)c3c2)cc1] | N-hydroxy-5-(4-methoxyphenyl-sulfonamido)-3-phenylbenzo[b]thiophene-2-carboxamide | (DMSOD6) δ ppm) 1 H: 10.78 (br s, 1 H), 10.15 (br s, 1 H), 9.19 (s, 1 H), 7.91 (d, J = 9.2 Hz, 1 H), 7.58 (d, J = 9.0 Hz, 2 H), 7.52-7.42 (m, 3 H), 7.24-7.19 (m, 4 H), 7.03 (d, J = 8.8 Hz, 2 H) LRMS (ESI): (calc.) 454.5 (found) 455.2 (MH)+ |
| 155 | 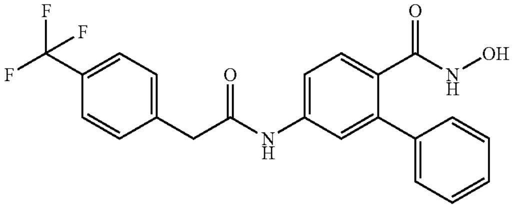 [SMILES: O=C(Cc1ccc(C(F)(F)F)cc1)Nc1ccc(C(=O)NO)c(-c2ccccc2)c1] | N-hydroxy-5-(2-(4-(trifluoromethyl)phenyl)acetamido)biphenyl-2-carboxamide | (DMSO-d6) d (ppm) 1 H: 10.71 (d, J = 1.6 Hz, 1 H), 10.45 (s, 1 H), 8.93 (d, J = 1.6 Hz, 1 H), 7.70 (d, J = 8.0 Hz, 2 H), 7.65 (d, J = 2.0 Hz, 1 H), 7.59 (dd, J = 8.4, 2.0 Hz, 1 H), 7.55 (d, J = 8.0 Hz, 2 H), 7.42-7.32 (m, 6 H), 3.80 (s, 2 H) LRMS (ESI): (calc) 414.38 (found) 415.2 (MH)+ |
| 156 | 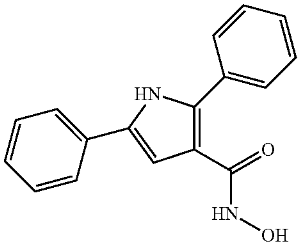 [SMILES: O=C(NO)c1cc(-c2ccccc2)[nH]c1-c1ccccc1] | N-hydroxy-2,5-diphenyl-1H-pyrrole-3-carboxamide | (DMSO-d6) d (ppm) 1 H: 11.56 (s, 1 H), 10.56 (s, 1 H), 8.75 (d, J = 1.6 Hz, 1 H), 7.74-7.72 (m, 2 H), 7.68-7.65 (m, 2 H), 7.42-7.37 (m, 4 H), 7.33-7.29 (m, 1 H), 7.24-7.20 (m, 1 H), 6.79 (d, J = 2.8 Hz, 1 H) LRMS (ESI): (calc) 278.11 (found) 279.2 (MH)+ |
| 157 | 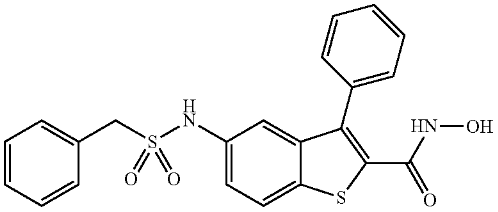 [SMILES: O=C(NO)c1sc2ccc(NS(=O)(=O)Cc3ccccc3)cc2c1-c1ccccc1] | N-hydroxy-3-phenyl-5-(phenylmethyl-sulfonamido)benzo[b]thiophene-2-carboxamide | (DMSO-d6) δ ppm) 1 H: 10.86 (br s, 1 H), 9.89 (br s, 1 H), 9.21 (s, 1 H), 8.01 (d, J = 8.8 Hz, 1 H), 7.54-7.42 (m, 6 H), 7.34-7.18 (m, 6 H), 4.39 (s, 2 H). LRMS (ESI): (calc.) 438.5 (found) 439.2 (MH)+ |
| 158 | 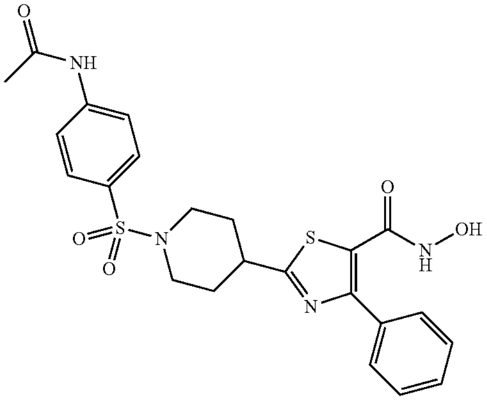 [SMILES: CC(=O)Nc1ccc(S(=O)(=O)N2CCC(c3nc(-c4ccccc4)c(C(=O)NO)s3)CC2)cc1] | 2-(1-(4-acetamidophenyl-sulfonyl)piperidin-4-yl)-N-hydroxy-4-phenylthiazole-5-carboxamide | (DMSO-d6) δ ppm) 1 H: 11.19 (br s, 1 H), 10.45 (s, 1 H), 9.36 (br s, 1 H), 7.91-7.85 (m, 2 H), 7.79-7.70 (m, 4 H), 7.49-7.38 (m, 3 H), 3.74-3.67 (m, 2 H), 3.20-3.09 (m, 1 H), 2.54-2.46 (m, 2 H), 2.21-2.13 (m, 5 H), 1.84-1.72 (m, 2 H) LRMS (ESI): (calc.) 500.6 (found) 501.5 (MH)+ |

TABLE 8-continued

| Cpd | Structure | Name | Characterization |
|---|---|---|---|
| 158a | 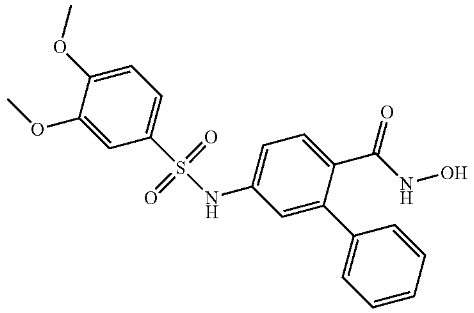 [SMILES: COc1ccc(S(=O)(=O)Nc2ccc(C(=O)NO)c(-c3ccccc3)c2)cc1OC] | 5-(3,4-dimethoxyphenyl-sulfonamido)-N-hydroxybiphenyl-2-carboxamide | (DMSO-d6) d (ppm) 1 H: 10.68 (d, J = 1.8 Hz, 1 H), 10.46 (s, 1 H), 8.92 (d, J = 2.0 Hz, 1 H), 7.41-7.24 (m, 8 H), 7.14-7.09 (m, 3 H), 3.80 (s, 3 H), 3.75 (s, 3 H) LRMS (ESI): (calc) 428.10 (found) 429.45 (MH)+ |
| 159 | 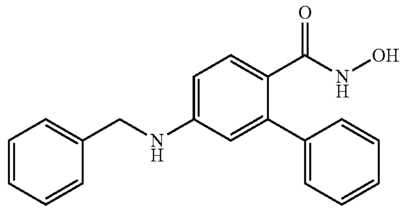 [SMILES: O=C(NO)c1ccc(NCc2ccccc2)cc1-c1ccccc1] | 5-(benzylamino)-N-hydroxybiphenyl-2-carboxamide | (DMSO-d6) d (ppm) 1 H: 10.46 (S, 1 H), 8.71 (s, 1 H), 7.36-7.21 (m, 10 H), 7.09 (d, J = 8.8 Hz, 1 H), 6.70 (t, J = 6.0 Hz, 1 H), 6.53-6.51 (m, 2 H), 4.33 (d, J = 6.4 Hz, 2 H) LRMS (ESI): (calc) 318.14 (found) 319.37 (MH)+ |
| 160 | 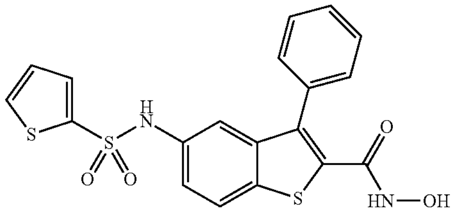 [SMILES: O=C(NO)c1sc2ccc(NS(=O)(=O)c3cccs3)cc2c1-c1ccccc1] | N-hydroxy-3-phenyl-5-(thiophene-2-sulfonamido)benzo[b](thiophene-2-carboxamide | (DMSO-d6) d (ppm) 1 H: 10.81 (br s, 1 H), 10.41 (br s, 1 H), 9.20 (s, 1 H), 7.97 (d, J = 8.8 Hz, 1 H), 7.89 (dd, J = 4.9 Hz, 1 H), 7.52-7, 41 (m, 4 H) 7.32-7.23 (m, 4 H), 7.11 (dd, J = 4.9, 3.7 Hz, 1 H). LRMS (ESI): (calc.) 430.5 (found) 431.4 (MH)+ |
| 161 | 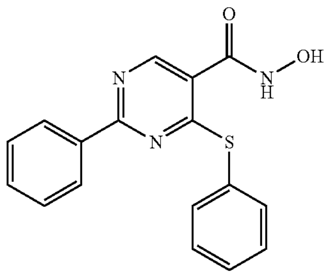 [SMILES: O=C(NO)c1cnc(-c2ccccc2)nc1Sc1ccccc1] | N-hydroxy-2-phenyl-4-(phenylthio) pyrimidine-5-carboxamide | (DMSO-d6) d (ppm) 1 H: 8.79 (s, 1 H), 7.96 (d, J = 7.0 Hz, 2 H), 7.69-7.56 (m, 5 H), 7.53-7.47 (m, 1 H), 7.44-7.37 (m, 2 H) LRMS (ESI): (calc.) 323.4 (found) 324.2 (MH)+ |
| 162 | 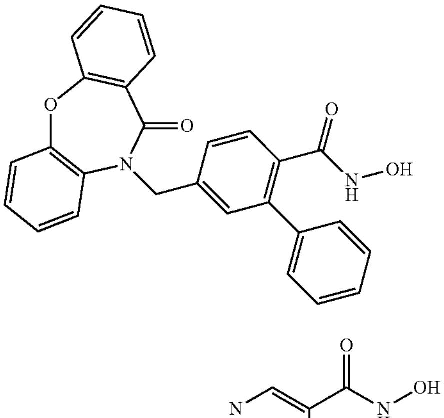 | N-hydroxy-5-((11-oxodibenzo[b,f][1,4]oxazepin-10(11H)-yl)methyl)biphenyl-2-carboxamide | (DMSO-d6) δ ppm) 1 H: 10.77 (s, 1 H), 8.96 (s, 1 H), 7.76 (dd, J = 7.6, 1.6 Hz, 1 H), 7.63-7.58 (m, 1 H), 7.55-7.52 (m, 1 H), 7.41-7.28 (m, 11 H), 7.24-7.17 (m, 2 H), 5.46 (s, 2 H) LRMS (ESI): (calc) 436.14 (found) 437.49 (MH)+ |
| 163 | 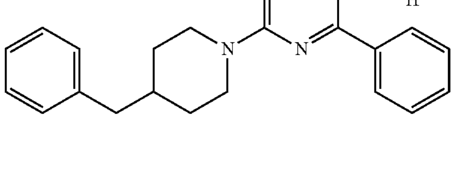 | 2-(4-benzylpiperidin-1-yl)-N-hydroxy-4-phenylpyrimidine-5-carboxamide | (MeOD-d4) d (ppm) 1 H: 8.37 (s, 1 H), 7.79-7.74 (m, 2 H), 7.50-7.43 (m, 3 H), 7.33-7.27 (m, 2 H), 7.24-7.18 (m, 3 H), 4.91 (m, 2 H), 3.00-2.90 (m, 2 H), 2.60 (d, J = 7.0 Hz, 2 H), 1.99-1.84 (m, 1 H), 1.82-1.72 (m, 2 H), 1.30-1.18 (m, 2 H) LRMS (ESI): (calc.) 388.5 (found) 389.4 (MH)+ |

TABLE 8-continued
| Cpd | Structure | Name | Characterization |
|---|---|---|---|
| 164 | 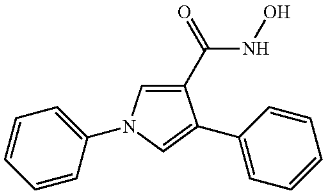 [SMILES: O=C(NO)c1cn(-c2ccccc2)cc1-c1ccccc1] | N-hydroxy-1,4-diphenyl-1H-pyrrole-3-carboxamide | (MeOD-d4) δ ppm) 1 H: 7.60-7.46 (m, 7 H), 7.38 (d, J = 2.5 Hz, 1 H), 7.36-7.29 (m, 3 H), 7.22 (t, J = 7.3 Hz, 1 H). LRMS (ESI): (calc.) 278.1 (found) 279.2 (MH)+ |
Scheme 16
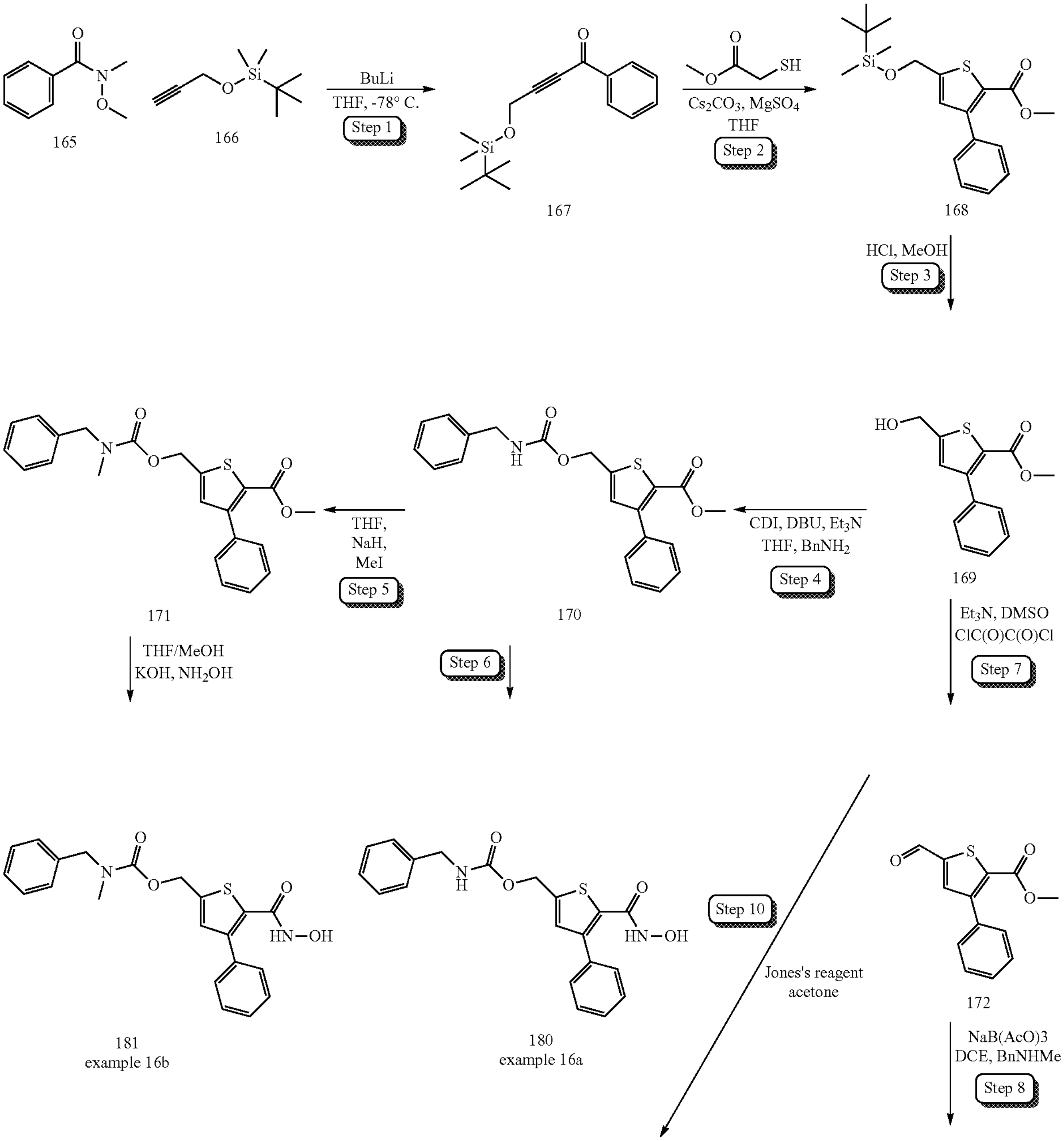
165
166
167
168
169
170
171
172
181
example 16b
180
example 16a -continued

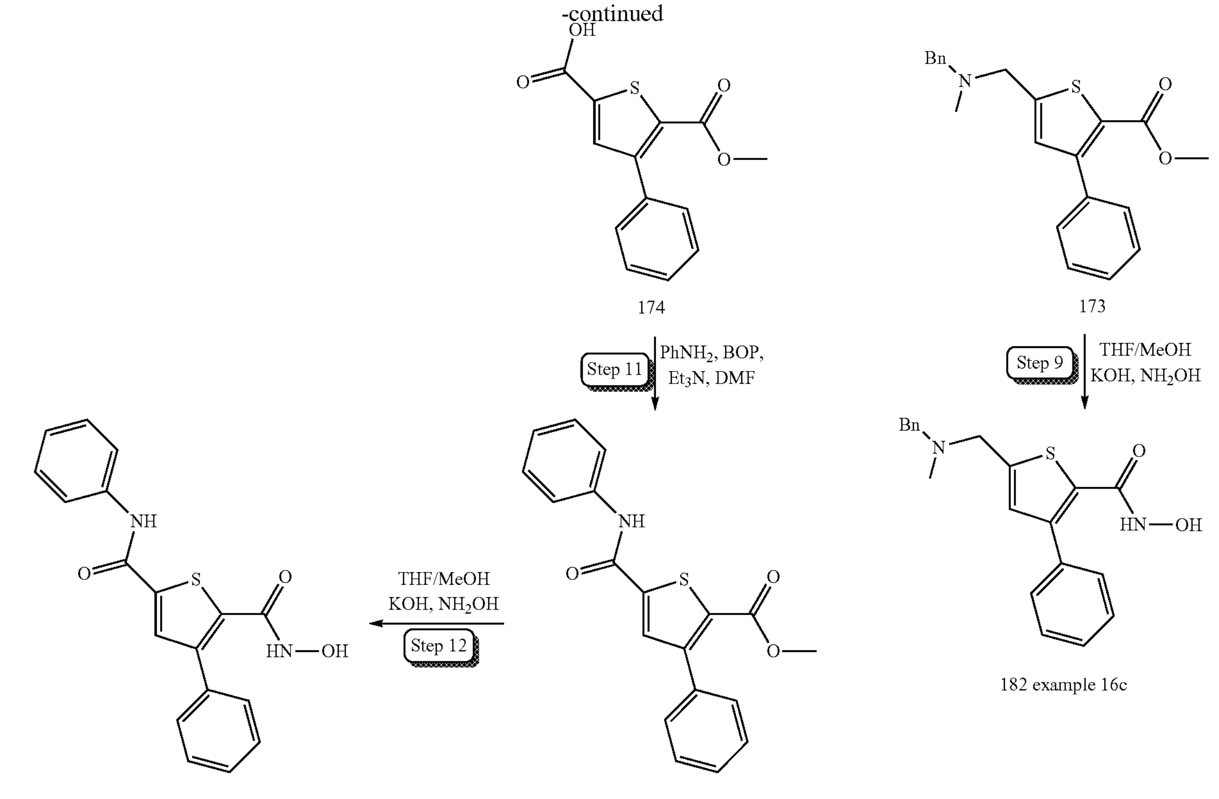

174

173

182 example 16c 183 example 16d

175

Example 16a, 16b, 16c, 16d (5-(hydroxycarbamoyl)-4-phenylthiophen-2-yl)methyl benzylcarbamate (180)

(5-(hydroxycarbamoyl)-4-phenylthiophen-2-yl)methyl benzyl(methyl)carbamate (181)

5-((benzyl(methylamino)methyl)-N-hydroxy-3-phenylthiophene-2-carboxamide (182)

N2-hydroxy-N5,3-diphenylthiophene-2,5-dicarboxamide (183)

Step 1: 4-(tert-butyldimethylsilyloxy)-1-phenylbut-2-yn-1-one (167)

To a solution of tert-Butyldimethyl(2-propynyloxy)silane 166 (7.99 mL, 39.4 mmol) in 80 mL of THF at −78° C. was added dropwise N-BUTYLLITHIUM (15.76 mL, 39.4 mmol). The resulting mixture was then warmed up slowly to −30° C. and stirred for 30 min. A solution of N-Methoxy-N-methylbenzamide 165 (5 mL, 32.8 mmol) in 5 mL of TIE was added dropwise and the solution was warmed slowly to room temperature and stirred 2 hours. Aqueous 5% HCl was added to quench the reaction and the product was extracted twice with ethyl acetate. The combined organic layers were washed with a saturated solution of bicarbonate and brine, dried over sodium sulfate and filtered. The solvents were removed in vacuo and the crude material was purified by ISCO (120 g column, 0-30% ethyl acetate in hexanes) to yield 99% of a yellow oil 167 (8.924 g)

LRMS (ESI): (calc) 274.14 (found) 275.05 (MH)+

Step 2: methyl 5-((tert-butyldimethylsilyloxy)methyl)-3-phenylthiophene-2-carboxylate (168)

To a solution of 167 (8.924 g, 32.5 mmol) in THF was added methyl thioglycolate (4.36 mL, 48.8 mmol) and stirred 2 hours at room temperature. MAGNESIUM SULFATE (3.91 g, 32.5 mmol) was added and the reaction mixture was stirred for 1 hour. Then CESIUM CARBONATE (10.60 g, 32.5 mmol) in 30 mL of MeOH was added and stirred for an additional 2 hours at room temperature. The reaction mixture was filtered and the filtrate was concentrated in vacuo. The residue was dissolved in ethyl acetate and washed with brine, dried over sodium sulfate and filtered. The solvent was evaporated and the residue was purified by silica gel chromatography (0%-5% ethyl acetate in hexanes) to yield 168 in 54% (6.389 g) as an orange solid LRMS (ESI): (calc) 362.14 (found) 363.38 (MH)+

Step 3: methyl 5-(hydroxymethyl)-3-phenylthiophene-2-carboxylate (169)

To a solution of 168 (6.389 g, 17.62 mmol) in 93 mL of MeOH was added concentrated HCl
(7 ml, 85 mmol) and stirred at room temperature for 45 min. The reaction mixture was concentrated under vacuum; the oil was dissolved in ethyl acetate, washed with a saturated solution of sodium bicarbonate, water, brine, dried with sodium sulfate, filtered and concentrated under vacuum. The residue was purified by ISCO (10%-50% ethyl acetate in hexanes) to yield 169 in 99% (4.35 g) as light brown oil LRMS (ESI): (calc) 248.05 (found) 249.14 (MH)+

Step 4: methyl 5-((benzylcarbamoyloxy)methyl)-3-phenylthiophene-2-carboxylate (170)

To a solution of 169 (0.900 g, 3.62 mmol) in THF was added 1,1'-carbonyldiimidazole (0.588 g, 3.62 mmol) and stirred at room temperature for 90 min. Then $BnNH_2$ (0.396 mL, 3.62 mmol), TEA (0.505 mL, 3.62 mmol) and 1,8-Diazabicyclo[5.4.0]undec-7-ene (0.546 mL, 3.62 mmol) were added and stirred at room temperature for an additional 2 hours. The reaction mixture was diluted with ethyl acetate, washed with water, brine, dried over sodium sulfate, filtered and concentrated under vacuum. The residue was purified by ISCO (40 g column, 0-45% ethyl acetate in hexanes) to yield in 82% (1.13 g) compound 170 as a pink solid.

Step 5: methyl 5-((benzyl(methyl)carbamoyloxy)methyl)-3-phenylthiophene-2-carboxylate (171)

To a solution of 170 (0.620 g, 1.625 mmol) in 10 mL of THF was added NaH (0.098 g, 2.438 mmol) and stirred at room temperature for 20 min. Then MeI (0.5 ml, 8.00 mmol) was added and stirred for an additional 2 hours at 50° C. The reaction mixture was cooled down at room temperature, quenched with 2 mL of MeOH, diluted with ethyl acetate, washed with brine, dried over sodium sulfate, filtered and concentrated under vacuum. The residue was purified by ISCO (40 g column, 5%-30% ethyl acetate in hexanes) to yield in 53% (342 mg) compound 171 as colorless oil.

LRMS (ESI): (calc) 395.12 (found) 396.40 (MH)+

Step 6: (5-(hydroxycarbamoyl)-4-phenylthiophen-2-yl)methyl benzylcarbamate (180)

The procedure was followed as outlined in Scheme 5, Step 3 replacing compound 49 with compound 170 to afford title compound 180 (46% yield, 110 mg) as a white solid after purification by Gilson (45%-95% MeOH in water).

LRMS (ESI): (calc) 382.10 (found) 383.11 (MH)+

(5-(hydroxycarbamoyl)-4-phenylthiophen-2-yl)methyl benzyl(methyl)carbamate (181)

The procedure was followed as outlined in Scheme 5, Step 3 replacing compound 49 with compound 171 to afford title compound 181 (37% yield, 127 mg) as colorless foam after purification by Gilson (50%-95% MeOH in water).

LRMS (ESI): (calc) 396.11 (found) 397.33 (MH)+

Step 7: methyl 5-formyl-3-phenylthiophene-2-carboxylate (172)

DMSO (0.643 ml, 9.06 mmol) in 4 mL of DCM at −70° C. was added dropwise to a solution of oxalyl chloride (0.529 ml, 6.04 mmol) in 10 mL of DCM at −78° C. and stirred for 10 min. Then 169 (0.75 g, 3.02 mmol) in 4 mL of DCM and TEA in 4 ml, DCM were added dropwise, stirred for an additional 10 min and warmed up slowly to 0° C. The reaction mixture was poured into an ice-cooled solution of $NaHCO_3$ (ss) and extract the product with DCM, washed with brine, dried over sodium sulfate, filtered, concentrated under vacuum to yield compound 172 (706 mg, 95%) as a beige solid.

LRMS (ESI): (calc) 246.04 (found) 247.16 (MH)+

Step 8: methyl 5-((benzyl(methyl)amino)methyl)-3-phenylthiophene-2-carboxylate (173)

To a solution of 172 (0.706 g, 2.87 mmol) in DCE (15 mL) was added N-Methylbenzylamine (0.388 mL, 3.01 mmol) and sodium triacetoxyborohydride (0.851 g, 4.01 mmol) and stirred for 18 hours. The reaction mixture was diluted in DCM and washed with a saturated solution of sodium bicarbonate. The organic layer was dried over sodium sulfate, filtered and evaporated. The crude residue was purified by ISCO (40 g column, 0-30% ethyl acetate in hexanes) to yield compound 173 (951 mg, 94%) a colorless oil.

LRMS (ESI): (calc) 351.13 (found) 352.33 (MH)+

Step 9: 5-((benzyl(methyl)amino)methyl)-N-hydroxy-3-phenylthiophene-2-carboxamide (182)

The procedure was followed as outlined in Scheme 5, Step 3 replacing compound 49 with compound 173 to afford title compound 182 (61% yield, 580 mg) as colorless foam after purification by ISCO (30%-60% Ethyl acetate in hexanes).

LRMS (ESI): (calc) 352.12 (found) 353.39 (MH)+

Step 10: 5-(methoxycarbonyl)-4-phenylthiophene-2-carboxylic Acid (174)

To a solution of 169 (1.20 g, 4.83 mmol) in 30 mL of acetone was added dropwise Jones reagent (5 mL, 1.3M, 6.5 mmol) and stirred at room temperature for 1 hour. The reaction mixture was quenched with 10 mL of IPA, stirred for 10 min, filtered over a pad of Celite®. The filtrate was concentrated under vacuum, diluted in ether, washed with brine, dried over sodium sulfate, filtered, concentrated under vacuum to yield compound 174 (1.156 g, 91%) as yellow solid.

LRMS (ESI): (calc) 262.03 (found) 261.16 (M−1)

Step 11: methyl 3-phenyl-5-(phenylcarbamoyl)thiophene-2-carboxylate (175)

To a solution of 174 (0.334 g, 1.273 mmol) in 6 mL DMF was added $PhNH_2$ (0.128 ml, 1.401 mmol), followed by BOP (0.620 g, 1.401 mmol) and TEA (0.355 ml, 2.55 mmol). The mixture was stirred for 1 h at room temperature and then poured into water. The product was extracted with ethyl acetate twice and the combined organic phases were washed with water and brine. The solution was dried over sodium sulfate, filtered and evaporated in vacuo. The crude residue was purified by ISCO (24 g column, 0%-100% ethyl acetate in hexanes) to yield compound 175 (285 mg, 66%) a off-white solid.

LRMS (ESI): (calc) 337.08 (found) 338.33 (MH)+

Step 12: N2-hydroxy-N5,3-diphenylthiophene-2,5-dicarboxamide (183)

The procedure was followed as outlined in Scheme 5, Step 3 replacing compound 49 with compound 175 to afford title compound 183 (64% yield, 182 mg) as a white solid after purification by Gilson (55%-95% MeOH in water).

LRMS (ESI): (calc) 338.07 (found) 339.31 (MH)+

TABLE 8

| Compounds according to Scheme 16 and Scheme 15 | | | | |
|---|---|---|---|---|
| Ex. | Cpd # | Structure | Name | Characterization |
| 16 | 180 | 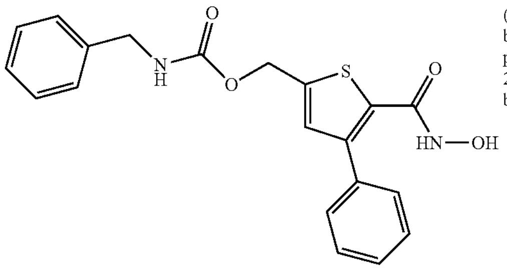 | (5- (hydroxycarbamoyl)-4-phenylthiophen-2-yl)methyl benzylcarbamate | (DMSO-d6) δppm) 1H: 10.91 (s, 1H), 9.18 (s, 1H), 7.91 (t, J = 6.3 Hz, 1H), 7.46-7.22 (m, 11H), 5.22 (s, 2H), 4.21 (d, J = 6.1 Hz, 2H) LEMS (ESI): (calc) 382.10 (found) 383.11 (MH)+ |
| | 181 | 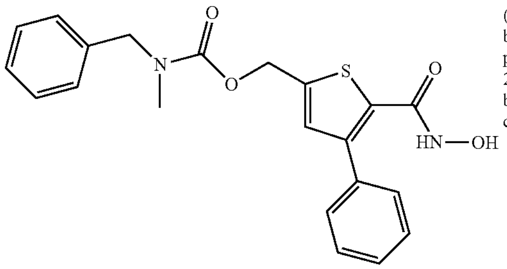 | (5- (hydroxycarbamoyl)-4-phenylthiophen-2-yl)methyl benzyl(methyl) carbamate | (MeOD-d4) δppm) 1H: 7.49-7.18 (m, 11H), 3.53 (d, J = 3.6 Hz, 2H), 4.50 (s, 2H), 2.89, 2.87 (2S, CH3, rotamers) LRMS (ESI): (calc) 396.11 (found) 397.33 (MH)+ |
| | 182 | 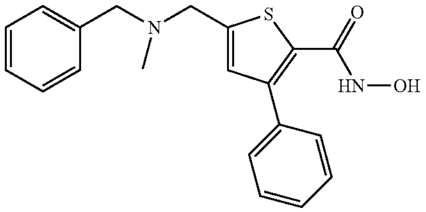 [SMILES: CN(Cc1ccccc1)Cc1cc(-c2ccccc2)c(C(=O)NO)s1] | 5- ((benzyl(methyl) amino)methyl)-N-hydroxy-3-phenylthiophene-2-carboxamide | (DMSO-d6) δppm) 1H: 10.85 (s, 1H), 9.13 (s, 1H), 7.47-7.45 (m, 2H), 7.41-7.24 (m, 8H), 7.14 (s, 1H), 3.74 (s, 2H), 3.57 (s, 2H), 2.19 (s, 3H) LRMS (ESI): (calc) 352.12 (found) 353.39 (MH)+ |
| | 183 | 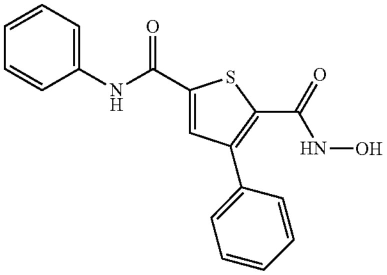 [SMILES: O=C(Nc1ccccc1)c1cc(-c2ccccc2)c(C(=O)NO)s1] | N2-hydroxy-N5,3-diphenylthiophene-2,5-dicarboxamide | (DMSO-d6) δppm) 1H: 11.15 (s, 1H), 10.35 (s, 1H), 9.33 (s, 1H), 8.21 (s, 1H), 7.75-7.72 (m, 2H), 7.55-7.53 (m, 2H), 7.48-7.45 (m, 2H), 7.42-7.36 (m, 3H), 7.15-7.11 (m, 1H) LRMS (ESI): (calc) 338.07 (found) 339.31 (MH)+ |

TABLE 8-continued
Compounds according to Scheme 16 and Scheme 15
| Ex. | Cpd # | Structure | Name | Characterization |
| --- | --- | --- | --- | --- |
| | 184 | 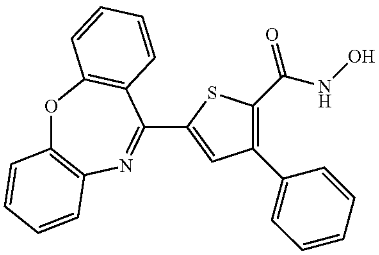 [SMILES: O=C(NO)c1sc(C2=Nc3ccccc3Oc3ccccc32)cc1-c1ccccc1] | (E)-5- (dibenzo[b,f][1,4]oxazepin-11-yl)-N-hydroxy-3-phenylthiophene-2-carboxamide | (DMSO-d6) δppm) 1H: 11.18 (s, 1H), 9.34 (s, 1H), 7.73-7.67 (m, 2H), 7.54-7.52 (m, 2H), 7.45-7.25 (m, 10H) LRMS (ESI): (calc) 412.09 (found) 413.30 (MH)+ |
Scheme 17
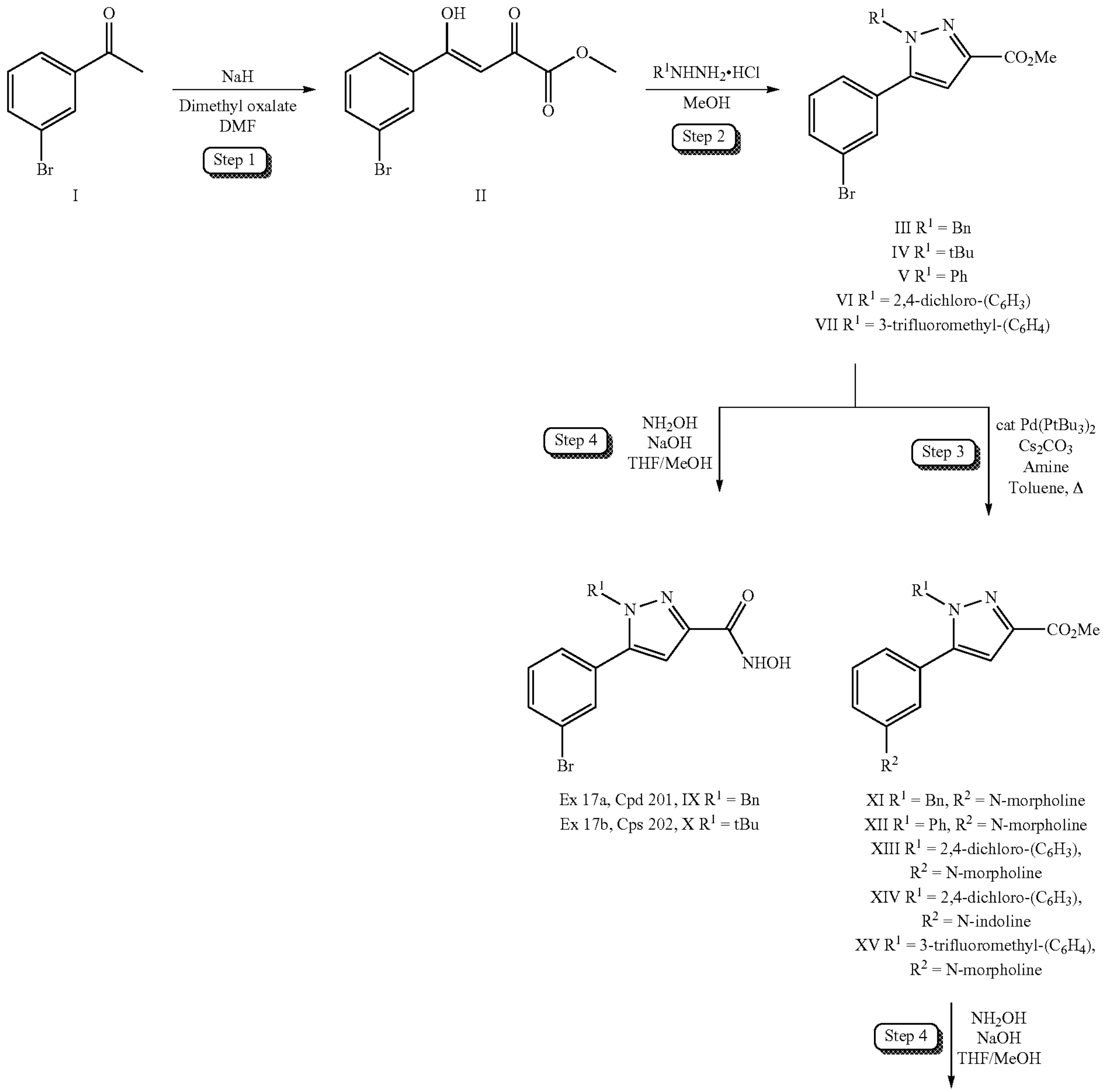

-continued

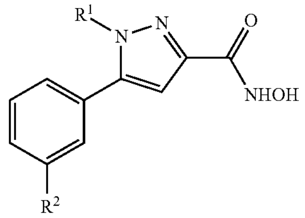

Ex 17c, Cpd 203, XVI $R^1$ = Bn, $R^2$ = N-morpholine
Ex 17d, Cpd 204, XVII $R^1$ = Ph, $R^2$ = N-morpholine
Ex 17e, Cpd 205, XVIII $R^1$ = 2,4-dichloro-($C_6H_3$), $R^2$ = N-morpholine
Ex 17f, Cpd 206, XIX $R^1$ = 2,4-dichloro-($C_6H_3$), $R^2$ = N-indoline
Ex 17g, Cpd 207, XX $R^1$ = 3-trifluoromethyl-($C_6H_4$), $R^2$ = N-morpholine Example 17a-g Compounds 201-207

Step 1: (Z)-methyl 4-(3-bromophenyl)-4-hydroxy-2-oxobut-3-enoate II

In a 100 mL round-bottomed flask was dissolved 3'-bromoacetophenone (I) (10.03 mL, 75 mmol) and dimethyl oxalate (8.90 g, 75 mmol) in DMF (25 mL) to give a pale orange suspension. Sodium hydride (3.62 g, 90 mmol) was added at 0° C. in portions, over 1 h (CAUTION! Vigorous bubbling!). The mixture was stirred at room temperature overnight, diluted with ethyl acetate, washed twice with water, then brine, then dried with $NaSO_4$, and the solvent evaporated in vacuo. The residue was treated with aqueous 3M HCl to obtain a brown suspension, which was triturated overnight and filtered to obtain product II as a yellow solid (18.4 g, 64.5 mmol, 86%).

Step 2: Preparation of III-VII

In a 15 ml pressure vessel, II (1 g, 3.51 mmol) and a functionalized hydrazine (HCl salt, 3.51 mmol) were dissolved in methanol (25 mL). (Four drops concentrated aqueous HCl was added if the hydrazine was used as its free base.) The flask was heated at 100° C. for 16 h. After cooling, the solvent was evaporated to yield the desired product.

Methyl 1-benzyl-5-(3-bromophenyl)-1H-pyrazole-3-carboxylate III

Using II (4.08 g, 14.3 mmol) and benzylhydrazide dihydrochloride (2.79 g, 14.3 mmol). 1.7 g (4.58 mmol, 32%) of III isolated as a thick yellow oil.

Methyl 5-(3-bromophenyl)-1-tert-butyl-1H-pyrazole-3-carboxylate IV

Using II (1 g, 3.51 mmol) and tert-butylhydrazine hydrochloride (0.437 g, 3.51 mmol). Purified by silica gel chromatography (0-25% EtOAc/Hex, 40 g silica column) get 742 mg (2.2 mmol, 63%) of IV as a yellow solid.

Methyl 5-(3-bromophenyl)-1-phenyl-1H-pyrazole-3-carboxylate V

Using II (1 g, 3.51 mmol) and phenylhydrazine (0.348 mL, 3.51 mmol). Purified by silica gel chromatography (0-20% EtOAc/Hex, 40 g silica column) to get 816 mg (2.2 mmol, 63%) of V as a yellow foam.

Methyl 5-(3-bromophenyl)-1-(2,4-dichlorophenyl)-1H-pyrazole-3-carboxylate VI

Using II (1 g, 3.51 mmol) and 2,4-dichlorophenylhydrazine hydrochloride (0.749 g, 3.51 mmol). Crude material was triturated in ether to obtain 920 mg (2.16 mmol, 62%) of VI as a light yellow powder.

Methyl 5-(3-bromophenyl)-1-(3-(trifluoromethyl)phenyl)-1H-pyrazole-3-carboxylate VII Using II (1 g, 3.51 mmol) and 3-(trifluoromethyl)phenylhydrazine (0.512 mL, 3.51 mmol). Crude material was triturated in hexanes to obtain 1.19 g (2.8 mmol, 80%) of VII as a light yellow powder.

Step 3: Preparation of XI-XV

The aryl bromide and bis(tri-t-butylphosphine)palladium (0) (0.044 equiv) were dissolved in Toluene (5 ml) in a 15 mL pressure flask, under a nitrogen atmosphere, to give an orange solution. An amine (1.3 equiv) and cesium carbonate (2.2 equiv) were then added and the mixture left to stir at 110° C. overnight. After cooling the suspension was filtered through Celite®, washed the solid with ethyl acetate, concentrated the filtrate and the residue was purified via silica-gel chromatography column (0-50% EtOAc/Hex) to obtain the desired product XI-XV.

Methyl 1-benzyl-5-(3-morpholinophenyl)-1H-pyrazole-3-carboxylate XI

Using III (500 mg, 1.34 mmol) and morpholine gave 369 mg (0.98 mmol, 73%) of XI as a yellow foam.

Methyl 5-(3-morpholinophenyl)-1-phenyl-1H-pyrazole-3-carboxylate XII

Using V (330 mg, 0.92 mmol) and morpholine gave 48 mg (0.13 mmol, 14%) of XII as a yellow foam.

Methyl 1-(2,4-dichlorophenyl)-5-(3-morpholinophenyl)-1H-pyrazole-3-carboxylate XIII Using VI (200 mg, 0.46 mmol) and morpholine gave 107 mg (0.24 mmol, 53%) of XIII as a colorless foam.

Methyl 1-(2,4-dichlorophenyl)-5-(3-(indolin-1-yl)phenyl)-1H-pyrazole-3-carboxylate XIV Using VI (200 mg, 0.46 mmol) and indoline gave 55 mg (0.12 mmol, 25%) of XIV as a colorless foam.

Methyl 5-(3-morpholinophenyl)-1-(3-(trifluoromethyl)phenyl)-1H-pyrazole-3-carboxylate XV Using VII (250 mg, 0.58 mmol) and morpholine gave 123 mg (0.28 mmol, 49%) of XV as a colorless foam.

Step 4: Preparation of IX, X and XVI-XX

The procedure was followed as outlined in Scheme 5, Step 3 replacing compound 49 with compound III, IV, XI-XV to afford title compound IX, X and XVI-XX, as a white powder.

1-benzyl-5-(3-bromophenyl)-N-hydroxy-1H-pyrazole-3-carboxamide IX (cpd 201)

200 mg of III yield 164 mg of 1× as a white solid (0.44 mmol, 85%).

5-(3-bromophenyl)-1-tert-butyl-N-hydroxy-1H-pyrazole-3-carboxamide X (cpd 202)

200 mg of IV yield 137 mg of X as a white solid (0.405 mmol, 68%).

1-Benzyl-N-hydroxy-5-(3-morpholinophenyl)-1H-pyrazole-3-carboxamide XVI (cpd 203)

Using XI (100 mg, 0.26 mmol) yield 68 mg (0.18 mmol, 68%) of XVI as a white powder.

N-Hydroxy-5-(3-morpholinophenyl)-1-phenyl-1H-pyrazole-3-carboxamide XVII (cpd 204)

Using XII (48 mg, 0.13 mmol) yield 40 mg (0.11 mmol, 83%) of XVII as a white powder.

1-(2,4-Dichlorophenyl)-N-hydroxy-5-(3-morpholinophenyl)-1H-pyrazole-3-carboxamide XVIII (cpd 205)

Using XIII (107 mg, 0.24 mmol) yield 62 mg (0.143 mmol, 58%) of XVIII as a white powder.

1-(2,4-Dichlorophenyl)-N-hydroxy-5-(3-(indolin-1-yl)phenyl)-1H-pyrazole-3-carboxamide XIX (cpd 206)

Using XIV (55 mg, 0.12 mmol) yield 45 mg (0.09 mmol, 82%) of XIX as a white powder.

N-Hydroxy-5-(3-morpholinophenyl)-1-(3-(trifluoromethyl)phenyl)-1H-pyrazole-3-carboxamide XX (cpd 207)

Using XV (123 mg, 0.28 mmol) yield 105 mg (0.24 mmol, 85%) of XX as a white powder.

Scheme 18

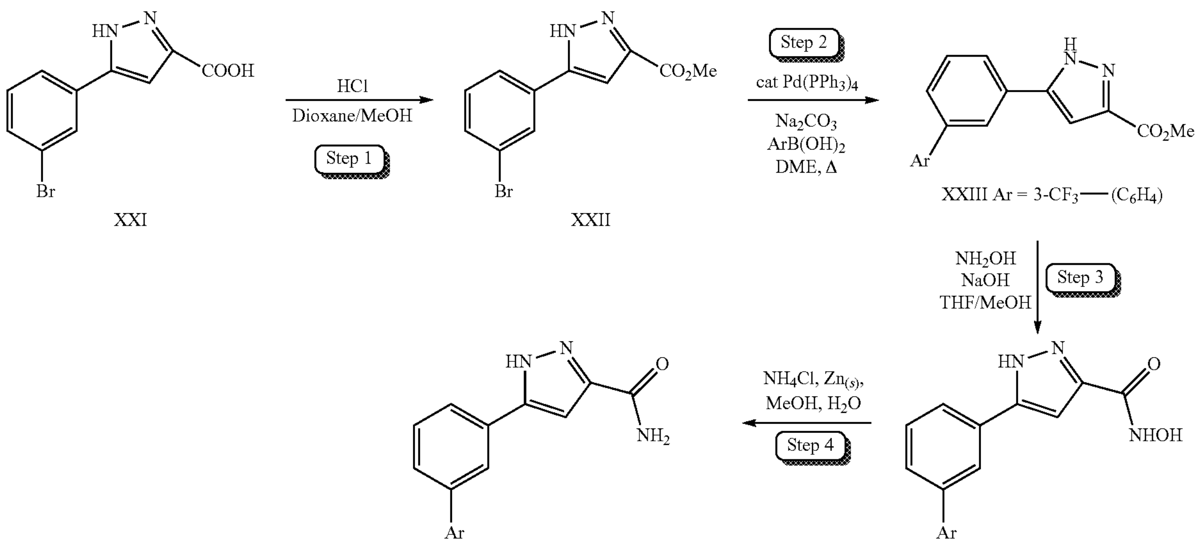

XXI

XXII

XXIII Ar = 3-$CF_3$—($C_6H_4$)

XIV Ar = 3-$CF_3$—($C_6H_4$)

Ex 18, Cpd 200, XV Ar = 3-$CF_3$—($C_6H_4$)

Example 18

5-(3'-(trifluoromethyl)biphenyl-4-yl)-1H-pyrazole-3-carboxamide (cpd 200, XV)

Step 1: methyl 5-(3-bromophenyl)-1H-pyrazole-3-carboxylate XXII

HCl in dioxane (4M, 3.56 mL, 14.23 mmol) was added to a solution of the carboxylic acid XXI (950 mg, 3.56 mmol) in MeOH (15 mL) and the reaction stirred at room temperature for 16 h. The solvent was removed in vacuo and the residue diluted with ethyl acetate and washed once with saturated sodium bicarbonate solution, twice with water, once with brine, dried ($MgSO_4$) and removed solvent in vacuo to obtain XXII as an off-white powder (810 mg, 2.88 mmol, 81%).

Step 2: methyl 5-(3'-(trifluoromethyl)biphenyl-3-yl)-1H-pyrazole-3-carboxylate XXIII In a 75 mL pressure flask, XXII (150 mg, 0.534 mmol), was dissolved in DME (5 mL) followed by addition of 3-trifluoromethylphenylboronic acid (111 mg, 0.587 mmol), and $Pd(PPh_3)_4$ (30.8 mg, 0.027 mmol) to give an orange solution. Sodium carbonate (2M solution, 0.320 mL, 0.640 mmol) was then added and refluxed overnight. The mixture was cooled to room temperature, filtered through silica and Celite®, washed the solids with ethyl acetate and the solvent was removed in vacuo. The residue was suspended in dichloromethane-ether, triturated and filtered to obtain XXIII as a white solid (98 mg, 0.283 mmol, 53%).

Step 3: N-hydroxy-5-(3'-(trifluoromethyl)biphenyl-3-yl)-1H-pyrazole-3-carboxamide XXIV The procedure was followed as outlined in Scheme 5, Step 3 replacing compound 49 with compound XXIII (98 mg, 0.283 mmol) to afford title compound MV as a white solid (75 mg, 0.216 mmol, 76%).

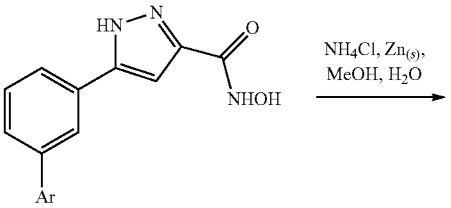

XIV Ar = 3-$CF_3$—($C_6H_4$)

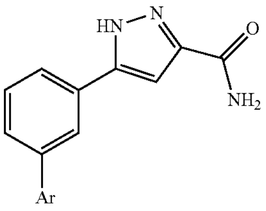

XV Ar = 3-$CF_3$—($C_6H_4$)

Step 4: 5-(3'-(trifluoromethyl)biphenyl-3-yl)-1H-pyrazole-3-carboxamide XXV (cpd 200)

To a solution of XIV (50 mg, 0.144 mmol) in MeOH (10 ml) and water (1 ml) was added ammonium chloride (15.40 mg, 0.288 mmol) and zinc powder (85 mg, 1.296 mmol) and the reaction mixture was heated to reflux for 4 hours. The reaction mixture was cooled down and filtered the suspension through Celite® and concentrated. The residue was purified via reverse phase column chromatography (40-80% MeOH/$H_2O$) to obtain XXV (5.8 mg, 0.018 mmol, 12%) as a white solid.

TABLE 9

The following additional compounds were prepared according to the procedures described herein and/or according to knowledge available to one of skill in the art.

| Cpd # | Structure | Name | Characterization |
|---|---|---|---|
| 200 | 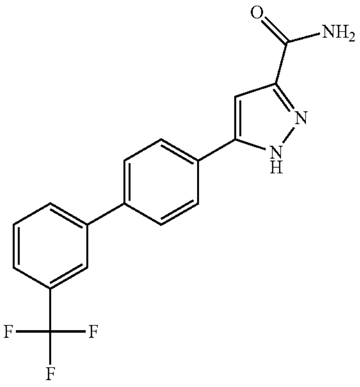 [SMILES: NC(=O)c1cc(-c2ccc(-c3cccc(C(F)(F)F)c3)cc2)[nH]n1] | 5-(3'-(trifluoromethyl) biphenyl-4-yl)-1H-pyrazole-3-carboxamide | (MeOD-d4) δppm) 1H: 7.66-7.95 (m, 8H), 7.13 (s, 1H). LRMS (ESI): (calc.) 331.09 (found) 332.37 (MH)+ |

TABLE 9-continued

The following additional compounds were prepared according to the procedures described herein and/or according to knowledge available to one of skill in the art.

| Cpd # | Structure | Name | Characterization |
|---|---|---|---|
| 201 | 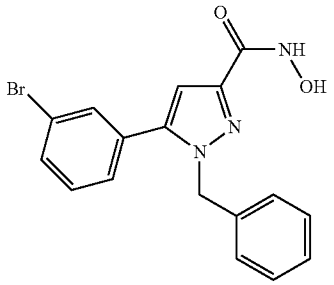 [SMILES: O=C(NO)c1cc(-c2cccc(Br)c2)n(Cc2ccccc2)n1] | 1-benzyl-5-(3-bromophenyl)-N-hydroxy-1H-pyrazole-3-carboxamide | (MeOD-d4) d (ppm) 1H: 7.59 (m, 1H), 7.48 (s, 1H), 7.24-7.34 (m, 5H), 7.03 (s, 1H), 7.02 (s, 1H), 6.83 (s, 1H), 5.41 (s, 2H). LRMS (ESI): (calc.) 371.3 (found) 372.17 (MH)+ |
| 202 | 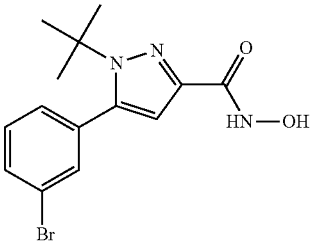 [SMILES: CC(C)(C)n1nc(C(=O)NO)cc1-c1cccc(Br)c1] | 5-(3-bromophenyl)-1-tert-butyl-N-hydroxy-1H-pyrazole-3-carboxamide | (MeOD-d4) d (ppm) 1H: 7.64 (m, 1H), 7.57 (s, 1H), 7.37 (m, 2H), 6.58 (s, 1H), 1.48 (s, 9H). LRMS (ESI): (calc.) 337.04 (found) 336.2 (M)− |
| 203 | 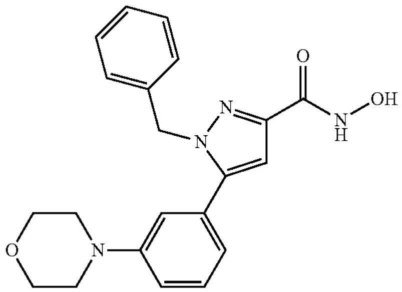 [SMILES: O=C(NO)c1cc(-c2cccc(N3CCOCC3)c2)n(Cc2ccccc2)n1] | 1-benzyl-N-hydroxy-5-(3-morpholinophenyl)-1H-pyrazole-3-carboxamide | (MeOD-d4) d (ppm) 1H: 7.29 (m, 4H), 7.03 (m, 3H), 6.75-6.85 (m, 3H), 5.41 (s, 2H), 3.74 (m, 4H), 2.97 (m, 4H). LRMS (ESI): (calc.) 378.17 (found) 379.36 (MH)+ |
| 204 | 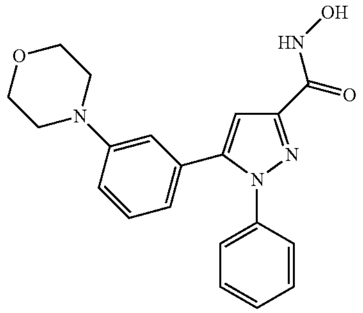 [SMILES: O=C(NO)c1cc(-c2cccc(N3CCOCC3)c2)n(-c2ccccc2)n1] | N-hydroxy-5-(3-morpholinophenyl)-1-phenyl-1H-pyrazole-3-carboxamide | (DMSO-d6) d (ppm) 1H: 11.1 (s, 1H), 9.0 (s, 1H), 7.43 (m, 3H), 7.32 (m, 2H), 7.17 (t, J = 8 Hz, 1H), 6.98 (s, 1H), 6.93 (dd, J = 1.6 Hz, 8.4 Hz, 1H), 6.79 (s, 1H), 6.62 (d, J = 7.6 Hz, 1H), 3.66 (t, J = 4.8 Hz, 4H), 2.97 (t, J = 4.8 Hz, 4H). LRMS (ESI): (calc.) 364.15 (found) 365.38 (MH)+ |

TABLE 9-continued

The following additional compounds were prepared according to the procedures described herein and/or according to knowledge available to one of skill in the art.

| Cpd # | Structure | Name | Characterization |
|---|---|---|---|
| 205 | 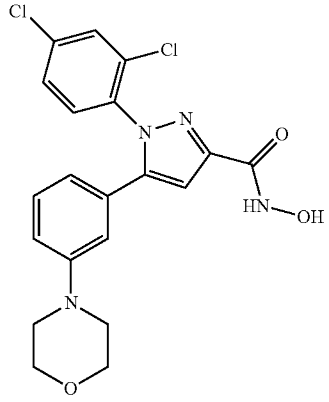 [SMILES: O=C(NO)c1cc(-c2cccc(N3CCOCC3)c2)n(-c2ccc(Cl)cc2Cl)n1] | 1-(2,4-dichlorophenyl)-N-hydroxy-5-(3-morpholinophenyl)-1H-pyrazole-3-carboxamide | (MeOD-d4) d (ppm) 1H: 7.17-7.63 (m, 4H), 6.91-6.99 (m, 2H), 6.71-6.76 (m, 2H), 3.76 (t, J = 4.8 Hz, 4H), 2.97 (t, J = 4.4 Hz, 4H). LRMS (ESI): (calc.) 432.08 (found) 431.13 (M)− |
| 206 | 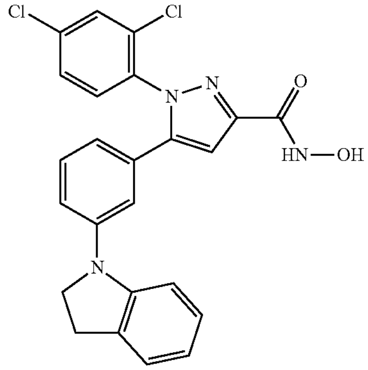 [SMILES: O=C(NO)c1cc(-c2cccc(N3CCc4ccccc43)c2)n(-c2ccc(Cl)cc2Cl)n1] | 1-(2,4-dichlorophenyl)-N-hydroxy-5-(3-(indolin-1-yl)phenyl)-1H-pyrazole-3-carboxamide | (MeOD-d4) d (ppm) 1H: 7.68 (m, 1H), 7.59 (m, 2H), 7.33 (t, J = 8 Hz, 1H), 7.12 (d, J = 7.6 Hz, 2H), 6.96 (m, 4H), 6.71 (t, J = 7.6 Hz, 1H), 6.44 (d, J = 8 Hz, 1H), 3.78 (t, J = 8 Hz, 2H), 3.04 (t, J = 8.4 Hz, 2H). LRMS (ESI): (calc.) 464.08 (found) 465.37 (MH)+ |
| 207 | 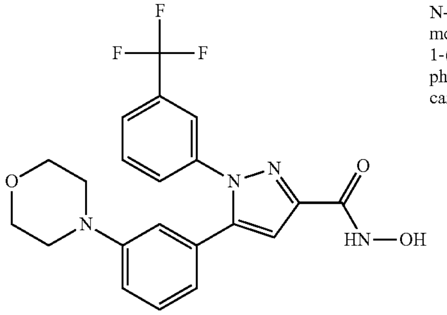 | N-hydroxy-5-(3-morpholinnophenyl)-1-(3-(trifluoromethyl) phenyl)-1H-pyrazole-3-carboxamide | (MeOD-d4) d (ppm) 1H: 7.69 (s, 2H), 7.59 (m, 2H), 7.25 (t, J = 8 Hz, 1H), 6.99 (m, 2H), 6.77 (m, 2H), 3.75 (t, J = 4.8 Hz, 4H), 2.99 (t, J = 4.8 Hz, 4H). LRMS (ESI): (calc.) 432.14 (found) 431.35 (M)− |
| 208 | 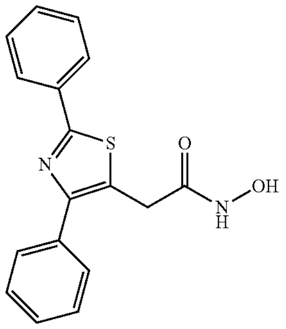 [SMILES: O=C(Cc1sc(-c2ccccc2)nc1-c1ccccc1)NO] | 2-(2,4-diphenylthiazol-5-yl)-N-hydroxyacetamide | (MeOD-d4) d (ppm) 1H: 8.02-7.96 (m, 2H), 7.75-7.71 (m, 2H), 7.56-7.44 (m, 6H), 3.79 (s, 2H) LRMS (ESI): (calc.) 310.4 (found) 311.2 (MH)+ |

TABLE 9-continued

The following additional compounds were prepared according to the procedures described herein and/or according to knowledge available to one of skill in the art.

| Cpd # | Structure | Name | Characterization |
|---|---|---|---|
| 209 | 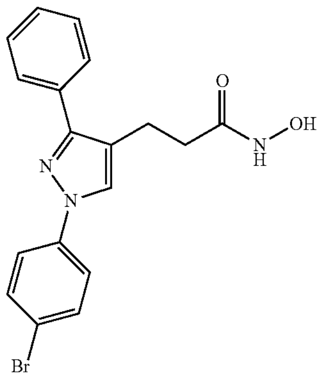 [SMILES: O=C(CCc1cn(-c2ccc(Br)cc2)nc1-c1ccccc1)NO] | 3-(1-(4-bromophenyl)-3-phenyl-1H-pyrazol-4-yl)-N-hydroxypropanamide | (DMSO-d6) d (ppm) 1H: 10.49 (br s, 1H), 8.79 (br s, 1H), 8.44 (s, 1H), 7.90-7.84 (m, 2H), 7.77-7.71 (m, 4H), 7.56-7.49 (m, 2H), 7.47-7.42 (m, 1H), 2.93 (t, J = 7.4 Hz, 2H), 2.37 (t, J = 7.2 Hz, 2H) LRMS (ESI): (calc.) 386.2 (found) 386.3 (MH)+ |

Where possible, the compounds in this application were named using Chemdraw Ultra version 9 or 10, which is available through Cambridgesoft.co, 100 Cambridge Park Drive, Cambridge, Mass. 02140, Meta- and para-substituted aryl or heteroaryl hydroxamates are very well known as HDAC inhibitors. Ortho-substitutions are detrimental for the potency of HDAC inhibitors; however small groups substituents such as halo can be tolerated.

We have unexpectedly found that o-substituted aryl or heteroaryl hydroxamates having a much bigger but flat aromatic or heteroaromatic substituent such as phenyl or thienyl are not only well tolerated but cause an increase in HDAC inhibitory activity and impart selectivity for histone deacetylase-4, -5, -6, -7, -8, -9 and/or -11.

Compositions

In a second aspect, the invention provides compositions comprising a compound according to the invention or an N-oxide, hydrate, solvate, pharmaceutically acceptable salt, complex or prodrug thereof, or a racemic or scalemic mixture, diastereomer, enantiomer or tautomer thereof, and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, intravenous or intrarectal. In certain embodiments, compounds of the invention are administered intravenously in a hospital setting. In certain other embodiments, administration may be by the oral route. The compositions may be in the form of liquid solutions or suspensions; for oral administration, formulations may be in the form of tablets or capsules; and for intranasal formulations, in the form of powders, nasal drops or aerosols. The compositions of the invention may be administered systemically or locally.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

In one embodiment of the second aspect, the composition comprises a compound, N-oxide, hydrate, solvate, pharmaceutically acceptable salt, complex or prodrug of a compound according to the present invention as described herein present in at least about 30% enantiomeric or diastereomeric excess. In certain embodiments of the invention, the compound, N-oxide, hydrates, solvate, pharmaceutically acceptable salt, complex or prodrug is present in at least about 50%, at least about 80%, or even at least about 90% enantiomeric or diastereomeric excess. In certain other embodiments of the invention, the compound, N-oxide, hydrate, solvate, pharmaceutically acceptable salt, complex or prodrug is present in at least about 95%, alternatively at least about 98% and alternatively at least about 99% enantiomeric or diastereomeric excess. In other embodiments of the invention, a compound, N-oxide, hydrate, solvate, pharmaceutically acceptable salt, complex or prodrug is present as a substantially racemic mixture. In certain embodiments, the composition further comprises an additional therapeutic or inhibitory agent.

As used herein, the term "pharmaceutically acceptable salts" is intended to mean salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate). As used herein, the term "salt" is also meant to encompass complexes, such as with an alkaline metal or an alkaline earth metal.

The active compound is included in the pharmaceutically acceptable carrier or diluent in an amount sufficient to deliver an inhibition or therapeutic effective amount without causing undesirable toxic effects. In certain embodiments, a dose of the active compound for all of the above-mentioned conditions is in the range from about 0.01 to 300 mg/kg, for example 0.1 to 100 mg/kg per day, alternatively 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

In certain embodiments of the second aspect of the invention, the composition further comprises an agent, such as an antisense oligonucleotide, that inhibits the expression of an HDAC gene. The combined use of a nucleic acid level inhibitor (e.g., antisense oligonucleotide) and a protein level inhibitor (i.e., inhibitor of HDAC enzyme activity) results in an improved inhibitory effect, thereby reducing the amounts of the inhibitors required to obtain a given inhibitory effect as compared to the amounts necessary when either is used individually. The antisense oligonucleotides according to this aspect of the invention are complementary to regions of RNA or double-stranded DNA that encode an HDAC gene. In other embodiments of the second aspect, the composition further comprises an additional agent that inhibits the enzymatic activity of the HDAC enzyme.

Additional inhibitory agents may also be present in the compositions of this invention, where the combination causes no unacceptable adverse effects.

Inhibition of HDAC Activity

In a third aspect, the invention provides a method of inhibiting HDAC activity, the method comprising contacting the HDAC with an inhibition effective amount of a compound according to the present invention, or with an inhibition effective amount of a composition according to the present invention. Inhibition of HDAC activity can be in a cell or a multicellular organism. If in a cell, the method according to this aspect comprises contacting the cell with an inhibition effective amount of a compound according to the present invention, or with an inhibition effective amount of a composition according to the present invention. If in a multicellular organism, the method according to this aspect of the invention comprises administering to the organism an inhibition effective amount of a compound according to the present invention, or an inhibition effective amount of a composition according to the present invention. In certain embodiments, the organism is a mammal, for example, a human. In certain embodiments, the method further comprises contacting the HDAC or the cell, with an effective amount of an additional inhibitory agent, or if in a multicellular organism, concurrently or sequentially administering an inhibition effective amount of an additional inhibitory agent.

In certain embodiments, the method is a method of treating a disease responsive to an inhibitor of HDAC activity and comprises administering to an individual in need thereof an effective amount of a compound or composition thereof according to the present invention. In certain embodiments, the method of treatment further comprises administering an effective amount of an additional therapeutic agent, wherein the additional therapeutic agent is a therapeutic agent appropriate for treating the disease.

Because compounds of the invention inhibit HDAC activity they are useful research tools for in vitro study of HDACs and their role in biological processes.

Measurement of the enzymatic activity of an HDAC can be achieved using known methodologies.

In some embodiments, the HDAC inhibitor interacts with and reduces the activity of fewer than all HDACs in the cell. In certain embodiments, the inhibitor interacts with and reduces the activity of HDAC4, HDAC5, HDAC6, HDAC7, HDAC8 and/or HDAC9, alternatively HDAC4, HDAC5, HDAC6, HDAC7 and/or HDAC8. In certain other embodiments, the inhibitor has an $IC_{50}$ for HDAC8 which is lower than the $IC_{50}$ for HDAC4, HDAC5, HDAC6 and/or HDAC7.

In certain embodiments of the present invention, the HDAC inhibitor of the present invention may be administered together with another HDAC inhibitor known in the art or which will be discovered. Administration of such HDAC inhibitor may be done sequentially or concurrently. In certain embodiments of the present invention the compositions comprise an HDAC inhibitor of the present invention and/or an antisense oligonucleotide and/or another HDAC inhibitor known in the art or which will be discovered. The active ingredients of such compositions for example act synergistically to produce a therapeutic effect.

In another embodiment of the third aspect, the method comprises inhibiting HDAC with a compound according to any of Formulae (I) to (Iaa) and Formula (II).

In another embodiment of the third aspect, the method comprises inhibiting HDAC with a compound selected from the group consisting of N-hydroxybiphenyl-2-carboxamide, N-hydroxy-2-phenoxybenzamide, N-hydroxy-2-(phenylamino)benzamide and 2-benzyl-N-hydroxybenzamide.

In another embodiment of the third aspect, the method of treating a disease responsive to an inhibitor of HDAC activity comprises administering to an individual in need thereof an effective amount of a compound according to any of Formulae (I) to (Iaa).

In another embodiment of the third aspect, the method of treating a disease responsive to an inhibitor of HDAC activity comprises administering to an individual in need thereof an effective amount of a compound selected from the group consisting of N-hydroxybiphenyl-2-carboxamide, N-hydroxy-2-phenoxybenzamide, N-hydroxy-2-(phenylamino)benzamide and 2-benzyl-N-hydroxybenzamide, or a composition thereof.

The following Examples are intended to further illustrate certain embodiments of the invention, and are not intended to limit the scope of the invention.

ASSAY EXAMPLES

Assay Example 1

Inhibition of Histone Deacetylase Enzymatic Activity

Inhibition of HDAC-1,2,3,6 and 8

The following protocol is used to assay the compounds of the invention. In the assay, the buffer used is 25 mM HEPES, pH 8.0, 137 mM NaCl, 2.7 mM KCl, 1 mM $MgCl_2$ and the substrate is Boc-Lys(Ac)-AMC in a 50 mM stock solution in DMSO. The enzyme stock solution is 4.08 μg/mL in buffer.

The compounds are pre-incubated (2 μl, in DMSO diluted to 13 μL in buffer for transfer to assay plate) with enzyme (20 μL of 4.08 μg/mL) for 10 minutes at room temperature (35 μL pre-incubation volume). The mixture is pre-incubated for 5 minutes at room temperature. The reaction is started by bringing the temperature to 37° C. and adding 15 μL substrate. Total reaction volume is 50 μL. The reaction is stopped after 20 minutes by addition of 50 μL developer, prepared as directed by Biomol (FLUOR DE LYS™ developer, Cat. # KI-105). A plate is incubated in the dark for 10 minutes at room temperature before reading ($\lambda_{Ex}$=360 nm, $\lambda_{Em}$=470 nm, Cutoff filter at 435 nm).

Inhibition of Class II HDAC and HDAC-11

A 30 mM stock of Boc-Lys(trifluoroacetyl)-AMC substrate is prepared in DMSO. 2 μL test compound in DMSO is diluted to 50 μL in buffer (25 mM HEPES, pH 8.0, 137 mM NaCl, 2.7 mM KCl, 1 mM $MgCl_2$, 0.1% BSA) and pre-incubated with HDAC enzyme (30 μL of a final enzyme concentration of 0.1-0.2 nM) for 10 minutes at room temperature. Reaction is started by adding 18 μL Boc-Lys(trifluoro-acetyl)-AMC substrate and incubating at 37° C. for 20-30 minutes. The reaction is stopped by adding 50 μL trypsin (1 mg/mL) and a known HDAC inhibitor. The plate is then incubated in the dark for 20 minutes at room temperature and read with Ex=360 nm, Em=470 nm, cutoff filter at 435 nm.

Compounds exemplified have an $IC_{50}$ value less than or equal to 12 μM against one or more of HDAC4, HDAC5, HDAC6, HDAC7, HDAC8, HDAC9 and HDAC11. The $IC_{50}$ values of some compounds according to the present invention are shown in Table 10. In the table, "a" represents an $IC_{50}$ value of less than 250 nM against one or more of HDAC4, HDAC5, HDAC6, HDAC7, HDAC8, HDAC9 and HDAC11; 250 nM≤"b"<500 nM; 500 nM≤"c"<750 nM; 750≤"d"<5000 nM.

TABLE 10

| Cpd No. | $IC_{50}$ code | Cpd No. | $IC_{50}$ code | Cpd No. | $IC_{50}$ code | Cpd No. | $IC_{50}$ code |
|---|---|---|---|---|---|---|---|
| 13 | d | 108 | d | 125 | a | 147 | a |
| 19 | d | 109 | a | 130 | a | 181 | a |
| 21 | d | 110 | a | 131 | c | 148 | a |
| 24 | d | 80 | a | 126 | c | 162 | a |
| 26 | d | 81 | a | 132 | a | 150 | a |
| 27 | d | 86 | a | 133 | a | 151 | a |
| 50 | d | 89 | b | 139 | d | 152 | a |
| 33 | c | 92 | a | 140 | c | 153 | b |
| 98 | c | 116 | a | 141 | b | 154 | c |
| 29 | c | 117 | a | 143 | b | 155 | a |
| 32 | c | 120 | a | 144 | a | 157 | a |
| 74 | a | 121 | a | 145 | a | 158 | a |
| 51 | a | 122 | a | 180 | a | 160 | b |
| 52 | a | 105 | c | 146 | a | | |
| 106 | b | 104 | a | 182 | a | | |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A compound or an N-oxide, hydrate, solvate, pharmaceutically acceptable salt, prodrug or complex thereof, in the form of a racemic or scalemic mixture, tautomer, diastereomer or enantiomer thereof, wherein the compound is selected from,

| # | Structure |
|---|---|
| 66 | 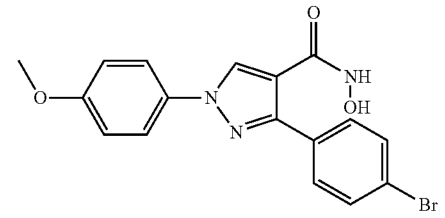 [SMILES: COc1ccc(-n2cc(C(=O)NO)c(-c3ccc(Br)cc3)n2)cc1] |
| 70 | 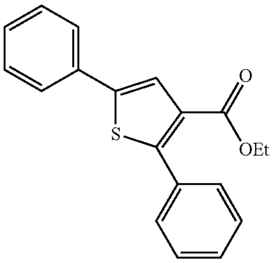 [SMILES: CCOC(=O)c1cc(-c2ccccc2)sc1-c1ccccc1] |
| 71 | 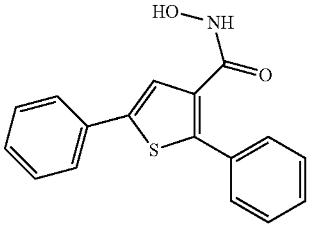 [SMILES: O=C(NO)c1cc(-c2ccccc2)sc1-c1ccccc1] |
| 74 | 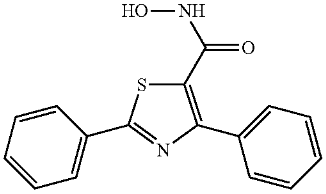 [SMILES: O=C(NO)c1sc(-c2ccccc2)nc1-c1ccccc1] |
| 80 | 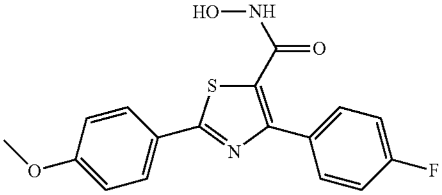 [SMILES: COc1ccc(-c2nc(-c3ccc(F)cc3)c(C(=O)NO)s2)cc1] |
| 81 | 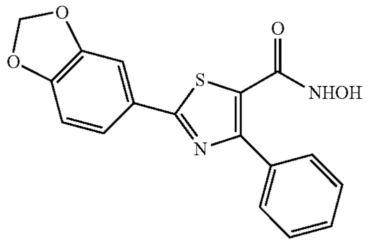 |
| 86 | 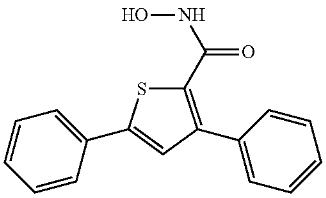 [SMILES: O=C(NO)c1sc(-c2ccccc2)cc1-c1ccccc1] |
-continued
| # | Structure |
|---|---|
| 106 | 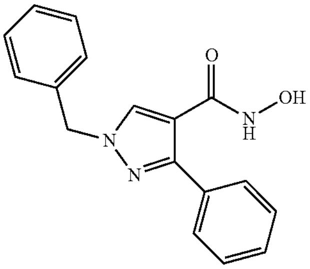 [SMILES: O=C(NO)c1cn(Cc2ccccc2)nc1-c1ccccc1] |
| 108 | 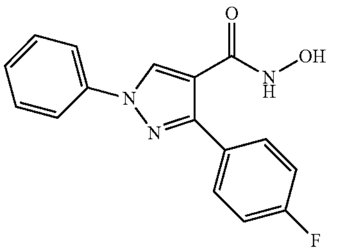 [SMILES: O=C(NO)c1cn(-c2ccccc2)nc1-c1ccc(F)cc1] |
| 109 | 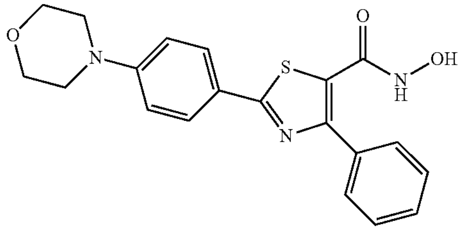 [SMILES: O=C(NO)c1sc(-c2ccc(N3CCOCC3)cc2)nc1-c1ccccc1] |
| 110 | 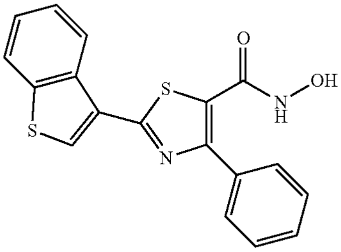 [SMILES: O=C(NO)c1sc(-c2csc3ccccc23)nc1-c1ccccc1] |
| 111 | 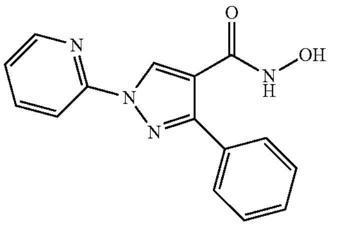 [SMILES: O=C(NO)c1cn(-c2ccccn2)nc1-c1ccccc1] |
| 112 | 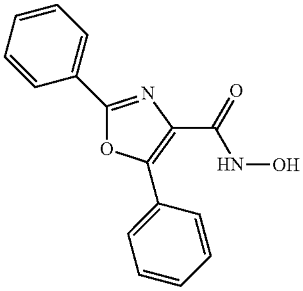 |

-continued
| # | Structure |
|---|---|
| 113 | 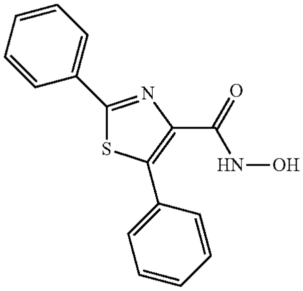 [SMILES: O=C(NO)c1nc(-c2ccccc2)oc1-c1ccccc1] |
| 114 | 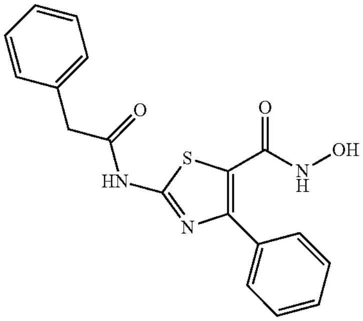 [SMILES: O=C(Cc1ccccc1)Nc1nc(-c2ccccc2)c(C(=O)NO)s1] |
| 117 | 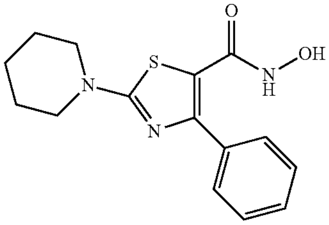 [SMILES: O=C(NO)c1sc(N2CCCCC2)nc1-c1ccccc1] |
| 120 | 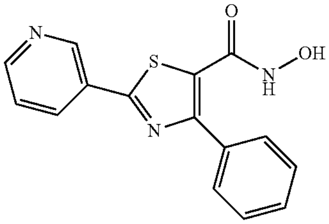 [SMILES: O=C(NO)c1sc(-c2cccnc2)nc1-c1ccccc1] |
| 122 | 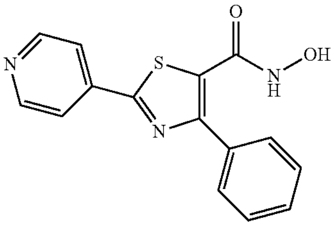 [SMILES: O=C(NO)c1sc(-c2ccncc2)nc1-c1ccccc1] |
| 125 | 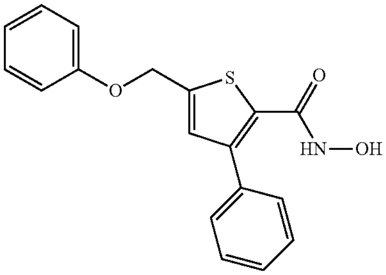 [SMILES: O=C(NO)c1sc(COc2ccccc2)cc1-c1ccccc1] |
-continued
| # | Structure |
|---|---|
| 130 | 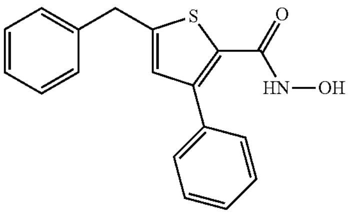 [SMILES: O=C(NO)c1sc(Cc2ccccc2)cc1-c1ccccc1] |
| 132 | 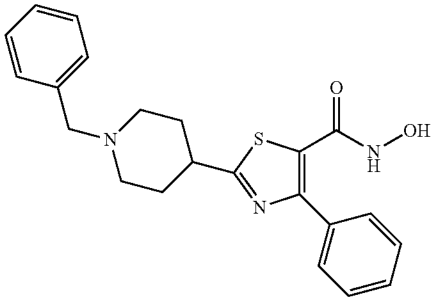 [SMILES: O=C(NO)c1sc(C2CCN(Cc3ccccc3)CC2)nc1-c1ccccc1] |
| 133 | 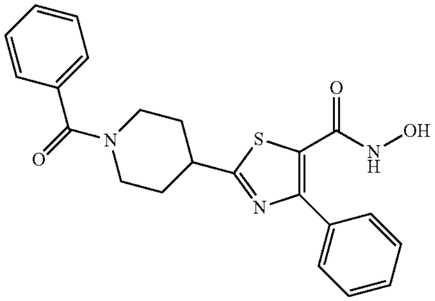 [SMILES: O=C(NO)c1sc(C2CCN(C(=O)c3ccccc3)CC2)nc1-c1ccccc1] |
| 139 | 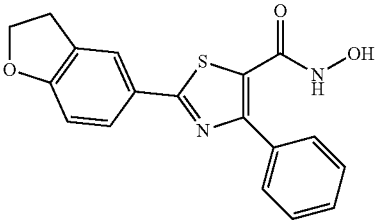 [SMILES: O=C(NO)c1sc(-c2ccc3c(c2)CCO3)nc1-c1ccccc1] |
| 140 | 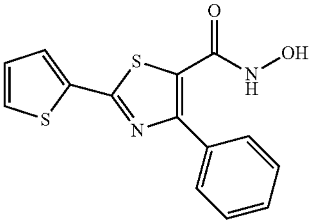 [SMILES: O=C(NO)c1sc(-c2cccs2)nc1-c1ccccc1] |
| 142 | 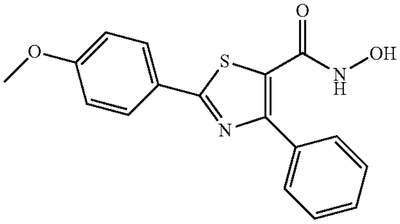 [SMILES: COc1ccc(-c2nc(-c3ccccc3)c(C(=O)NO)s2)cc1] |

-continued
| # | Structure |
|---|---|
| 144 | 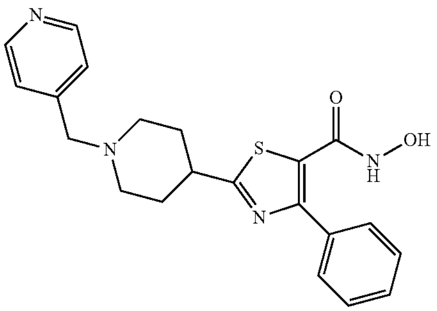 [SMILES: O=C(NO)c1sc(C2CCN(Cc3ccncc3)CC2)nc1-c1ccccc1] |
| 145 | 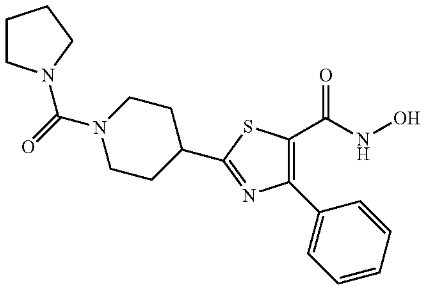 [SMILES: O=C(NO)c1sc(C2CCN(C(=O)N3CCCC3)CC2)nc1-c1ccccc1] |
| 147 | 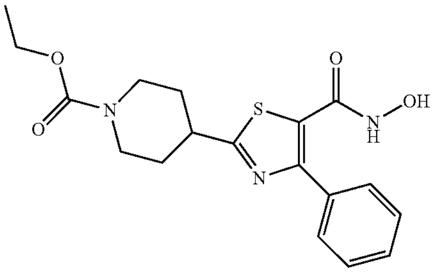 [SMILES: CCOC(=O)N1CCC(c2nc(-c3ccccc3)c(C(=O)NO)s2)CC1] |
| 148 | 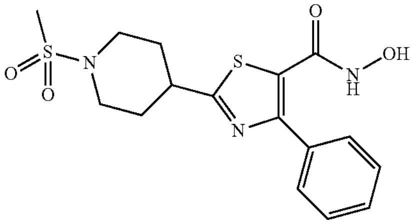 [SMILES: CS(=O)(=O)N1CCC(c2nc(-c3ccccc3)c(C(=O)NO)s2)CC1] |
| 150 | 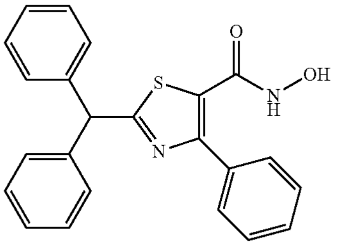 [SMILES: O=C(NO)c1sc(C(c2ccccc2)c2ccccc2)nc1-c1ccccc1] |
-continued
| # | Structure |
|---|---|
| 151 | 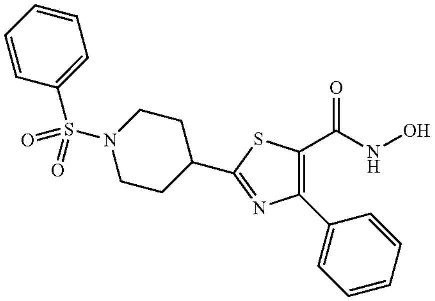 [SMILES: O=C(NO)c1sc(C2CCN(S(=O)(=O)c3ccccc3)CC2)nc1-c1ccccc1] |
| 152 | 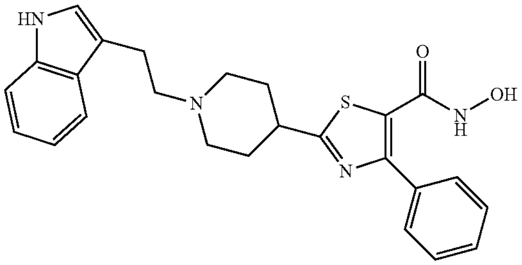 [SMILES: O=C(NO)c1sc(C2CCN(CCc3c[nH]c4ccccc34)CC2)nc1-c1ccccc1] |
| 153 | 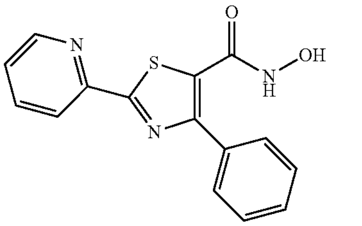 [SMILES: O=C(NO)c1sc(-c2ccccn2)nc1-c1ccccc1] |
| 156 | 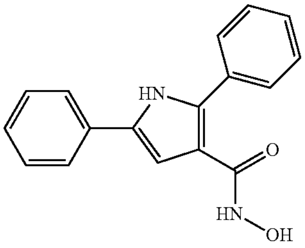 [SMILES: O=C(NO)c1cc(-c2ccccc2)[nH]c1-c1ccccc1] |
| 158 | 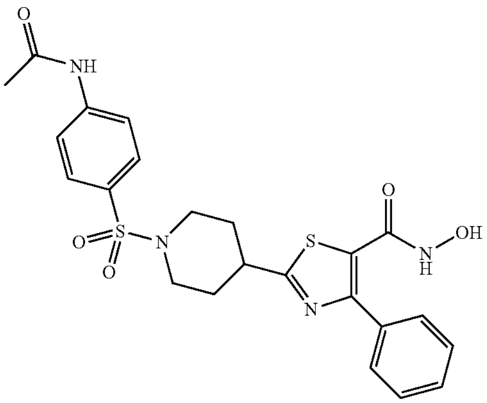 [SMILES: CC(=O)Nc1ccc(S(=O)(=O)N2CCC(c3nc(-c4ccccc4)c(C(=O)NO)s3)CC2)cc1] |

-continued
| # | Structure |
| --- | --- |
| 164 | 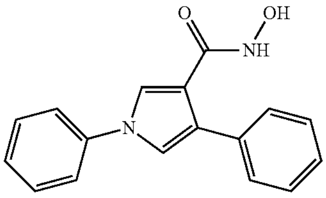 [SMILES: O=C(NO)c1cn(-c2ccccc2)cc1-c1ccccc1] |
| 180 | 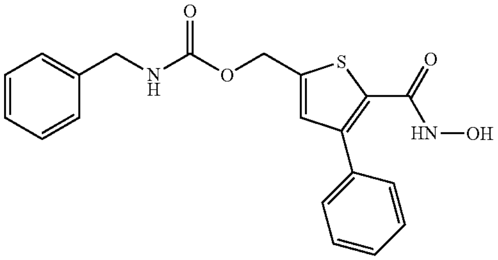 [SMILES: O=C(NCc1ccccc1)OCc1cc(-c2ccccc2)c(C(=O)NO)s1] |
| 181 | 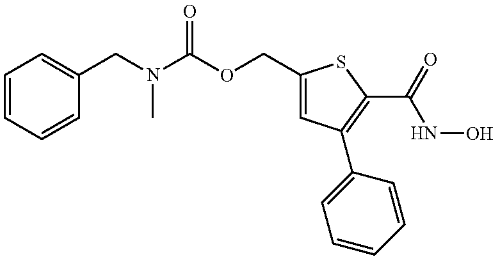 [SMILES: CN(Cc1ccccc1)C(=O)OCc1cc(-c2ccccc2)c(C(=O)NO)s1] |
| 182 | 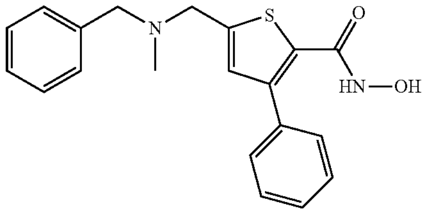 [SMILES: CN(Cc1ccccc1)Cc1cc(-c2ccccc2)c(C(=O)NO)s1] |
| 183 | 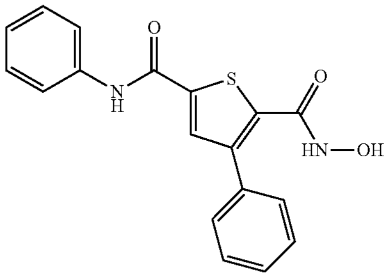 [SMILES: O=C(Nc1ccccc1)c1cc(-c2ccccc2)c(C(=O)NO)s1] |
| 201 | 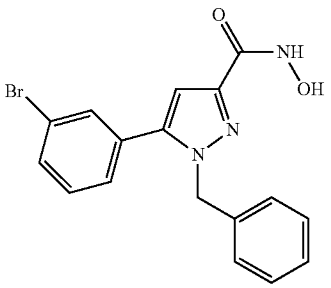 [SMILES: O=C(NO)c1cc(-c2cccc(Br)c2)n(Cc2ccccc2)n1] |
-continued
| # | Structure |
| --- | --- |
| 202 | 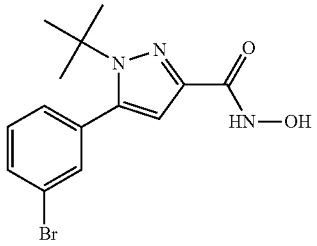 [SMILES: CC(C)(C)n1nc(C(=O)NO)cc1-c1cccc(Br)c1] |
| 203 | 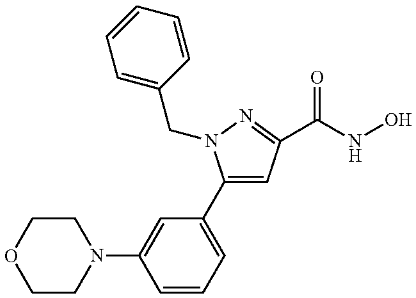 [SMILES: O=C(NO)c1cc(-c2cccc(N3CCOCC3)c2)n(Cc2ccccc2)n1] |
| 204 | 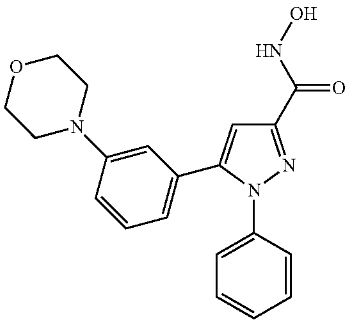 [SMILES: O=C(NO)c1cc(-c2cccc(N3CCOCC3)c2)n(-c2ccccc2)n1] |
| 205 | 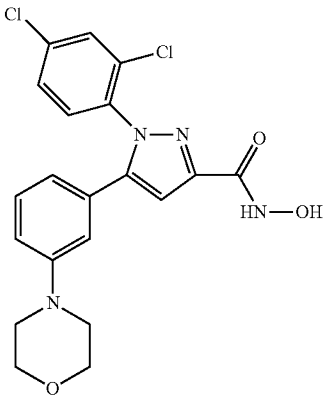 [SMILES: O=C(NO)c1cc(-c2cccc(N3CCOCC3)c2)n(-c2ccc(Cl)cc2Cl)n1] |

-continued
| # | Structure |
|---|---|
| 206 | 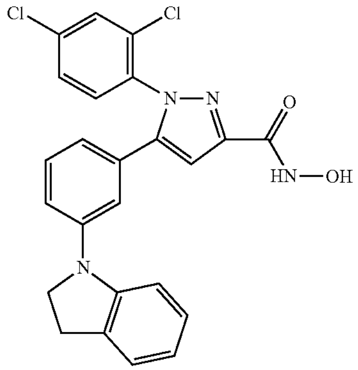 [SMILES: O=C(NO)c1cc(-c2cccc(N3CCc4ccccc43)c2)n(-c2ccc(Cl)cc2Cl)n1] |
or
-continued
| # | Structure |
|---|---|
| 207 | 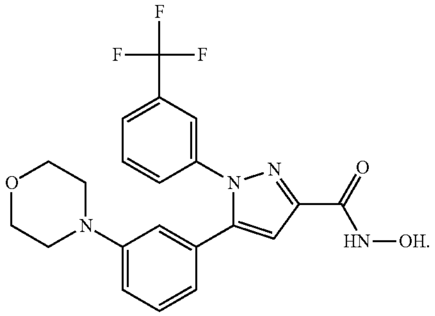 [SMILES: O=C(NO)c1cc(-c2cccc(N3CCOCC3)c2)n(-c2cccc(C(F)(F)F)c2)n1] |
2. A composition comprising a compound according to claim 1 and a pharmaceutically acceptable carrier.
* * * * *